US011834430B2

United States Patent
Ho et al.

(10) Patent No.: US 11,834,430 B2
(45) Date of Patent: Dec. 5, 2023

(54) COMPOUNDS USEFUL AS INHIBITORS OF ISOPRENYLCYSTEINE CARBOXYL METHYLTRANSFERASE

(71) Applicant: AGENCY FOR SCIENCE, TECHNOLOGY AND RESEARCH, Singapore (SG)

(72) Inventors: Soo Yei Ho, Singapore (SG); Anders Poulsen, Singapore (SG); Sum Wai Eldwin Tan, Singapore (SG); Shi Hua Ang, Singapore (SG); Thomas Hugo Keller, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/646,693

(22) PCT Filed: Sep. 12, 2018

(86) PCT No.: PCT/SG2018/050466
§ 371 (c)(1),
(2) Date: Mar. 12, 2020

(87) PCT Pub. No.: WO2019/054944
PCT Pub. Date: Mar. 21, 2019

(65) Prior Publication Data
US 2021/0130317 A1 May 6, 2021

(30) Foreign Application Priority Data
Sep. 12, 2017 (SG) .......................... 10201707444W

(51) Int. Cl.
*C07D 401/04* (2006.01)
*C07D 231/12* (2006.01)
*C07D 233/12* (2006.01)
*C07D 249/08* (2006.01)
*C07D 401/12* (2006.01)
*C07D 401/14* (2006.01)
*A61P 35/00* (2006.01)
*C07D 233/06* (2006.01)
*C07D 233/60* (2006.01)
*C07D 261/08* (2006.01)
*C07D 277/24* (2006.01)
*C07D 403/12* (2006.01)

(52) U.S. Cl.
CPC ............ *C07D 401/04* (2013.01); *A61P 35/00* (2018.01); *C07D 231/12* (2013.01); *C07D 233/06* (2013.01); *C07D 233/60* (2013.01); *C07D 249/08* (2013.01); *C07D 261/08* (2013.01); *C07D 277/24* (2013.01); *C07D 401/12* (2013.01); *C07D 401/14* (2013.01); *C07D 403/12* (2013.01)

(58) Field of Classification Search
CPC .. C07D 401/04; C07D 231/12; C07D 233/12; C07D 249/08; C07D 401/12; C07D 401/14
See application file for complete search history.

(56) References Cited

U.S. PATENT DOCUMENTS

| 2,196,576 A | 4/1940 | Coleman et al. |
| 2,248,491 A | 7/1941 | Coleman et al. |
| 4,537,617 A | 8/1985 | Plath et al. |
| (Continued) | | |

FOREIGN PATENT DOCUMENTS

| CN | 1432013 A | 7/2003 |
| CN | 1505625 A | 6/2004 |
| (Continued) | | |

OTHER PUBLICATIONS

Watanbe, et al. Document No. 116:235652, retrieved from STN; entered in STN on Jun. 13, 1992.*
(Continued)

*Primary Examiner* — Shawquia Jackson
(74) *Attorney, Agent, or Firm* — MARSHALL, GERSTEIN & BORUN LLP

(57) ABSTRACT

The present invention relates to compounds of general Formula (I), and/or tautomers, enantiomers, solvates, hydrates, and pharmaceutically acceptable salts thereof. The present invention also relates to compounds of Formula (I) for use in therapy, methods of treating isoprenylcysteine carboxyl methyltransferase (ICMT) related disorders or uses of compounds of Formula (I) in the manufacture of a medicament for the treatment of ICMT-related disorders, wherein the disorder is cancer and/or progeria. The present invention further relates to processes for synthesizing compounds of Formula (I).

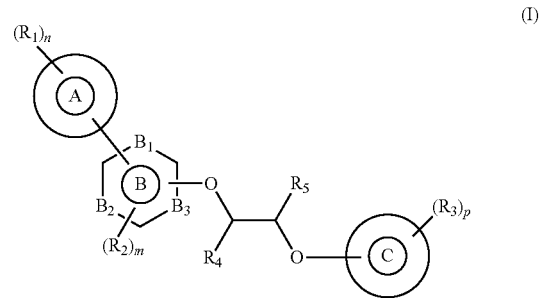

20 Claims, 8 Drawing Sheets

(56) References Cited

U.S. PATENT DOCUMENTS

| | | | |
|---|---|---|---|
| 6,204,293 | B1 | 3/2001 | Sebti et al. |
| 6,465,467 | B1 | 10/2002 | Nilsson et al. |
| 6,727,364 | B2 | 4/2004 | Tullis et al. |
| 6,958,353 | B2 | 10/2005 | Konno et al. |
| 8,227,500 | B2 | 7/2012 | Shimizu et al. |
| 8,742,100 | B2 | 6/2014 | Leow et al. |
| 10,626,095 | B2 | 4/2020 | Sato et al. |
| 2008/0070866 | A1 | 3/2008 | Deng et al. |
| 2009/0105253 | A1 | 4/2009 | Kubo et al. |
| 2010/0099675 | A1 | 4/2010 | Kawashima et al. |

FOREIGN PATENT DOCUMENTS

| | | |
|---|---|---|
| CN | 1944383 A | 4/2007 |
| CN | 102574787 A | 7/2012 |
| DE | 3331692 A1 | 3/1985 |
| EP | 135838 A2 | 4/1985 |
| EP | 658548 A1 | 6/1995 |
| JP | 2004-262890 A | 9/2004 |
| JP | 2005-298406 A | 10/2005 |
| JP | 2008-239614 A | 10/2008 |
| JP | 2009-545597 A | 12/2009 |
| JP | 2016-525069 A | 8/2016 |
| KR | 1020090077091 | 7/2009 |
| WO | WO-02/00648 A1 | 1/2002 |
| WO | WO-02/08200 A2 | 1/2002 |
| WO | WO-03/097163 A2 | 11/2003 |
| WO | WO-2006/109846 A1 | 10/2006 |
| WO | WO-2008/016674 A1 | 2/2008 |
| WO | WO-2008/126899 A1 | 10/2008 |
| WO | WO-2010/058417 A1 | 5/2010 |
| WO | WO-2012/104875 A1 | 8/2012 |
| WO | WO-2014/041349 A1 | 3/2014 |
| WO | WO-2015/008872 A1 | 1/2015 |
| WO | WO-2016/044556 A2 | 3/2016 |
| WO | WO-2016/118666 A1 | 7/2016 |
| WO | WO-2017/136699 A1 | 8/2017 |
| WO | WO-2018/119357 A1 | 6/2018 |

OTHER PUBLICATIONS

WO 2002006237 A1 (Harada, et al.) Jan. 24, 2002 (abstract) STN [database online]. CAPLUS [retrieved on Aug. 30, 2021]. Accession No. 2002:72052.*

U.S. Pat. No. 20130109697 A1 (Heckel, et al.) May 2, 2013 (abstract) STN [database online]. CAPLUS [retrieved on Aug. 30, 2021]. Accession No. 2013:681953.*

WO 2002000648 A1 (Konno, et al.) Jan. 3, 2002 (abstract) STN [database online]. CAPLUS [retrieved on Aug. 30, 2021]. Accession No. 2002:10467.*

WO 2005063732 A1 (Pearson, et al.) Jul. 14, 2005 (abstract) STN [database online]. CAPLUS [retrieved on Aug. 30, 2021]. Accession No. 2005:612274.*

Cancer and Metastasis Reviews (1998), 17(1), 91-106.*

Science (1999), vol. 286, 531-537.*

Cancer [online], [retrieved on Jul. 6, 2007]. Retrieved from the internet, URL http://www.nlm.nih.gov/medlineplus/cancer.html>.*

Extended European Search Report in EP Application No. 18856093.2 dated Jan. 22, 2021, 15 pages.

Morimoto et al., Modifications and Structure-Activity Relationships at the 2-Position of 4-Sulfonamidopyrimidine Derivatives as Potent Endothelin Antagonists, Bioorganic & Medicinal Chemistry Letters, vol. 12, 2002, pp. 81-84.

Database Registry [Online] Chemical Abstracts Service, Columbus, Ohio, US, Jul. 5, 2015, XP002801468, Database Assession No. 1794288-61-1, abstract.

Database Registry [Online] Chemical Abstracts Service, Columbus, Ohio, US, Aug. 23, 2011, XP002801469, Database Assession No. 1322079-46-8, abstract.

Database Registry [Online] Chemical Abstracts Service, Columbus, Ohio, US, Aug. 21, 2011, XP002801470, Database Assession No. 1320667-01-3, abstract.

Yang et al., "Isoprenyl Carboxyl Methyltransferase Inhibitors: a Brief Review Including Recent Patents", Amino Acids, vol. 49, 2017, pp. 1469-1485.

More et al., "Discovery of Target Based Novel Pyrrolyl Phenoxy Derivatives as Antimycobacterial Agents: An in Silico Approach", European Journal of Medicinal Chemistry 94, 2015, pp. 317-339.

Goud et al., "One-Pot Synthesis of Bis(4,5-diphenylimidazol-2-yl-phenyl)glycols and Evaluation of Their Antimicrobial Activity", Russian Journal of General Chemistry, vol. 85, No. 3, 2015, pp. 673-678.

Search Report and Written Opinion in International Application No. PCT/SG2018/050466 dated Dec. 4, 2018, 18 pages.

Mahmoud et al, "Discovery of New Heat Shock Protein 90 Inhibitors Using Virtual Co-crystallized Pharmacophore Generation", Journal of Enzyme Inhibition and Medicinal Chemistry, vol. 31, No. 54, Aug. 12, 2016, pp. 64-77.

Search Report and Written Opinion in SG Application No. 11202002267U dated Aug. 17, 2021, 12 pages.

Office Action in EP Application No. 18856093.2 dated Nov. 23, 2021, 12 pages.

Chemical Abstract Registry No. 1798056-84-4, Benzonitrile, 2-[2-[3-(1H-1,2,4-triazol-1-yl)phenoxy]ethoxy]-, entered Jul. 9, 2015.

Chemical Abstract Registry No. 1794887-30-1, 1H-Tetrazole, 1-[3-[2-(4-fluorophenoxy)ethoxy]phenyl]-, entered Jul. 5, 2015.

Chemical Abstract Registry No. 1607309-75-0, Benzonitrile, 3-[2-[3-(1H-1,2,4-triazol-1-yl)phenoxy]ethoxy]-, entered May 20, 2014.

Chemical Abstract Registry No. 1424456-53-0, 1H-Tetrazole, 1-[3-(2-phenoxyethoxy)phenyl]-, entered Mar. 17, 2013.

Chemical Abstract Registry No. 1286626-09-2, 1H-Tetrazole, 1-[3-[2-(2,6-dimethylphenoxy)ethoxy]phenyl]-, entered Apr. 27, 2011.

Chemical Abstract Registry No. 1285917-66-9, 1H-Tetrazole, 1-[3-[2-(2-methylphenoxy)ethoxy]phenyl]-, entered Apr. 26, 2011.

Chemical Abstract Registry No. 1276433-33-0, 1H-Tetrazole, 1-[3-[2-(3-chlorophenoxy)ethoxy]phenyl]-, entered Apr. 7, 2011.

Chemical Abstract Registry No. 1197591-14-2, Benzonitrile, 4-[2-[3-(1H-tetrazol-1-yl)phenoxy]ethoxy]-, entered Dec. 16, 2009.

Chemical Abstract Registry No. 1110902-15-2, 1H-Tetrazole, 1-[3-[2-(2,6-dichlorophenoxy)ethoxy]phenyl]-, entered Feb. 24, 2009.

Chemical Abstract Registry No. 1090566-29-2, 1H-Tetrazole, 1-[3-[2-(2-bromo-4-chlorophenoxy)ethoxy]phenyl]-, entered Dec. 28, 2008.

Chemical Abstract Registry No. 1031644-68-4, Ethanone, 1-[2-[2-[3-(1H-tetrazol-1-yl)phenoxy]ethoxy]phenyl]-, entered Jun. 29, 2008.

Chemical Abstract Registry No. 949678-80-2, 1H-Tetrazole, 1-[3-[2-(4-methoxyphenoxy)ethoxy]phenyl]-, entered Oct. 9, 2007.

Chemical Abstract Registry No. 877967-21-0, 1H-Tetrazole, 1-[3-[2-(4-bromophenoxy)ethoxy]phenyl]-, entered Mar. 24, 2006.

Chemical Abstract Registry No. 874623-87-7, 1H-Tetrazole, 1-[3-[2-(3-bromophenoxy)ethoxy]phenyl]-, entered Feb. 20, 2006.

Office Action in JP Application No. 2020-515184 dated Oct. 4, 2022, 10 pages.

Office Action in CN Application No. 201880072698.4 dated Oct. 27, 2022, 14 pages.

Chemical Abstract Registry No. 1794288-61-1, 1,2,4-Oxadiazole, 3-[3-[2-(2-chlorophenoxy)ethoxy]phenyl]-5-methyl-, entered Jul. 5, 2015.

Chemical Abstract Registry No. 1322079-46-8, 1,2,4-Oxadiazole, 3-[3-[2-(3-bromophenoxy)ethoxy]phenyl]-5-methyl-, entered Aug. 23, 2011.

Chemical Abstract Registry No. 1320667-01-3, 1,2,4-Oxadiazole, 3-[3-[2-(4-bromophenoxy)ethoxy]phenyl]-5-methyl-, entered Aug. 21, 2011.

Khwaja et al., "Comparison of Quantitative Structure-activity Relationships of the Inhibition of Leukemia Cells in Culture With the Inhibition of Dihydrofolate Reductase From Leukemia Cells and Other Cell Types", J. Med. Chem, vol. 25, 1982, pp. 153-156.

* cited by examiner

COMPOUNDS USEFUL AS INHIBITORS OF ISOPRENYLCYSTEINE CARBOXYL METHYLTRANSFERASE

TECHNICAL FIELD

The present invention generally relates to compounds which act as inhibitors of isoprenylcysteine carboxyl methyltransferase (ICMT). The present invention also relates to the compounds for use in therapy, methods of treating ICMT-related disorders, or uses of the compounds in the manufacture of a medicament for the treatment of ICMT-related disorders. The present invention further relates to processes for synthesizing said compounds.

BACKGROUND ART

The members of the Ras family of signalling molecules and other proteins that terminate with a -CaaX motif undergo a three step post translational modification to carry out their cellular function. In the first step of the modification, a 15-carbon farnesyl or a 20-carbon geranylgeranyl lipid is covalently attached to the Cysteine residue of the CaaX motif. This is carried out by farnesyltransferase (FTase) or geranylgeranyltransferase (GGTase) type I enzymes. The second step involves the cleaving of the three amino acids (i.e., the -aaX) by the membrane associated Rce1 (Ras converting enzyme 1) protease. In the last step of the modification the newly exposed isoprenylated cysteine residue is methylated by ICMT. The post translational modification increases the hydrophobicity of the signalling molecules and directs it to the membrane.

The Ras family of GTPases are implicated in oncogenesis and tumour progression. K-Ras is the most commonly mutated form of Ras found in human malignancies, particularly in solid malignancies. Activating mutations in Ras have been found in almost 30% of all cancers, including 50% of colon cancers and up to 90% of pancreatic cancers. The transforming abilities of Ras require processing through the prenylation pathway. Hence, the protein prenyltransferases are important targets for many drug discovery programs. Inhibitors of FTase (FTIs) have been explored in the past but have not proven effective in clinical trials. One of the grounds of lack of efficacy might be due to the ability of GGTase to be effective in the post translational modification in the absence of FTase.

Genetic and pharmacological inactivation of ICMT have defined the specific requirement of CAAX motif methylation for Ras function. ICMT is required for the proper membrane targeting of H-, N-, and K-RAS. It has been shown that, inactivating ICMT in mouse fibroblasts inhibited cell growth and K-RAS-induced oncogenic transformation. Further, ICMT inactivation ameliorates K-Ras induced myeloproliferative disease. Hence, inhibitors of ICMT may be a better strategy to overcome the RAS proteins from associating with the plasma membrane.

With rising evidence for the importance of ICMT-catalyzed CaaX protein methylation in oncogenesis, there is a clear need for specific pharmacological agents to target this process. However, the only such agents available to date have been analogs of the substrate, like isoprenoid-modified analogs of the minimal ICMT substrate N-acetyl-S-farnesyl cysteine prenylcysteine or indole-based small-molecule inhibitor of Icmt. These compounds either had low potency or suffered from poor physicochemical and PK properties.

The other rationale for targeting ICMT includes treating progeroid disorders. Hutchinson-Gilford progeria syndrome (HGPS) is a rare dominant genetic disorder that mimics premature, rapid aging. This disease is caused by the accumulation of a mutant form of prelamin A that cannot be processed to mature lamin A. HGPS is most commonly caused by a de novo point mutation in exon 11 of LMNA. This mutation, which occurs in codon 608, activates a cryptic splice site and leads to the in-frame deletion of 50 aa within prelamin A. This deletion leaves the CAAX motif intact; hence, the mutant prelamin A (progerin) is predicted to undergo farnesylation, release of the_AAX, and carboxyl methylation. However, the site for the second endoproteolytic cleavage step, ZMPSTE24-recognition site is eliminated by the deletion.

A more severe form of progeria is caused by the loss of ZMPSTE24 protease activity through genetic mutation. In all forms of progeria, the lack of proteolysis of farnesylated and carboxymethylated prelamin A results in the accumulation of an incompletely processed molecule, termed progerin, on the nuclear envelope, where it triggers a range of molecular disturbances that lead to premature ageing. The presence of progerin adversely affects the integrity of the nuclear lamina, resulting in misshapen nuclei and nuclear blebs.

A possible treatment strategy for HGPS was tested using FTIs. A gene-targeted mouse model of HGPS was generated with genetically identical primary mouse embryonic fibroblasts and then FTIs effect on nuclear blebbing was examined. Using immunofluoresence microscopy the mislocalized progerin was observed to be away from the nuclear envelope to the nucleoplasm. So far, only modest effect has been observed in clinical trials.

Another strategy is to target ICMT in Progeria. The introduction of a hypomorphic allele of ICMT into the Zmpste24−/− mouse model of progeria largely rescued both the premature ageing phenotype and premature death. Thus, reducing isoprenylcysteine methylation pharmacologically may be helpful for children affected by Progeria.

ICMT has emerged as a promising target for drug discovery due to its role in protein prenylation pathway, a pathway that can be targeted for cancer and premature ageing disorders.

There is therefore a need to provide compounds that inhibit ICMT, and overcome, or at least ameliorate, one or more of the disadvantages described above.

SUMMARY

In one aspect of the present disclosure, there is provided a compound having the following Formula (I):

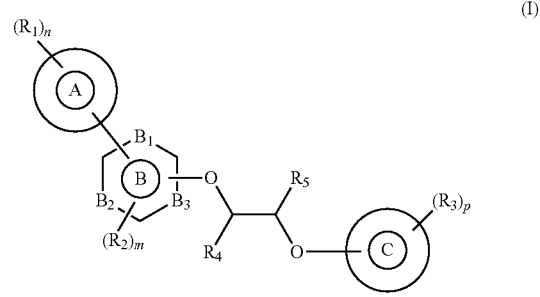

and/or tautomers, enantiomers, solvates, hydrates, prodrugs and pharmaceutically acceptable salts thereof;

wherein:

represents an aromatic ring system;

Ring A is a 5- or 6-membered carbocyclic ring system, wherein 1 to 4 carbon atoms may be optionally replaced with a heteroatom;

$B_1$, $B_2$ and $B_3$ are independently selected from C, CH, or N;

Ring C is a 5- or 6-membered carbocyclic ring system, wherein 1 to 3 carbon atoms may be optionally replaced with a heteroatom;

$R_1$, $R_2$, and $R_3$ are independently absent or selected from H, OH, cyano, halogen, optionally substituted alkyl, haloalkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl;

$R_4$ and $R_5$ are independently selected from H or aliphatic;

n is an integer selected from 0 to 5, wherein when n is more than 1, each $R_1$ substituted on Ring A may be the same or different;

m is an integer selected from 0 to 4, wherein when m is more than 1, each $R_2$ substituted on Ring B may be the same or different; and p is an integer selected from 0 to 5, wherein when p is more than 1, each $R_3$ substituted on Ring C may be the same or different.

In another aspect of the present disclosure, there is provided a compound having the following Formula (I):

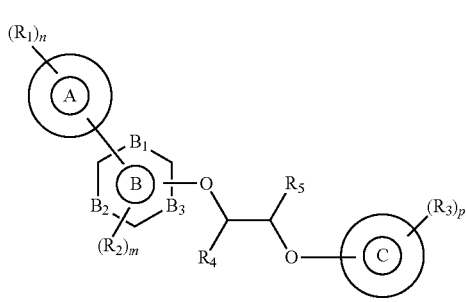

(I)

and/or tautomers, enantiomers, solvates, hydrates, prodrugs and pharmaceutically acceptable salts thereof;

wherein:

represents an aromatic ring system;

Ring A is a 5- or 6-membered carbocyclic ring system, wherein 1 to 4 carbon atoms may be optionally replaced with a heteroatom;

$B_1$, $B_2$ and $B_3$ are independently selected from C, CH, or N, wherein when one of $B_1$, $B_2$ or $B_3$ is N, the remaining $B_1$, $B_2$ or $B_3$ is C or CH;

Ring C is a 5- or 6-membered carbocyclic ring system, wherein 1 to 3 carbon atoms may be optionally replaced with a heteroatom;

$R_1$ is absent or selected from H, OH, halogen, optionally substituted alkyl, haloalkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl;

$R_2$ is absent or selected from H, OH, cyano, halogen, optionally substituted alkyl, haloalkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl;

$R_3$ is absent or selected from H, OH, cyano, halogen, optionally substituted alkyl, haloalkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, or optionally substituted aryl;

$R_4$ and $R_5$ are independently selected from H or aliphatic;

n is an integer selected from 0 to 5, wherein when n is more than 1, each $R_1$ substituted on Ring A may be the same or different;

m is an integer selected from 0 to 4, wherein when m is more than 1, each $R_2$ substituted on Ring B may be the same or different, and m is 1 when $R_2$ is halogen; and p is an integer selected from 0 to 5, wherein when p is more than 1, each $R_3$ substituted on Ring C may be the same or different.

In yet another aspect of the present disclosure, there is provided a pharmaceutical composition comprising a compound as defined herein, or a pharmaceutically acceptable form or prodrug thereof, and a pharmaceutically acceptable excipient.

In a further aspect of the present disclosure, there is provided a method of inhibiting methylation of isoprenylated cysteine or isoprenylcysteine caused by isoprenylcysteine carboxyl methyltransferase (ICMT) comprising contacting the compound as defined herein, or a pharmaceutical composition as defined herein, with ICMT.

In another aspect of the present disclosure, there is provided a method of inhibiting ICMT in a cell comprising contacting said cell with a compound as defined herein, or a pharmaceutically acceptable form or prodrug thereof, or a pharmaceutical composition as defined herein.

In yet another aspect of the present disclosure, there is provided a method of treating a ICMT-related disorder comprising administering to a subject in need of treatment a compound as defined herein, or pharmaceutical, or a composition as defined herein.

In a further aspect of the present disclosure, there is provided a compound as defined herein, or a pharmaceutically form or prodrug thereof, or a composition as defined herein for use in therapy.

In another aspect of the present disclosure, there is provided a compound as defined herein, or a pharmaceutically form or prodrug thereof, or a composition as defined herein for use in the treatment and/or prevention of cancer and/or progeroid diseases.

In yet another aspect of the present disclosure, there is provided a compound as defined herein, or a pharmaceutically form or prodrug thereof, or a composition as defined herein, for use in the treatment of a ICMT-related disorder.

In a further aspect of the present disclosure, there is provided a use of a compound as defined herein, or a pharmaceutically form or prodrug thereof, or a composition as defined herein, in the manufacture of a medicament for the treatment and/or prevention of cancer and/or progeroid diseases.

In another aspect of the present disclosure, there is provided a use of a compound as defined herein, or a pharmaceutically form or prodrug thereof, or a composition as defined herein, in the manufacture of a medicament for the treatment of a ICMT-related disorder.

In yet another aspect of the present disclosure, there is provided a process for synthesizing a compound as defined herein, comprising:

(a) reacting a compound of formula (III):

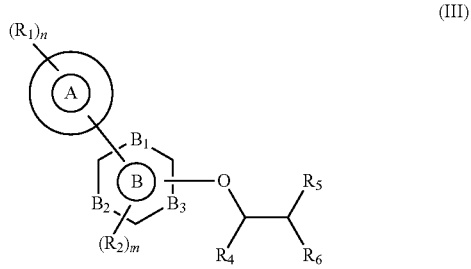

(III)

wherein $R_1$, $R_2$, $R_4$, $R_5$, $B_1$, $B_2$, $B_3$, n and m are as defined herein, and $R_6$ is a leaving group, in an organic solvent in the presence of a base with a compound of formula (IV):

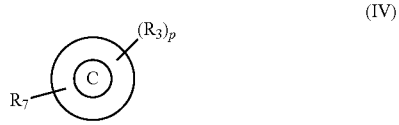

(IV)

wherein $R_3$ and p are as defined herein, and $R_7$ is —OH;

or (b) reacting a compound of formula (III):

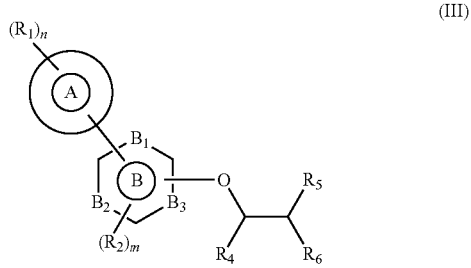

(III)

wherein $R_1$, $R_2$, $R_4$, $R_5$, $B_1$, $B_2$, $B_3$, n and m are as defined herein, and $R_6$ is OH or an alkoxide, in an organic solvent in the presence of a base with a compound of formula (IV):

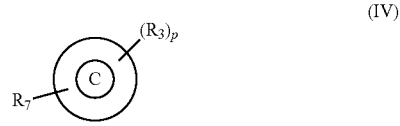

(IV)

wherein $R_3$ and p are as defined herein, and $R_7$ is halogen.

Advantageously, the compounds of the present disclosure and pharmaceutical compositions comprising them may inhibit ICMT effectively at low concentrations. Said compounds and pharmaceutical compositions comprising them may be useful for the prophylaxis and/or treatment of diseases linked to ICMT. Advantageously, the compounds or pharmaceutical compositions comprising them may offer a treatment to cancer, premature ageing, or Hutchinson-Gilford progeria syndrome (HGPS), including without limitation a cancer linked to mutant Ras overactivity such as hepatocellular carcinoma cancer, breast cancer, ovarian cancer, colorectal carcinoma, lung cancer, pancreatic cancer or leukaemia, and other diseases linked to high ICMT expression.

Advantageously, compared to known compounds of the prior art, the compounds of the present disclosure may show high effectiveness in ICMT inhibition combined with a desirable excellent anti-proliferative and anti-ageing activity. The compounds of the present disclosure can further be processed well into formulation for further drug testing.

Definitions

The following words and terms used herein shall have the meaning indicated:

"Acyl" means an R—C(=O)— group in which the R group may be an optionally substituted alkyl, optionally substituted cycloalkyl, optionally substituted heterocycloalkyl, optionally substituted aryl or optionally substituted heteroaryl group as defined herein. Examples of acyl include acetyl, benzoyl and amino acid derived aminoacyl. The group may be a terminal group or a bridging group. If the group is a terminal group it is bonded to the remainder of the molecule through the carbonyl carbon.

"Aliphatic" refers to an organic moiety wherein the carbon and hydrogen atoms are arranged in saturated or unsaturated straight or branched chains, including alkanes, alkenes and alkynes.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkoxy" refers to an alkyl-O— group in which alkyl is as defined herein. Preferably the alkyloxy is a $C_1$-$C_6$ alkyloxy. Examples include, but are not limited to methoxy and ethoxy. The group may be a terminal group or a bridging group. The term alkoxy may be used interchangeably with the term "alkyloxy".

"Alkyl" or "alkylene" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Amino" refers to groups of the form —$NR_aR_b$ wherein $R_a$ and $R_b$ are individually selected from the group including but not limited to hydrogen, optionally substituted alkyl, optionally substituted alkenyl, optionally substituted alkynyl, and optionally substituted aryl groups.

"Aryl" as a group or part of a group denotes (i) an optionally substituted monocyclic, or fused polycyclic, aromatic carbocycle (ring structure having ring atoms that are all carbon) preferably having from 6 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Azidoalkyl" refers to an alkyl group in which alkyl is as defined herein and which is substituted by an —$N_3$ group. Preferably the azidoalkyl is a $C_1$-$C_6$ azidoalkyl. Examples include, but are not limited to azidomethyl and azidoethyl.

"Carbocyclic" refers to any stable 3, 4, 5, 6, or 7-membered monocyclic or bicyclic or 7, 8, 9, 10, 11, 12, or 13-membered bicyclic or tricyclic ring system, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl". Carbocycles may be optionally substituted.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or bridged or spiro polycyclic, carbocycle preferably containing from 3 to 9 carbon atoms per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Haloalkyl" refers to an alkylgroup in which alkyl is as defined herein and the alkyl is substitueted by at least one halogen. Preferably the alkyl group is substituted by 1 to 5 halogen atoms. Preferably the alkyloxy is a $C_1$-$C_6$ haloalkyl. Examples include, but are not limited to chloromethyl, fluoromethyl and trifluoromethyl. The group may be a terminal group or a bridging group.

"Halogen" or "halo" represents chlorine, fluorine, bromine or iodine.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridinyl, 2-, 3-, 4-, 5-, or 8-quinolinyl, 1-, 3-, 4-, or 5-isoquinolinyl 1-, 2-, or 3-indolyl, and 2-, or 3 thiophenyl. A heteroaryl group is typically a $C_1$-$C_{18}$ heteroaryl group. A heteroaryl group may comprise 3 to 8 ring atoms. A heteroaryl group may comprise 1 to 3 heteroatoms independently selected from the group consisting of N, O and S. The group may be a terminal group or a bridging group.

"Heterocyclyl" refers to saturated or partially unsaturated monocyclic, bicyclic or polycyclic ring system containing at least one heteroatom selected from the group consisting of nitrogen, sulfur and oxygen as a ring atom. Examples of heterocyclic moieties include heterocycloalkyl and heterocycloalkenyl.

"Heterocycloalkenyl" refers to a heterocycloalkyl as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, fused or bridged or spiro polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidinyl, tetrahydrofuranyl, tetrahydrothiofuranyl, piperidinyl, piperazinyl, tetrahydropyranyl, morpholino, 1,3-diazapane, 1,4-diazapane, 1,4-oxazepane, and 1,4 oxathiapane. A heterocycloalkyl group typically is a $C_2$-$C_{12}$ heterocycloalkyl group. A heterocycloalkyl group may comprise 3 to 9 ring atoms. A heterocycloalkyl group may comprise 1 to 3 heteroatoms independently selected from the group consisting of N, O and S. The group may be a terminal group or a bridging group.

It is understood that included in the family of compounds of Formula (I) are isomeric forms including diastereomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

The term "optionally substituted" as used herein means the group to which this term refers may be unsubstituted, or may be substituted with one or more groups independently selected from optionally substituted aryl, optionally substituted heteroarylyl, alkyl, including an alkylene bride representing two substitutents, alkenyl, alkynyl, thioalkyl, cycloalkyl, aminocycloalkyl, cycloalkylalkyl, cycloalkenyl, cycloalkylalkenyl, heterocycloalkyl, cycloalkylheteroalkyl, cycloalkyloxy, cycloalkylaminocarbonyl, cycloalkenyloxy, cycloamino, halo, carboxyl, haloalkyl, haloalkenyl, haloalkynyl, alkynyloxy, heteroalkyl, heteroalkyloxy, hydroxyl, hydroxyalkyl, alkoxy, alkoxyalkyl, alkyloxyalkyloxyalkyl, cycloalkylalkyloxyalkyl, thioalkoxy, alkenyloxy, haloalkoxy, haloalkenyloxy, nitro, halogen, amino, aminocarbonyl, aminocarbonylalkyl, azidoalkyl, nitroalkyl, nitroalkenyl, nitroalkynyl, nitroheterocyclyl, alkylamino, alkylaminocarbonyl, dialkylamino, dialkylaminoalkyl, alkenylamine, alkylcarbonylamino, aminoalkyl, alkynylamino, acyl, oxo, alkyloxy, alkyloxyalkyl, alkyloxyaryl, alkyloxycarbonyl, alkyloxycycloalkyl, alkyloxyheteroaryl, alkyloxyheterocycloalkyl, alkenoyl, alkynoyl, acylamino, diacylamino, acyloxy, alkylsulfonyloxy, heterocyclic, heterocycloalkenyl, heterocycloalkyl, heterocycloalkylalkyl, heterocycloalkylalkenyl, heterocycloalkylheteroalkyl, heterocycloalkyloxy, heterocycloalkenyloxy, heterocycloxy, heterocycloamino, haloheterocycloalkyl, alkylsulfinyl, alkylsulfonyl, alkylsulfenyl, alkylcarbonyloxy, alkylthio, acylthio, aminosulfonyl, phosphorus-containing groups such as phosphono and phosphinyl, sulfinyl, sulfinylamino, sulfonyl, sulfonylamino, alkylsulfamoyl, aryl, heteroaryl, heteroarylalkyl, heteroarylalkenyl, heteroarylheteroalkyl, heteroarylamino, heteroaryloxy, arylalkenyl, arylalkyl, alkylaryl, alkylheteroaryl, aryloxy, arylsulfonyl, cyano, cyanate, isocyanate, —C(O)NH(alkyl), and —C(O)N(alkyl)$_2$. The number of carbon and hetero atoms in the groups of the optional substituents is as defined for the groups mentioned above e.g. every alkyl or alkylene moiety can be a $C_1$-$C_{12}$ alkyl, methyl, ethyl, n-propyl, 2-propyl, etc. Accordingly a haloalkoxy group is for instance defined as an alkoxy group as referred to above which is substituted by at least one halogen atom. Where the optional substituents are themselves optionally substituted there substituents can be chosen from the list of optional substituents and such substituents are not further substituted.

Preferred optional substituents are defined as one to three groups selected from halogen, $C_1$-$C_3$-alkyl, or $C_3$-$C_7$-cycloalkyl, nitro, halogen, $C_1$-$C_4$ haloalkyl having 1 to 5 halogen atoms, $C_1$-$C_4$ hydroxyalkyl, optionally halogen substituted $C_3$-$C_7$-cycloalkyl, aminocarbonyl-$C_1$-$C_3$-alkyl, optionally $C_1$-$C_3$-alkyl substituted and/or halogen substituted heteroaryl having 5 to 6 ring members and 1 to two hetero atoms selected from N or O, or optionally halogen, $C_1$-$C_3$-alkyl, $C_1$-$C_4$ hydroxyalkyl and/or azido $C_1$-$C_3$-alkyl substituted phenyl. Preferred optional substituents are also two substituents forming an optionally $C_1$-$C_3$-alkyl substituted $C_1$-$C_4$-alkylene bridge.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, PA 1995. In the case of agents that are solids, it is understood by those skilled in the art that the inventive compounds, agents and salts may exist in different crystalline or polymorphic forms, all of which are intended to be within the scope of the present disclosure and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be converted by hydrolysis in vivo to the parent molecule. Suitable esters of compounds of formula (I) containing a hydroxyl group, are for example formates, acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates, and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be converted by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007).

In the context of this invention the term "administering" and variations of that term including "administer" and "administration", includes contacting, applying, delivering or providing a compound or composition of the invention to an organism, or a surface by any appropriate means.

The term "treatment", refers to any and all uses which remedy a disease state or symptoms, prevent the establishment of disease, or otherwise prevent, hinder, retard, or reverse the progression of disease or other undesirable symptoms in any way whatsoever.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF EMBODIMENTS

Figure 1A:
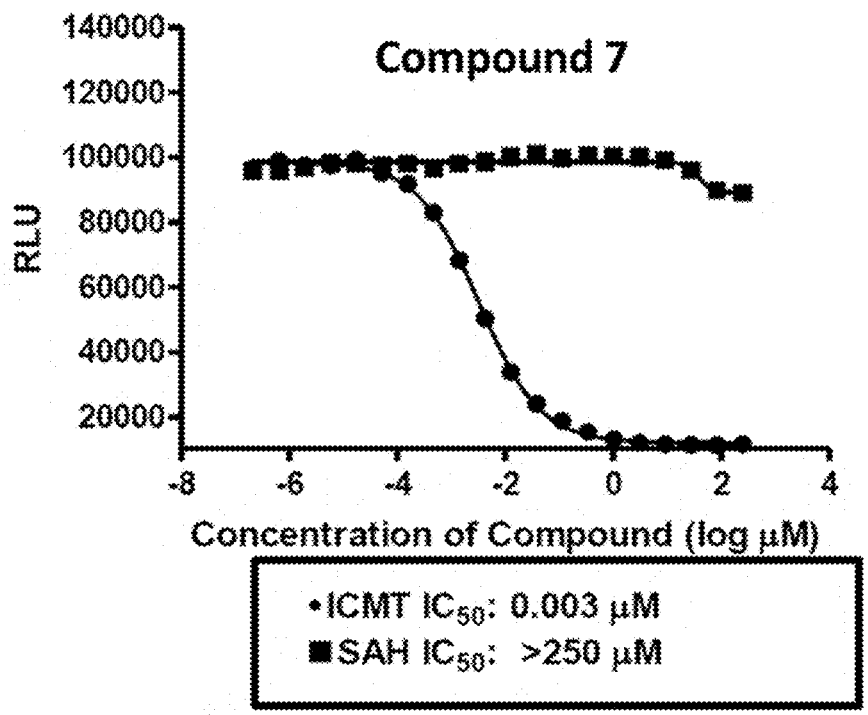
FIG. 1 shows dose response curves showing the effects of compounds on the enzymatic activity of isoprenylcysteine carboxyl methyltransferase; for compound 7 (FIG. 1A); for compound 71 (FIG. 1B); for compound 53 (FIG. 1C); for compound 70 (FIG. 1D); for compound 59 (FIG. 1E); for compound 69 (FIG. 1F); and for compound 78 (FIG. 1G).
Figure 1B:
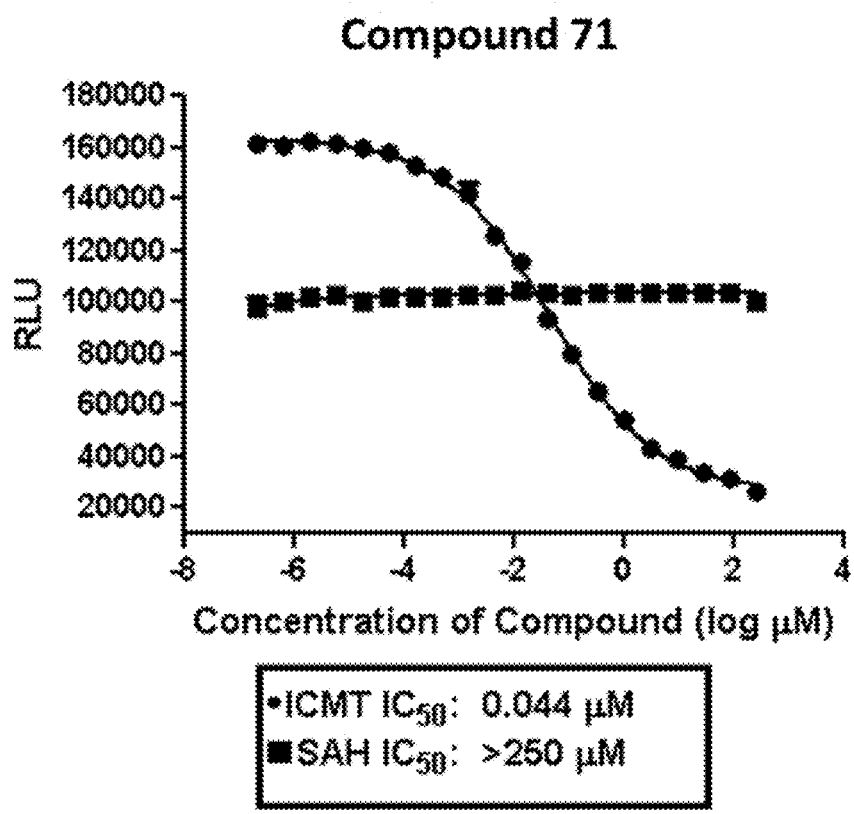
Figure 1C:
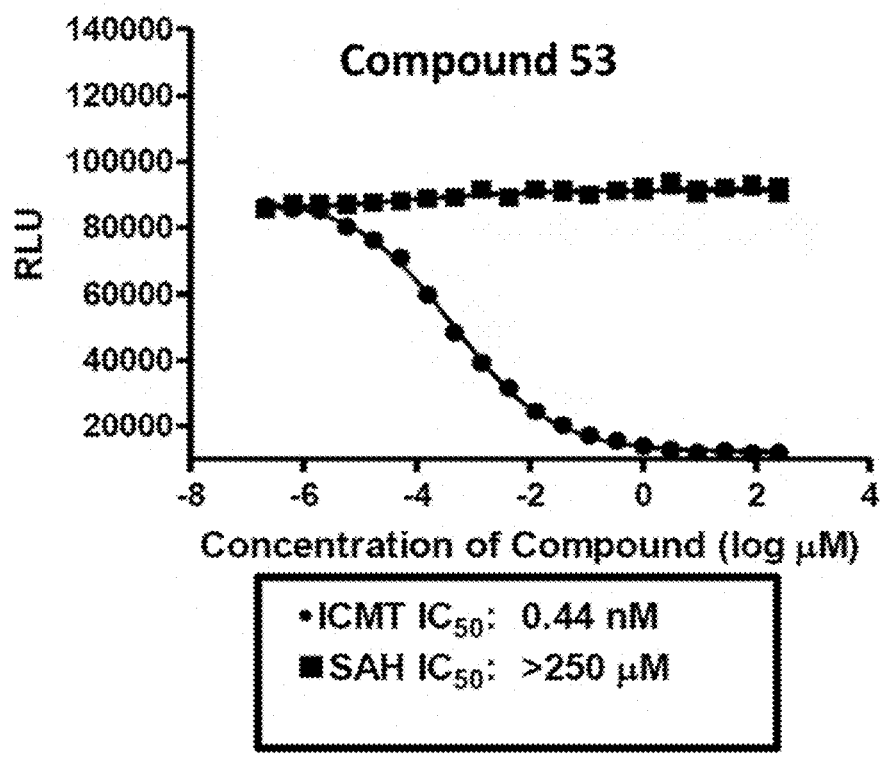
Figure 1D:
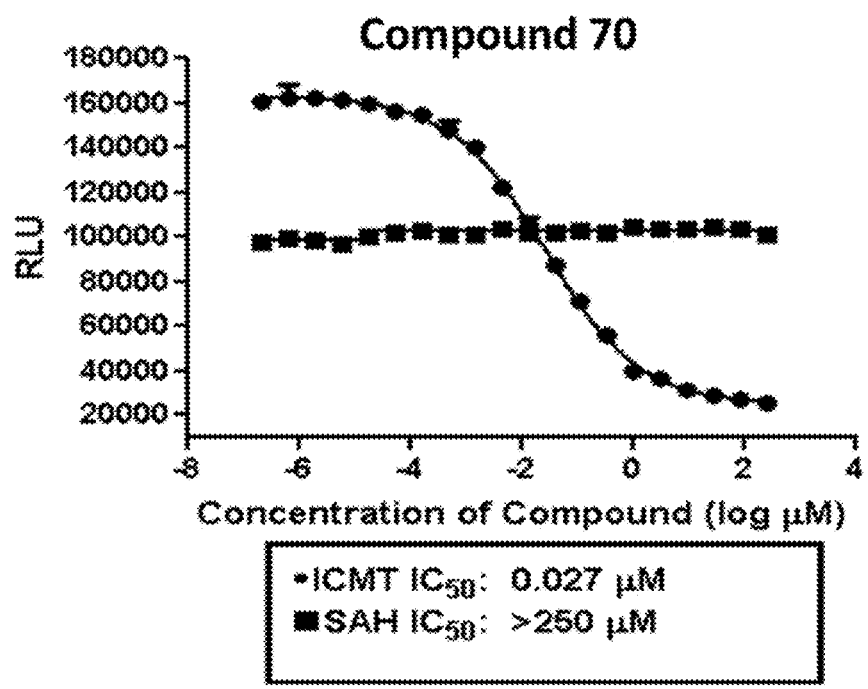
Figure 1E:
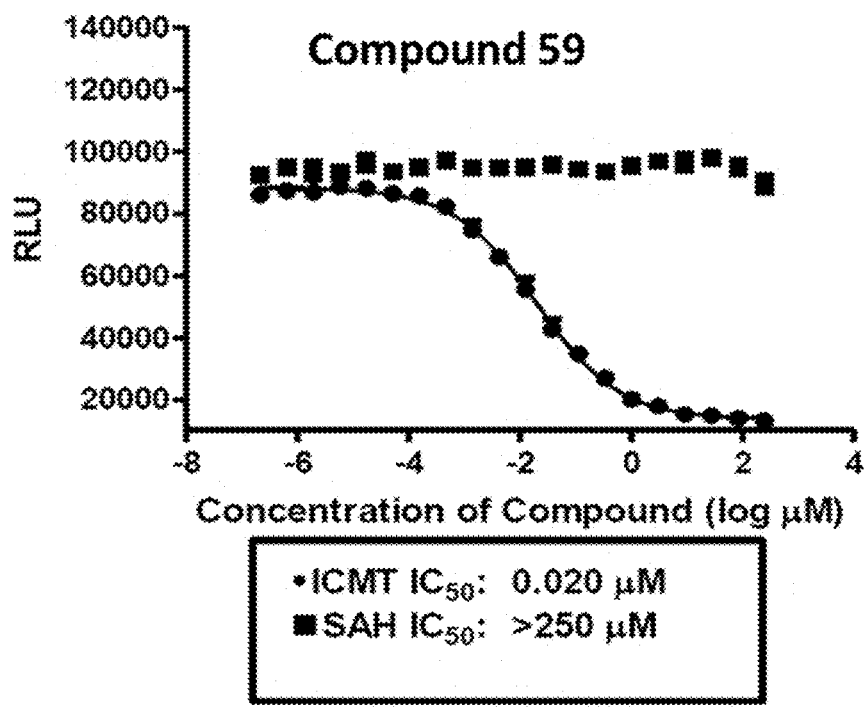
Figure 1F:
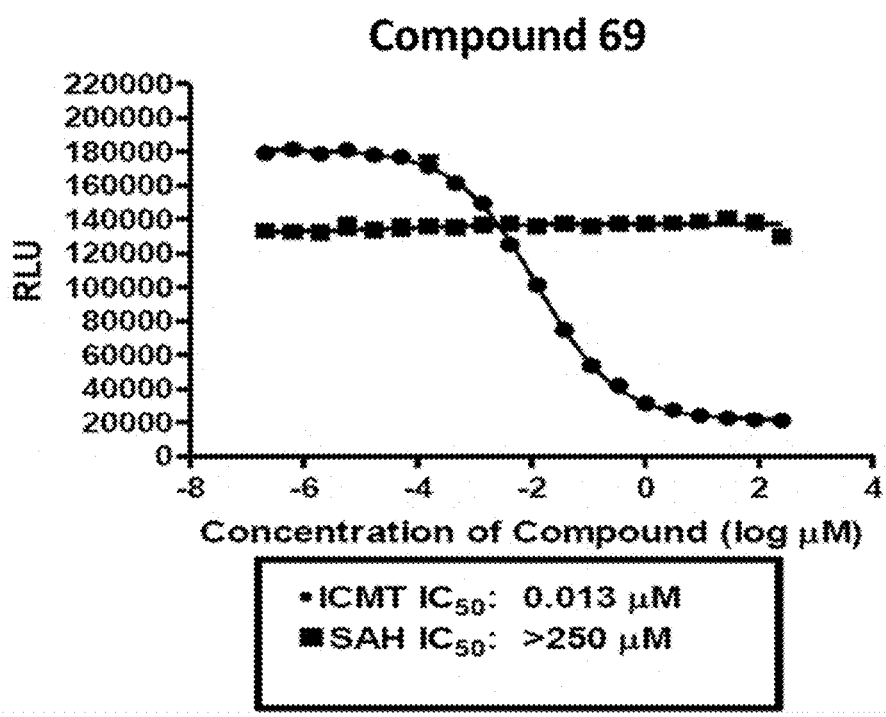
Figure 1G:
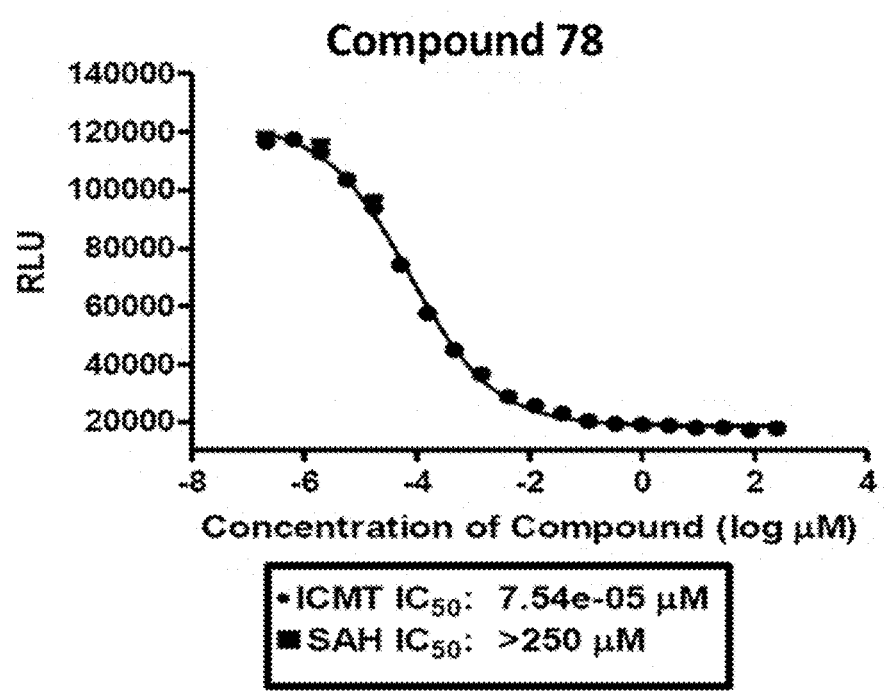
Figure 2:
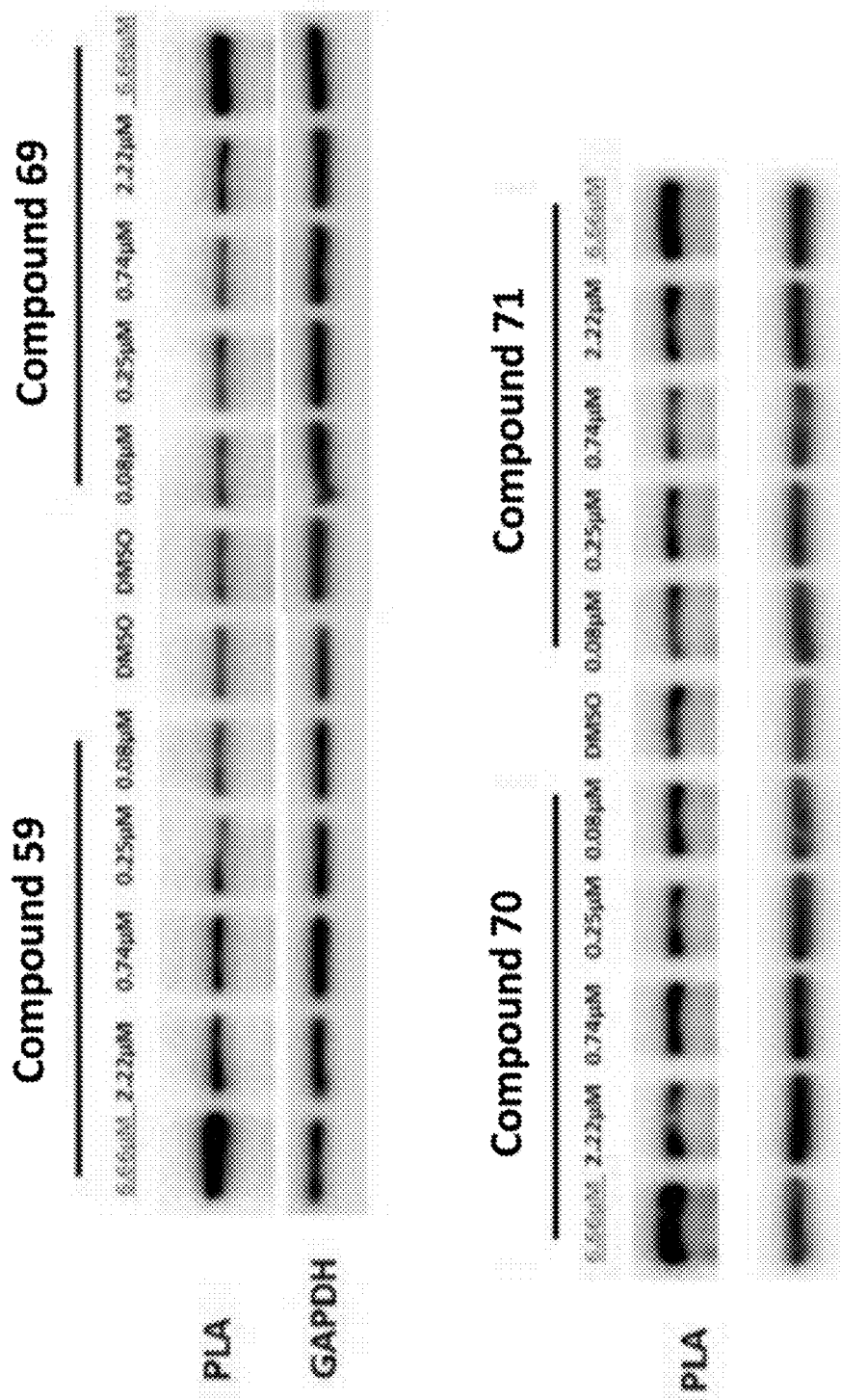
FIG. 2 shows a Western blot image showing Prelamin A accumulation in MIAPaCa-2 cells following treatment with various concentrations of compound 59, 69, 70 and 71.
Figure 3A:
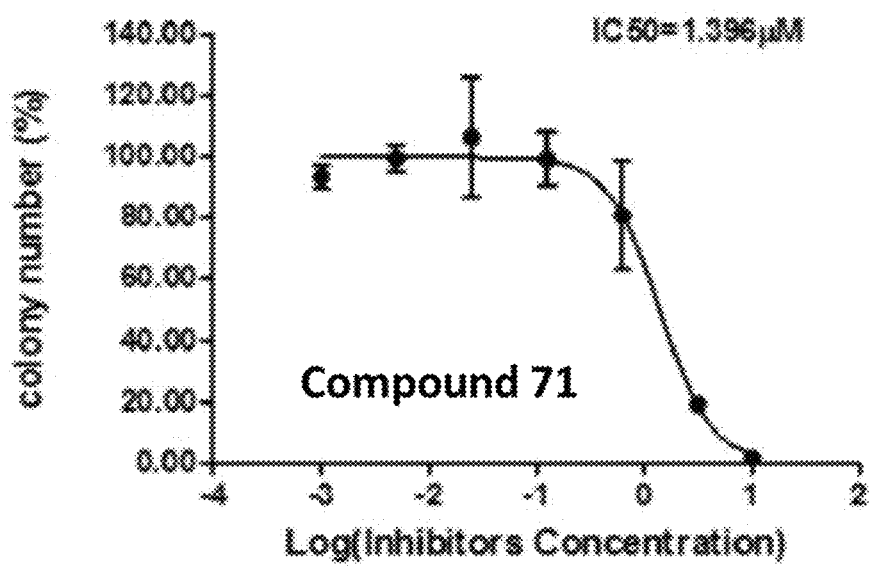
FIG. 3 is the dose response curves showing the effects of compounds on the growth of MIAPaCa-2 cells; for compound 71 (FIG. 3A); for compound 53 (FIG. 3B); for compound 70 (FIG. 3C); for compound 59 (FIG. 3D); for compound 69 (FIG. 3E); and for compound 78 (FIG. 3F).
Figure 3B:
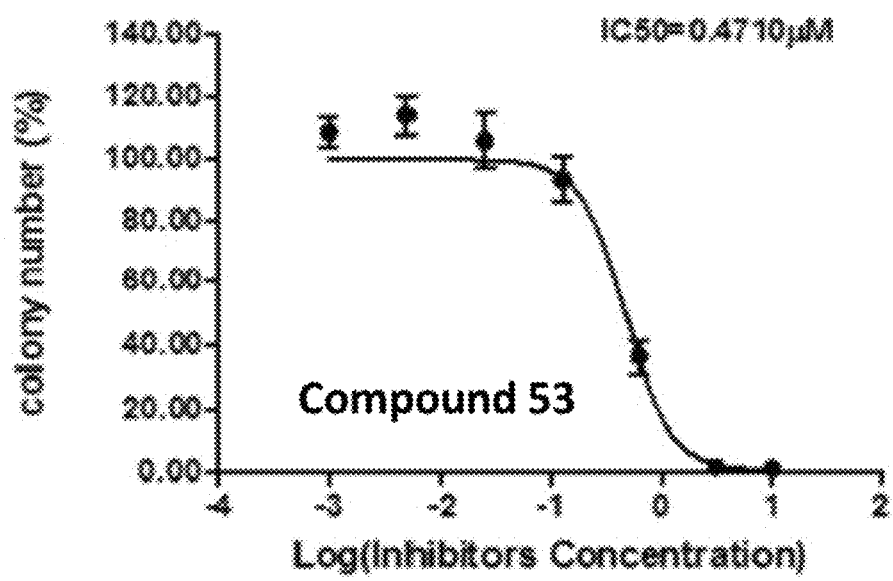
Figure 3C:
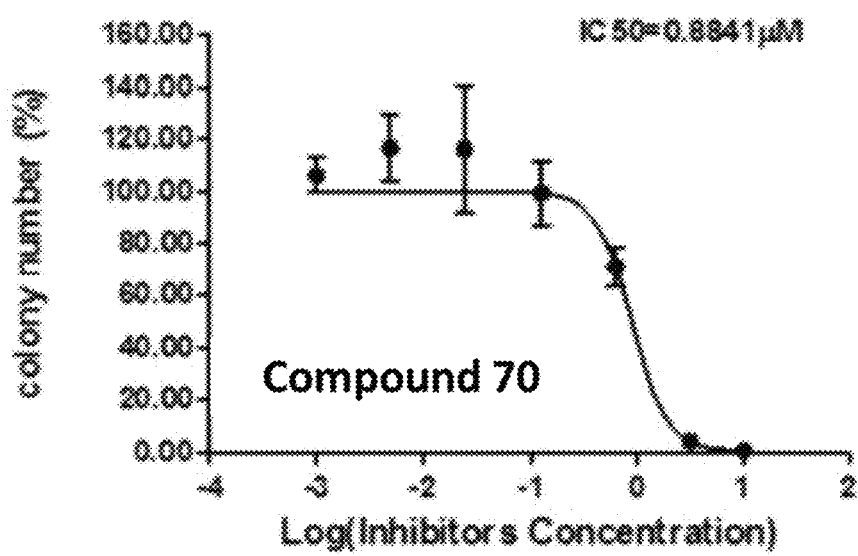
Figure 3D:
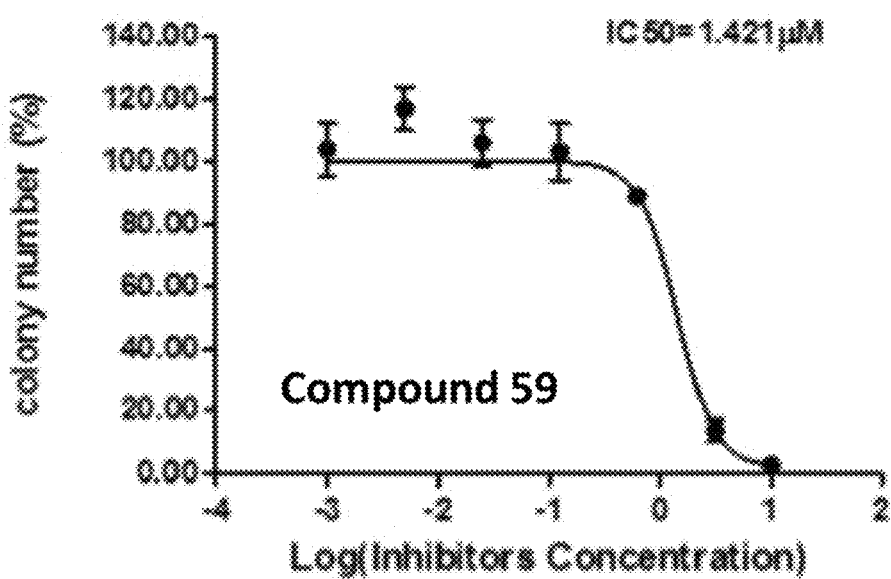
Figure 3E:
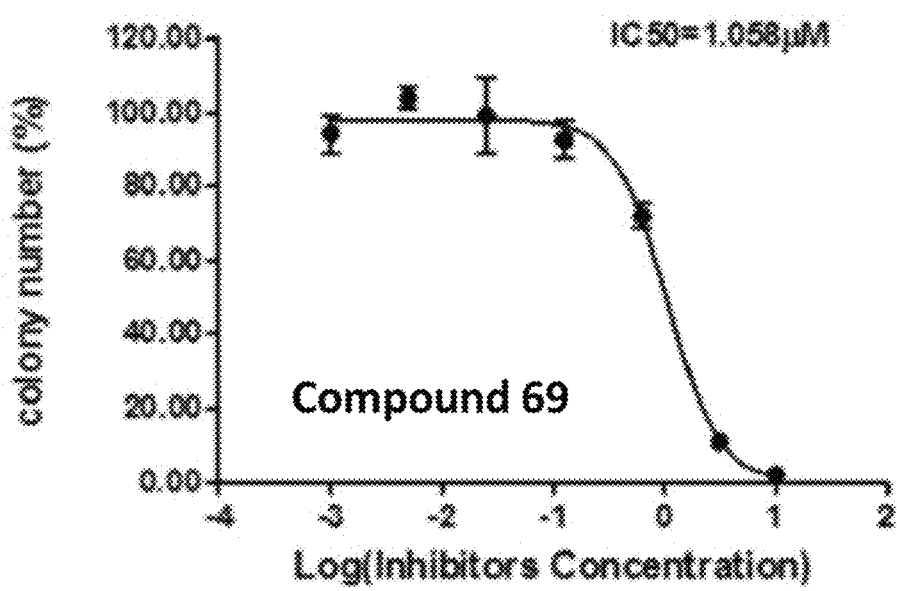
Figure 3F:
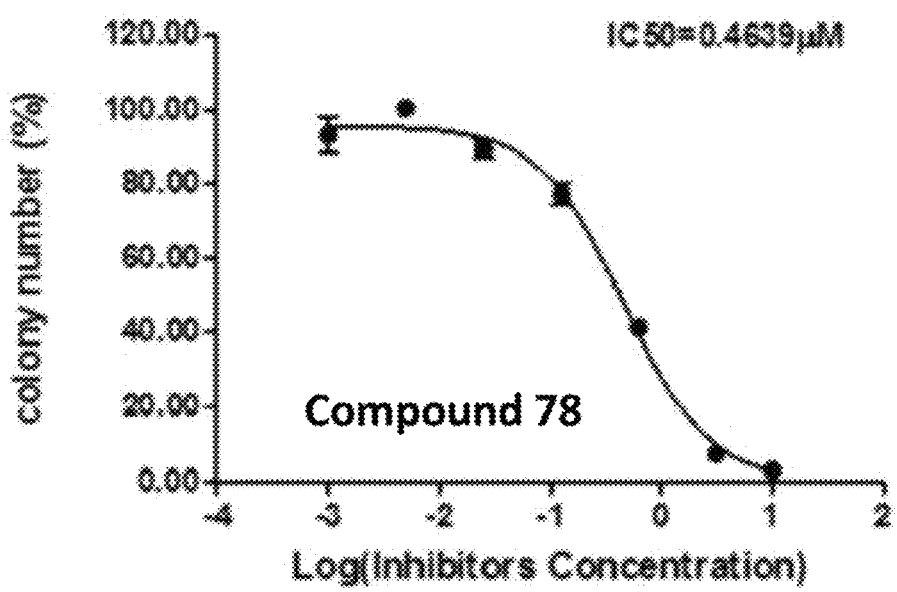

The present invention relates to compounds having the following Formula (I):

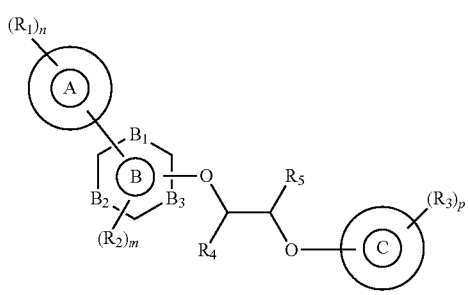

(I)

and/or tautomers, enantiomers, solvates, hydrates, prodrugs and pharmaceutically acceptable salts thereof;

wherein:

represents an aromatic ring system;

Ring A is a 5- or 6-membered carbocyclic ring system, wherein 1 to 4 carbon atoms may be optionally replaced with a heteroatom;

$B_1$, $B_2$ and $B_3$ are independently selected from C, CH, or N, wherein when one of $B_1$, $B_2$ or $B_3$ is N, the remaining $B_1$, $B_2$ or $B_3$ is C or CH;

Ring C is a 5- or 6-membered carbocyclic ring system, wherein 1 to 3 carbon atoms may be optionally replaced with a heteroatom;

$B_1$, $B_2$ and $B_3$ are independently selected from C, CH, or N;

Ring C is a 5- or 6-membered carbocyclic ring system, wherein 1 to 3 carbon atoms may be optionally replaced with a heteroatom;

$R_1$, $R_2$, and $R_3$ are independently absent or selected from H, OH, cyano, halogen, optionally substituted alkyl, haloalkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl;

$R_4$ and $R_5$ are independently selected from H or aliphatic;

n is an integer selected from 0 to 5, wherein when n is more than 1, each $R_1$ substituted on Ring A may be the same or different;

m is an integer selected from 0 to 4, wherein when m is more than 1, each $R_2$ substituted on Ring B may be the same or different; and p is an integer selected from 0 to 5, wherein when p is more than 1, each $R_3$ substituted on Ring C may be the same or different.

The present invention also relates to compounds having the following Formula (I):

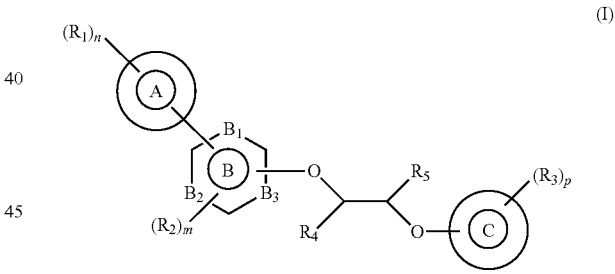

(I)

and/or tautomers, enantiomers, solvates, hydrates, prodrugs and pharmaceutically acceptable salts thereof;

wherein:

represents an aromatic ring system;

Ring A is a 5- or 6-membered carbocyclic ring system, wherein 1 to 4 carbon atoms may be optionally replaced with a heteroatom;

$B_1$, $B_2$ and $B_3$ are independently selected from C, CH, or N;

Ring C is a 5- or 6-membered carbocyclic ring system, wherein 1 to 3 carbon atoms may be optionally replaced with a heteroatom;

R₁ is absent or selected from H, OH, halogen, optionally substituted alkyl, optionally substituted alkenyl, haloalkyl, CF₃, CHF₂, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl;

R₂ is absent or selected from H, OH, cyano, halogen, optionally substituted alkyl, haloalkyl, CF₃, CHF₂, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl;

R₃ is absent or selected from H, OH, cyano, halogen, optionally substituted alkyl, haloalkyl, CF₃, CHF₂, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, or optionally substituted aryl;

R₄ and R₅ are independently selected from H or aliphatic;

n is an integer selected from 0 to 5, wherein when n is more than 1, each R₁ substituted on Ring A may be the same or different;

m is an integer selected from 0 to 4, wherein when m is more than 1, each R₂ substituted on Ring B may be the same or different, and m is 1 when R₂ is halogen; and p is an integer selected from 0 to 5, wherein when p is more than 1, each R₃ substituted on Ring C may be the same or different.

The present invention further relates to compounds having the following Formula (IA):

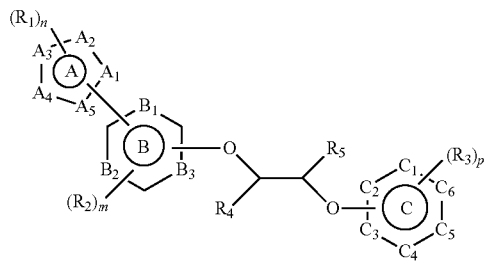

(IA)

and/or tautomers, enantiomers, solvates, hydrates, prodrugs and pharmaceutically acceptable salts thereof, wherein:

represents an aromatic ring system; and

A₁, A₂, A₃, A₄ and A₅, R₁, n, B₁, B₂, B₃, R₂, m, R₄, R₅, C₁, C₂, C₃, C₄, C₅, C₆, R₃ and p are as defined herein.

The present invention also relates to compounds of the following Formula (IE) or Formula (IF):

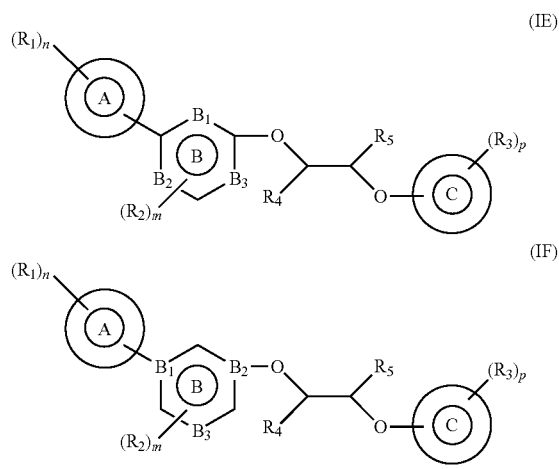

(IE)

(IF)

and/or tautomers, enantiomers, solvates, hydrates, prodrugs and pharmaceutically acceptable salts thereof, wherein:

represents an aromatic ring system; and

A₁, A₂, A₃, A₄ and A₅, R₁, n, B₁, B₂, B₃, R₂, m, R₄, R₅, C₁, C₂, C₃, C₄, C₅, C₆, R₃ and p are as defined herein.

In the formulas disclosed herein, Ring A may be of the formula (aa):

(aa)

wherein:

* represents the point of attachment to Ring B; and

A₁, A₂, A₃, A₄ and A₅ are independently selected from C, CH, N, O or S.

In the formulas disclosed herein, Ring A may be of the formula (ab):

(ab)

wherein:

* represents the point of attachment to Ring B; and

A₁ is N or C;
A₂ is N, S, CH, or C;
A₃ is C, CH, N, or O;
A₄ is N; and
A₅ is C, CH, O, or N.

In the formulas disclosed herein, Ring A may be of formula (ac):

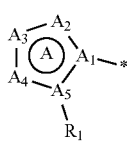

(ac)

wherein:
* represents the point of attachment to Ring B; and
$A_1$ is N or C;
$A_2$ is N, S, CH, or C;
$A_3$ is C, CH, N, or O;
$A_4$ is N; and
$A_5$ is C, O, or N.

In the formulas disclosed herein, Ring A may be selected from the group consisting of formulas (a1) to (a8):

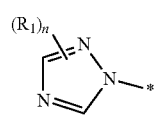

(a1)

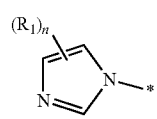

(a2)

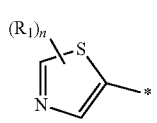

(A3)

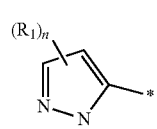

(a4)

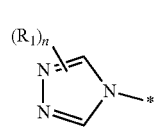

(a5)

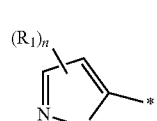

(a6)

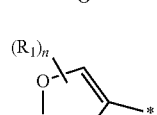

(a7)

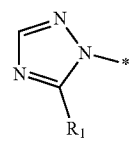

(a8)

In the formulas disclosed herein, Ring A may be selected from the group consisting of formulas (a1') to (a8'):

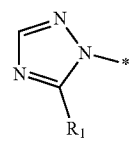

(a1')

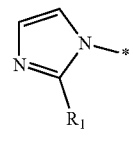

(a2')

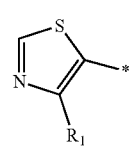

(a3')

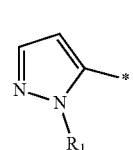

(a4')

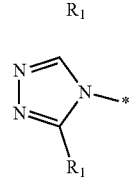

(a5')

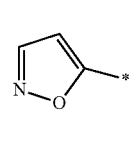

(a6')

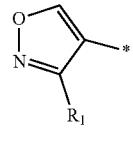

(a7')

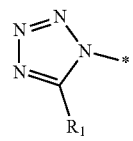

(a8')

In the formulas disclosed herein, Ring A may be selected from the group consisting of formulas (a1") to (a10"):

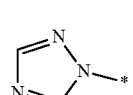

(a1")

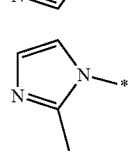

(a2")

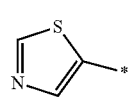

(a3")

-continued

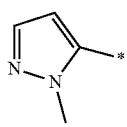
(a4″)

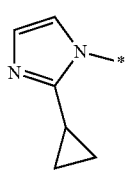
(a5″)

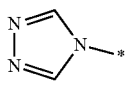
(a6″)

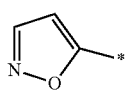
(a7″)

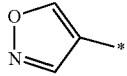
(a8″)

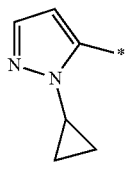
(a9″)

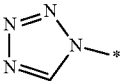
(a10″)

wherein * represents the point of attachment to Ring B.

In the formulas disclosed herein, $R_1$ may be absent or H, OH, cyano, halogen (such as F, Cl, Br, I), optionally substituted alkyl, haloalkyl, $CF_3$, $CHF_2$, $CH_2F$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl.

The optionally substituted alkyl of $R_1$ may be an optionally substituted $C_1$-$C_{12}$ alkyl, or optionally substituted $C_1$ alkyl, optionally substituted $C_2$ alkyl, optionally substituted $C_3$ alkyl, optionally substituted $C_4$ alkyl, optionally substituted $C_5$ alkyl, optionally substituted $C_6$ alkyl, optionally substituted $C_7$ alkyl, optionally substituted $C_8$ alkyl, optionally substituted $C_9$ alkyl, optionally substituted $C_{10}$ alkyl, optionally substituted $C_{11}$ alkyl, or optionally substituted $C_{12}$ alkyl. The optionally substituted alkyl may of $R_1$ be methyl, ethyl, propyl, butyl, pentyl, hexyl, or a haloalkyl, such as $CF_3$, $CHF_2$, or $CH_2F$. The optionally substituted alkoxy of $R_1$ may be an optionally substituted $C_1$-$C_{12}$ alkoxy, or optionally substituted $C_1$ alkoxy, optionally substituted $C_2$ alkoxy, optionally substituted $C_3$ alkoxy, optionally substituted $C_4$ alkoxy, optionally substituted $C_5$ alkoxy, optionally substituted $C_6$ alkoxy, optionally substituted $C_7$ alkoxy, optionally substituted $C_8$ alkoxy, optionally substituted $C_9$ alkoxy, optionally substituted $C_{10}$ alkoxy, optionally substituted $C_{11}$ alkoxy, or optionally substituted $C_{12}$ alkoxy. The optionally substituted cycloalkyl of $R_1$ may be an optionally substituted $C_3$-$C_9$ cycloalkyl, or optionally substituted $C_3$ cycloalkyl, optionally substituted $C_4$ cycloalkyl, optionally substituted $C_5$ cycloalkyl, optionally substituted $C_6$ cycloalkyl, optionally substituted $C_7$ cycloalkyl, optionally substituted $C_8$ cycloalkyl, or optionally substituted $C_9$ cycloalkyl. The optionally substituted cycloalkyl may be cyclopropyl. The optionally substituted cycloalkenyl of $R_1$ may be an optionally substituted $C_3$-$C_9$ cycloalkenyl, or optionally substituted $C_3$ cycloalkenyl, optionally substituted $C_4$ cycloalkenyl, optionally substituted $C_5$ cycloalkenyl, optionally substituted $C_6$ cycloalkenyl, optionally substituted $C_7$ cycloalkenyl, optionally substituted $C_8$ cycloalkenyl, or optionally substituted $C_9$ cycloalkenyl. The optionally substituted heterocycloalkyl of $R_1$ may be an optionally substituted heterocycloalkyl having a ring atom number of 3 to 8 (such as a ring atom number of 3, 4, 5, 6, 7, 8) and having 1 to 3 heteroatoms (such as 1, 2, 3 heteroatoms) independently selected from the group consisting of N, O and S. The optionally substituted aryl of $R_1$ may be an optionally substituted $C_6$-$C_{18}$ aryl, or optionally substituted $C_6$ aryl, optionally substituted $C_7$ aryl, optionally substituted $C_8$ aryl, optionally substituted $C_9$ aryl, optionally substituted $C_{10}$ aryl, optionally substituted $C_{11}$ aryl, or optionally substituted $C_{12}$ aryl, optionally substituted $C_{13}$ aryl, optionally substituted $C_{14}$ aryl, or optionally substituted $C_{15}$ aryl, optionally substituted $C_{16}$ aryl, optionally substituted $C_{17}$ aryl, or optionally substituted $C_{18}$ aryl. The optionally substituted heteroaryl of $R_1$ may be an optionally substituted heteroaryl having a ring atom number of 3 to 8 (such as a ring atom number of 3, 4, 5, 6, 7, 8) and having 1 to 3 heteroatoms (such as 1, 2, 3 heteroatoms) independently selected from the group consisting of N, O and S. The optionally substituted alkenyl of $R_1$ may be an optionally substituted $C_2$-$C_{12}$ alkenyl, or optionally substituted $C_2$ alkenyl, optionally substituted $C_3$ alkenyl, optionally substituted $C_4$ alkenyl, optionally substituted $C_5$ alkenyl, optionally substituted $C_6$ alkenyl, optionally substituted $C_7$ alkenyl, optionally substituted $C_8$ alkenyl, optionally substituted $C_9$ alkenyl, optionally substituted $C_{10}$ alkenyl, optionally substituted $C_{11}$ alkenyl, or optionally substituted $C_{12}$ alkenyl. The optionally substituted alkynyl of $R_1$ may be an optionally substituted $C_2$-$C_{12}$ alkynyl, or optionally substituted $C_2$ alkynyl, optionally substituted $C_3$ alkynyl, optionally substituted $C_4$ alkynyl, optionally substituted $C_5$ alkynyl, optionally substituted $C_6$ alkynyl, optionally substituted $C_7$ alkynyl, optionally substituted $C_8$ alkynyl, optionally substituted $C_9$ alkynyl, optionally substituted $C_{10}$ alkynyl, optionally substituted $C_{11}$ alkynyl, or optionally substituted $C_{12}$ alkynyl.

In the formulas disclosed herein, $R_2$ may be absent or H, OH, cyano, halogen (such as F, Cl, Br, I), optionally substituted alkyl, haloalkyl, $CF_3$, $CHF_2$, $CH_2F$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl.

The optionally substituted alkyl of $R_2$ may be an optionally substituted $C_1$-$C_{12}$ alkyl, or optionally substituted $C_1$ alkyl, optionally substituted $C_2$ alkyl, optionally substituted $C_3$ alkyl, optionally substituted $C_4$ alkyl, optionally substituted $C_5$ alkyl, optionally substituted $C_6$ alkyl, optionally substituted $C_7$ alkyl, optionally substituted $C_8$ alkyl, optionally substituted $C_9$ alkyl, optionally substituted $C_{10}$ alkyl, optionally substituted $C_{11}$ alkyl, or optionally substituted $C_{12}$ alkyl. The optionally substituted alkoxy of $R_2$ may be an optionally substituted $C_1$-$C_{12}$ alkoxy, or optionally substituted $C_1$ alkoxy, optionally substituted $C_2$ alkoxy, optionally substituted $C_3$ alkoxy, optionally substituted $C_4$ alkoxy, optionally substituted $C_5$ alkoxy, optionally substituted $C_6$ alkoxy, optionally substituted $C_7$ alkoxy, optionally substituted $C_8$ alkoxy, optionally substituted $C_9$ alkoxy, optionally substituted $C_{10}$ alkoxy, optionally substituted $C_{11}$ alkoxy, or optionally substituted $C_{12}$ alkoxy. The optionally substituted cycloalkyl of $R_2$ may be an optionally substituted $C_3$-$C_9$ cycloalkyl, or optionally substituted $C_3$ cycloalkyl, optionally substituted $C_4$ cycloalkyl, optionally substituted $C_5$ cycloalkyl, optionally substituted $C_6$ cycloalkyl, optionally substituted $C_7$ cycloalkyl, optionally substituted $C_8$ cycloalkyl, or optionally substituted $C_9$ cycloalkyl. The optionally substituted cycloalkenyl of $R_2$ may be an optionally substituted $C_3$-$C_9$ cycloalkenyl, or optionally substituted $C_3$ cycloalkenyl, optionally substituted $C_4$ cycloalkenyl, optionally substituted $C_5$ cycloalkenyl, optionally substituted $C_6$ cycloalkenyl, optionally substituted $C_7$ cycloalkenyl, optionally substituted $C_8$ cycloalkenyl, or optionally substituted $C_9$ cycloalkenyl. The optionally substituted heterocycloalkyl of $R_2$ may be an optionally substituted heterocycloalkyl having a ring atom number of 3 to 8 (such as a ring atom number of 3, 4, 5, 6, 7, 8) and having 1 to 3 heteroatoms (such as 1, 2, 3 heteroatoms) independently selected from the group consisting of N, O and S. The optionally substituted aryl of $R_2$ may be an optionally substituted $C_6$-$C_{18}$ aryl, or optionally substituted $C_6$ aryl, optionally substituted $C_7$ aryl, optionally substituted $C_8$ aryl, optionally substituted $C_9$ aryl, optionally substituted $C_{10}$ aryl, optionally substituted $C_{11}$ aryl, or optionally substituted $C_{12}$ aryl, optionally substituted $C_{13}$ aryl, optionally substituted $C_{14}$ aryl, or optionally substituted $C_{15}$ aryl, optionally substituted $C_{16}$ aryl, optionally substituted $C_{17}$ aryl, or optionally substituted $C_{18}$ aryl. The optionally substituted heteroaryl of $R_2$ may be an optionally substituted heteroaryl having a ring atom number of 3 to 8 (such as a ring atom number of 3, 4, 5, 6, 7, 8) and having 1 to 3 heteroatoms (such as 1, 2, 3 heteroatoms) independently selected from the group consisting of N, O and S. The optionally substituted alkenyl of $R_2$ may be an optionally substituted $C_2$-$C_{12}$ alkenyl, or optionally substituted $C_2$ alkenyl, optionally substituted $C_3$ alkenyl, optionally substituted $C_4$ alkenyl, optionally substituted $C_5$ alkenyl, optionally substituted $C_6$ alkenyl, optionally substituted $C_7$ alkenyl, optionally substituted $C_8$ alkenyl, optionally substituted $C_9$ alkenyl, optionally substituted $C_{10}$ alkenyl, optionally substituted $C_{11}$ alkenyl, or optionally substituted $C_{12}$ alkenyl. The optionally substituted alkynyl of $R_2$ may be an optionally substituted $C_2$-$C_{12}$ alkynyl, or optionally substituted $C_2$ alkynyl, optionally substituted $C_3$ alkynyl, optionally substituted $C_4$ alkynyl, optionally substituted $C_5$ alkynyl, optionally substituted $C_6$ alkynyl, optionally substituted $C_7$ alkynyl, optionally substituted $C_8$ alkynyl, optionally substituted $C_9$ alkynyl, optionally substituted $C_{10}$ alkynyl, optionally substituted $C_{11}$ alkynyl, or optionally substituted $C_{12}$ alkynyl. $R_2$ may be H or F.

In the formulas disclosed herein, $R_3$ may be absent or H, OH, cyano, halogen (such as F, Cl, Br, I), optionally substituted alkyl, haloalkyl, $CF_3$, $CHF_2$, $CH_2F$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl or optionally substituted heteroaryl.

The optionally substituted alkyl of $R_3$ may be an optionally substituted $C_1$-$C_{12}$ alkyl, or optionally substituted $C_1$ alkyl, optionally substituted $C_2$ alkyl, optionally substituted $C_3$ alkyl, optionally substituted $C_4$ alkyl, optionally substituted $C_5$ alkyl, optionally substituted $C_6$ alkyl, optionally substituted $C_7$ alkyl, optionally substituted $C_8$ alkyl, optionally substituted $C_9$ alkyl, optionally substituted $C_{10}$ alkyl, optionally substituted $C_{11}$ alkyl, or optionally substituted $C_{12}$ alkyl. The optionally substituted alkoxy of $R_3$ may be an optionally substituted $C_1$-$C_{12}$ alkoxy, or optionally substituted $C_1$ alkoxy, optionally substituted $C_2$ alkoxy, optionally substituted $C_3$ alkoxy, optionally substituted $C_4$ alkoxy, optionally substituted $C_5$ alkoxy, optionally substituted $C_6$ alkoxy, optionally substituted $C_7$ alkoxy, optionally substituted $C_8$ alkoxy, optionally substituted $C_9$ alkoxy, optionally substituted $C_{10}$ alkoxy, optionally substituted $C_{11}$ alkoxy, or optionally substituted $C_{12}$ alkoxy. The optionally substituted cycloalkyl of $R_3$ may be an optionally substituted $C_3$-$C_9$ cycloalkyl, or optionally substituted $C_3$ cycloalkyl, optionally substituted $C_4$ cycloalkyl, optionally substituted $C_5$ cycloalkyl, optionally substituted $C_6$ cycloalkyl, optionally substituted $C_7$ cycloalkyl, optionally substituted $C_8$ cycloalkyl, or optionally substituted $C_9$ cycloalkyl. The optionally substituted cycloalkenyl of $R_3$ may be an optionally substituted $C_3$-$C_9$ cycloalkenyl, or optionally substituted $C_3$ cycloalkenyl, optionally substituted $C_4$ cycloalkenyl, optionally substituted $C_5$ cycloalkenyl, optionally substituted $C_6$ cycloalkenyl, optionally substituted $C_7$ cycloalkenyl, optionally substituted $C_8$ cycloalkenyl, or optionally substituted $C_9$ cycloalkenyl. The optionally substituted heterocycloalkyl of $R_3$ may be an optionally substituted heterocycloalkyl having a ring atom number of 3 to 8 (such as a ring atom number of 3, 4, 5, 6, 7, 8) and having 1 to 3 heteroatoms (such as 1, 2, 3 heteroatoms) independently selected from the group consisting of N, O and S. The optionally substituted aryl of $R_3$ may be an optionally substituted $C_6$-$C_{18}$ aryl, or optionally substituted $C_6$ aryl, optionally substituted $C_7$ aryl, optionally substituted $C_8$ aryl, optionally substituted $C_9$ aryl, optionally substituted $C_{10}$ aryl, optionally substituted $C_{11}$ aryl, or optionally substituted $C_{12}$ aryl, optionally substituted $C_{13}$ aryl, optionally substituted $C_{14}$ aryl, or optionally substituted $C_{15}$ aryl, optionally substituted $C_{16}$ aryl, optionally substituted $C_{17}$ aryl, or optionally substituted Cis aryl. The optionally substituted heteroaryl of $R_3$ may be an optionally substituted heteroaryl having a ring atom number of 3 to 8 (such as a ring atom number of 3, 4, 5, 6, 7, 8) and having 1 to 3 heteroatoms (such as 1, 2, 3 heteroatoms) independently selected from the group consisting of N, O and S. The optionally substituted alkenyl of $R_3$ may be an optionally substituted $C_2$-$C_{12}$ alkenyl, or optionally substituted $C_2$ alkenyl, optionally substituted $C_3$ alkenyl, optionally substituted $C_4$ alkenyl, optionally substituted $C_5$ alkenyl, optionally substituted $C_6$ alkenyl, optionally substituted $C_7$ alkenyl, optionally substituted $C_8$ alkenyl, optionally substituted $C_9$ alkenyl, optionally substituted $C_{10}$ alkenyl, optionally substituted $C_{11}$ alkenyl, or optionally substituted $C_{12}$ alkenyl. The optionally substituted alkynyl of $R_3$ may be an optionally substituted $C_2$-$C_{12}$ alkynyl, or optionally substituted $C_2$ alkynyl, optionally substituted $C_3$ alkynyl, optionally substituted $C_4$ alkynyl, optionally substituted $C_5$ alkynyl, optionally substituted $C_6$ alkynyl, optionally substituted $C_7$ alkynyl, optionally substituted $C_8$ alkynyl, optionally substituted $C_9$ alkynyl, optionally substituted $C_{10}$ alkynyl, optionally substituted $C_{11}$ alkynyl, or optionally substituted $C_{12}$ alkynyl. $R_3$ may be halogen (such as F, Cl, Br, I), —CN, alkoxy (such as methoxy, ethoxy, propoxy, butoxy, pentoxy), amino, haloalkyl (such as —CF$_3$, —CHF$_2$, —CH$_2$F), haloalkyloxy (such as —OCF$_3$, —OCHF$_2$, —OCH$_2$F), or alkyl (such as methyl, ethyl, propyl, butyl, pentyl, hexyl).

R$_3$ may be fluoro, chloro, bromo, —CN, methoxy, methyl, —NH$_2$, —OCF$_3$ or —CF$_3$.

R$_4$ may be H or aliphatic. R$_4$ may be H or optionally substituted alkyl. R$_4$ may be H or optionally substituted C$_1$-C$_{12}$ alkyl, optionally substituted C$_1$-C$_{12}$ alkenyl, or optionally substituted C$_1$-C$_{12}$ alkynyl. R$_4$ may be optionally substituted C$_1$ alkyl, optionally substituted C$_2$ alkyl, optionally substituted C$_3$ alkyl, optionally substituted C$_4$ alkyl, optionally substituted C$_5$ alkyl, optionally substituted C$_6$ alkyl, optionally substituted C$_7$ alkyl, optionally substituted C$_8$ alkyl, optionally substituted C$_9$ alkyl, optionally substituted C$_{10}$ alkyl, optionally substituted C$_{11}$ alkyl, or optionally substituted C$_{12}$ alkyl. R$_4$ may be optionally substituted C$_2$ alkenyl, optionally substituted C$_3$ alkenyl, optionally substituted C$_4$ alkenyl, optionally substituted C$_5$ alkenyl, optionally substituted C$_6$ alkenyl, optionally substituted C$_7$ alkenyl, optionally substituted C$_8$ alkenyl, optionally substituted C$_9$ alkenyl, optionally substituted C$_{10}$ alkenyl, optionally substituted C$_{11}$ alkenyl, or optionally substituted C$_{12}$ alkenyl. R$_4$ may be optionally substituted C$_2$ alkenyl, optionally substituted C$_3$ alkenyl, optionally substituted C$_4$ alkenyl, optionally substituted C$_5$ alkenyl, optionally substituted C$_6$ alkenyl, optionally substituted C$_7$ alkenyl, optionally substituted C$_8$ alkenyl, optionally substituted C$_9$ alkenyl, optionally substituted C$_{10}$ alkenyl, optionally substituted C$_{11}$ alkenyl, or optionally substituted C$_{12}$ alkenyl. R$_4$ may be H or methyl, ethyl, propyl, butyl, pentyl, or hexyl.

R$_5$ may be H or aliphatic. R$_5$ may be H or optionally substituted alkyl. R$_5$ may be H or optionally substituted C$_1$-C$_{12}$ alkyl, optionally substituted C$_1$-C$_{12}$ alkenyl, or optionally substituted C$_1$-C$_{12}$ alkynyl. R$_4$ may be optionally substituted C$_1$ alkyl, optionally substituted C$_2$ alkyl, optionally substituted C$_3$ alkyl, optionally substituted C$_4$ alkyl, optionally substituted C$_5$ alkyl, optionally substituted C$_6$ alkyl, optionally substituted C$_7$ alkyl, optionally substituted C$_8$ alkyl, optionally substituted C$_9$ alkyl, optionally substituted C$_{10}$ alkyl, optionally substituted C$_{11}$ alkyl, or optionally substituted C$_{12}$ alkyl. R$_5$ may be optionally substituted C$_2$ alkenyl, optionally substituted C$_3$ alkenyl, optionally substituted C$_4$ alkenyl, optionally substituted C$_5$ alkenyl, optionally substituted C$_6$ alkenyl, optionally substituted C$_7$ alkenyl, optionally substituted C$_8$ alkenyl, optionally substituted C$_9$ alkenyl, optionally substituted C$_{10}$ alkenyl, optionally substituted C$_{11}$ alkenyl, or optionally substituted C$_{12}$ alkenyl. R$_5$ may be optionally substituted C$_2$ alkenyl, optionally substituted C$_3$ alkenyl, optionally substituted C$_4$ alkenyl, optionally substituted C$_5$ alkenyl, optionally substituted C$_6$ alkenyl, optionally substituted C$_7$ alkenyl, optionally substituted C$_8$ alkenyl, optionally substituted C$_9$ alkenyl, optionally substituted C$_{10}$ alkenyl, optionally substituted C$_{11}$ alkenyl, or optionally substituted C$_{12}$ alkenyl. R$_5$ may be H or methyl, ethyl, propyl, butyl, pentyl, or hexyl.

R$_4$ and R$_5$ may be H; or R$_4$ is H and R$_5$ is methyl; or R$_4$ is methyl and R$_5$ is H; or R$_4$ is methyl and R$_5$ is methyl.

In the formulas disclosed herein, Ring B may be of formula (bb1) or formula (bb2):

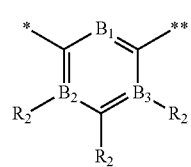
(bb1)

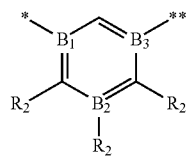
(bb2)

wherein:

* represents the point of attachment to Ring A; and

** represents the point of attachment to the —O(CHR$_4$)— moiety of formula (I).

In the formulas disclosed herein, Ring B may be selected from the group consisting of formulas (b1) to (b5):

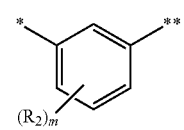
(b1)

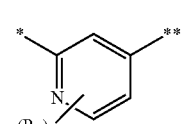
(b2)

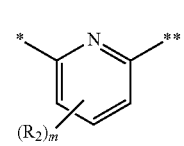
(b3)

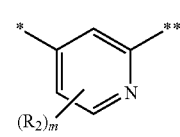
(b4)

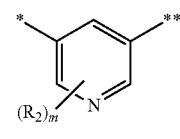
(b5)

In the formulas disclosed herein, Ring B may be selected from the group consisting of formulas (b1') to (b9'):

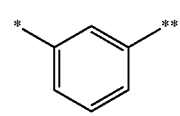
(b1')

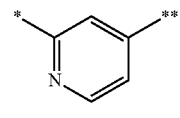
(b2')

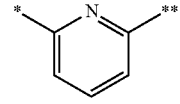
(b3')

-continued

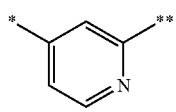 (b4′)

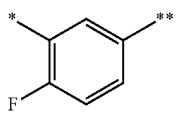 (b5′)

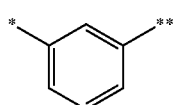 (b6′)

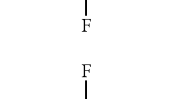 (b7′)

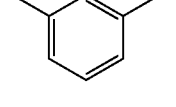 (b8′)

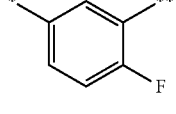 (b9′)

wherein:

* represents the point of attachment to Ring A; and

** represents the point of attachment to the —O(CHR$_4$)— moiety of formula (I).

In the formulas disclosed herein, Ring C may be of formula (ca):

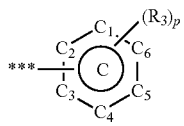 (ca)

wherein:

represents an aromatic ring system;

*** represents the point of attachment to the —O(CHR$_5$)— moiety of formula (I); and $C_1$, $C_2$, $C_3$, $C_4$, $C_5$ and $C_6$ are independently selected from C, CH, or N.

In the formulas disclosed herein, Ring C may be of the formula (cb):

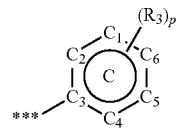 (cb)

wherein:

represents an aromatic ring system;

*** represents the point of attachment to the —O(CHR$_5$)— moiety of formula (I);

$C_1$ and $C_2$ are independently C, CH or N;

$C_4$, $C_5$, and $C_6$ are independently C or CH; and $C_3$ is C.

In the formulas disclosed herein, Ring C may be of formula (cc):

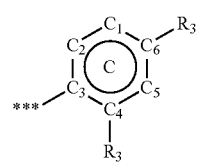 (cc)

wherein:

represents an aromatic ring system;

*** represents the point of attachment to the —O(CHR$_5$)— moiety of formula (I);

$C_1$ and $C_2$ are independently CH or N;

$C_5$ is CH; and $C_3$, $C_4$, and $C_6$ are C.

In the formulas disclosed herein, Ring C may be selected from the group consisting of formulas (c1) to (c4):

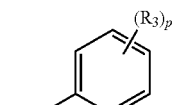 (c1)

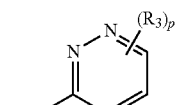 (c2)

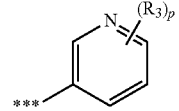 (c3)

-continued
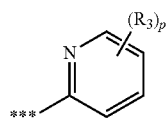 (c4)
In the formulas disclosed herein, Ring C may be selected from the group consisting of formulas (c1') to (c6'):
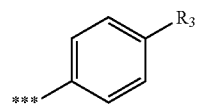 (c1')
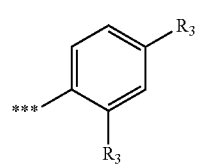 (c2')
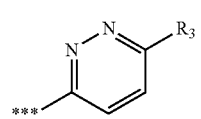 (c3')
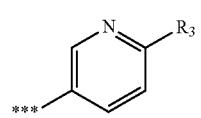 (c4')
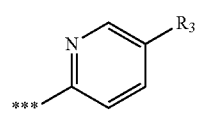 (c5')
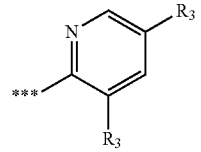 (c6')
wherein:
\*\*\* represents the point of attachment to the —O(CHR$_5$)— moiety of formula (I).
In the formulas disclosed herein, Ring C may be selected from the group consisting of (c1″) to (c22″):
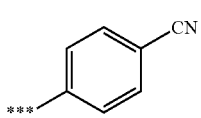 (c1″)
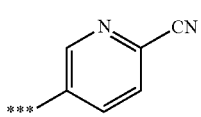 (c2″)
-continued
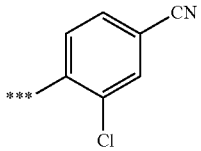 (c3″)
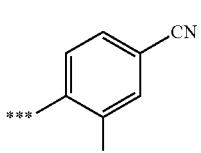 (c4″)
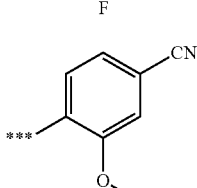 (c5″)
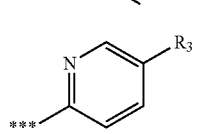 (c6″)
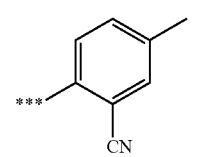 (c7″)
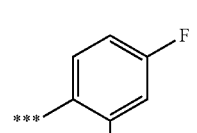 (c8″)
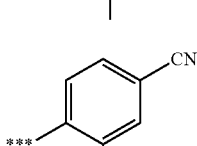 (c9″)
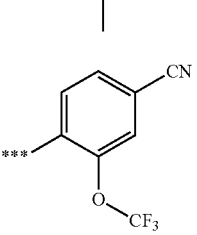 (c10″)
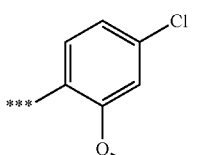 (c11″)
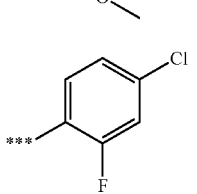 (c12″)

-continued

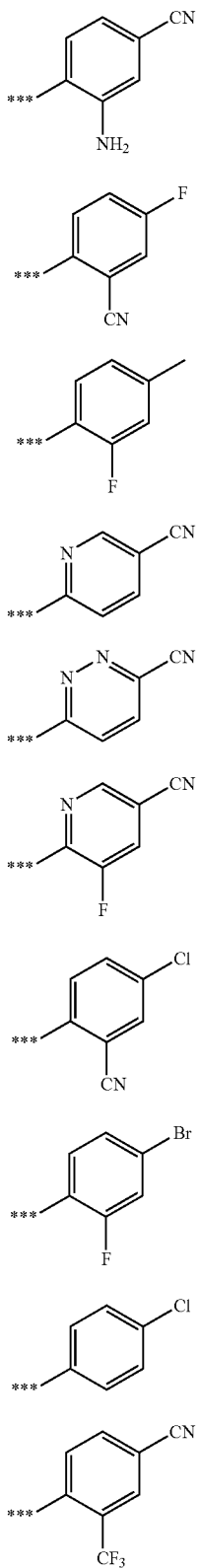

wherein:
*** represents the point of attachment to the —O(CHR₅)— moiety of formula (I).

Ring A may be a 5-membered carbocylic ring system, wherein 1 to 4 (such as 1, 2, 3, 4) carbon atoms is replaced with a heteroatom; and Ring B is of formula (bb1) or formula (bb2).

Ring A may be a 5-membered heteroaryl, and Ring B is of formula (bb1) or formula (bb2).

The compounds of the formulas disclosed herein may be selected from the group consisting of:

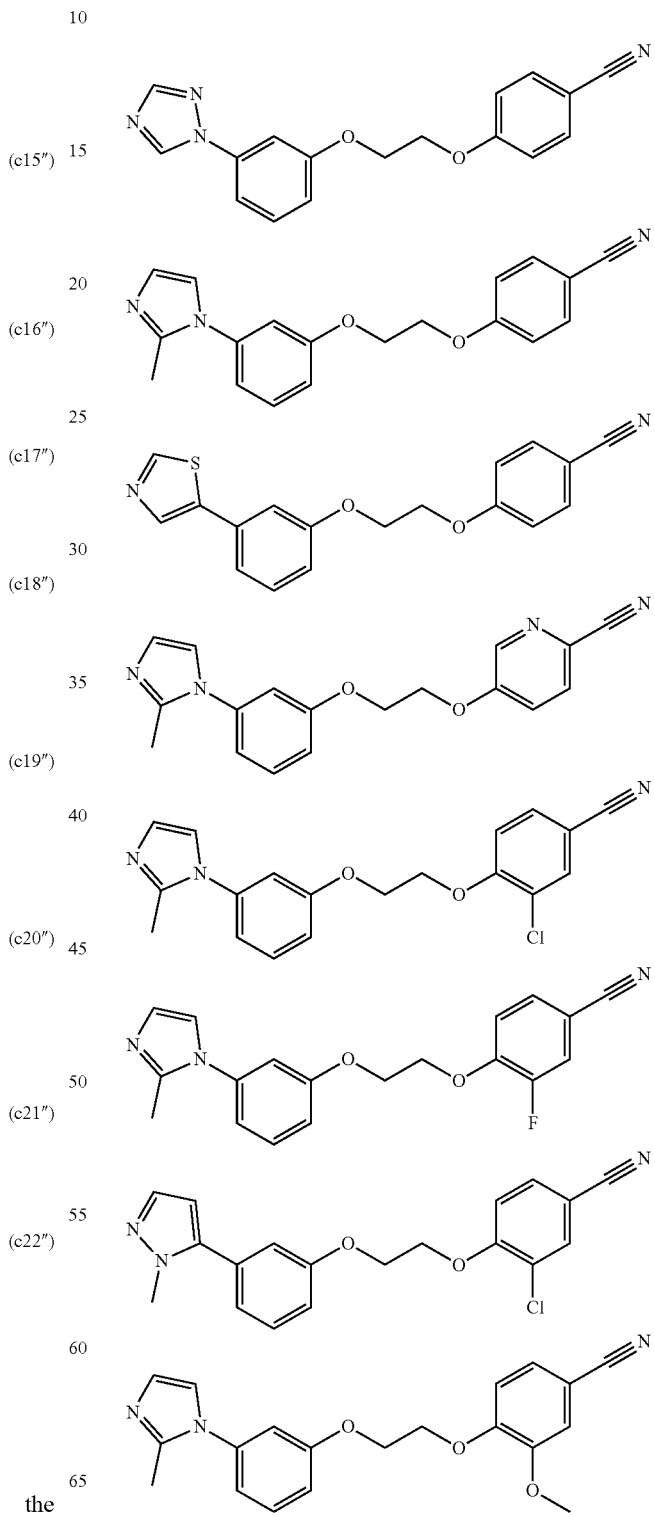

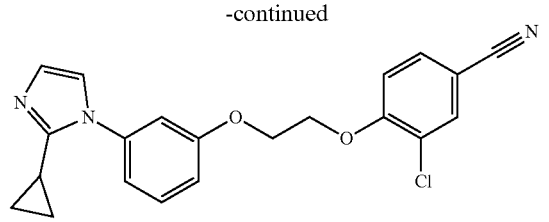
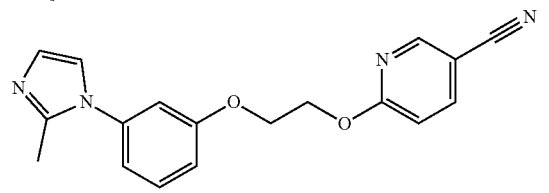
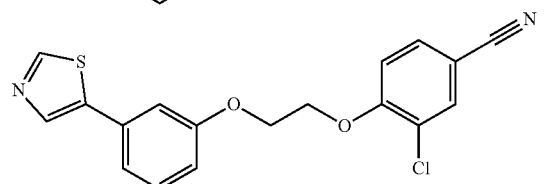
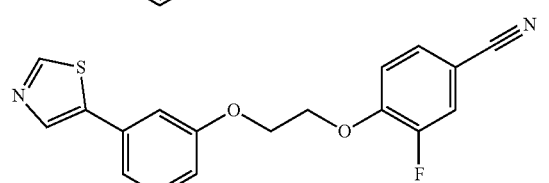
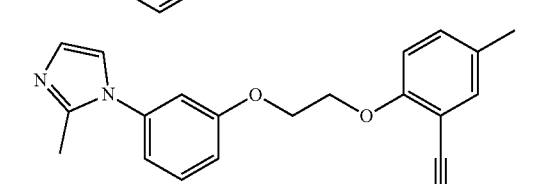
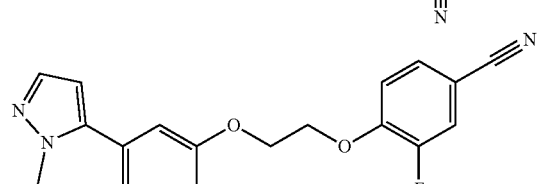
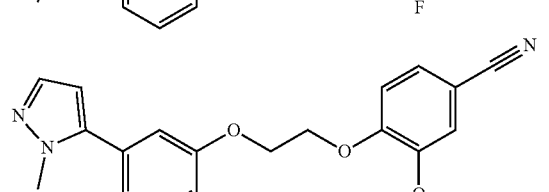
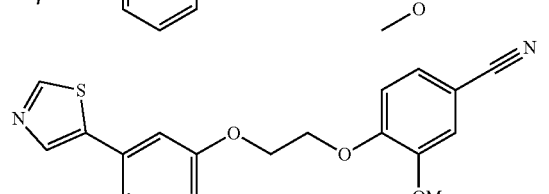
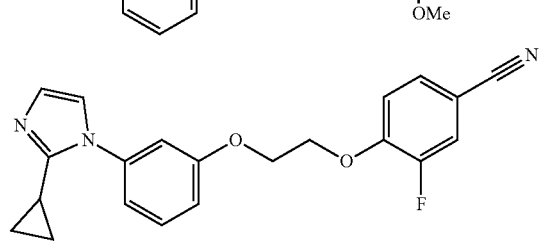
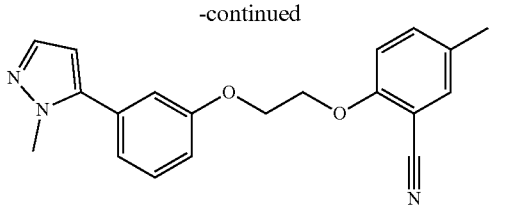
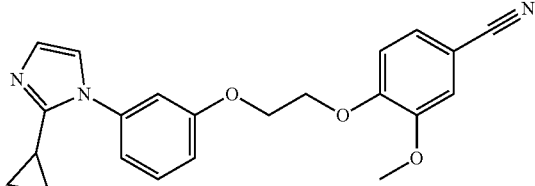
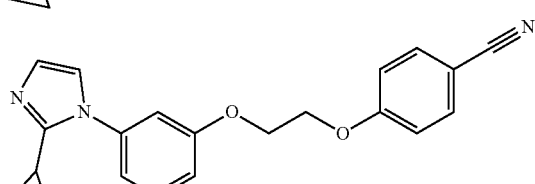
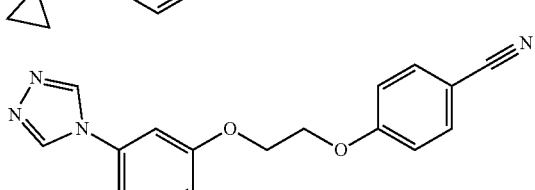
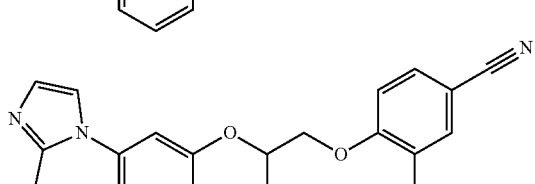
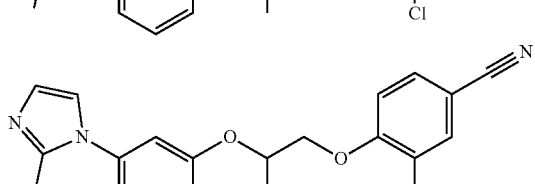
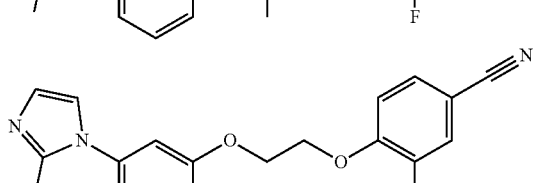
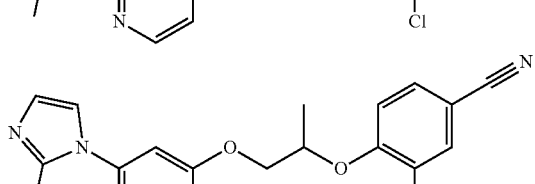
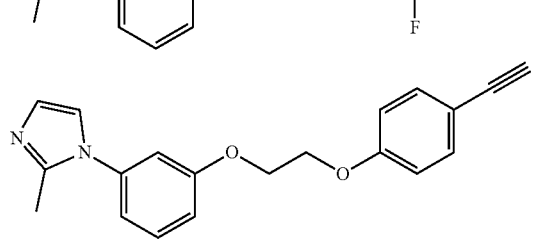

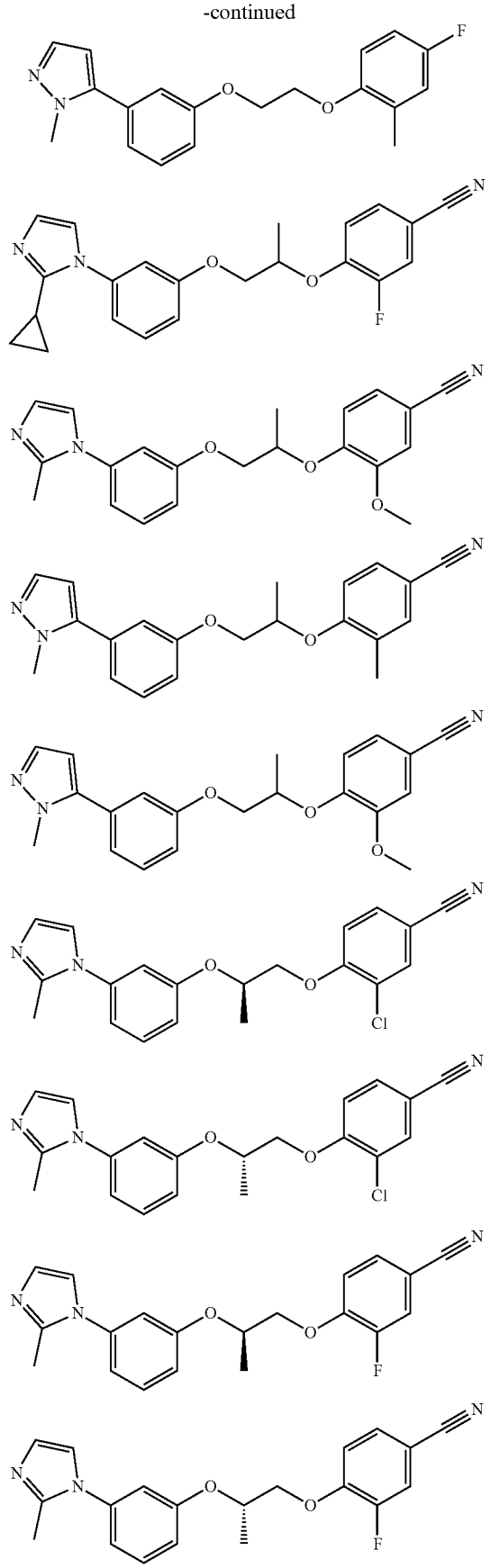
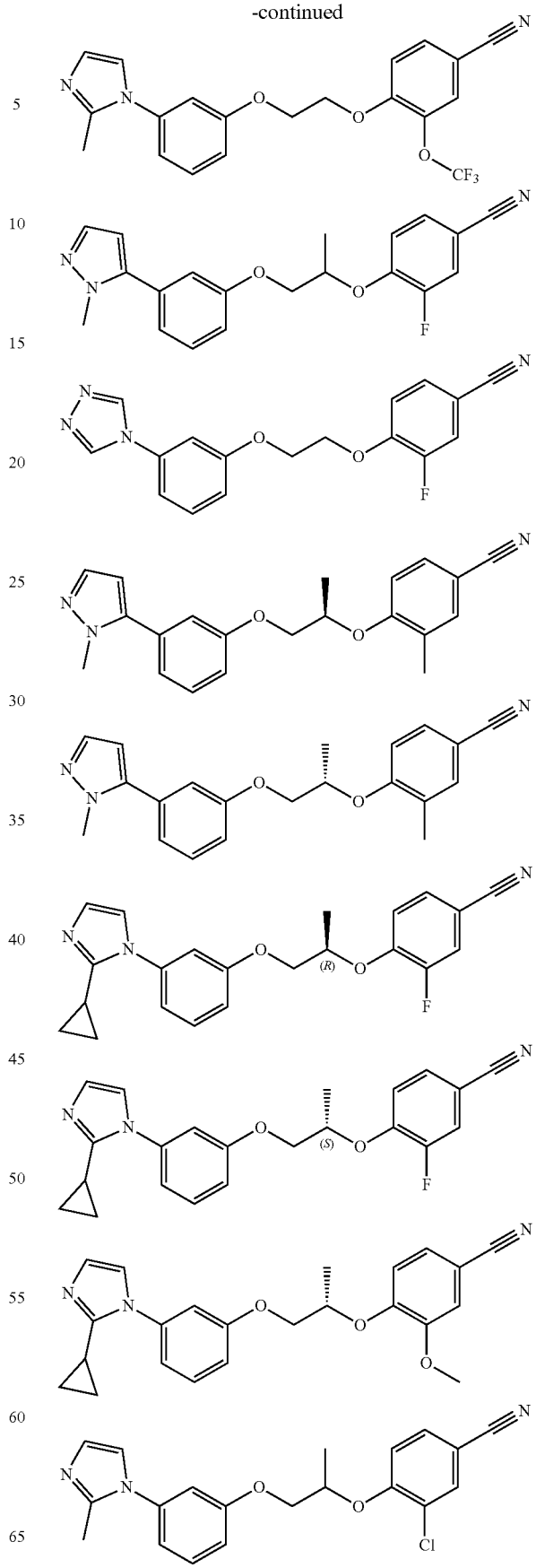

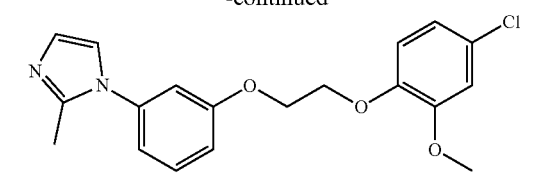
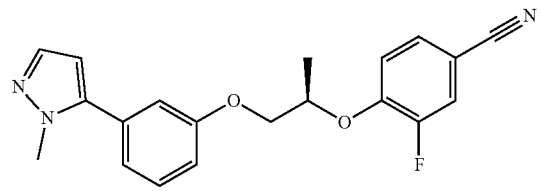
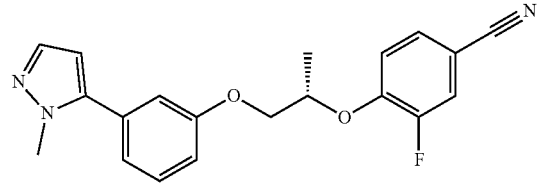
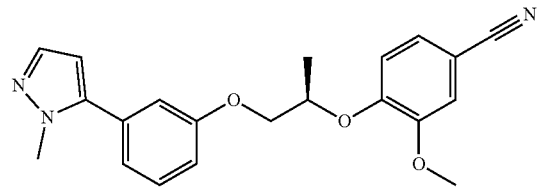
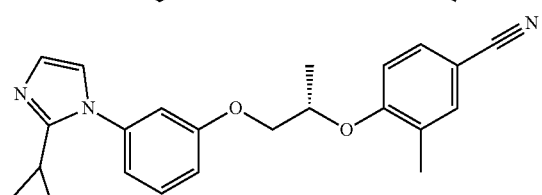
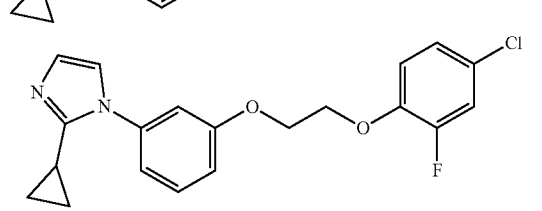
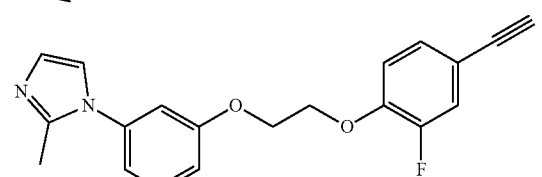
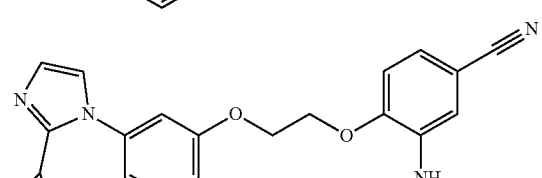
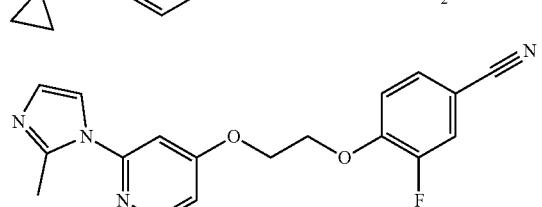
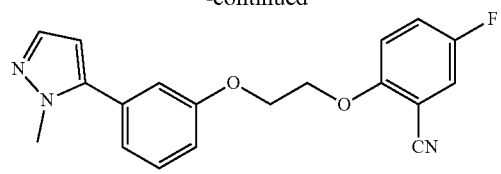
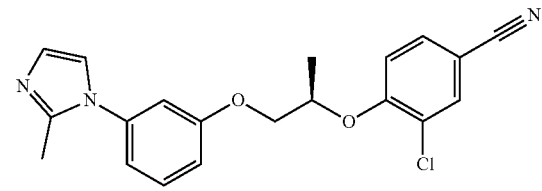
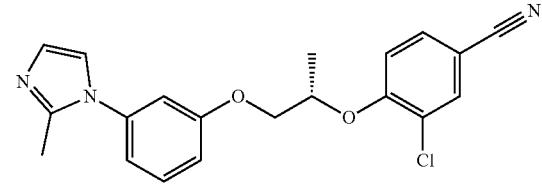
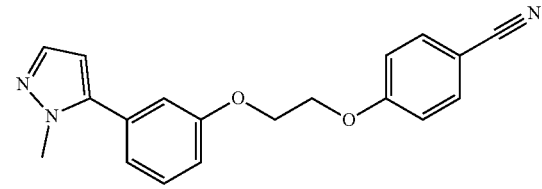
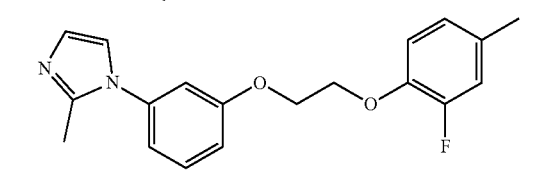
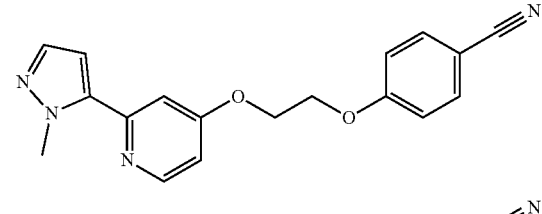
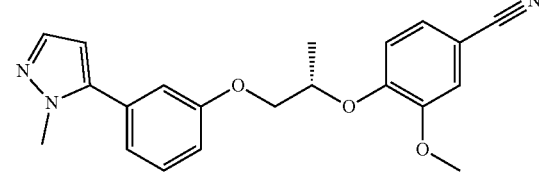
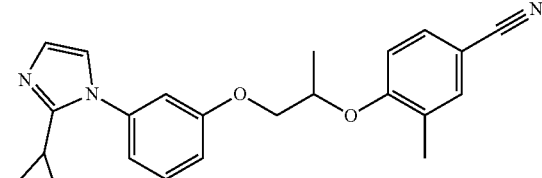
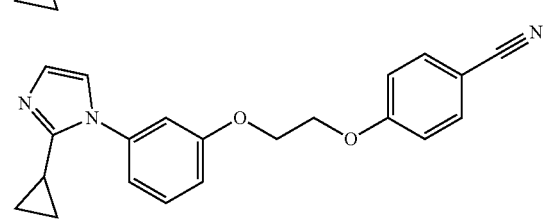

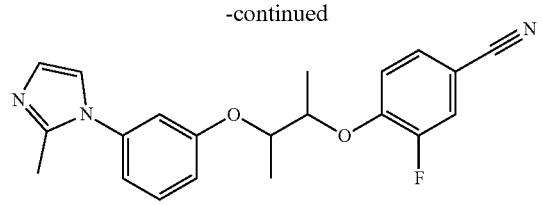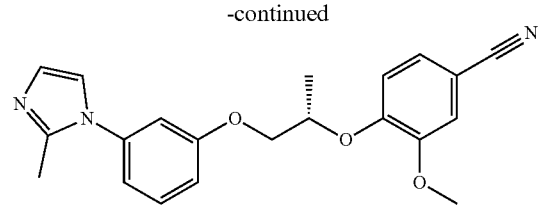

37
-continued
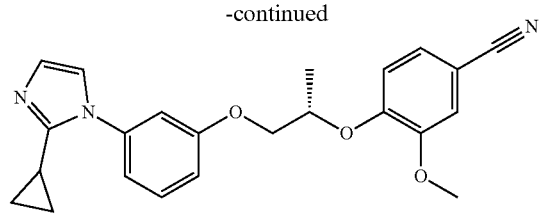
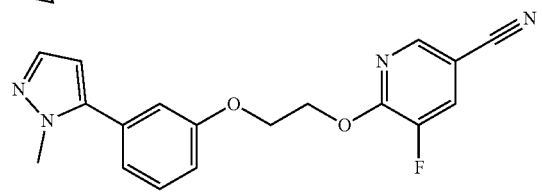
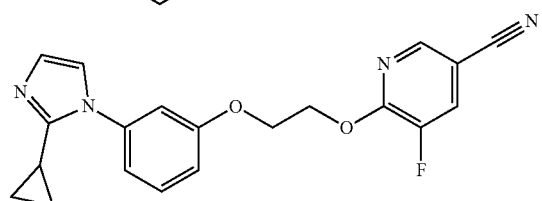
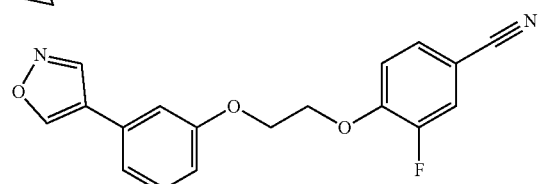
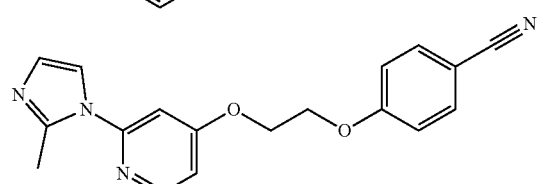
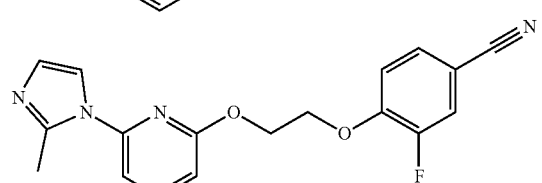
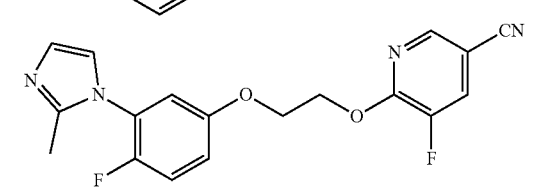
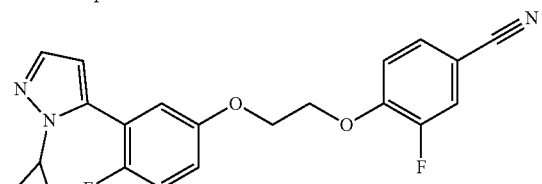
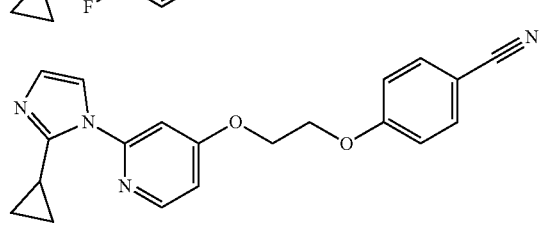
38
-continued
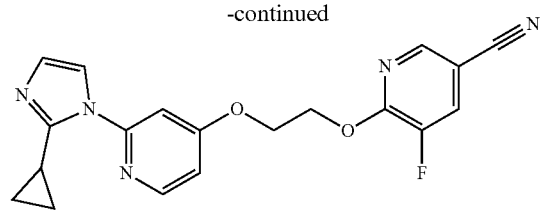
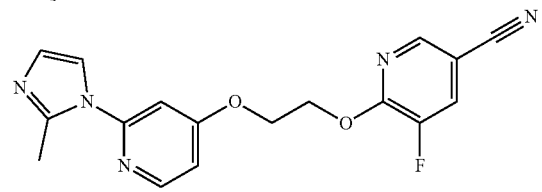
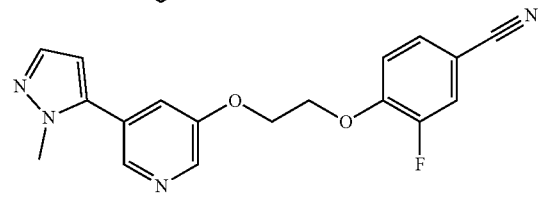
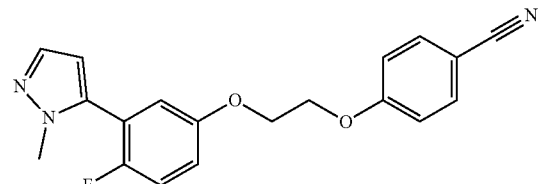
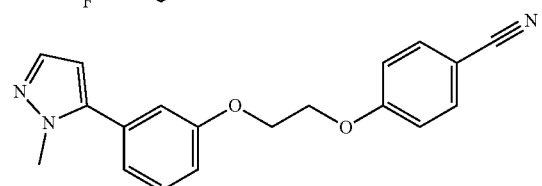
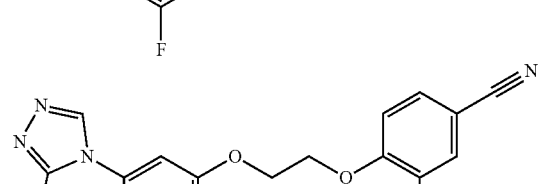
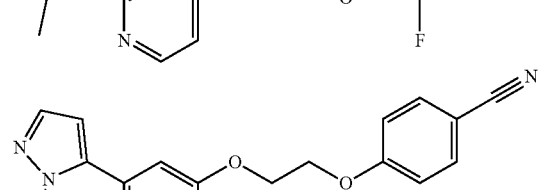
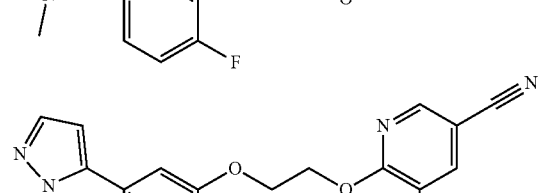
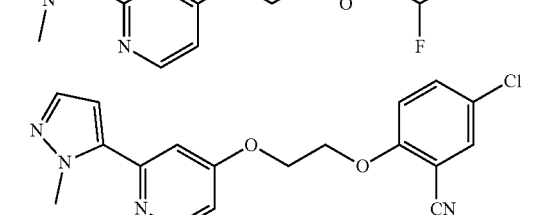

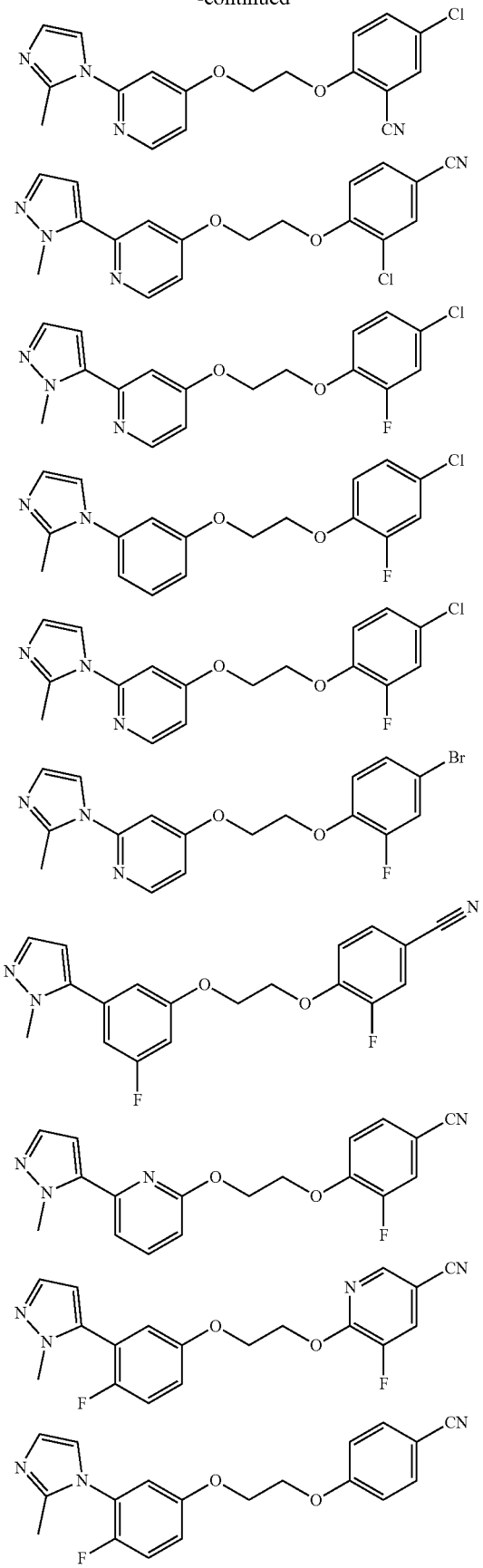
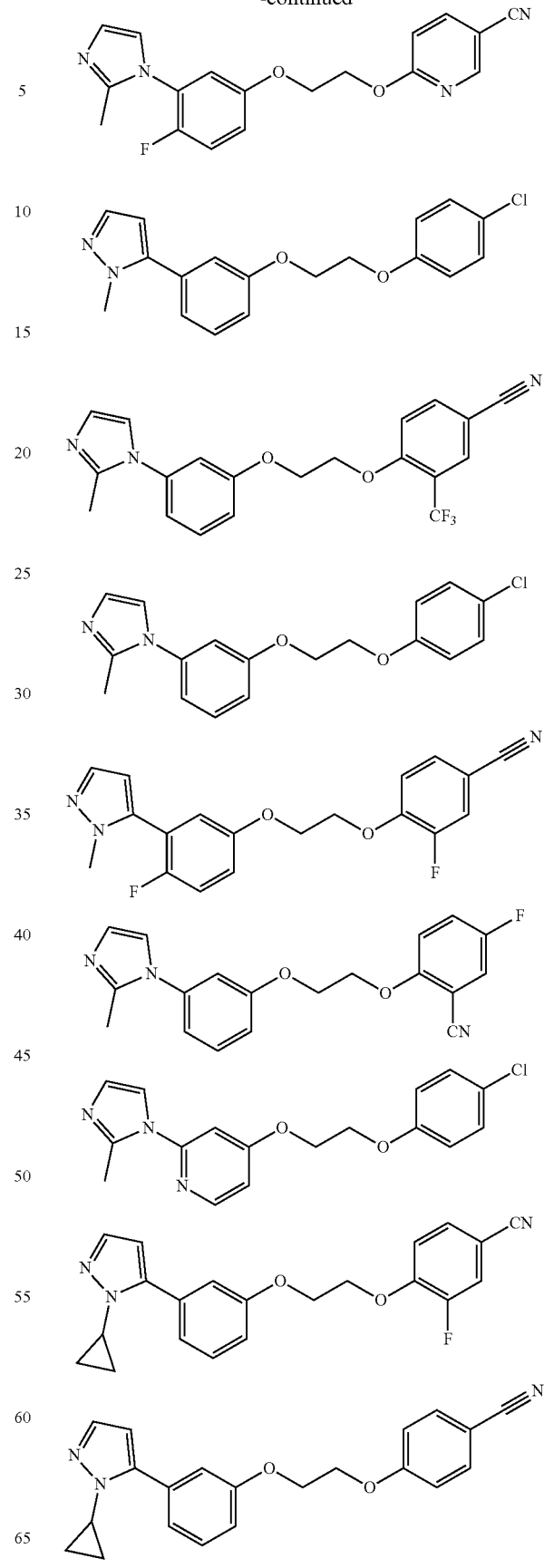

-continued

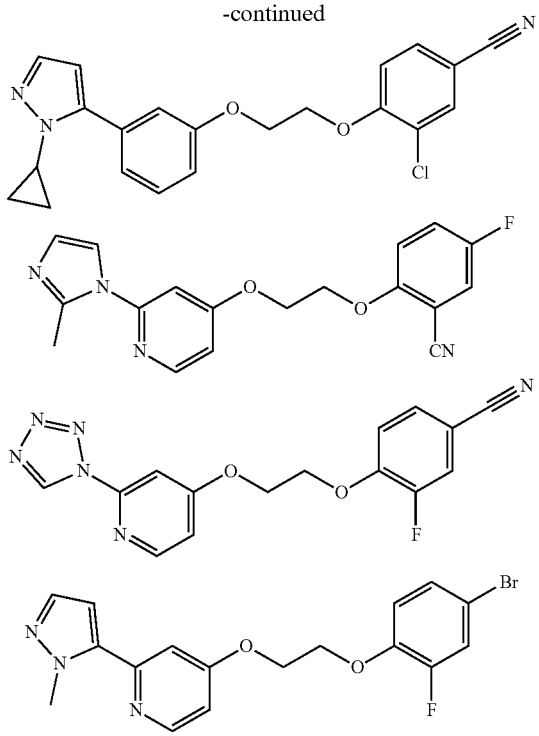

There is provided a pharmaceutical composition comprising a compound disclosed herein, or a pharmaceutically acceptable form or prodrug thereof, and a pharmaceutically acceptable excipient.

The amount of compound in the compositions may be such that it is effective to measurably inhibit ICMT in a biological sample or in a patient. The composition may be formulated for administration to a patient in need of such composition.

In using the compounds, they may be administered in any form or mode which may make the compound bioavailable. One skilled in the art of preparing formulations can readily select the proper form and mode of administration depending upon the particular characteristics of the compound selected, the condition to be treated, the stage of the condition to be treated and other relevant circumstances.

The term "pharmaceutically acceptable excipient" may refer to a non-toxic carrier, adjuvant, or vehicle that does not destroy the pharmacological activity of the compound with which it is formulated. Pharmaceutically acceptable carriers, adjuvants or vehicles that may be used in the compositions of this disclosure may include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol or wool fat.

Compositions as defined above may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions as defined above may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Pharmaceutical compositions for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds may be incorporated into slow release or targeted delivery systems such as polymer matrices, liposomes, and microspheres.

The injectable formulations may be sterilized, for example, by filtration through a bacterial-retaining filter, or by incorporating sterilizing agents in the form of sterile solid compositions that can be dissolved or dispersed in sterile water or other sterile injectable medium just prior to use.

Alternatively, pharmaceutically acceptable compositions as defined above may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions as defined above may also be administered topically, especially when the target of treatment includes areas or organs readily accessible by topical application, including diseases of the eye, the skin, or the lower intestinal tract. Suitable topical formulations may be readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of compounds as defined above may include, but are not limited to, mineral oil, liquid petrolatum, white petrolatum, propylene glycol, polyoxyethylene, polyoxypropylene compound, emulsifying wax and water. Alternatively, the pharmaceutically acceptable compositions may be formulated in a suitable lotion or cream containing the active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions as defined above may also be administered by nasal aerosol or inhalation. Such compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions as defined above may be formulated for oral administration. Such formulations may be administered with or without food. In some embodiments, pharmaceutically acceptable compositions as defined above may be administered without food. In other embodiments, pharmaceutically acceptable compositions as defined above may be administered with food.

The amount of compound that may be combined with the carrier materials to produce a composition in a single dosage form may vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

There is provided a method of inhibiting methylation of isoprenylated cysteine or isoprenylcysteine caused by isoprenylcysteine carboxyl methyltransferase (ICMT) comprising contacting the compound disclosed herein, or a pharmaceutical composition disclosed herein, with ICMT.

There is also provided a method of inhibiting ICMT in a cell comprising contacting said cell with a compound disclosed herein, or a pharmaceutically acceptable form or prodrug thereof, or a pharmaceutical composition disclosed herein.

The inhibition of ICMT may further comprise the inhibition of cell proliferation.

There is further provided a method of treating a ICMT-related disorder comprising administering to a subject in need of treatment a compound disclosed herein, or pharmaceutical, or a composition disclosed herein. The method may further comprise the step of administering an additional therapeutic agent to the subject.

The disorder may be cancer, premature ageing, or Hutchinson-Gilford progeria syndrome (HGPS). The cancer may be linked to mutant Ras overactivity. The cancer may be selected from the group consisting of hepatocellular carcinoma cancer, breast cancer, ovarian cancer, colorectal carcinoma, lung cancer, pancreatic cancer or leukemia.

There is also provided a compound disclosed herein, or a pharmaceutically form or prodrug thereof, or a composition disclosed herein for use in therapy. The compound may be administered in combination with an additional therapeutic agent.

There is also provided a compound disclosed herein, or a pharmaceutically form or prodrug thereof, or a composition disclosed herein for use in the treatment and/or prevention of cancer and/or progeroid diseases.

There is also provided a compound disclosed herein, or a pharmaceutically form or prodrug thereof, or a composition disclosed herein for use in the treatment of a ICMT-related disorder. The disorder may be cancer, premature ageing, or Hutchinson-Gilford progeria syndrome (HGPS). The cancer may be one linked to mutant Ras overactivity. The cancer may be hepatocellular carcinoma cancer, breast cancer, ovarian cancer, colorectal carcinoma, lung cancer, pancreatic cancer or leukemia.

There is also provided a use of a compound disclosed herein, or a pharmaceutically form or prodrug thereof, or a composition disclosed herein, in the manufacture of a medicament for the treatment and/or prevention of cancer and/or progeroid diseases. The medicament may be administered in combination with an additional therapeutic agent.

There is also provided a use of a compound disclosed herein, or a pharmaceutically form or prodrug thereof, or a composition disclosed herein, in the manufacture of a medicament for the treatment of a ICMT-related disorder. The disorder may be cancer, premature ageing, or Hutchinson-Gilford progeria syndrome (HGPS). The cancer may be one linked to mutant Ras overactivity. The cancer may be hepatocellular carcinoma cancer, breast cancer, ovarian cancer, colorectal carcinoma, lung cancer, pancreatic cancer or leukemia.

The compounds of the present invention may have an ICMT IC50 of less than about 5 μM. The compounds of the present invention may have an ICMT IC50 of about 0.001 μM to about 5 μM.

There is also provided a process for synthesizing a compound disclosed herein, comprising:

(a) reacting a compound of formula (III):

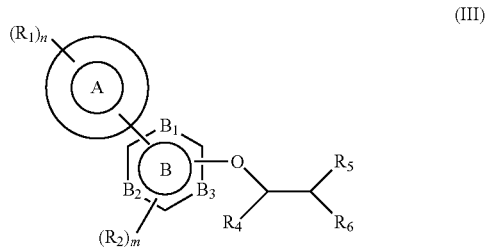

wherein $R_1$, $R_2$, $R_4$, $R_5$, $B_1$, $B_2$, $B_3$, n and m are as defined herein, and $R_6$ is a leaving group, in an organic solvent in the presence of a base with a compound of formula (IV):

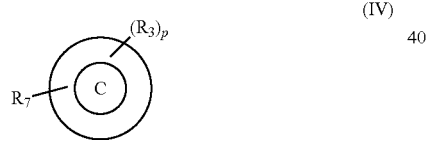

wherein $R_3$ and p are as defined herein, and $R_7$ is —OH.

$R_6$ being a leaving group may be any suitable leaving group and may be a mesylate (OMs), tosylate (OTs), perfluoroalkylsulfonates (trifluoromethanesulfonate), bromide or iodide.

The organic solvent for the above process (a) may be N-methylpyrrolidone, dimethylformamide, tetrahydrofuran, ethyl acetate, acetone, acetonitrile or dimethylsulfoxide.

The base for the above process (a) may be selected from a variety of bases including inorganic bases or nitrogen bases such as triethylamine, pyridine, sodium hydroxide, potassium hydroxide, lithium hydroxide, ammonium hydroxide, calcium hydroxide, lithium carbonate, sodium carbonate, potassium carbonate caesium carbonate, sodium hydride or sodium bicarbonate.

The above process (a) may be performed at a temperature that depends on the type of solvent and base used. As a guideline, the temperature may generally be in the range of about 40° C. to about 80° C. Process (a) may be performed at a temperature range of about 40° C. to about 80° C., about 45° C. to about 80° C., about 50° C. to about 80° C., about 55° C. to about 80° C., about 60° C. to about 80° C., about 65° C. to about 80° C., about 70° C. to about 80° C., about 75° C. to about 80° C., about 40° C. to about 75° C., about 40° C. to about 70° C., about 40° C. to about 65° C., about 40° C. to about 60° C., about 40° C. to about 55° C., about 40° C. to about 50° C., about 40° C. to about 45° C., or about 40° C., about 45° C., about 50° C., about 55° C., about 60° C., about 65° C., about 70° C., about 75° C., about 80° C., or any value or range therein, The above process (a) may be performed for a time duration that depends on the type of solvent and base used. As a guideline, the time duration may generally be in the range of about 12 hours to about 20 hours. Process (a) may be performed for about 12 hours to about 20 hours, about 13 hours to about 20 hours, about 14 hours to about 20 hours, about 15 hours to about 20 hours, about 16 hours to about 20 hours, about 17 hours to about 20 hours, about 18 hours to about 20 hours, about 19 hours to about 20 hours, about 12 hours to about 19 hours, about 12 hours to about 18 hours, about 12 hours to about 17 hours, about 12 hours to about 16 hours, about 12 hours to about 15 hours, about 12 hours to about 14 hours, about 12 hours to about 13 hours, or about 12 hours, about 13 hours, about 14 hours, about 15 hours, about 16 hours, about 17 hours, about 18 hours, about 19 hours, about 20 hours, or any value or range therein.

There is also provided another process for synthesizing a compound disclosed herein, comprising:

(b) reacting a compound of formula (III):

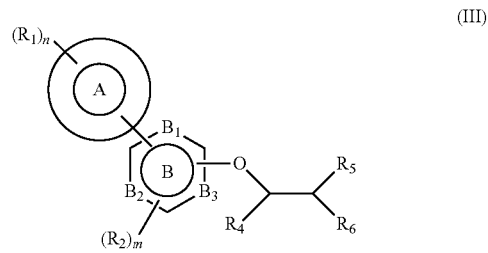

wherein $R_1$, $R_2$, $R_4$, $R_5$, $B_1$, $B_2$, $B_3$, n and m are as defined herein, and $R_6$ is OH or an alkoxide, in an organic solvent in the presence of a base with a compound of formula (IV):

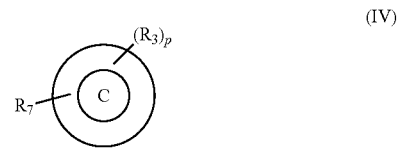

wherein $R_3$ and p are as defined herein, and $R_7$ is halogen.

The organic solvent for the above process (b) may be N-methylpyrrolidone, dimethylformamide, tetrahydrofuran, ethyl acetate, acetone, acetonitrile, dimethylsulfoxide, propylene carbonate or nitromethane.

The base for the above process (b) may be selected from a variety of bases including inorganic bases or nitrogen bases such as triethylamine, pyridine, sodium hydroxide, potassium hydroxide, lithium hydroxide, lithium carbonate, sodium carbonate, potassium carbonate or caesium carbonate.

The above process (b) may be performed at a temperature that depends on the type of solvent and base used. As a guideline, the temperature may generally be in the range of about 80° C. to about 120° C. Process (b) may be performed at a temperature range of about 80° C. to about 120° C., about 85° C. to about 120° C., about 90° C. to about 120° C., about 95° C. to about 120° C., about 100° C. to about 120° C., about 105° C. to about 120° C., about 110° C. to about 120° C., about 115° C. to about 120° C., about 80° C. to about 115° C., about 80° C. to about 110° C., about 80° C. to about 105° C., about 80° C. to about 100° C., about 80° C. to about 95° C., about 80° C. to about 90° C., about 80° C. to about 85° C., or about 80° C., about 85° C., about 90° C., about 95° C., about 100° C., about 105° C., about 110° C., about 115° C., about 120° C., or any value or range therein.

The above process (b) may be performed for a time duration that depends on the type of solvent and base used. As a guideline, the time duration may generally be in the range of about 12 hours to about 20 hours. Process (b) may be performed for about 12 hours to about 20 hours, about 13 hours to about 20 hours, about 14 hours to about 20 hours, about 15 hours to about 20 hours, about 16 hours to about 20 hours, about 17 hours to about 20 hours, about 18 hours to about 20 hours, about 19 hours to about 20 hours, about 12 hours to about 19 hours, about 12 hours to about 18 hours, about 12 hours to about 17 hours, about 12 hours to about 16 hours, about 12 hours to about 15 hours, about 12 hours to about 14 hours, about 12 hours to about 13 hours, or about 12 hours, about 13 hours, about 14 hours, about 15 hours, about 16 hours, about 17 hours, about 18 hours, about 19 hours, about 20 hours, or any value or range therein.

EXAMPLES

Non-limiting examples of the invention will be further described in greater detail by reference to specific Examples, which should not be construed as in any way limiting the scope of the invention.

Example 1: Expression and Purification of ICMT Enzyme

Recombinant human ICMT was prepared by infection of Sf9 cells with a recombinant baculovirus containing the entire open reading frame of the human ICMT cDNA.

Briefly, Sf9 cells in log phase growth were diluted to $1\times10^6$ cells/ml and infected with recombinant baculovirus at a multiplicity of infection of 2. Cells producing ICMT were harvested 66 hours post-infection. The cells are homogenized and resuspended in 5 mM $NaHPO_4$ (pH 7.0), and a cocktail of protease inhibitors. The membrane was pelleted, after removal of nuclei and debris, at 100,000×g for 1 hour. Membranes were resuspended in 5 mM $NaHPO_4$ (pH 7.0) with 5 mM EDTA at 10-12 mg/ml. The suspension was stored at −80° C. in multiple aliquots.

Example 2: ICMT Biochemical Assay

An ICMT enzymatic assay was developed using Promega's Methyltransferase-Glo™reagents. In the assay, ICMT catalyzes the methylation of the N-Acetyl-S-farnesyl-L-cysteine by transferring a methyl group from SAM to the farnesylated cysteine and further converts the SAM to SAH. The methyltransferase activity is measured based on the amount of SAH produced from the reaction through the use of coupling enzymes that convert the SAH to ATP. The MTase-Glo detection solution then catalyzes the formation of light from ATP.

For the IC50 determination, the compounds were incubated for 30 minutes with 0.04 ug/well ICMT membrane extract from Sf-9 cells. A final concentration of 2.0 μM and 20 μM of SAM and peptide were added and further incubated for 90 minutes at room temperature before adding the MTase Glo and detection reagent. Reaction signals were detected using microplate readers on luminescent mode (Satire Tecan). The IC50 was determined by nonlinear regression, using GraphPad Prism version, 5.03.

Example 3: Prelamin a Accumulation Assay

The MIAPaCa-2 cells were seeded in 6-well plates. After seeding for 24 hours, the cells were treated with either DMSO or varying concentration of the compound and incubated for 48 hours. The cells were trypsinized and the lysate was extracted with RIPA buffer (Santa Cruz). The total protein concentration of lysate is quantified using the standard Bradford assay (Biorad protein assay, microplate standard assay).

Western blot analysis was performed using antibody against Prelamin A in MIAPaCa cells treated with compound at various concentration for 48 hours. 15.0 μg of cell lysate was run on a SDS-PAGE and then transferred to nitrocellulose membrane. The membrane was then incubated in blocking buffer [PBS (phosphate buffered saline) with 0.1% Tween 20 and 5% dry milk] at room temperature for 1 hour, followed by incubation with Prelamin A antibody (rat monoclonal antibody) at 1:2500 dilution in PBS, 0.1% Tween 20 and 5% dry milk overnight at 4° C., followed by three washes (15 minutes each wash) in PBS, 0.1% Tween 20 on the next day.

The nitrocellulose membrane was then incubated with secondary antibody solution at room temperature for 1 hour, washed three times before developed with enhanced Chemiluminescence (ECL) mixture (Amersham, Aylesbury, United Kingdom), incubated for 5 minutes and exposed using Fluor Chem E System instrument (Protein Simple).

Example 4: Soft Agar Assay

MIAPaCa-2 cells were purchased from ATCC. For the soft agar assay, 600 μL of 0.6% agar was added to 24-well plate to form the base layer. This is followed by the addition of 500 μL of 0.36% agar middle layer (containing MIAPacCa-2 cells). Lastly, 500 μL of fresh growth medium (containing the corresponding serially diluted compound) was added above the middle layer. The plates were incubated at 37° C. with 5% carbon dioxide in a humidified incubator for 1 to 2 weeks, with media changes every 3 days. 70 μL of thiazolyl blue tetrazolium bromide (5 mg/mL, Sigma Catalogue No: M5655) was added to each well and the plates were incubated at room temperature overnight. The plates with colonies imaged with dissecting microscope (4× magnification). The images were then analysed with ImageJ software for colony counts, which were plotted against compound concentrations using Graphpad Prism software. In addition, the software was used to perform non-linear curve fitting and the calculation of IC50.

Example 5: Cell Proliferation Assay

Cell proliferation assay was performed using CellTiter-Glo Luminescent Cell Viability Assay (Promega) following manufacturer's instructions. The MIAPaCa-2 cells (ATCC) were treated with compounds that were serial diluted in the media (DMEM). Plates were incubated for 3 days at 37° C. in 5% $CO_2$. After 3 days, an equal volume of Cell Titer Glo reagent was added. Plates were rocked on a rotator for 2 hours. 100 μL of each well was transferred to a 96-well opaque plate, and luminescence emitted was measured with the Tecan Safire II. The data for selected compounds is summarized in Table 1.

TABLE 1

Summary of MIAPaCa-2 cells proliferation assay data for selected compounds.

| Compound | GI$_{50}$ (μM) |
|---|---|
| 71 | 12.66 |
| 53 | 2.2 |
| 70 | 5.99 |
| 59 | 5.52 |
| 69 | 5.05 |
| 78 | 6.02 |

Example 6: Preparation of Phenol Intermediates

General Procedure 1

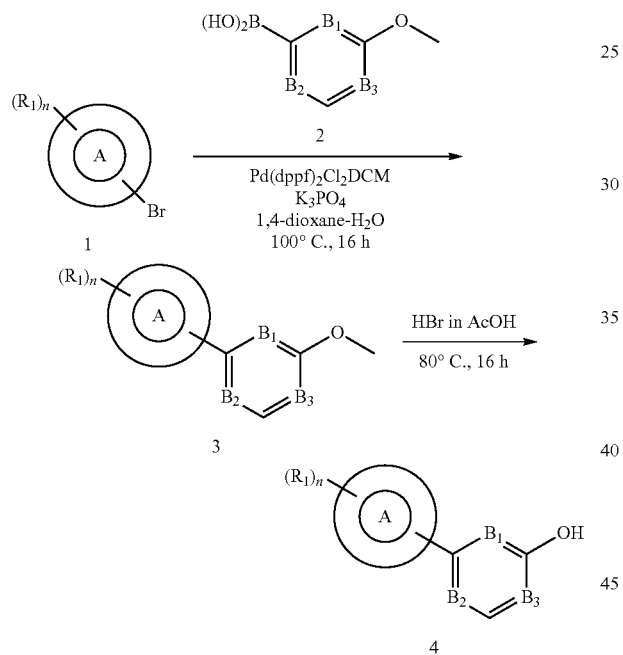

To a well stirred solution of the respective halide, 1 (1 molar equiv.) in 4:1 ratio of 1,4-dioxane-water (0.6 M) were added boronic acid, 2 (1.2 molar equiv.), K$_3$PO$_4$ (2 molar equiv.) and Pd(dppf)Cl$_2$·DCM (0.05 molar equiv.) sequentially at room temperature and degassed with argon for 5 minutes. The reaction mixture was heated at 100° C. for 16 hours. The reaction mixture was cooled to room temperature, poured into ice-cold water and extracted with ethyl acetate. The combined organics was washed with water, brine, dried over sodium sulphate, filtered and concentrated under reduced pressure to give the crude product. This crude product was purified by column chromatography to afford the desired product, 3.

To a well stirred solution of 3 in excess HBr in acetic acid was heated at 80° C. for 16 hours. The reaction mixture was concentrated under reduced pressure. The crude material was basified with saturated sodium bicarbonate and pH was adjusted to 8 and extracted with ethyl acetate. The combined organics was washed with water and brine solution, dried over anhydrous sodium sulphate, filtered, concentrated under reduced pressure to afford the desired phenol, 4.

Preparation of 3-(thiazol-5-yl)phenol

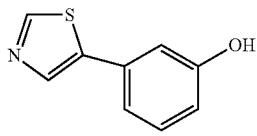 [SMILES: Oc1cccc(-c2cncs2)c1]

$^1$HNMR (400 MHz, CDCl$_3$) δ (ppm): 8.75 (s, 1H), 8.07 (s, 1H), 7.33 (t, J=8.0 Hz, 1H), 7.20-7.15 (m, 1H), 7.11 (t, J=2.2 Hz, 1H), 6.91-6.88 (m, 1H), 3.86 (s, 3H). MS (ESI) m/z 178.2 [C$_9$H$_7$NOS+H]$^+$.

Preparation of 3-(1-methyl-1H-pyrazol-5-yl) phenol

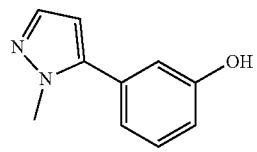

$^1$H NMR (400 MHz, CDCl$_3$) δ (ppm): 7.52 (d, J=2.0 Hz, 1H), 7.32-7.25 (m, 1H), 6.96-6.86 (m, 3H), 6.38 (t, J=2.4 Hz, 1H), 6.30 (dd, J=6.8, 2.0 Hz, 1H), 3.93 (s, 3H). MS (ESI) m/z 175.2 [C$_{10}$H$_{10}$N$_2$O+H]$^+$.

Preparation of 2-(1-methyl-1H-pyrazol-5-yl) pyridin-4-ol

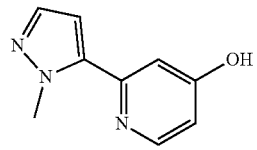

$^1$H NMR (400 MHz, CDCl$_3$) δ (ppm): 10.8 (s, 1H), 8.49 (d, J=6.0 Hz, 1H), 7.49 (s, 1H), 7.07 (s, 1H), 6.79 (t, J=2.0 Hz, 1H), 6.54 (s, 1H), 4.2 (s, 3H). MS (ESI) m/z 176.2 [C$_9$H$_9$N$_3$O+H]$^+$.

Preparation of 3-(isoxazol-4-yl)phenol

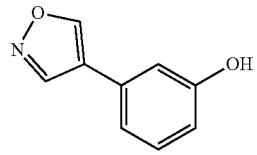

$^1$H NMR (400 MHz, CDCl$_3$) δ (ppm): 8.66 (d, J=6.8 Hz, 1H), 8.52 (d, J=3.6 Hz, 1H), 7.27 (t, J=7.6 Hz, 1H), 7.05 (d, J=8.0 Hz, 1H), 6.81 (dd, J=8.4, 2.0 Hz, 1H), 4.98 (s, 1H). MS (ESI) m/z 162.2 [C$_9$H$_7$NO$_2$+H]$^+$.

Preparation of 3-(isoxazol-4-yl)phenol

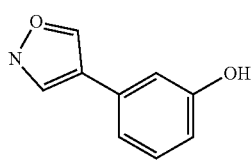

¹H NMR (400 MHz, CDCl₃) δ (ppm): 8.66 (d, J=6.8 Hz, 1H), 8.52 (d, J=3.6 Hz, 1H), 7.27 (t, J=7.6 Hz, 1H), 7.05 (d, J=8.0 Hz, 1H), 6.81 (dd, J=8.4, 2.0 Hz, 1H), 4.98 (s, 1H). MS (ESI) m/z 162.2 [C$_9$H$_7$NO$_2$+H]$^+$.

Preparation of
3-fluoro-5-(1-methyl-1H-pyrazol-5-yl)phenol

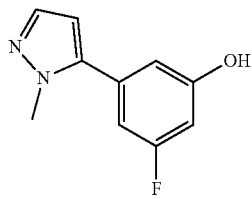

¹H NMR (DMSO-d₆, 400 MHz): δ 10. 527 (brs, 1H), 7.434 (d, 1H, J=1.6 Hz), 6.765 (d, 1H, J=9.6 Hz), 6.715 (s, 1H), 6.623 (dd, 1H, J=10.8 & 2.0 Hz), 6.379 (d, 1H, J=1.6 Hz), 3.815 (s, 3H). MS (ESI) m/z 193.1 [C$_{10}$H$_9$FN$_2$O+H]$^+$.

Preparation of
5-(1-methyl-1H-pyrazol-5-yl)pyridin-3-ol

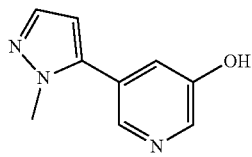

MS (ESI) m/z 176.1 [C$_9$H$_9$N$_3$O]$^+$.

Preparation of
6-(1-methyl-1H-pyrazol-5-yl)pyridin-2-ol

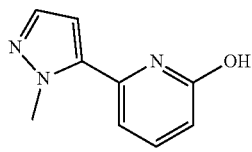

¹H NMR (CDCl₃, 400 MHz): δ 7.542 (t, 0.5H, J=8.0 Hz), 7.444 (t, 0.5H, J=8.0 Hz), 7.082 (d, 0.5H, J=7.2 Hz), 6.924 (d, 0.5H, J=7.2 Hz), 6.735 (d, 0.5H, J=8.0 Hz), 6.703 (d, 0.5H, J=8.0 Hz), 4.462-4.440 (m, 2H), 3.964-3.942 (m, 2H). MS (ESI) m/z 176.1 [C9H9N3O+H]$^+$.

Preparation of
4-fluoro-3-(1-methyl-1H-pyrazol-5-yl)phenol

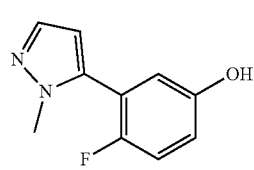

¹H NMR (CDCl₃, 400 MHz): δ 7.54-7.53 (d, J=1.6 Hz, 1H), 7.10 (t, J=9.0 Hz, 1H), 6.97-6.93 (m, 1H), 6.87-6.85 (m, 1H), 6.32-6.31 (d, J=2.0 Hz, 1H), 4.09-4.07 (m, 2H), 3.98-3.96 (m, 2H), 3.82 (s, 3H). MS (ESI) m/z 193.1 [C10H9FN2O+H]$^+$.

General Procedure 2

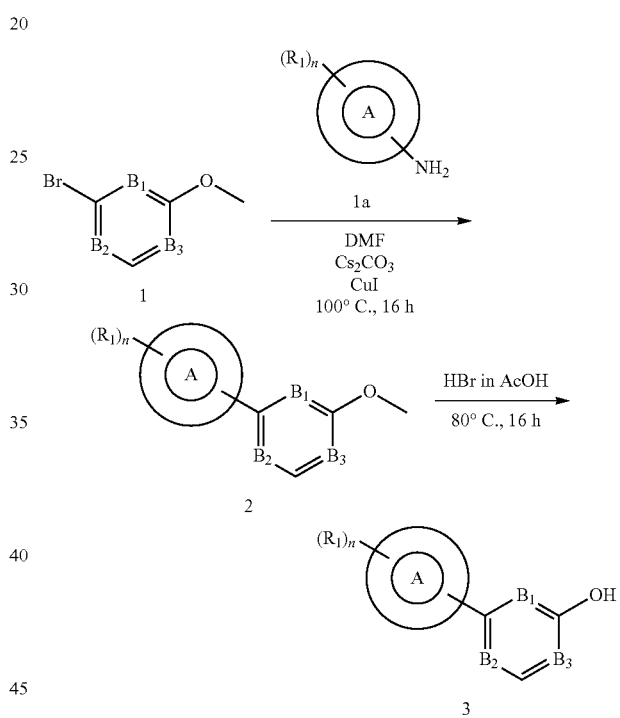

To a well stirred solution of 1-bromo-3-methoxybenzene, 1 (1 molar equiv.) in DMF (0.85 M) were added the respective amine, 1a (1.5 molar equiv.) and caesium carbonate (2 molar equiv.) and copper(I) iodide (0.1 molar equiv.). The reaction mixture was heated at 100° C. for 16 hours. The reaction mixture was cooled and poured into water and extracted with ethyl acetate. The combined organics was washed with water and brine, dried over sodium sulphate and concentrated under reduced pressure. The crude product was purified by column chromatography to afford the desired intermediate, 2.

To a well stirred solution of 2 in excess HBr in acetic acid was heated at 80° C. for 16 hours. The reaction mixture was concentrated under reduced pressure. The crude material was basified with saturated sodium bicarbonate and pH was adjusted to 8 and extracted with ethyl acetate. The combined organics was washed with water and brine solution, dried over anhydrous sodium sulphate, filtered, concentrated under reduced pressure to afford the desired phenol, 3.

Preparation of 3-(1H-1,2,4-triazol-1-yl)phenol

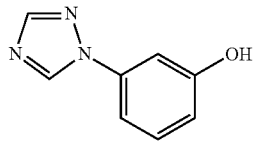 [SMILES: Oc1cccc(-n2cncn2)c1]

¹H NMR (400 MHz, DMSO-d₆) δ (ppm): 9.97 (s, 1H), 9.22 (s, 1H), 8.19 (s, 1H), 7.34-7.24 (m, 3H), 6.80-6.78 (m, 1H). MS (m/z): 162.2 [C₈H₇N₃O+H]⁺.

Preparation of 3-(4H-1,2,4-triazol-4-yl)phenol

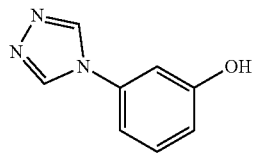 [SMILES: Oc1cccc(-n2cnnc2)c1]

¹H NMR (400 MHz, CDCl₃) δ (ppm): 9.94 (s, 1H), 9.23 (s, 1H), 8.19 (s, 1H), 7.35-7.24 (m, 3H), 6.93 (dd, J=1.6 Hz, 8.0 Hz, 1H). MS (ESI) m/z 162.2 [C₈H₇N₃O+H]⁺.

Preparation of 2-(3-methyl-4H-1,2,4-triazol-4-yl)pyridin-4-ol

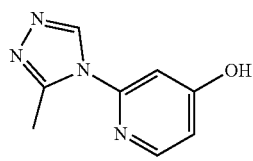

MS (ESI) m/z 177.1 [C₈H₈N₄O]⁺.

Preparation of 2-(1H-tetrazo-1-yl)pyridin-4-ol

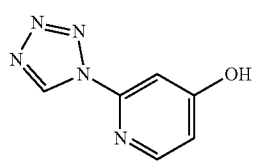 [SMILES: Oc1ccnc(-n2cnnn2)c1]

MS (ESI) m/z 177.1 [C₆H₅N₅O]⁺.

Preparation of 3-(2-methyl-1H-imidazol-1-yl)phenol

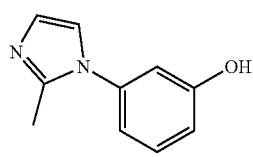

¹H NMR (400 MHz, DMSO-d₆) δ (ppm): 9.91 (s, 1H), 7.32-7.28 (m, 1H), 7.23 (m, 1H), 6.68 (m, 1H), 6.84-6.81 (m, 2H), 6.75 (m, 1H), 2.26 (s, 3H); MS (ESI) m/z 175.1 [C₁₀H₁₀N₂O+H]⁺.

Preparation of 4-methoxy-2-(2-methyl-1H-imidazol-1-yl)pyridine

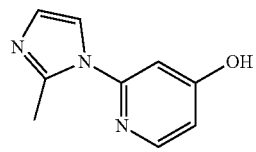

¹H NMR (400 MHz, DMSO-d₆) δ (ppm): 11.08 (s, 1H), 8.23 (d, J=6.0 Hz, 1H), 7.45 (d, J=1.6 Hz, 1H), 6.87-6.80 (m, 3H), 2.23 (s, 3H). MS (ESI) m/z 176.2 [C₉H₉N₃O+H]⁺.

Preparation of 6-(2-methyl-1H-imidazol-1-yl)pyridin-2-ol

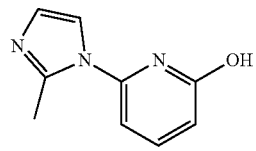

MS (ESI) m/z 176.0 [C₉H₉N₃O]⁺.

Preparation of 3-(2-cyclopropyl-1H-imidazol-1-yl)phenol

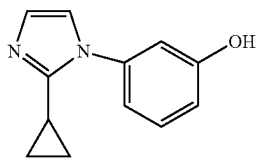 [SMILES: Oc1cccc(-n2ccnc2C2CC2)c1]

¹HNMR (400 MHz, DMSO-d₆) δ (ppm): 9.89 (s, 1H), 7.32 (t, J=8.4 Hz, 1H), 7.19 (d, J=1.1 Hz, 1H), 6.89 (dd, J=1.4 and 2.5 Hz, 1H), 6.84-6.82 (m, 3H), 1.80-1.74 (m, 1H), 0.88-0.82 (m, 4H). MS (ESI) m/z 201.2 [C₁₂H₁₂N₂O+H]⁺.

Preparation of 4-fluoro-3-(2-methyl-1H-imidazol-1-yl)phenol

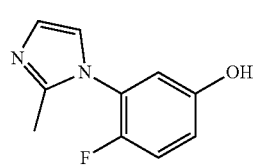

¹H NMR (DMSO, 400 MHz) δ 9.88 (s, 1H), 7.27 (t, J=9.4 Hz, 1H), 7.22 (s, 1H), 6.92 (s, 1H), 6.91-6.87 (m, 1H), 6.80-6.78 (m, 1H), 2.17 (s, 3H). MS (ESI) m/z 192.8 $[C_{10}H_9FN_2O+H]^+$.

Preparation of Ethyl 2-(3-(2-methyl-1H-imidazol-1-yl)phenoxy)propanoate

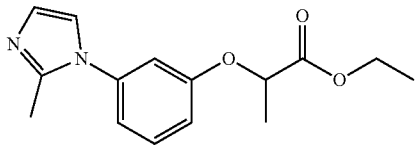 [SMILES: CCOC(=O)C(C)Oc1cccc(-n2ccnc2C)c1]

To a well stirred solution of 3-(2-methyl-1H-imidazol-1-yl)phenol (1 molar equiv.) in DMF (0.3 M) were added ethyl 2-bromopropanoate (2 molar equiv.) and $K_2CO_3$ (3 molar equiv.). The reaction mixture was heated at 100° C. for 16 hours. The reaction mixture was cooled and poured in to water (200 mL) and extracted with EtOAc (3×200 mL). The combined organic layer was washed with water and brine, dried over $Na_2SO_4$ and concentrated under reduced pressure. The crude product was purified by column chromatography to afford ethyl 2-(3-(2-methyl-1H-imidazol-1-yl)phenoxy) propanoate as a colorless gummy liquid.

¹H NMR (400 MHz, $CDCl_3$) δ (ppm): 7.37 (t, J=8.0 Hz, 1H), 7.01-6.89 (m, 4H), 6.81 (d, J=1.6 Hz, 1H), 4.78-4.73 (m, 1H), 4.25-4.20 (s, 2H), 2.37 (d, J=6.0 Hz, 3H), 1.28 (t, J=7.6 Hz, 3H).

Preparation of 2-(3-(2-methyl-1H-imidazol-1-yl) phenoxy)propan-1-ol

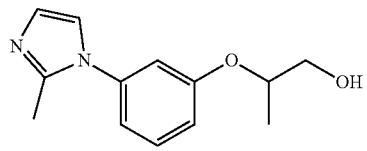 [SMILES: Cc1nccn1-c1cccc(OC(C)CO)c1]

To a well stirred solution of ethyl 2-(3-(2-methyl-1H-imidazol-1-yl)phenoxy)propanoate (0.07 M) in THF (20 mL) were added LAH (2 M in THF) (2 molar equiv.). The reaction mixture was cooled at 0° C. to room temperature for 16 hours. The reaction mixture was cooled and quenched with saturated $NaSO_4$ and extracted with EtOAc. The combined organic layer was washed with water and brine, dried over $Na_2SO_4$ and concentrated under reduced pressure. The crude product was purified by column chromatography to afford 2-(3-(2-methyl-1H-imidazol-1-yl)phenoxy)propan-1-ol.

1H NMR (400 MHz, $CDCl_3$) δ (ppm): 7.38 (t, 1H), 7.05-6.90 (m, 4H), 6.85 (d, 1H), 4.58 (m, 1H), 3.78 (s, 2H), 2.37 (s, 3H), 1.28 (s, 3H).

Preparation of 1-(3-(1-methyl-1H-pyrazol-5-yl)phenoxy)propan-2-ol

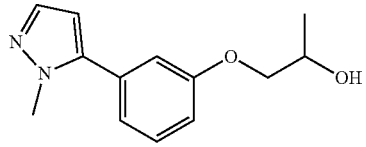 [SMILES: CC(O)COc1cccc(-c2ccnn2C)c1]

To a well stirred solution of 3-(1-methyl-1H-pyrazol-5-yl) phenol (500 mg, 2.8 mmol) in DMSO (0.5 M) were added 1-chloropropan-2-ol (1.5 molar equiv.) and $K_2CO_3$ (3 molar equiv.). The reaction mixture was heated at 100° C. for 16 hours. The reaction mixture was cooled and poured in to water and extracted with EtOAc. The combined organic layer was washed with water and brine, dried over $Na_2SO_4$ and concentrated under reduced pressure. The crude product was purified by column chromatography to afford 1-(3-(1-methyl-1H-pyrazol-5-yl)phenoxy)propan-2-ol.

1H NMR (400 MHz, $CDCl_3$) δ (ppm): 7.50 (d, J=1.6 Hz, 1H), 7.39-7.24 (m, 1H), 7.02-6.95 (m, 3H), 6.29 (d, J=2.0 Hz, 1H), 4.25-4.20 (m, 1H), 4.04-3.96 (m, 1H), 3.96-3.82 (m, 4H), 2.31 (d, J=3.6 Hz, 1H), 1.31-1.24 (m, 3H).

Preparation of 1-(3-(2-methyl-1H-imidazol-1-yl) phenoxy)propan-2-ol

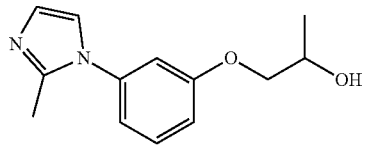 [SMILES: Cc1nccn1-c1cccc(OCC(C)O)c1]

To a well stirred solution of 3-(2-methyl-1H-imidazol-1-yl) phenol (1 equiv.) in DMSO (0.2 M) were added 1-chloropropan-2-ol (2 molar equiv.) and $K_2CO_3$ (3 molar equiv.). The reaction mixture was heated at 100° C. for 16 hours. The reaction mixture was cooled and poured in to water and extracted with EtOAc. The combined organic layer was washed with water and brine, dried over $Na_2SO_4$ and concentrated under reduced pressure. The crude product was purified by column chromatography to afford 1-(3-(2-methyl-1H-imidazol-1-yl)phenoxy)propan-2-ol.

1H NMR (400 MHz, $CDCl_3$) δ (ppm): 7.37 (t, J=8.0 Hz, 1H), 7.27 (d, J=1.2 Hz, 1H), 7.03-6.97 (m, 3H), 6.89 (d, J=1.2 Hz, 1H), 4.89 (d, J=4.4 Hz, 1H), 3.97-3.84 (m, 3H), 2.29 (s, 3H), 1.15 (d, J=6.4 Hz, 3H).

Preparation of (S)-1-(3-(2-cyclopropyl-1H-imidazol-1-yl)phenoxy)propan-2-ol

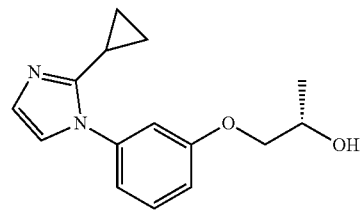 [SMILES: C[C@H](O)COc1cccc(-n2ccnc2C2CC2)c1]

To a well stirred solution of 3-(2-cyclopropyl-1H-imidazol-1-yl)phenol (1 molar equiv.) in DMSO (0.3 M) were added (S)-1-chloropropan-2-ol (2 molar equiv.) and $K_2CO_3$ (3 molar equiv.). The reaction mixture was heated at 100° C. for 16 hours. The reaction mixture was cooled and poured in to water and extracted with EtOAc. The combined organic layer was washed with water and brine, dried over $Na_2SO_4$ and concentrated under reduced pressure. The crude product was purified by column chromatography to afford (S)-1-(3-(2-cyclopropyl-1H-imidazol-1-yl)phenoxy)propan-2-ol.

$^1$H NMR (400 MHz, CDCl$_3$) δ (ppm): 7.41-7.36 (m, 1H), 7.02 (t, J=8.0 Hz, 4H), 4.25-4.20 (m, 1H), 3.97 (dd, J=4.0, 12.0 Hz, 1H), 3.85 (t, J=8.0 Hz, 1H), 2.34 (s, 1H), 1.82-1.75 (m, 1H), 1.30 (d, J=4.0 Hz, 3H), 1.12-1.09 (m, 2H), 0.92-0.87 (m, 2H); MS (ESI) m/z 259.21 [$C_{15}H_{18}N_2O_2$+H]$^+$.

Preparation of (R)-1-(3-(2-cyclopropyl-1H-imidazol-1-yl)phenoxy)propan-2-ol

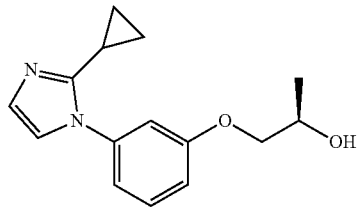 [SMILES: C[C@@H](O)COc1cccc(-n2ccnc2C2CC2)c1]

To a well stirred solution of 3-(2-cyclopropyl-1H-imidazol-1-yl)phenol (1 molar equiv.) in DMSO (0.3 M) were added (R)-1-chloropropan-2-ol (2 molar equiv.) and $K_2CO_3$ (3 molar equiv.). The reaction mixture was heated at 100° C. for 16 hours. The reaction mixture was cooled and poured in to water and extracted with EtOAc. The combined organic layer was washed with water and brine, dried over $Na_2SO_4$ and concentrated under reduced pressure. The crude product was purified by column chromatography to afford (R)-1-(3-(2-cyclopropyl-1H-imidazol-1-yl)phenoxy)propan-2-ol.

$^1$H NMR (400 MHz, CDCl$_3$) δ (ppm): 7.41-7.36 (m, 1H), 7.02 (t, J=8.0 Hz, 4H), 4.25-4.20 (m, 1H), 3.97 (dd, J=4.0, 12.0 Hz, 1H), 3.85 (t, J=8.0 Hz, 1H), 2.34 (s, 1H), 1.82-1.75 (m, 1H), 1.30 (d, J=4.0 Hz, 3H), 1.12-1.09 (m, 2H), 0.92-0.87 (m, 2H); MS (ESI) m/z 259.21 [$C_{15}H_{18}N_2O_2$+H]$^+$.

Preparation of 3-(3-(2-methyl-1H-imidazol-1-yl)phenoxy)butan-2-one

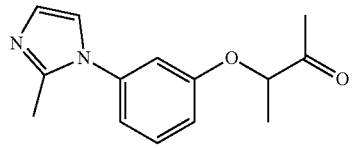 [SMILES: CC(=O)C(C)Oc1cccc(-n2ccnc2C)c1]

To a well stirred solution of 3-(2-methyl-1H-imidazol-1-yl) phenol (1 molar equiv.) in DMSO (0.14 M) were added 3-bromobutan-2-one (1.5 molar equiv.) and $K_2CO_3$ (3 molar equiv.). The reaction mixture was heated at 100° C. for 16 hours. The reaction mixture was cooled and poured in to water and extracted with EtOAc. The combined organic layer was washed with water and brine, dried over $Na_2SO_4$ and concentrated under reduced pressure. The crude product was purified by column chromatography to afford 3-(3-(2-methyl-1H-imidazol-1-yl)phenoxy)butan-2-one.

MS (ESI) m/z 245.2 [$C_{14}H_{16}N_2O_2$+H]$^+$.

Preparation of 3-(3-(2-methyl-1H-imidazol-1-yl)phenoxy)butan-2-ol

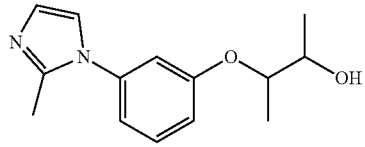 [SMILES: Cc1nccn1-c1cccc(OC(C)C(C)O)c1]

To a well stirred solution of 3-(3-(2-methyl-1H-imidazol-1-yl)phenoxy)butan-2-one (1 molar equiv.) in methanol (0.12 M) was added NaBH$^4$ (1.5 molar equiv.) at 0-5° C. and stirred the reaction mixture at room temperature for 4 hours. The reaction mixture was concentrated and diluted with water and extracted into EtOAc. The combined organic layer was washed with water and brine, dried over $Na_2SO_4$ and concentrated under reduced pressure to give crude product. This crude product was purified by column chromatography to afford 3-(3-(2-methyl-1H-imidazol-1-yl)phenoxy)butan-2-ol.

MS (ESI) m/z 247.2 [$C_{14}H_{18}N_2O_2$+H]$^+$.

Example 7: Preparation of Final Compounds

General Procedure A

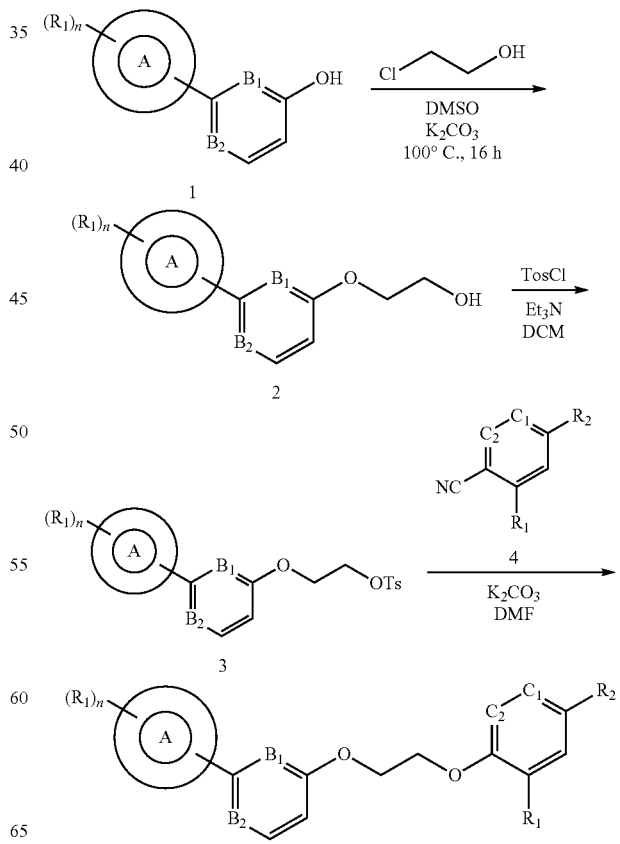

To a well stirred solution of the respective phenol, 1 (1 molar equiv.) in DMSO (0.25 M) were added 2-chloroethanol (2 molar equiv.) and $K_2CO_3$ (3 molar equiv.). The reaction mixture was heated at 100° C. for 16 hours. Upon completion of reaction, the reaction mixture was cooled and poured into water and extracted with ethyl acetate. The combined organics was washed with water and brine, dried over sodium sulphate and concentrated under reduced pressure. The crude product was purified by column chromatography to afford the desired product, 2.

To a solution of the respective compound 2 (1 molar equiv.) in dichloromethane (0.4 M) was added trimethylamine (3 molar equiv.) and tosyl chloride (1.5 molar equiv.) at 0° C. The reaction mixture was stirred at room temperature for 16 hours. Upon completion of the reaction, the crude product was extracted with dichloromethane and washed with water. The combined organics was dried over sodium sulphate and concentrated under reduced pressure to obtain the crude compound which was purified by column chromatography to afford the respective tosylate, 3.

To a well stirred solution of the respective phenol, 4 (1 molar equiv.) in DMF (0.15 M) was added the respective tosylate, 3 (1.1 molar equiv.) and $K_2CO_3$ (3 molar equiv.). The reaction mixture was heated at 60° C. for 16 hours. Upon completion of reaction, the reaction mixture was cooled to room temperature and concentrated under reduced pressure. The crude product was diluted with ethyl acetate and washed with water. The combined organics was dried over sodium sulphate and washed concentrated under reduced pressure to obtain the crude product which was then purified further by column chromatography.

Preparation of 4-(2-(3-(1H-1,2,4-triazol-1-yl)phenoxy)ethoxy)benzonitrile, Compound 1

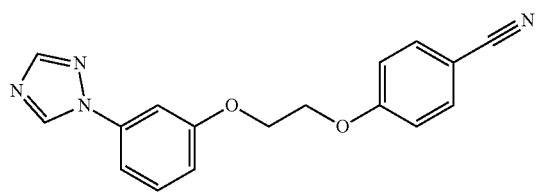 [SMILES: N#Cc1ccc(OCCOc2cccc(-n3cncn3)c2)cc1]

¹H NMR (400 MHz, CDCl$_3$) δ (ppm): 8.55 (s, 1H), 8.11 (s, 1H), 7.63-7.60 (m, 2H), 7.43 (t, J=8.0 Hz, 1H), 7.34 (t, J=2.4 Hz, 1H), 7.29-7.28 (m, 1H), 7.03-6.99 (m, 2H), 6.97 (dd, J=0.8 and 5.6 Hz, 1H), 4.42-4.41 (m, 4H). MS (m/z): 307.1 $[C_{17}H_{14}N_4O_2+H]^+$.

Preparation of 4-(2-(3-(2-methyl-1H-imidazol-1-yl)phenoxy)ethoxy)benzonitrile, Compound 2

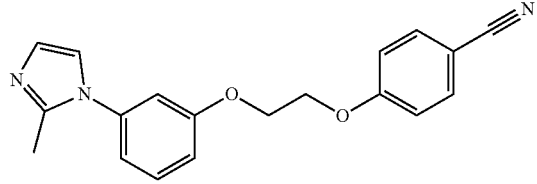 [SMILES: Cc1nccn1-c1cccc(OCCOc2ccc(C#N)cc2)c1]

¹H NMR (400 MHz, CDCl$_3$) δ (ppm): 7.62 (d, J=8.8 Hz, 2H), 7.40 (t, J=8.0 Hz, 1H), 7.02-6.98 (m, 3H), 7.01 (d, J=8.8 Hz, 2H), 6.94-6.91 (m, 1H), 6.87 (t, J=2.0 Hz, 1H), 4.41-4.37 (m, 4H), 2.37 (s, 3H). MS (m/z): 320.2 $[C_{19}H_{17}N_3O_2+H]^+$.

Preparation of 4-(2-(3-(thiazol-5-yl)phenoxy)ethoxy)benzonitrile, Compound 3

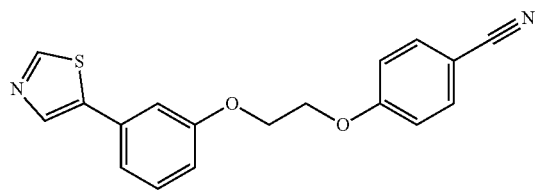 [SMILES: N#Cc1ccc(OCCOc2cccc(-c3cncs3)c2)cc1]

1H NMR (400 MHz, CDCl$_3$) δ (ppm): 8.76 (s, 1H), 8.07 (s, 1H), 7.62 (d, J=8.8 Hz, 2H), 7.35 (t, J=8.0 Hz, 1H), 7.22 (d, J=7.6 Hz, 1H), 7.16 (s, 1H), 7.04 (d, J=8.8 Hz, 2H), 6.92 (dd, J=2.4 and 8.2 Hz, 1H), 4.40 (s, 4H). MS (m/z): 322.9 $[C_{18}H_{14}N_2O_2S+H]^+$.

Preparation of 5-(2-(3-(2-methyl-1H-imidazol-1-yl)phenoxy)ethoxy)picolinonitrile, Compound 4

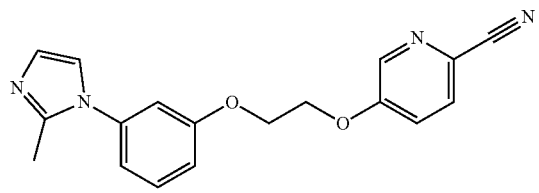 [SMILES: Cc1nccn1-c1cccc(OCCOc2ccc(C#N)nc2)c1]

1H NMR (400 MHz, DMSO-d$_6$) δ (ppm): 8.50 (d, J=2.0 Hz, 1H), 8.03 (d, J=8.8 Hz, 1H), 7.66 (dd, J=5.2, 2.4 Hz, 3H), 7.45 (t, J=8.4 Hz, 1H), 7.28 (s, 1H), 7.04 (dd, J=16.4, 7.2 Hz, 3H), 6.90 (s, 1H), 4.54-4.43 (m, 4H), 2.29 (s, 3H); MS (ESI) m/z 321.23 $[C_{18}H_{16}N_4O_2+H]^+$.

Preparation of 3-chloro-4-(2-(3-(2-methyl-1H-imidazol-1-yl)phenoxy)ethoxy)benzonitrile, Compound 5

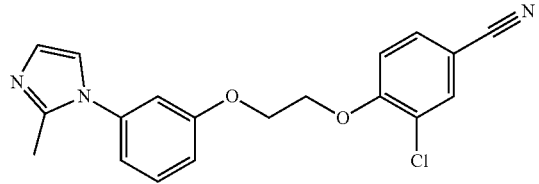 [SMILES: Cc1nccn1-c1cccc(OCCOc2ccc(C#N)cc2Cl)c1]

1H NMR (400 MHz, CDCl$_3$) δ (ppm): 7.67 (d, J=1.9 Hz, 1H), 7.57 (dd, J=2.0 and 8.5 Hz, 1H), 7.40 (t, J=8.1 Hz, 1H), 7.06 (d, J=8.5 Hz, 1H), 7.04-7.00 (m, 3H), 6.96-6.90 (m, 1H), 6.89 (t, J=2.1 Hz, 1H), 4.48-4.43 (m, 4H), 2.37 (s, 3H). MS (m/z): 354.3 $[C_{19}H_{16}ClN_3O_2+H]^+$.

Preparation of 3-fluoro-4-(2-(3-(2-methyl-1H-imidazol-1-yl)phenoxy)ethoxy)benzonitrile, Compound 6

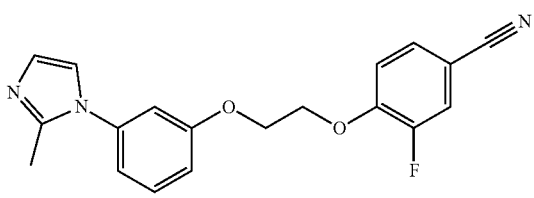 [SMILES: Cc1nccn1-c1cccc(OCCOc2ccc(C#N)cc2F)c1]

1H NMR (400 MHz, DMSO-d$_6$) δ (ppm): 7.85 (d, J=11.2 Hz, 1H), 7.70 (d, J=8.4 Hz, 1H), 7.45 (t, J=8.8 Hz, 2H), 7.29 (s, 1H), 7.05 (dd, J=17.6, 6.8 Hz, 3H), 6.90 (s, 1H), 4.53 (d, J=4.0 Hz, 2H), 4.44 (d, J=3.2 Hz, 2H), 2.30 (s, 3H). MS (ESI) m/z 338.20 [C$_{19}$H$_{16}$FN$_3$O$_2$+H]$^+$.

Preparation of 3-chloro-4-(2-(3-(2-cyclopropyl-1H-imidazol-1-yl)phenoxy)ethoxy)benzonitrile, Compound 9

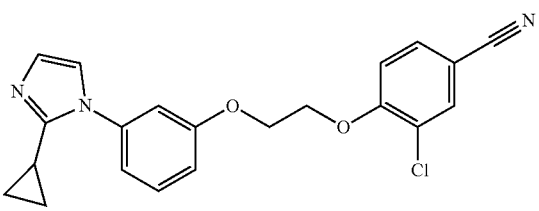 [SMILES: N#Cc1ccc(OCCOc2cccc(-n3ccnc3C3CC3)c2)c(Cl)c1]

1H NMR (400 MHz, CDCl$_3$) δ (ppm): 7.68 (d, J=1.9 Hz, 1H), 7.56 (dd, J=1.9 and 8.5 Hz, 1H), 7.41 (t, J=7.8 Hz, 1H), 7.07-6.98 (m, 6H), 4.48-4.44 (m, 4H), 1.82-1.75 (m, 1H), 1.13-1.09 (m, 2H), 0.92-0.86 (m, 2H); MS (m/z): 380.3 [C$_{21}$H$_{18}$ClN$_3$O$_2$+H]$^+$.

Preparation of 3-chloro-4-(2-(3-(thiazol-5-yl)phenoxy)ethoxy)benzonitrile, Compound 11

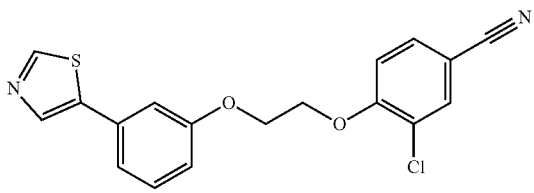 [SMILES: N#Cc1ccc(OCCOc2cccc(-c3cncs3)c2)c(Cl)c1]

1H NMR (400 MHz, CDCl$_3$) δ (ppm): 8.76 (s, 1H), 8.07 (s, 1H), 7.68 (d, J=2.0 Hz, 1H), 7.57 (dd, J=2.0 and 8.5 Hz, 1H), 7.36 (t, J=7.9 Hz, 1H), 7.21 (dd, J=0.8 and 7.7 Hz, 1H), 7.15 (t, J=2.2 Hz, 1H), 7.07 (d, J=8.5 Hz, 1H), 6.96-6.93 (m, 1H), 4.47 (s, 4H); MS (m/z): 357.3 [C$_{18}$H$_{13}$ClN$_2$O$_2$S+H]$^+$.

Preparation of 3-fluoro-4-(2-(3-(thiazol-5-yl)phenoxy)ethoxy)benzonitrile, Compound 12

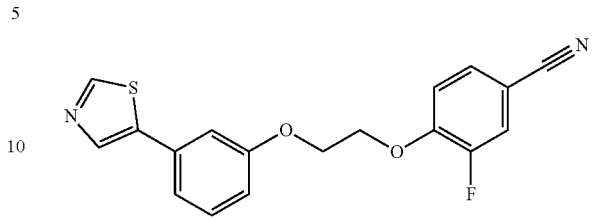

1H NMR (400 MHz, CDCl$_3$) δ (ppm): 8.76 (s, 1H), 8.07 (s, 1H), 7.47-7.43 (m, 1H), 7.40 (dd, J=1.9 and 10.4 Hz, 1H), 7.35 (t, J=7.9 Hz, 1H), 7.23-7.20 (m, 1H), 7.15 (t, J=2.24 Hz, 1H), 7.11 (t, J=8.3 Hz, 1H), 6.95-6.91 (m, 1H), 4.50-4.47 (m, 2H), 4.44-4.42 (m, 2H); MS (m/z): 339.4 [C$_{18}$H$_{13}$FN$_2$O$_2$S+H]$^+$.

Preparation of 5-(3-(2-(4-fluoro-2-methylphenoxy)ethoxy)phenyl)-1-methyl-1H-pyrazole, Compound 27

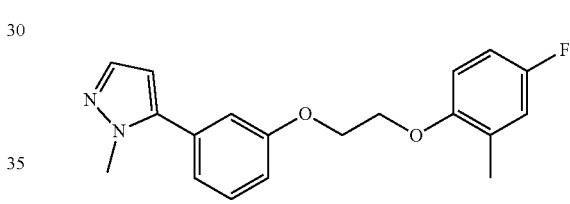

1H NMR (400 MHz, DMSO-d$_6$)) δ (ppm): 7.45 (d, J=2 Hz, 1H), 7.41 (t, J=8.2 Hz, 1H), 7.11-7.09 (m, 2H), 7.08-7.05 (m, 1H), 7.03-6.93 (m, 3H), 6.40 (d, J=2 Hz, 1H), 4.40-4.38 (m, 2H), 4.32-4.30 (m, 2H), 3.85 (s, 3H), 2.12 (s, 3H); MS (ESI) m/z 327.1 [C$_{19}$H$_{19}$FN$_2$O$_2$$^+$H]$^+$.

Preparation of 1-(3-(2-(4-chloro-2-fluorophenoxy)ethoxy)phenyl)-2-cyclopropyl-1H-imidazole, Compound 50

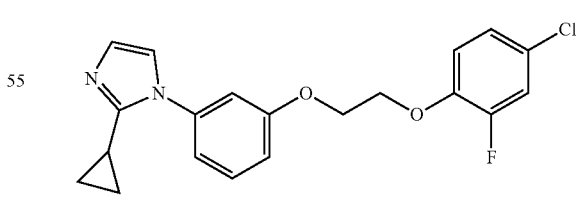

1H NMR (400 MHz, DMSO-d$_6$) δ 7.48-7.42 (m, 2H), 7.31-7.22 (m, 3H), 7.10-7.07 (m, 3H), 6.85 (d, J=1.2 Hz, 1H), 4.42 (s, 4H), 1.85-1.79 (m, 1H), 0.90-0.85 (m, 4H); MS (ESI) m/z 373.1 [C$_{20}$H$_{18}$ClFN$_2$O$_2$+H]$^+$.

Preparation of 4-(2-(3-(1-methyl-1H-pyrazol-5-yl)phenoxy)ethoxy)benzonitrile, Compound

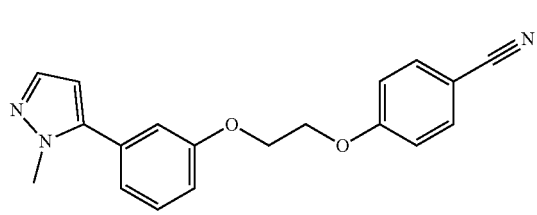 [SMILES: Cn1nccc1-c1cccc(OCCOc2ccc(C#N)cc2)c1]

1H NMR (400 MHz, DMSO-d$_6$) δ 7.80-7.77 (m, 2H), 7.45 (d, J=2.0 Hz, 1H), 7.42 (t, J=8.0 Hz, 1H), 7.19-7.16 (m, 2H), 7.12-7.10 (m, 2H), 7.07-7.04 (m, 1H), 6.41 (d, J=1.6 Hz, 1H), 4.45-4.41 (m, 4H), 3.85 (s, 3H); MS (ESI) m/z 320.1 [C$_{19}$H$_{17}$N$_3$O$_2$+H]$^+$.

Preparation of 1-(3-(2-(2-fluoro-4-methylphenoxy)ethoxy)phenyl)-2-methyl-1H-imidazole, Compound 58

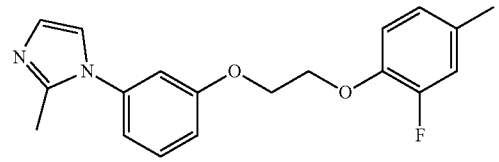 [SMILES: Cc1ccc(OCCOc2cccc(-n3ccnc3C)c2)c(F)c1]

1H NMR (400 MHz, CDCl$_3$) δ (ppm): 7.38 (t, J=8.0 Hz, 1H), 7.0 (d, J=8.4 Hz, 3H), 6.94-6.84 (m, 5H), 4.37 (d, J=5.2 Hz, 4H), 2.37 (s, 3H), 2.28 (s, 3H); MS (ESI) m/z 327.14 [C$_{19}$H$_{19}$FN$_2$O$_2$+H]$^+$.

Preparation of 4-(2-(3-(2-cyclopropyl-1H-imidazol-1-yl)phenoxy)ethoxy)benzonitrile, Compound 62

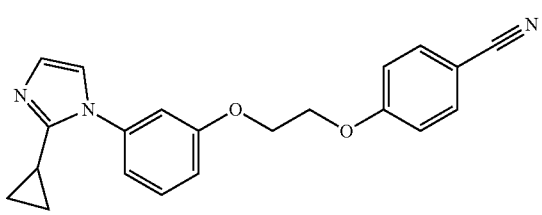 [SMILES: N#Cc1ccc(OCCOc2cccc(-n3ccnc3C3CC3)c2)cc1]

1H NMR (400 MHz, DMSO-d$_6$) δ 7.80-7.78 (m, 2H), 7.47 (t, J=7.6 Hz, 1H), 7.26 (d, J=0.8 Hz, 1H), 7.18-7.16 (m, 2H), 7.10-7.07 (m, 3H), 6.85 (s, 1H), 4.44-4.43 (m, 4H), 1.84-1.80 (m, 1H), 0.90-0.85 (m, 4H); MS (ESI) m/z 346.1 [C$_{21}$H$_{19}$N$_3$O$_2$+H]$^+$.

Preparation of 4-(2-(3-(isoxazol-4-yl)phenoxy)ethoxy)benzonitrile, Compound 67

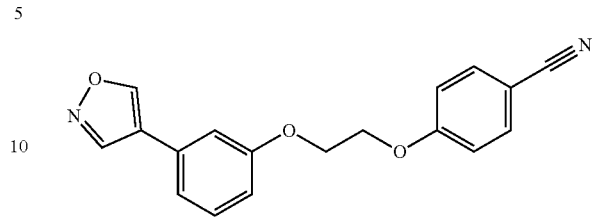

1H NMR (400 MHz, CDCl$_3$) δ (ppm): 8.66 (s, 1H), 8.53 (s, 1H), 7.61 (d, J=8.8 Hz, 2H), 7.35 (t, J=8.4 Hz, 1H), 7.10 (d, J=7.6 Hz, 1H), 7.05 (dd, J=19.2, 2.0 Hz, 3H), 6.90 (dd, J=8.4, 1.6 Hz, 1H), 4.39 (m, 4H); MS (ESI) m/z 307.22 [C$_{18}$H$_{14}$N$_2$O$_3$+H]$^+$.

Preparation of 4-(2-((2-(2-methyl-1H-imidazol-1-yl)pyridin-4-yl)oxy)ethoxy)benzonitrile, Compound 85

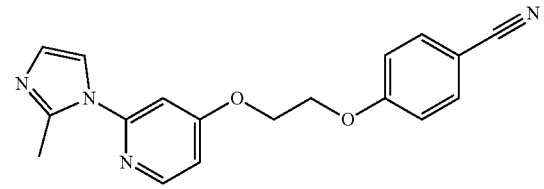 [SMILES: Cc1nccn1-c1cc(OCCOc2ccc(C#N)cc2)ccn1]

1H NMR (400 MHz, CDCl$_3$) δ 8.41-8.40 (m, 1H), 7.64-7.61 (m, 2H), 7.25 (s, 1H), 7.03-6.99 (m, 3H), 6.89-6.86 (m, 2H), 4.46-4.43 (m, 4H), 2.60 (s, 3H); MS (ESI) m/z 321.1 [C$_{18}$H$_{16}$N$_4$O$_2$+H]$^+$.

Preparation of 3-fluoro-4-(2-((6-(2-methyl-1H-imidazol-1-yl)pyridin-2-yl)oxy)ethoxy)benzonitrile, Compound 86

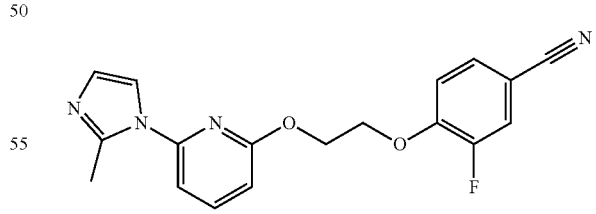

1H NMR (400 MHz, DMSO-d$_6$) δ 7.95-7.87 (m, 1H), 7.83 (dd, J=11.2, 1.6 Hz, 1H), 7.72-7.65 (m, 1H), 7.57 (s, 1H), 7.48-7.40 (m, 1H), 7.19 (d, J=7.6 Hz, 1H), 6.93-6.85 (m, 2H), 4.75-4.65 (m, 2H), 4.60-4.50 (m, 2H), 2.54 (s, 3H); MS (ESI) m/z 339.1 [C$_{18}$H$_{15}$N$_4$O$_2$+H]$^+$.

Preparation of 5-fluoro-6-(2-(4-fluoro-3-(2-methyl-1H-imidazol-1-yl)phenoxy)ethoxy)nicotinonitrile, Compound 87

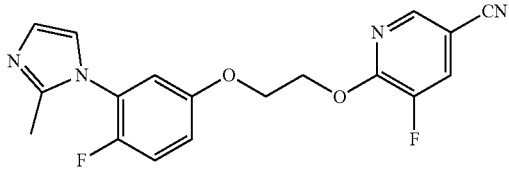 [SMILES: Cc1nccn1-c1cc(OCCOc2ncc(C#N)cc2F)ccc1F]

1H NMR (CDCl$_3$, 400 MHz) δ 8.22-8.21 (d, J=2.8 Hz, 1H), 7.68-7.65 (dd, J=6.8, 2.8 Hz, 1H), 7.24 (t, J=6.0 Hz, 1H), 7.19-7.17 (m, 1H), 7.04-6.99 (m, 2H), 6.88-6.86 (m, 1H), 4.76 (t, J=4.8 Hz, 1H), 4.35 (t, J=4.6 Hz, 1H), 2.35 (s, 3H); MS (ESI) m/z 357.2 [C$_{18}$H$_{14}$F$_2$N$_4$O$_2$+H]$^+$.

Preparation of 4-(2-(3-(1-cyclopropyl-1H-pyrazol-5-yl)-4-fluorophenoxy)ethoxy)-3-fluorobenzonitrile, Compound 88

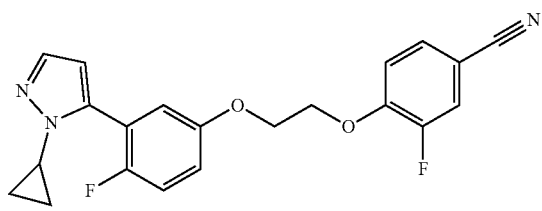 [SMILES: N#Cc1ccc(OCCOc2ccc(F)c(-c3ccnn3C3CC3)c2)c(F)c1]

1H NMR (400 MHz, DMSO-d$_6$) δ 7.88-7.84 (dd, J=11.2, 1.6 Hz, 1H), 7.71-7.69 (m, 1H), 7.48-7.41 (m, 2H), 7.33-7.28 (m, 1H), 7.14-7.09 (m, 2H), 6.4 (s, 1H), 4.52-4.51 (m, 2H), 4.42 (m, 2H), 3.60-3.55 (m, 1H), 0.92-0.91 (m, 2H), 0.9-0.87 (m, 2H); MS (ESI) m/z 353.1 [C$_{19}$H$_{17}$FN$_4$O$_2$+H]$^+$.

Preparation of 4-(2-((2-(2-cyclopropyl-1H-imidazol-1-yl)pyridin-4-yl)oxy)ethoxy)benzonitrile, Compound 89

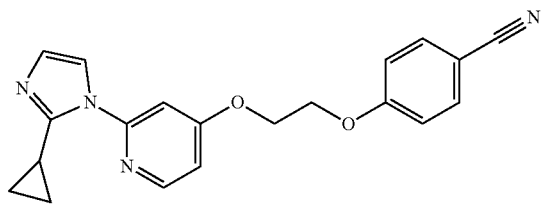 [SMILES: N#Cc1ccc(OCCOc2ccnc(-n3ccnc3C3CC3)c2)cc1]

1H NMR (400 MHz, DMSO-d$_6$) δ 8.39 (d, J=5.6 Hz, 1H), 7.81-7.78 (m, 2H), 7.49 (s, 1H), 7.25 (d, J=2.0 Hz, 1H), 7.19-7.16 (m, 2H), 7.11-7.09 (m, 1H), 6.85 (s. 1H), 4.56-4.55 (m, 2H), 4.49-4.48 (m, 2H), 2.40-2.34 (m, 1H), 0.90-0.88 (m, 4H); MS (ESI) m/z 347.1 [C$_{20}$H$_{18}$N$_4$O$_2$+H]$^+$.

Preparation of 3-fluoro-4-(2-((5-(1-methyl-1H-pyrazol-5-yl)pyridin-3-yl)oxy)ethoxy)benzonitrile, Compound 92

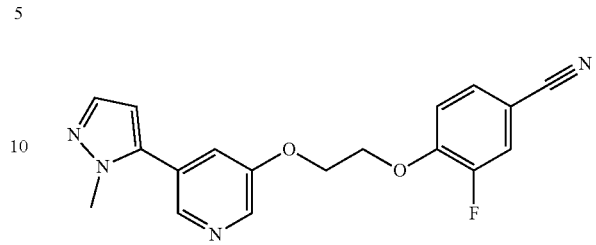

1H NMR (400 MHz, DMSO-d$_6$) δ 8.39-8.36 (m, 1H), 7.88-7.85 (m, 1H), 7.73-7.70 (m, 1H), 7.63-7.62 (m, 1H), 7.51 (d, J=2.0 Hz, 1H), 7.45 (t, J=8.4 Hz, 1H), 6.54 (d, J=1.6 Hz, 1H), 4.56 (s, 4H), 3.89 (s, 3H); MS (ESI) m/z 339.1 [C$_{18}$H$_{15}$FN$_4$O$_2$]$^+$.

Preparation of 4-(2-(3-fluoro-5-(1-methyl-1H-pyrazol-5-yl)phenoxy)ethoxy)benzonitrile, Compound 94

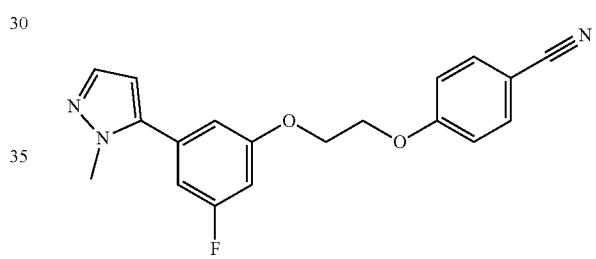

1H NMR (400 MHz, DMSO-d$_6$) δ 7.80-7.78 (m, 2H), 7.47 (m, 1H), 7.18-7.16 (m, 2H), 7.02-6.98 (m, 3H), 6.48 (s. 1H), 4.44 (s, 4H), 3.88 (m, 3H); MS (ESI) m/z 338.1 [C$_{19}$H$_{16}$FN$_3$O$_2$]$^+$.

Preparation of 3-fluoro-4-(2-((2-(3-methyl-4H-1,2,4-triazol-4-yl)pyridin-4-yl)oxy)ethoxy)benzonitrile, Compound 95

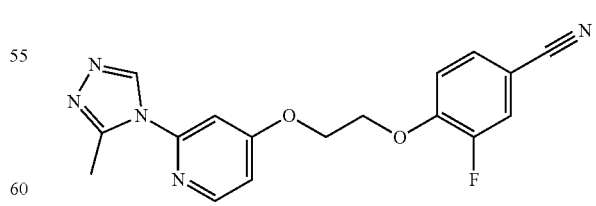

1H NMR (400 MHz, DMSO-d$_6$) δ 8.40 (d, J=6.0 Hz, 1H), 8.06 (s, 1H), 7.88-7.85 (m, 1H), 7.72-7.69 (m, 1H), 7.45 (t, J=8.4 Hz, 1H), 7.39 (d, J=2.4 Hz, 1H), 7.13-7.11 (m, 1H), 4.58 (s, 4H), 2.74 (s, 3H); MS (ESI) m/z 340.1 [C$_{17}$H$_{14}$FN$_5$O$_2$]$^+$.

Preparation of 4-(2-(2-fluoro-5-(1-methyl-1H-pyrazol-5-yl)phenoxy)ethoxy)benzonitrile, Compound 96

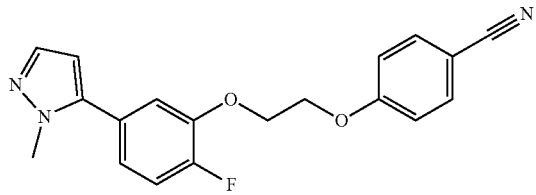 [SMILES: Cn1nccc1-c1ccc(F)c(OCCOc2ccc(C#N)cc2)c1]

1H NMR (400 MHz, DMSO-$d_6$) δ 7.80 (s, 1H), 7.78 (s, 1H), 7.46 (s, 1H), 7.40-7.30 (m, 2H), 7.18 (s, 1H), 7.16 (s, 1H), 7.14-7.08 (m, 1H), 6.42 (s, 1H), 4.55-4.50 (m, 2H), 4.50-4.45 (m, 2H), 3.85 (s, 3H); MS (ESI) m/z 338.1 $[C_{19}H_{16}FN_3O_2+H]^+$.

Preparation of 5-fluoro-6-(2-((2-(1-methyl-1H-pyrazol-5-yl)pyridin-4-yl)oxy)ethoxy)nicotinonitrile, Compound 97

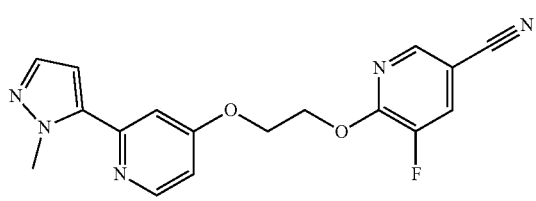 [SMILES: Cn1nccc1-c1cc(OCCOc2ncc(C#N)cc2F)ccn1]

1H NMR (CDCl$_3$, 400 MHz): δ 8.54-8.53 (d, J=4.8 Hz, 1H), 8.49-8.43 (m, 2H), 7.46 (d, J=2.0 Hz, 1H), 7.37 (d, J=2.0 Hz, 1H), 7.04-7.02 (m, 1H), 6.82 (d, J=1.6 Hz, 1H), 4.77-4.75 (m, 2H), 4.56-4.54 (m, 2H), 4.12 (s, 3H); MS (ESI) m/z 340.16 $[C_{17}H_{14}FN_5O_2+H]^+$.

Preparation of 4-(2-(4-chloro-2-fluorophenoxy)ethoxy)-2-(1-methyl-1H-pyrazol-5-yl)pyridine, Compound 101

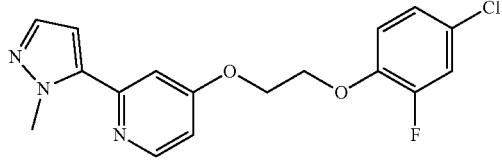

1H NMR (400 MHz, DMSO-$d_6$) δ 8.49 (d, J=6.0 Hz, 1H), 7.47-7.43 (m, 2H), 7.38 (d, J=2.4 Hz, 1H), 7.31-7.22 (m, 2H), 7.04-7.01 (m, 1H), 6.82 (d, J=2.0 Hz, 1H), 4.53-4.51 (m, 2H), 4.46-4.43 (m, 1H), 4.13 (s, 3H); MS (ESI) m/z 348.0 $[C_{17}H_{15}ClFN_3O_2+H]^+$.

Preparation of 1-(3-(2-(4-chloro-2-fluorophenoxy)ethoxy)phenyl)-2-methyl-1H-imidazole, Compound 102

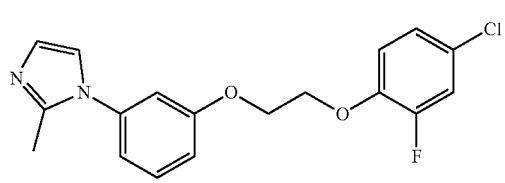 [SMILES: Cc1nccn1-c1cccc(OCCOc2ccc(Cl)cc2F)c1]

1H NMR (400 MHz, DMSO-$d_6$) δ 7.42-7.45 (m, 2H), 7.21-7.30 (m, 3H), 7.00-7.07 (m, 3H), 6.89 (s, 1H), 4.41 (s, 4H), 2.29 (s, 3H); MS (ESI) m/z 347.0 $[C_{18}H_{16}ClFN_2O_2+H]^+$.

Preparation of 4-(2-(4-chloro-2-fluorophenoxy)ethoxy)-2-(2-methyl-1H-imidazol-1-yl)pyridine, Compound 103

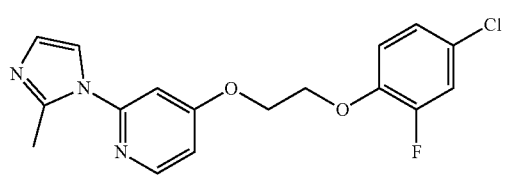

1H NMR (400 MHz, DMSO-$d_6$) δ 8.37 (d, J=5.6 Hz, 1H), 7.56 (d, J=1.2 Hz, 1H), 7.45 (dd, J=11.2, 2.4 Hz, 1H), 7.32-7.18 (m, 3H), 7.10-7.03 (m, 1H), 6.90 (d, J=1.2 Hz, 1H), 4.60-4.50 (m, 2H), 4.50-4.40 (m, 2H), 2.49 (s, 3H); MS (ESI) m/z 348.1 $[C_{17}H_{15}ClFN_3O_2+H]^+$.

Preparation of 4-(2-(4-bromo-2-fluorophenoxy)ethoxy)-2-(2-methyl-1H-imidazol-1-yl)pyridine, Compound 104

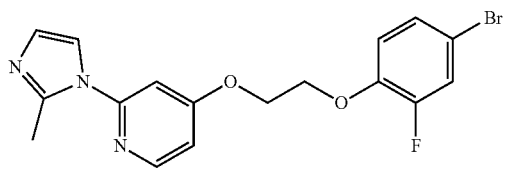 [SMILES: Cc1nccn1-c1cc(OCCOc2ccc(Br)cc2F)ccn1]

1H NMR (400 MHz, DMSO-$d_6$) δ 8.37 (d, J=6.0 Hz, 1H), 7.60-7.50 (m, 2H), 7.40-7.32 (m, 1H), 7.28-7.20 (m, 2H), 7.10-7.03 (m, 1H), 6.90 (d, J=1.6 Hz, 1H), 4.60-4.50 (m, 2H), 4.50-4.40 (m, 2H), 2.49 (s, 3H); MS (ESI) m/z 394.0 $[C_{17}H_{15}BrFN_3O_2+H]^+$.

Preparation of 5-fluoro-6-(2-(4-fluoro-3-(1-methyl-1H-pyrazol-5-yl)phenoxy)ethoxy)nicotinonitrile, Compound 107

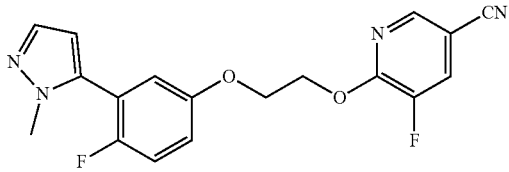 [SMILES: Cn1nccc1-c1cc(OCCOc2ncc(C#N)cc2F)ccc1F]

1H NMR (CDCl$_3$, 400 MHz) δ 8.21 (d, J=3.2 Hz, 1H), 7.67-7.64 (dd, J=3.2, 7.2 Hz, 1H), 7.53 (d, J=1.6 Hz, 1H), 7.11 (t, J=9.2 Hz, 1H), 7.01-6.97 (m, 1H), 6.89-6.87 (dd, J=3.2, 5.6 Hz, 1H), 6.32-6.31 (d, J=2.0 Hz, 1H), 4.75 (t, J=4.8 Hz, 2H), 4.34 (t, J=5.0 Hz, 2H), 3.82-3.81 (d, J=1.2 Hz, 1H); MS (ESI) m/z 357.1 [C$_{18}$H$_{14}$F$_2$N$_4$O$_2$+H]$^+$.

Preparation of 6-(2-(4-fluoro-3-(2-methyl-1H-imidazol-1-yl)phenoxy)ethoxy)nicotinonitrile, Compound 109

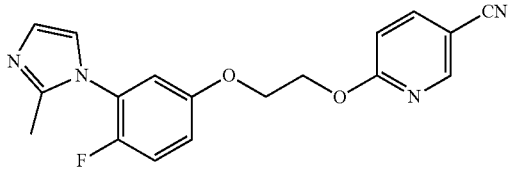 [SMILES: Cc1nccn1-c1cc(OCCOc2ccc(C#N)cn2)ccc1F]

1H NMR (CDCl$_3$, 400 MHz) δ 8.48 (d, J=2.4 Hz, 1H), 7.82-7.80 (dd, J=8.8, 2.4 Hz, 1H), 7.18 (t, J=9.2 Hz, 1H), 7.05 (s, 1H), 7.01-6.96 (m, 1H), 6.95 (s, 1H), 6.89-6.87 (d, J=8.4 Hz, 1H), 6.86-6.85 (m, 1H), 4.74 (t, J=4.6 Hz, 1H), 4.31 (t, J=4.8 Hz, 1H), 2.30 (s, 3H); MS (ESI) m/z 339.1 [C$_{18}$H$_{15}$FN$_4$O$_2$+H]$^+$.

Preparation of 5-(3-(2-(4-chlorophenoxy)ethoxy)phenyl)-1-methyl-1H-pyrazole, Compound 110

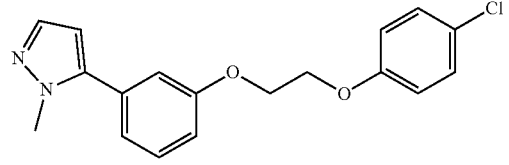 [SMILES: Cn1nccc1-c1cccc(OCCOc2ccc(Cl)cc2)c1]

1H NMR (400 MHz, DMSO-d$_6$) δ 7.51 (d, J=2.0 Hz, 1H), 7.38-7.36 (m, 1H), 7.26-7.24 (m, 2H), 7.04-7.02 (m, 1H), 7.01-6.98 (m, 2H), 6.90-6.88 (m, 2H), 6.3 (d, J=1.6 Hz, 1H), 4.35-4.32 (m, 4H), 3.89 (s, 3H); MS (ESI) m/z 329.1 [C$_{18}$H$_{17}$ClN$_2$O$_2$+H]$^+$.

Preparation of 1-(3-(2-(4-chlorophenoxy)ethoxy)phenyl)-2-methyl-1H-imidazole, Compound 112

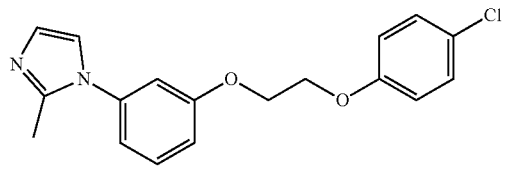 [SMILES: Cc1nccn1-c1cccc(OCCOc2ccc(Cl)cc2)c1]

1H NMR (CDCl$_3$, 400 MHz) δ 7.41 (t, J=8.1 Hz, 1H), 7.28-7.26 (m, 2H), 7.04-7.03 (m, 3H), 6.94-6.89 (m, 4H), 4.37-4.33 (m, 4H), 2.39 (s, 3H). MS (ESI) m/z 329.2 [C$_{18}$H$_{17}$ClN$_2$O$_2$+H]$^+$.

Preparation of 3-fluoro-4-(2-(4-fluoro-3-(1-methyl-1H-pyrazol-5-yl)phenoxy)ethoxy)benzonitrile, Compound 113

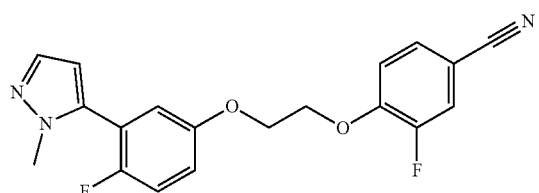

1H NMR (CDCl$_3$, 400 MHz) δ 7.56 (d, 1H, J=2.0 Hz), 7.44 (dt, 1H, J=8.8 & 0.8 Hz), 7.39 (dd, 1H, J=10.4 & 2.0 Hz), 7.15-7.07 (m, 2H), 6.984 (dt, 1H, J=8.8 & 3.6 Hz), 6.89 (dd, 1H, J=6.0 & 3.0 Hz), 4.47-4.45 (m, 2H), 4.38-4.36 (m, 2H), 3.83 (d, 3H, J=1.2 Hz); MS (ESI) m/z 356.1 [C$_{19}$H$_{15}$F$_2$N$_3$O$_2$+H]$^+$.

Preparation of 4-(2-(4-chlorophenoxy)ethoxy)-2-(2-methyl-1H-imidazol-1-yl)pyridine, Compound 115

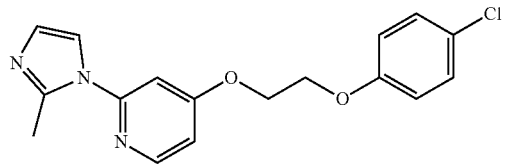 [SMILES: Cc1nccn1-c1cc(OCCOc2ccc(Cl)cc2)ccn1]

1H NMR (400 MHz, DMSO-d$_6$) δ 8.38-8.36 (d, J=6.0 Hz, 1H), 7.57 (d, J=1.2 Hz, 1H), 7.35-7.32 (m, 2H), 7.21-7.20 (d, J=1.2 Hz, 1H), 7.09-7.07 (dd, J=6.0, 1.2 Hz, 1H), 7.03-7.00 (m, 2H), 6.92 (d, J=1.2 Hz, 1H), 4.53-4.51 (m, 2H), 4.37-4.34 (m, 2H); MS (ESI) m/z 330.1 [C$_{17}$H$_{16}$ClN$_3$O$_2$+H]$^+$.

Preparation of 5-fluoro-2-(2-((2-(2-methyl-1H-imidazol-1-yl)pyridin-4-yl)oxy)ethoxy)benzonitrile, Compound 119

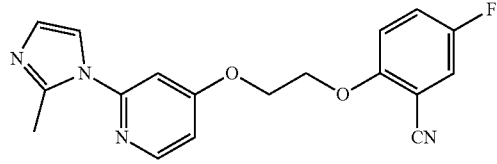 [SMILES: Cc1nccn1-c1cc(OCCOc2ccc(F)cc2C#N)ccn1]

1H NMR (400 MHz, DMSO-$d_6$) δ 8.38-8.37 (d, J=5.6 Hz, 1H), 7.77-7.74 (dd, J=8.4, 2.8 Hz, 1H), 7.62-7.57 (m, 2H), 7.39-7.35 (dd, J=9.2, 4.0 Hz, 1H), 7.23-7.22 (d, J=2.4 Hz, 1H), 7.10-7.08 (dd, J=6.0, 2.4 Hz, 1H), 6.96-6.95 (d, J=1.6 Hz, 1H), 4.58-4.56 (m, 2H), 4.54-4.53 (m, 2H); MS (ESI) m/z 339.2 $[C_{18}H_{15}FN_4O_2+H]^+$.

Preparation of 4-(2-((2-(1H-tetrazol-1-yl)pyridin-4-yl)oxy)ethoxy)-3-fluorobenzonitrile, Compound 120

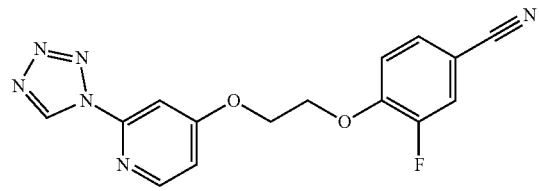 [SMILES: N#Cc1ccc(OCCOc2ccnc(-n3cnnn3)c2)c(F)c1]

1H NMR (400 MHz, DMSO-$d_6$) δ 10.15 (s, 1H), 8.47 (t, J=6.0 Hz, 1H), 7.88-7.85 (m, 1H), 7.73-7.70 (m, 1H), 7.65 (d, J=2.4 Hz, 1H), 7.45 (t, J=8.8 Hz, 1H), 7.28-7.26 (m, 1H), 4.67-4.65 (m, 2H), 4.60-4.58 (m, 2H); MS (ESI) m/z 327.1 $[C_{15}H_{11}FN_6O_2+H]^+$.

Preparation of 4-(2-(4-bromo-2-fluorophenoxy)ethoxy)-2-(1-methyl-1H-pyrazol-5-yl)pyridine, Compound 121

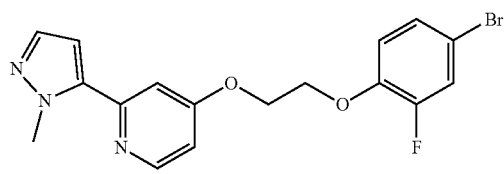 [SMILES: Cn1nccc1-c1cc(OCCOc2ccc(Br)cc2F)ccn1]

1H NMR (CDCl$_3$, 400 MHz) δ 8.51 (d, J=6 Hz, 1H), 7.50 (d, J=2 Hz, 1H), 7.28-7.25 (m, 2H), 7.23-7.20 (m, 1H), 7.12 (d, J=2.4 Hz, 1H), 6.91 (t, J=8.4 Hz, 1H), 6.83 (dd, J=6 Hz, 2.4 Hz, 1H), 6.55 (d, J=2 Hz, 1H), 4.45-4.40 (m, 4H), 4.20 (s, 3H); MS (ESI) m/z 392.1 $[C_{17}H_{15}BrFN_3O_2+H]^+$.

General Procedure B

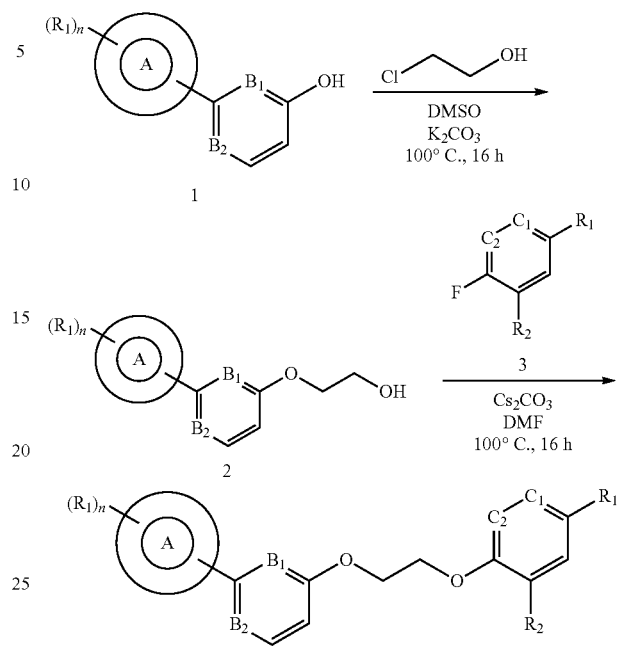

To a well stirred solution of the respective phenol, 1 (1 molar equiv.) in DMSO (0.25M) were added 2-chloroethanol (2 molar equiv.) and K$_2$CO$_3$ (3 molar equiv.). The reaction mixture was heated at 100° C. for 16 hours. Upon completion of reaction, the reaction mixture was cooled and poured into water and extracted with ethyl acetate. The combined organics was washed with water and brine, dried over sodium sulphate and concentrated under reduced pressure. The crude product was purified by column chromatography to afford the desired product, 2.

To a well stirred solution of 2 (1 molar equiv.) in DMF (0.1 M) were added the respective fluoro compound, 3 (1.3 molar equiv.) and Cs$_2$CO$_3$ (3.2 molar equiv.). The reaction mixture was heated at 100° C. for 16 hours. The reaction mixture was cooled and poured into water and extracted with ethyl acetate. The combined organics was washed with water and brine, dried over sodium sulphate and concentrated under reduced pressure to give the crude product. This crude product was purified by column chromatography to afford the desired product.

Preparation of 3-chloro-4-(2-(3-(1-methyl-1H-pyrazol-5-yl)phenoxy)ethoxy)benzonitrile, Compound 7

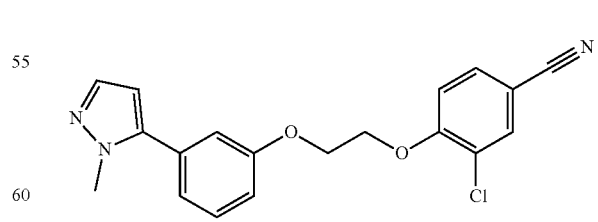

1H NMR (400 MHz, DMSO-$d_6$) δ (ppm): 8.02 (d, J=2.0 Hz, 1H), 7.84 (dd, J=8.4, 2.0 Hz, 1H), 7.45-7.39 (m, 3H)), 7.12-7.05 (m, 3H), 6.40 (d, J=1.2 Hz, 1H), 4.55 (dd, J=4.8, 3.6 Hz, 2H), 4.45 (dd, J=6.4, 2.0 Hz, 2H), 3.85 (s, 3H); MS (ESI) m/z 354.21 $[C_{19}H_{16}ClN_3O_2+H]^+$.

Preparation of 3-methoxy-4-(2-(3-(2-methyl-1H-imidazol-1-yl)phenoxy)ethoxy)benzonitrile, Compound 8

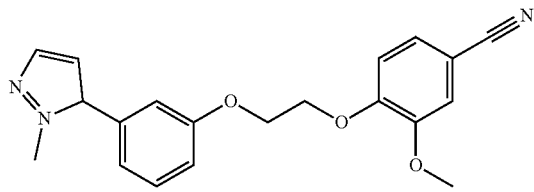

1H NMR (400 MHz, DMSO-d$_6$) δ (ppm): 7.46-7.41 (m, 3H), 7.29 (d, J=0.8 Hz, 1H), 7.20 (d, J=8.4 Hz, 1H), 7.07-7.01 (m, 3H), 6.89 (d, J=0.8 Hz, 1H), 4.54-4.31 (m, 4H), 3.78 (s, 3H), 2.30 (s, 3H); MS (ESI) m/z 350.28 [C$_{20}$H$_{19}$N$_3$O$_3$+H]$^+$.

Preparation of 6-(2-(3-(2-methyl-1H-imidazol-1-yl)phenoxy)ethoxy)nicotinonitrile, Compound 10

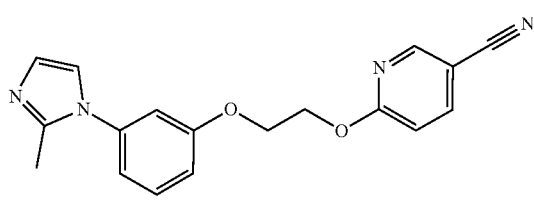 [SMILES: Cc1nccn1-c1cccc(OCCOc2ccc(C#N)cn2)c1]

1H NMR (400 MHz, DMSO-d$_6$) δ (ppm): 8.70 (d, J=1.6 Hz, 1H), 8.17 (d, J=8.8, 2.0 Hz, 1H), 7.44 (t, J=16 Hz, 1H), 7.28 (s, 1H), 7.07-7.01 (m, 4H), 6.90 (s, 1H), 4.68 (d, J=4.4 Hz, 2H), 4.41 (d, J=4.4 Hz, 2H), 2.29 (s, 3H); MS (ESI) m/z 321.23 [C$_{18}$H$_{16}$N$_4$O$_2$+H]$^+$.

Preparation of 5-methyl-2-(2-(3-(2-methyl-1H-imidazol-1-yl)phenoxy)ethoxy)benzonitrile, Compound 13

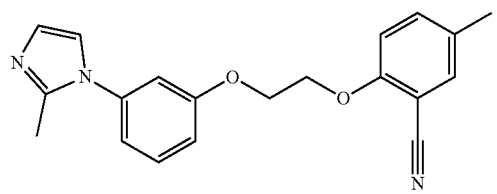 [SMILES: Cc1ccc(OCCOc2cccc(-n3ccnc3C)c2)c(C#N)c1]

1H NMR (400 MHz, DMSO-d$_6$) δ (ppm): 7.53-7.42 (m, 3H), 7.31 (s, 1H), 7.23 (d, J=8.8, Hz, 1H), 7.10-7.02 (m, 3H), 6.93 (s, 1H), 4.46 (d, J=4.8 Hz, 2H), 4.43 (d, J=5.6 Hz, 2H), 2.32 (s, 6H); MS (ESI) m/z 334.26 [C$_{20}$H$_{19}$N$_3$O$_2$+H]$^+$.

Preparation of 3-fluoro-4-(2-(3-(1-methyl-1H-pyrazol-5-yl)phenoxy)ethoxy)benzonitrile, Compound 14

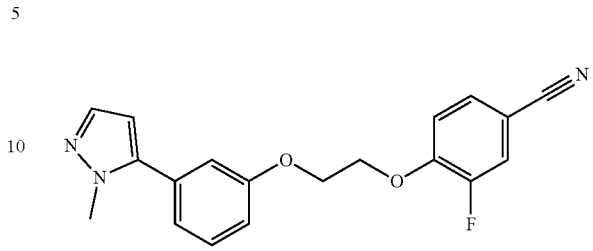

1H NMR (400 MHz, DMSO-d$_6$) δ (ppm): 7.92-7.84 (m, 1H), 7.75-7.69 (t, J=16.4 Hz, 1H)), 7.57-7.39 (m, 3H)), 7.12-7.05 (m, 3H), 6.40 (d, J=2.0 Hz, 1H), 4.53 (dd, J=4.4, 3.6 Hz, 2H), 4.43 (dd, J=6.0, 2.0 Hz, 2H), 3.85 (s, 3H); MS (ESI) m/z 338.27 [C$_{19}$H$_{16}$FN$_3$O$_2$+H]$^+$.

Preparation of 3-methoxy-4-(2-(3-(1-methyl-1H-pyrazol-5-yl)phenoxy)ethoxy)benzonitrile, Compound 15

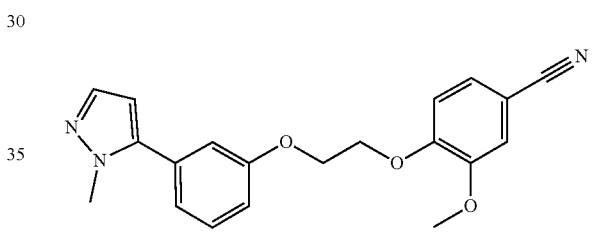

1H NMR (400 MHz, DMSO-d$_6$) δ (ppm): 7.46-7.39 (m, 4H), 7.20 (d, J=7.6 Hz, 1H), 7.12-7.04 (m, 3H), 6.41 (d, J=1.2 Hz, 1H), 4.41 (m, 4H), 3.80 (s, 6H); MS (ESI) m/z 350.28 [C$_{20}$H$_{19}$N$_3$O$_3$+H]$^+$.

Preparation of 3-methoxy-4-(2-(3-(thiazol-5-yl)phenoxy)ethoxy)benzonitrile, Compound 16

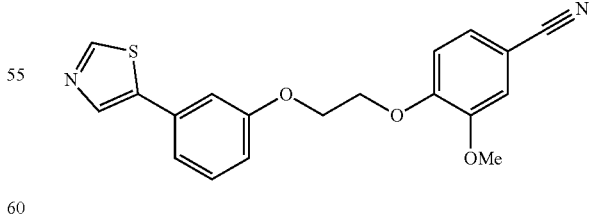

1H NMR (400 MHz, DMSO-d$_6$) δ (ppm): 9.08 (s, 1H), 8.35 (s, 1H), 7.45-7.43 (m, 3H), 7.31-7.20 (m, 3H), 7.01-6.99 (dd, J=2.0, 2.0 Hz, 1H), 4.42 (m, 4H), 3.79 (s, 3H); MS (ESI) m/z 353.16 [C$_{19}$H$_{16}$N$_2$O$_3$S+H]$^+$.

Preparation of 4-(2-(3-(2-cyclopropyl-1H-imidazol-1-yl)phenoxy)ethoxy)-3-fluorobenzonitrile, Compound 17

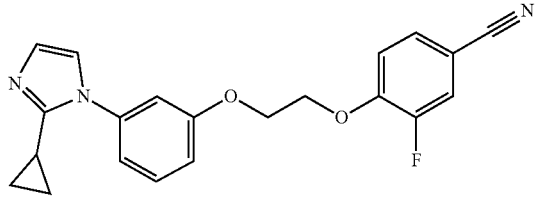 [SMILES: N#Cc1ccc(OCCOc2cccc(-n3ccnc3C3CC3)c2)c(F)c1]

1H NMR (400 MHz, DMSO-d$_6$) δ 7.88-7.85 (m, 1H), 7.70 (d, J=8.4 Hz, 1H), 7.48-7.42 (m, 2H), 7.26 (d, J=1.2 Hz, 1H), 7.10-7.06 (m, 3H), 6.85 ((d, J=1.2 Hz, 1H), 4.55-4.53 (m, 2H), 4.46-4.44 (m, 2H), 1.84-1.80 (m, 1H), 0.90-0.84 (m, 4H); MS (ESI) m/z 364.1 [C$_{21}$H$_{18}$FN$_3$O$_2$]$^+$.

Preparation of 5-methyl-2-(2-(3-(1-methyl-1H-pyrazol-5-yl)phenoxy)ethoxy)benzonitrile, Compound 18

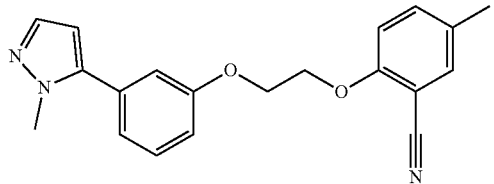 [SMILES: Cc1ccc(OCCOc2cccc(-c3ccnn3C)c2)c(C#N)c1]

1H NMR (400 MHz, DMSO-d$_6$) δ 7.54 (s, 1H), 7.49 (d, J=8.8 Hz, 1H), 7.46 (d, J=1.6 Hz, 1H), 7.42 (t, J=8 Hz, 1H), 7.24 (d, J=8.8 Hz, 1H), 7.12-7.10 (m, 2H), 7.09-7.06 (m, 1H), 6.41 (d, J=1.6 Hz, 1H), 4.49-4.47 (m, 2H), 4.43-4.41 (m, 2H), 3.95 (s, 3H), 2.27 (s, 3H); MS (ESI) m/z 334.4 [C$_{20}$H$_{19}$N$_3$O$_2$+H]$^+$.

Preparation of 4-(2-(3-(2-cyclopropyl-1H-imidazol-1-yl)phenoxy)ethoxy)-3-methoxybenzonitrile, Compound 19

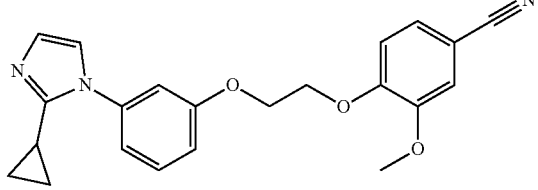

1H NMR (400 MHz, DMSO-d$_6$) δ 7.50-7.38 (m, 3H), 7.27 (d, J=0.8 Hz, 1H), 7.23-7.17 (m, 1H), 7.15-7.05 (m, 3H), 6.85 (d, J=0.8 Hz, 1H), 4.43 (s, 4H), 3.78 (s, 3H), 1.90-1.80 (m, 1H), 0.95-0.80 (m, 4H); MS (ESI) m/z 376.1 [C$_{22}$H$_{21}$N$_3$O$_3$+H]$^+$.

Preparation of 4-(2-(3-(2-cyclopropyl-1H-imidazol-1-yl)phenoxy)ethoxy)benzonitrile, Compound 20

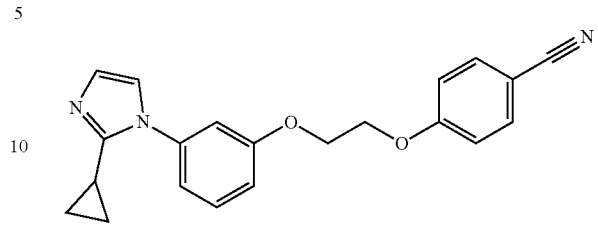

1H NMR (400 MHz, DMSO-d$_6$) δ 7.79 (d, J=8.8 Hz, 2H), 7.46 (t, J=8.0 Hz, 1H), 7.27 (d, J=1.6 Hz, 1H), 7.20-7.13 (m, 2H), 7.13-7.05 (m, 3H), 6.85 (d, J=1.2 Hz, 1H), 4.50-4.40 (m, 4H), 1.85-1.75 (m, 1H), 0.95-0.80 (m, 4H); MS (ESI) m/z 346.1 [C$_{21}$H$_{19}$N$_3$O$_2$+H]$^+$.

Preparation of -(4H-1,2,4-triazol-4-yl)phenoxy)ethoxy)benzonitrile, Compound 21

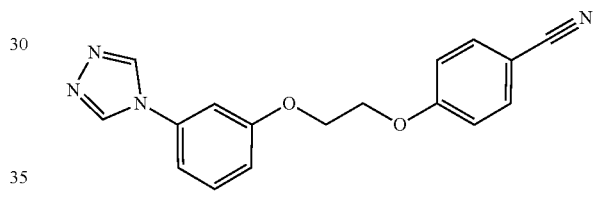

1H NMR (400 MHz, CDCl$_3$) δ (ppm): 8.54 (s, 1H), 8.09 (s, 1H), 7.60 (d, J=8.8 Hz, 2H), 7.42 (t, J=8.0 Hz, 1H), 7.33-7.25 (m, 2H), 7.02-6.96 (m, 3H), 4.43-4.39 (m, 4H); MS (ESI) m/z 307.29 [C$_{17}$H$_{14}$N$_4$O$_2$+H]$^+$.

Preparation of 3-chloro-4-(2-(3-(2-methyl-1H-imidazol-1-yl)phenoxy)propoxy)benzonitrile, Compound 22

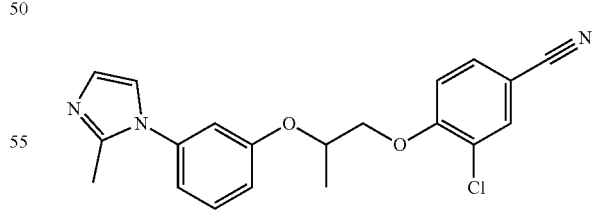

1H NMR (400 MHz, DMSO-d$_6$) δ (ppm): 7.99 (d, J=1.2 Hz, 1H), 7.81 (d, J=8.0 Hz, 1H), 7.42 (dd, J=16.8, 16.4 Hz, 2H), 7.25 (s, 1H), 7.05 (d, J=6.4 Hz, 2H), 7.00 (d, J=8.0 Hz, 1H), 6.88 (s, 1H), 5.01-4.98 (m, 1H), 4.38 (dd, J=16.8, 16 Hz, 2H), 2.27 (s, 3H), 1.39 (d, J=5.6 Hz, 3H); MS (ESI) m/z 368.33 [C$_{20}$H$_{18}$ClN$_3$O$_2$+H]$^+$.

Preparation of 3-fluoro-4-(2-(3-(2-methyl-1H-imidazol-1-yl) phenoxy) propoxy)benzonitrile, Compound 23

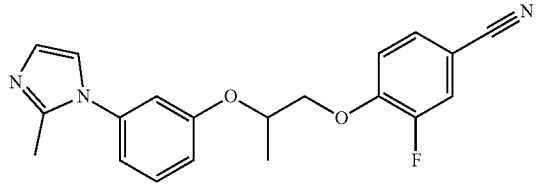 [SMILES: Cc1nccn1-c1cccc(OC(C)COc2ccc(C#N)cc2F)c1]

1H NMR (400 MHz, DMSO-d$_6$) δ (ppm): 7.81 (d, J=11.2 Hz, 1H), 7.66 (d, J=8.8 Hz, 1H), 7.41 (d, J=8.4 Hz, 2H), 7.25 (s, 1H), 7.05 (d, J=8.4 Hz, 2H), 6.98 (d, J=8.4 Hz, 1H), 6.88 (s, 1H), 5.01-4.64 (m, 1H), 4.38 (t, J=2.4 Hz, 2H), 2.27 (s, 3H), 1.38 (d, J=6.4 Hz, 3H); MS (ESI) m/z 352.12 [C$_{20}$H$_{18}$FN$_3$O$_2$+H]$^+$.

Preparation of 3-chloro-4-(2-((2-(2-methyl-1H-imidazol-1-yl)pyridin-4-yl)oxy)ethoxy)benzonitrile, Compound 24

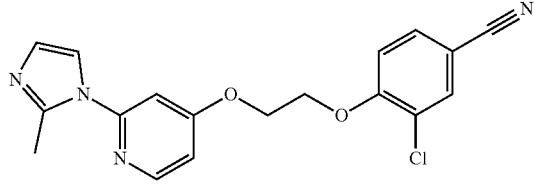 [SMILES: Cc1nccn1-c1cc(OCCOc2ccc(C#N)cc2Cl)ccn1]

1H NMR (400 MHz, DMSO-d$_6$) δ (ppm): 8.41 (d, J=5.6 Hz, 1H), 8.03 (d, J=2.0 Hz, 1H), 7.86-7.84 (dd, J=2.0 Hz, 1H), 7.75 (s, 1H), 7.41 (d, J=8.8 Hz, 1H), 7.32 (d, J=2.0 Hz, 1H), 7.21-7.26 (m, 2H), 4.62-4.58 (dd, J=4.8, 5.2 Hz, 4H), 2.58 (s, 3H); MS (ESI) m/z 355.27 [C$_{18}$H$_{15}$ClN$_4$O$_2$+H]$^+$.

Preparation of 3-fluoro-4-((1-(3-(2-methyl-1H-imidazol-1-yl)phenoxy)propan-2-yl)oxy)benzonitrile. Compound 25

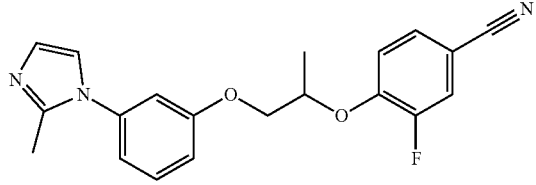 [SMILES: Cc1nccn1-c1cccc(OCC(C)Oc2ccc(C#N)cc2F)c1]

1H NMR (400 MHz, CDCl$_3$) δ (ppm): 7.42-7.35 (m, 3H), 7.14 (t, J=8.4 Hz, 1H), 7.02-6.89 (m, 4H), 6.81 (t, J=2.0 Hz, 1H), 2.36 (s, 3H), 1.50 (d, J=6.4 Hz, 3H); MS (ESI) m/z 352.14 [C$_{20}$H$_{18}$FN$_3$O$_2$+H]$^+$.

Preparation of 1-(3-(2-(4-ethynylphenoxy)ethoxy)phenyl)-2-methyl-1H-imidazole, Compound 26

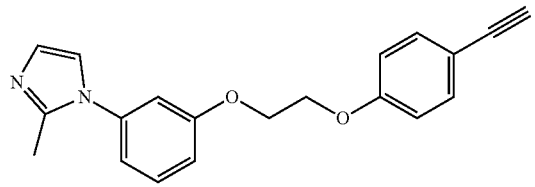 [SMILES: C#Cc1ccc(OCCOc2cccc(-n3ccnc3C)c2)cc1]

1H NMR (400 MHz, DMSO-d$_6$) δ (ppm): 7.47-7.39 (m, 3H), 7.28 (d, J=1.6 Hz, 1H), 7.10-6.96 (m, 5H), 6.89 (d, J=1.2 Hz, 1H), 4.45-4.30 (m, 4H), 4.01 (s, 1H), 2.30 (s, 3H); MS (ESI) m/z 319.1 [C$_{20}$H$_{18}$N$_2$O$_2$+H]$^+$.

Preparation of 4-((1-(3-(2-cyclopropyl-1H-imidazol-1-yl)phenoxy)propan-2-yl)oxy)-3-fluorobenzonitrile, Compound 28

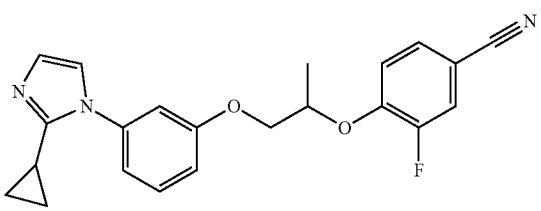 [SMILES: CC(COc1cccc(-n2ccnc2C2CC2)c1)Oc1ccc(C#N)cc1F]

1H NMR (400 MHz, DMSO-d$_6$) δ (ppm): 7.80 (dd, J=11.2 Hz, 2.0 Hz, 1H), 7.64 (d, J=8.4 Hz, 1H), 7.49-7.39 (m, 2H), 7.22 (s, 1H), 7.06-6.98 (m, 3H), 6.82 (s, 1H), 5.90-5.05 (m, 1H), 4.29-4.21 (m, 2H), 1.80-1.73 (m, 1H), 1.36 (t, J=6.4 Hz, 3H), 0.91-0.79 (m, 4H); MS (ESI) m/z 378.21 [C$_{22}$H$_{20}$FN$_3$O$_2$+H]$^+$.

Preparation of 3-methoxy-4-((1-(3-(2-methyl-1H-imidazol-1-yl)phenoxy)propan-2-yl)oxy)benzonitrile, Compound 29

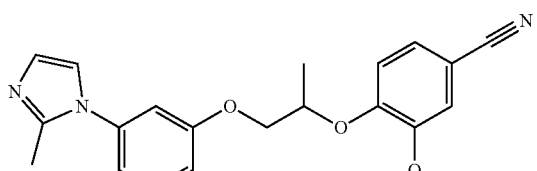

1H NMR (400 MHz, CDCl$_3$) δ (ppm): 7.36 (t, J=8.0 Hz, 1H), 7.26-7.24 (m, 1H), 7.10 (d, J=8.8 Hz, 1H), 7.06-6.88 (m, 5H), 6.83 (s, 1H), 4.86-4.82 (m, 1H), 4.26-4.22 (m, 1H), 4.12-4.09 (m, 1H), 3.84 (s, 3H), 2.36 (s, 3H) 1.49 (d, J=6.4 Hz, 3H); MS (ESI) m/z 364.16 [C$_{21}$H$_{21}$N$_3$O$_3$+H]$^+$.

Preparation of 3-methyl-4-((1-(3-(1-methyl-1H-pyrazol-5-yl)phenoxy)propan-2-yl)oxy)benzonitrile, Compound 30

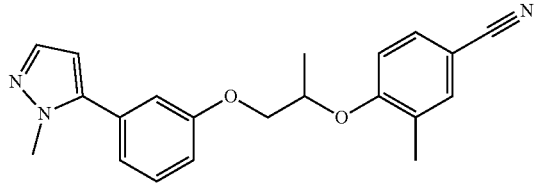 [SMILES: Cc1cc(C#N)ccc1OC(C)COc1cccc(-c2ccnn2C)c1]

1H NMR (400 MHz, DMSO-d$_6$) δ (ppm): 7.50-7.42 (m, 3H), 7.38-7.34 (m, 1H), 7.03-6.92 (m, 4H)), 6.28 (d, J=2.0 Hz, 1H), 4.87-4.82 (dd, J=6.4, 5.6 Hz, 1H), 4.23-4.19 (dd, J=6.4, 5.6 Hz, 1H), 4.11-3.88 (d, J=4.4 Hz, 1H), 3.88 (s, 3H), 2.19 (s, 3H), 1.48 (d, J=6.4 Hz, 3H); MS (ESI) m/z 348.29 [C$_{21}$H$_{21}$N$_3$O$_2$+H]$^+$.

Preparation of 3-methoxy-4-((1-(3-(1-methyl-1H-pyrazol-5-yl)phenoxy)propan-2-yl)oxy)benzonitrile, Compound 31

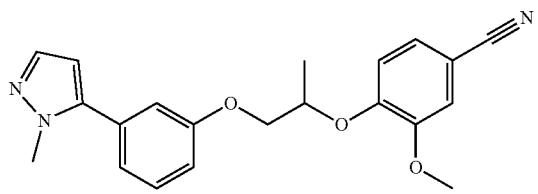 [SMILES: COc1cc(C#N)ccc1OC(C)COc1cccc(-c2ccnn2C)c1]

1H NMR (400 MHz, DMSO-d$_6$) δ (ppm): 7.50 (d, J=1.6 Hz, 1H), 7.37-7.31 (m, 1H), 7.26 (s, 1H) 7.09 (d, J=1.2 Hz, 1H), 7.04-6.99 (m, 2H), 6.93 (d, J=7.6 Hz, 2H), 6.28 (d, J=1.2 Hz, 1H), 4.84 (dd, J=6.0, 2.0 Hz, 1H), 4.26 (dd, J=9.6, 6.4 Hz, 1H), 4.13-4.09 (m, 1H), 3.88 (s, 3H), 3.84 (s, 3H), 1.50 (d, J=6.4 Hz, 3H); MS (ESI) m/z 364.26 [C$_{21}$H$_{21}$N$_3$O$_3$+H]$^+$.

Preparation of (R)-3-chloro-4-(2-(3-(2-methyl-1H-imidazol-1-yl)phenoxy)propoxy)benzonitrile, Compound 32

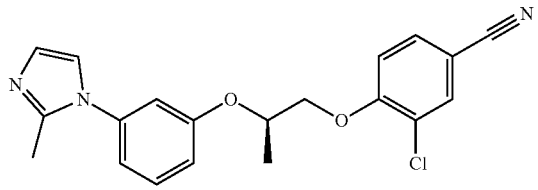 [SMILES: Cc1nccn1-c1cccc(O[C@H](C)COc2ccc(C#N)cc2Cl)c1]

1H NMR (400 MHz, DMSO-d$_6$) δ (ppm): 7.99 (d, J=1.2 Hz, 1H), 7.81 (d, J=8.0 Hz, 1H), 7.42 (dd, J=16.8, 16.4 Hz, 2H), 7.25 (s, 1H), 7.05 (d, J=6.4 Hz, 2H), 7.00 (d, J=8.0 Hz, 1H), 6.88 (s, 1H), 5.01-4.98 (m, 1H), 4.38 (dd, J=16.8, 16 Hz, 2H), 2.27 (s, 3H), 1.39 (d, J=5.6 Hz, 3H); MS (ESI) m/z 368.33 [C$_{20}$H$_{18}$ClN$_3$O$_2$+H]$^+$.

Preparation of (S)-3-chloro-4-(2-(3-(2-methyl-1H-imidazol-1-yl)phenoxy)propoxy)benzonitrile, Compound 33

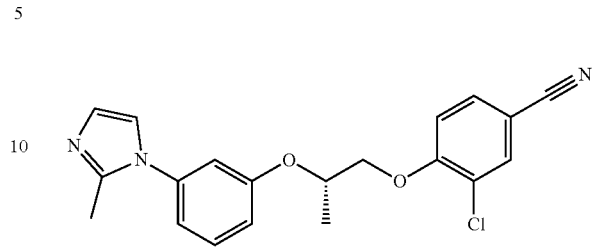

1H NMR (400 MHz, DMSO-d$_6$) δ (ppm): 7.99 (d, J=1.2 Hz, 1H), 7.81 (d, J=8.0 Hz, 1H), 7.42 (dd, J=16.8, 16.4 Hz, 2H), 7.25 (s, 1H), 7.05 (d, J=6.4 Hz, 2H), 7.00 (d, J=8.0 Hz, 1H), 6.88 (s, 1H), 5.01-4.98 (m, 1H), 4.38 (dd, J=16.8, 16 Hz, 2H), 2.27 (s, 3H), 1.39 (d, J=5.6 Hz, 3H); MS (ESI) m/z 368.33 [C$_{20}$H$_{18}$ClN$_3$O$_2$+H]$^+$.

Preparation of (R)-3-fluoro-4-(2-(3-(2-methyl-1H-imidazol-1-yl)phenoxy)propoxy)benzonitrile, Compound 34

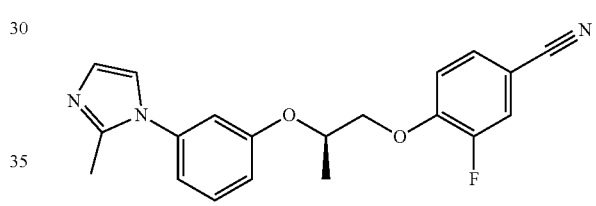

1H NMR (400 MHz, DMSO-d$_6$) δ (ppm): 7.84 (dd, J=11.6, 1.6 Hz, 1H), 7.68 (d, J=8.8 Hz, 1H), 7.44-7.39 (m, 2H), 7.26 (d, J=1.2 Hz, 1H), 7.05-6.98 (m, 3H), 6.89 (d, J=1.2 Hz, 1H), 5.01-4.97 (m, 1H), 4.38-4.31 (m, 2H), 2.28 (s, 3H), 1.37 (d, J=6.0 Hz, 3H); MS (ESI) m/z 352.25 [C$_{20}$H$_{18}$FN$_3$O$_2$+H]$^+$.

Preparation of (S)-3-fluoro-4-(2-(3-(2-methyl-1H-imidazol-1-yl)phenoxy)propoxy)benzonitrile, Compound 35

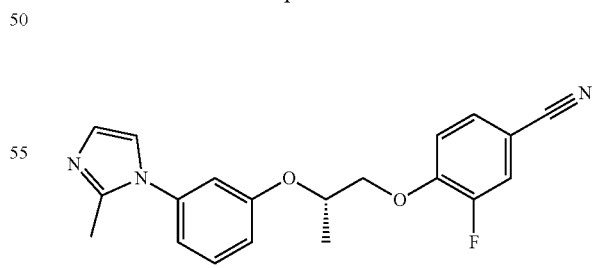

1H NMR (400 MHz, DMSO-d$_6$) δ (ppm): 7.84 (dd, J=11.6, 1.6 Hz, 1H), 7.68 (d, J=8.8 Hz, 1H), 7.44-7.39 (m, 2H), 7.26 (d, J=1.2 Hz, 1H), 7.05-6.98 (m, 3H), 6.89 (d, J=1.2 Hz, 1H), 5.01-4.97 (m, 1H), 4.38-4.31 (m, 2H), 2.28 (s, 3H), 1.37 (d, J=6.0 Hz, 3H); MS (ESI) m/z 352.25 [C$_{20}$H$_{18}$FN$_3$O$_2$+H]$^+$.

Preparation of 4-(2-(3-(2-methyl-1H-imidazol-1-yl)phenoxy)ethoxy)-3-(trifluoromethoxy)benzonitrile, Compound 36

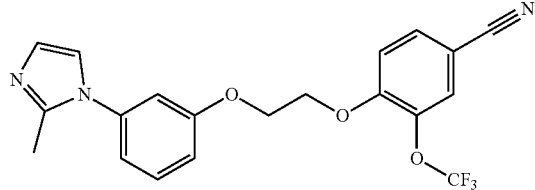 [SMILES: Cc1nccn1-c1cccc(OCCOc2ccc(C#N)cc2OC(F)(F)F)c1]

1H NMR (400 MHz, DMSO-$d_6$) δ (ppm): 7.78-7.69 (m, 2H), 7.49-7.39 (m, 2H), 7.18 (d, J=1.2 Hz, 1H), 7.13-7.08 (m, 1H), 7.02-6.95 (m, 3H), 4.60-4.50 (m, 2H), 4.50-4.40 (m, 2H), 2.33 (m, 3H); MS (ESI) m/z 404.1 $[C_{20}H_{18}F_3N_3O_3+H]^+$.

Preparation of 4-(2-(3-(4H-1,2,4-triazol-4-yl)phenoxy)ethoxy)-3-fluorobenzonitrile, Compound 38

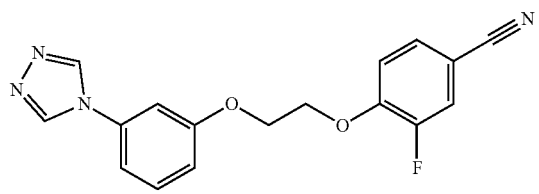 [SMILES: N#Cc1ccc(OCCOc2cccc(-n3cnnc3)c2)c(F)c1]

1H NMR (400 MHz, CDCl$_3$) δ (ppm): 8.54 (s, 1H), 8.09 (s, 1H), 7.45-7.26 (m, 5H), 7.10 (t, J=8.4 Hz, 1H), 6.97 (dd, J=2.0, 8.0 Hz, 1H), 4.49-4.45 (m, 4H); MS (ESI) m/z 325.10 $[C_{17}H_{13}FN_4O_2+H]^+$.

Preparation of 3-fluoro-4-((1-(3-(1-methyl-1H-pyrazol-5-yl)phenoxy)propan-2-yl)oxy)benzonitrile, Compound 37

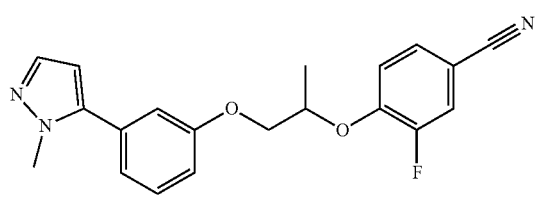

1H NMR (400 MHz, DMSO-$d_6$) δ (ppm): 7.50 (d, J=2.0 Hz, 1H), 7.42-7.34 (m, 3H), 7.17 (t, 3H), 7.03-6.99 (m, 1H), 6.92-6.91 (m, 2H), 6.28 (d, J=1.6 Hz, 1H), 4.91-4.87 (dd, J=10.8, 6.4 Hz, 1H), 4.25-4.21 (m, 1H), 4.14-4.10 (m, 1H), 3.88 (d, J=4.4 Hz, 1H), 1.55-1.47 (m, 3H); MS (ESI) m/z 352.25 $[C_{20}H_{18}FN_3O_2+H]^+$.

Preparation of (R)-3-methyl-4-((1-(3-(1-methyl-1H-pyrazol-5-yl)phenoxy)propan-2-yl)oxy)benzonitrile, Compound 39

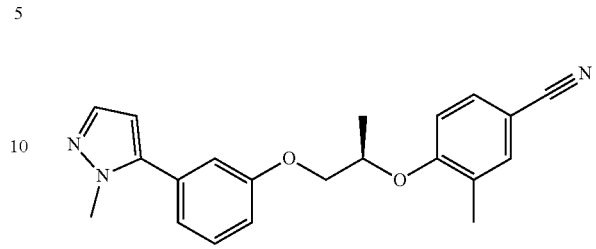

1H NMR (400 MHz, DMSO-$d_6$) δ (ppm): 7.50-7.42 (m, 3H), 7.38-7.34 (m, 1H), 7.03-6.92 (m, 4H)), 6.28 (d, J=2.0 Hz, 1H), 4.87-4.82 (dd, J=6.4, 5.6 Hz, 1H), 4.23-4.19 (dd, J=6.4, 5.6 Hz, 1H), 4.11-3.88 (d, J=4.4 Hz, 1H), 3.88 (s, 3H), 2.19 (s, 3H), 1.48 (d, J=6.4 Hz, 3H); MS (ESI) m/z 348.29 $[C_{21}H_{21}N_3O_2+H]^+$.

Preparation of (S)-3-methyl-4-((1-(3-(1-methyl-1H-pyrazol-5-yl)phenoxy)propan-2-yl)oxy)benzonitrile, Compound 40

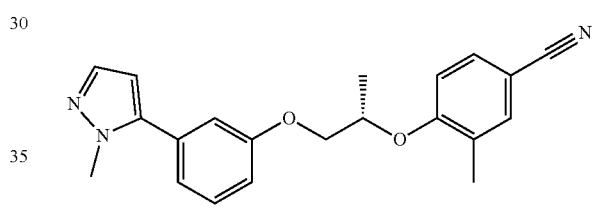

1H NMR (400 MHz, DMSO-$d_6$) δ (ppm): 7.50-7.42 (m, 3H), 7.38-7.34 (m, 1H), 7.03-6.92 (m, 4H)), 6.28 (d, J=2.0 Hz, 1H), 4.87-4.82 (dd, J=6.4, 5.6 Hz, 1H), 4.23-4.19 (dd, J=6.4, 5.6 Hz, 1H), 4.11-3.88 (d, J=4.4 Hz, 1H), 3.88 (s, 3H), 2.19 (s, 3H), 1.48 (d, J=6.4 Hz, 3H); MS (ESI) m/z 348.29 $[C_{21}H_{21}N_3O_2+H]^+$.

Preparation of (R)-4-(1-(3-(2-cyclopropyl-1H-imidazol-1-yl)phenoxy)propan-2-yloxy)-3-fluorobenzonitrile, Compound 41

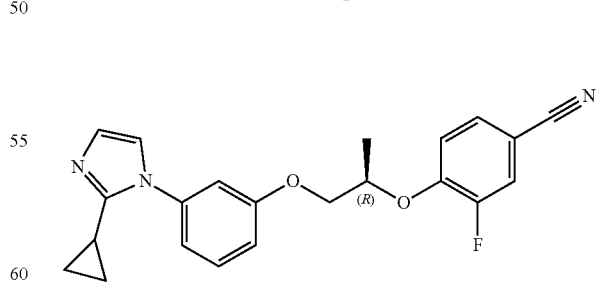

1H NMR (400 MHz, CDCl$_3$) δ (ppm): 7.41-7.36 (m, 1H), 7.02 (t, J=8.0 Hz, 4H), 4.25-4.20 (m, 1H), 3.97 (dd, J=4.0, 12.0 Hz, 1H), 3.85 (t, J=8.0 Hz, 1H), 2.34 (s, 1H), 1.82-1.75 (m, 1H), 1.30 (d, J=4.0 Hz, 3H), 1.12-1.09 (m, 2H), 0.92-0.87 (m, 2H); MS (ESI) m/z 259.21 $[C_{15}H_{18}N_2O_2+H]^+$.

Preparation of (S)-4-((1-(3-(2-cyclopropyl-1H-imidazol-1-yl)phenoxy)propan-2-yl)oxy)-3-fluorobenzonitrile, Compound 42

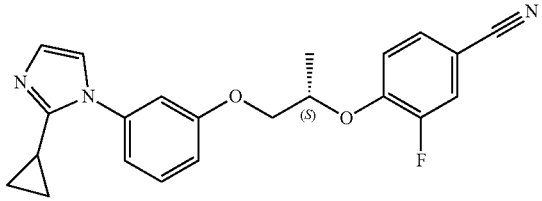

1H NMR (400 MHz, DMSO-d$_6$) δ (ppm): 7.84 (dd, J=2.0 Hz, 11.2 Hz, 1H), 7.66 (d, J=8.0 Hz, 1H), 7.52-7.42 (m, 2H), 7.26 (d, J=0.8 Hz, 1H), 7.09-7.01 (m, 3H), 6.86 (s, 1H), 5.11-5.07 (m, 1H), 4.31-4.23 (m, 2H), 1.81-1.77 (m, 1H), 1.39 (d, J=6.4 Hz, 3H), 0.91-0.82 (m, 4H); MS (ESI) m/z 378.26 [C$_{22}$H$_{20}$FN$_3$O$_2$+H]$^+$.

Preparation of (S)-4-((1-(3-(2-cyclopropyl-1H-imidazol-1-yl)phenoxy)propan-2-yl)oxy)-3-methoxybenzonitrile, Compound 43

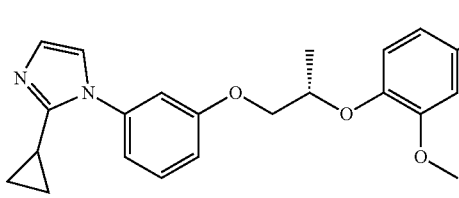

1H NMR (400 MHz, DMSO-d$_6$) δ (ppm): 7.43-7.35 (m, 3H), 7.23 (dd, J=2.0 Hz, 3.2 Hz, 2H), 7.06-6.99 (m, 3H), 6.82 (s, 1H), 4.95 (dd, J=13.2 Hz, 11.2 Hz, 1H), 4.22 (d, J=4.4 Hz, 2H), 3.73 (s, 3H), 1.79-1.75 (m, 1H), 1.34 (dd, J=8.0, 11.2 Hz, 3H), 0.88-0.79 (m, 4H); MS (ESI) m/z 390.27 [C$_{23}$H$_{23}$N$_3$O$_3$+H]$^+$.

Preparation of 3-chloro-4-((1-(3-(2-methyl-1H-imidazol-1-yl)phenoxy)propan-2-yl)oxy)benzonitrile, Compound 44

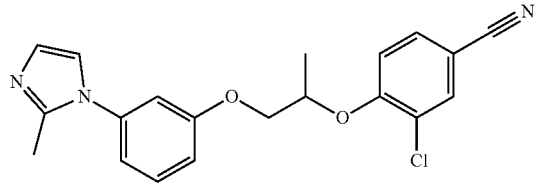

1H NMR (400 MHz, CDCl$_3$) δ (ppm): 7.66 (d, J=2.0 Hz, 1H), 7.53 (dd, J=2.0 Hz, 8.8 Hz, 1H), 7.37 (t, J=8.4 Hz, 1H), 7.15 (d, J=8.8 Hz, 1H), 7.01-6.90 (m, 4H), 6.82 (s, 1H), 4.91-4.87 (m, 1H), 4.27-4.23 (m, 1H), 4.15-4.12 (m, 1H), 2.36 (s, 3H), 1.54 (d, J=13.2 Hz, 3H); MS (ESI) m/z 368.11 [C$_{20}$H$_{18}$ClN$_3$O$_2$+H]$^+$.

Preparation of 1-(3-(2-(4-chloro-2-methoxyphenoxy)ethoxy)phenyl)-2-methyl-1H-imidazole, Compound 45

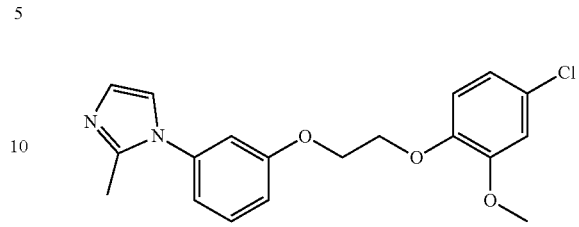

1H NMR (400 MHz, DMSO-d$_6$) δ (ppm): 7.92-7.84 (m, 1H), 7.75-7.69 (t, J=16.4 Hz, 1H)), 7.57-7.39 (m, 3H)), 7.12-7.05 (m, 3H), 6.40 (d, J=2.0 Hz, 1H), 4.53 (dd, J=4.4, 3.6 Hz, 2H), 4.43 (dd, J=6.0, 2.0 Hz, 2H), 3.85 (s, 3H); MS (ESI) m/z 338.27 [C$_{19}$H$_{16}$FN$_3$O$_2$+H]$^+$.

Preparation of (R)-3-fluoro-4-((1-(3-(1-methyl-1H-pyrazol-5-yl)phenoxy)propan-2-yl)oxy)benzonitrile, Compound 46

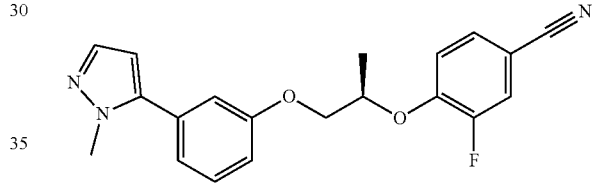

1H NMR (400 MHz, DMSO-d$_6$) δ (ppm): 7.51 (d, J=2.0 Hz, 1H), 7.43-7.34 (m, 3H), 7.17-7.13 (m, 3H), 7.03-7.01 (m, 1H), 6.92-6.91 (m, 2H), 6.29 (d, J=1.6 Hz, 1H), 4.91-4.87 (dd, J=10.8, 6.4 Hz, 1H), 4.26-4.21 (m, 1H), 4.14-4.11 (m, 1H), 3.89 (d, J=4.4 Hz, 1H), 1.52-1.47 (m, 3H); MS (ESI) m/z 352.25 [C$_{20}$H$_{18}$FN$_3$O$_2$+H]$^+$.

Preparation of (S)-3-fluoro-4-((1-(3-(1-methyl-1H-pyrazol-5-yl)phenoxy)propan-2-yl)oxy)benzonitrile, Compound 47

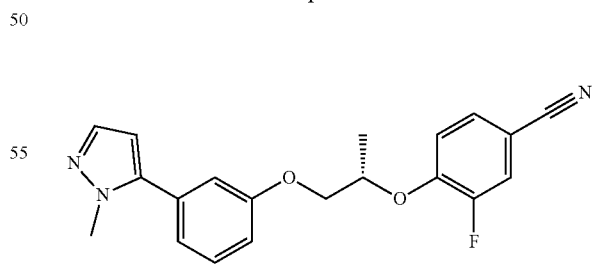

1H NMR (400 MHz, DMSO-d$_6$) δ (ppm): 7.51 (d, J=2.0 Hz, 1H), 7.43-7.34 (m, 3H), 7.17-7.13 (m, 3H), 7.03-7.01 (m, 1H), 6.92-6.91 (m, 2H), 6.29 (d, J=1.6 Hz, 1H), 4.91-4.87 (dd, J=10.8, 6.4 Hz, 1H), 4.26-4.21 (m, 1H), 4.14-4.11 (m, 1H), 3.89 (d, J=4.4 Hz, 1H), 1.52-1.47 (m, 3H); MS (ESI) m/z 352.25 [C$_{20}$H$_{18}$FN$_3$O$_2$+H]$^+$.

Preparation of (R)-3-methoxy-4-((1-(3-(1-methyl-1H-pyrazol-5-yl)phenoxy)propan-2-yl)oxy)benzonitrile, Compound 48

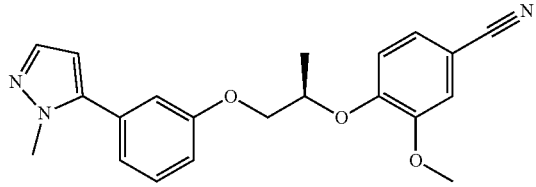 [SMILES: COc1cc(C#N)ccc1O[C@H](C)COc1cccc(-c2ccnn2C)c1]

1H NMR (400 MHz, DMSO-d$_6$) δ (ppm): 7.51 (s, 1H), 7.36 (t, 1H), 7.26 (s, 1H), 7.10 (s, 1H), 7.04-7.01 (m, 2H), 6.96-6.92 (m, 2H), 6.29 (s, 2H), 4.90-4.83 (m, 1H), 4.26 (dd, J=10.0, 6.4 Hz, 1H), 4.11 (dd, J=10.0, 4.4 Hz, 1H), 3.89 (s, 1H), 3.84 (s, 3H), 1.51 (d, J=6.4 Hz, 3H); MS (ESI) m/z 364.26 [C$_{21}$H$_{21}$N$_3$O$_3$+H]$^+$.

Preparation of (S)-4-((1-(3-(2-cyclopropyl-1H-imidazol-1-yl)phenoxy)propan-2-yl)oxy)-3-methylbenzonitrile, Compound 49

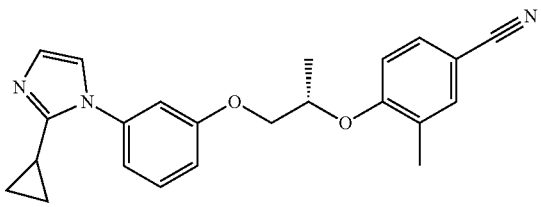

1H NMR (400 MHz, DMSO-d$_6$) δ (ppm): 7.62 (t, J=8.4 Hz, 2H), 7.43 (t, J=8.0 Hz, 1H), 7.24 (d, J=7.6 Hz, 2H), 7.05 (t, J=10.8 Hz, 3H), 6.84 (s, 1H), 4.99 (d, J=4.4 Hz, 1H), 4.27 (d, J=13.2 Hz, 2H), 2.09 (s, 3H), 1.76 (dd, J=4.8, 10 Hz, 1H), 1.37 (d, J=6.4 Hz, 3H), 0.88-0.80 (m, 4H); MS (ESI) m/z 374.30 [C$_{23}$H$_{23}$N$_3$O$_2$+H]$^+$.

Preparation of 1-(3-(2-(4-ethynyl-2-fluorophenoxy)ethoxy)phenyl)-2-methyl-1H-imidazole, Compound 51

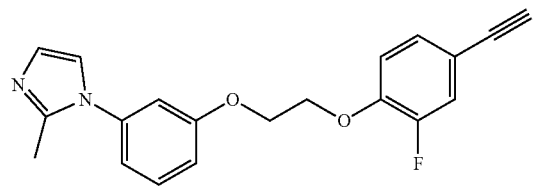

1H NMR (400 MHz, DMSO-d$_6$) δ 7.44 (t, J=8.2 Hz, 1H), 7.37 (dd, J=1.6, 2 Hz, 1H), 7.31-7.22 (m, 3H), 7.08-7.06 (m, 2H), 7.02 (d, J=8.4 Hz, 1H), 6.89 (d, J=0.8 Hz, 1H), 4.45-4.41 (m, 4H), 4.13 (s, 1H), 2.30 (s, 3H); MS (ESI) m/z 337.1 [C$_{20}$H$_{17}$FN$_2$O$_2$+H]$^+$.

Preparation of 3-amino-4-(2-(3-(2-cyclopropyl-1H-imidazol-1-yl)phenoxy)ethoxy)benzonitrile, Compound 52

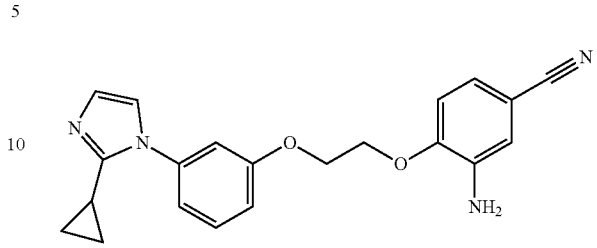

1H NMR (400 MHz, DMSO-d$_6$) δ 7.47 (t, J=8.0 Hz, 1H), 7.17-7.05 (m, 4H), 7.03-6.95 (m, 3H), 6.88-6.92 (m, 1H), 4.50-4.40 (m, 4H), 1.90-1.75 (m, 1H), 1.00-0.85 (m, 4H); MS (ESI) m/z 361.1 [C$_{21}$H$_{20}$N$_4$O$_2$+H]$^+$.

Preparation of 3-fluoro-4-(2-((2-(2-methyl-1H-imidazol-1-yl)pyridin-4-yl)oxy)ethoxy)benzonitrile, Compound 53

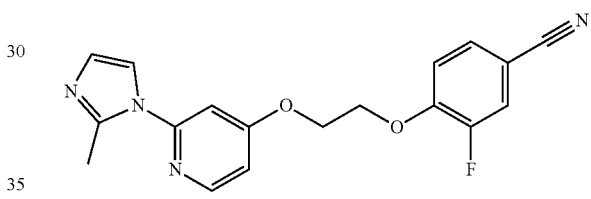

1H NMR (400 MHz, DMSO-d$_6$) δ (ppm): 8.37 (d, J=6.0 Hz, 1H), 7.84-7.85 (dd, J=1.6, 11.2 Hz, 1H), 7.71 (d, J=8.0 Hz, 1H), 7.56 (s, 1H), 7.44 (t, 1H), 7.21 (d, J=2.0 Hz, 1H), 7.09-7.07 (dd, J=2.0, 6.0 Hz, 1H), 6.91 (s, 1H), 4.58-4.57 (m, 4H), 3.31 (s, 3H); MS (ESI) m/z 339.23 [C$_{18}$H$_{15}$FN$_4$O$_2$+H]$^+$.

Preparation of 5-fluoro-2-(2-(3-(1-methyl-1H-pyrazol-5-yl)phenoxy)ethoxy)benzonitrile, Compound 54

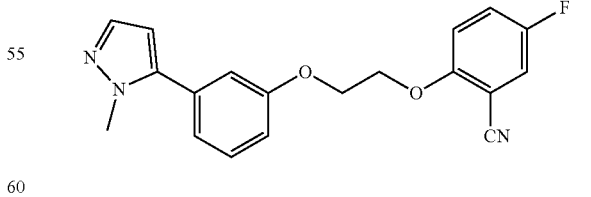

1H NMR (400 MHz, CDCl$_3$) δ (ppm): 7.50 (d, J=1.6 Hz, 1H), 7.38 (t, J=7.6 Hz, 1H), 7.29 (s, 1H), 7.26 (d, J=7.2 Hz, 1H), 7.05-6.97 (m, 4H), 6.30 (d, J=2.0 Hz, 1H), 4.43 (q, J=2.8 Hz, 4H), 3.89 (s, 3H); MS (ESI) m/z 338.26 [C$_{19}$H$_{16}$FN$_3$O$_2$+H]$^+$.

Preparation of (R)-3-chloro-4-((1-(3-(2-methyl-1H-imidazol-1-yl)phenoxy)propan-2-yl)oxy)benzonitrile, Compound 55

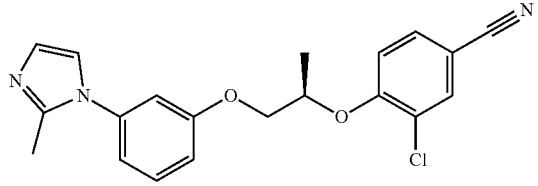 [SMILES: Cc1nccn1-c1cccc(OC[C@@H](C)Oc2ccc(C#N)cc2Cl)c1]

1H NMR (400 MHz, CDCl₃) δ (ppm): 7.66 (d, J=2.0 Hz, 1H), 7.53 (dd, J=2.0 Hz, 8.8 Hz, 1H), 7.37 (t, J=8.4 Hz, 1H), 7.15 (d, J=8.8 Hz, 1H), 7.01-6.90 (m, 4H), 6.82 (s, 1H), 4.91-4.87 (m, 1H), 4.27-4.23 (m, 1H), 4.15-4.12 (m, 1H), 2.36 (s, 3H), 1.54 (d, J=13.2 Hz, 3H); MS (ESI) m/z 368.11 [C₂₀H₁₈ClN₃O₂+H]⁺.

Preparation of (S)-3-chloro-4-((1-(3-(2-methyl-1H-imidazol-1-yl)phenoxy)propan-2-yl)oxy)benzonitrile, Compound 56

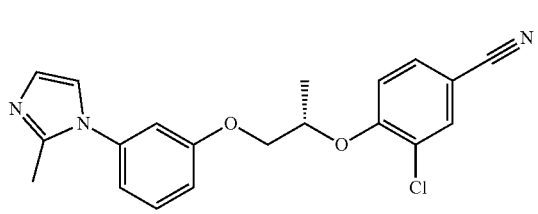 [SMILES: Cc1nccn1-c1cccc(OC[C@H](C)Oc2ccc(C#N)cc2Cl)c1]

1H NMR (400 MHz, CDCl₃) δ (ppm): 7.66 (d, J=2.0 Hz, 1H), 7.53 (dd, J=2.0 Hz, 8.8 Hz, 1H), 7.37 (t, J=8.4 Hz, 1H), 7.15 (d, J=8.8 Hz, 1H), 7.01-6.90 (m, 4H), 6.82 (s, 1H), 4.91-4.87 (m, 1H), 4.27-4.23 (m, 1H), 4.15-4.12 (m, 1H), 2.36 (s, 3H), 1.54 (d, J=13.2 Hz, 3H); MS (ESI) m/z 368.11 [C₂₀H₁₈ClN₃O₂+H]⁺.

Preparation of 4-(2-((2-(1-methyl-1H-pyrazol-5-yl)pyridin-4-yl)oxy)ethoxy)benzonitrile, Compound 59

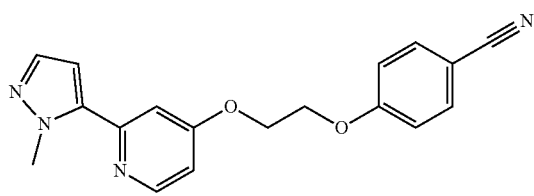 [SMILES: Cn1nccc1-c1cc(OCCOc2ccc(C#N)cc2)ccn1]

1H NMR (400 MHz, CDCl₃) δ (ppm): 8.52 (d, J=9.6 Hz, 1H), 7.61 (d, J=8.8 Hz, 2H), 7.49 (s, 1H), 7.11 (s, 1H), 7.03 (d, J=8.8 Hz, 2H), 6.82 (d, J=4.0 Hz, 1H), 6.53 (s, 1H), 4.42 (d, J=6.4 Hz, 4H), 4.20 (s, 3H); MS (ESI) m/z 321.30 [C₁₈H₁₆N₄O₂+H]⁺.

Preparation of (S)-3-methoxy-4-((1-(3-(1-methyl-1H-pyrazol-5-yl)phenoxy)propan-2-yl)oxy)benzonitrile, Compound 60

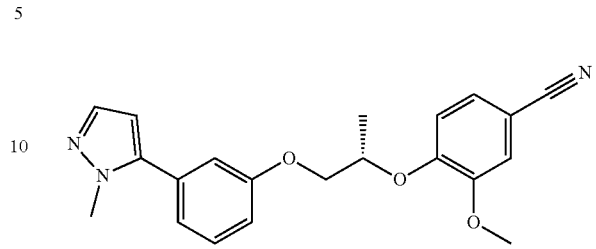

1H NMR (400 MHz, DMSO-d₆) δ (ppm): 7.50 (d, J=1.6 Hz, 1H), 7.37-7.31 (m, 1H), 7.26 (s, 1H) 7.09 (d, J=1.2 Hz, 1H), 7.04-6.99 (m, 2H), 6.93 (d, J=7.6 Hz, 2H), 6.28 (d, J=1.2 Hz, 1H), 4.84 (dd, J=6.0, 2.0 Hz, 1H), 4.26 (dd, J=9.6, 6.4 Hz, 1H), 4.13-4.09 (m, 1H), 3.88 (s, 3H), 3.84 (s, 3H), 1.50 (d, J=6.4 Hz, 3H); MS (ESI) m/z 364.26 [C₂₁H₂₁N₃O₃+H]⁺.

Preparation of 4-((1-(3-(2-cyclopropyl-1H-imidazol-1-yl)phenoxy)propan-2-yl)oxy)-3-methylbenzonitrile, Compound 61

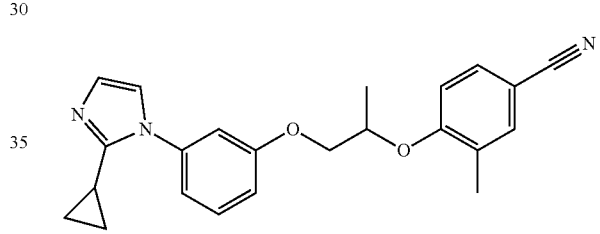

1H NMR (400 MHz, DMSO-d₆) δ (ppm): 7.62 (t, J=8.4 Hz, 2H), 7.43 (t, J=8.0 Hz, 1H), 7.24 (d, J=7.6 Hz, 2H), 7.05 (t, J=10.8 Hz, 3H), 6.84 (s, 1H), 4.99 (d, J=4.4 Hz, 1H), 4.27 (d, J=13.2 Hz, 2H), 2.09 (s, 3H), 1.76 (dd, J=4.8, 10 Hz, 1H), 1.37 (d, J=6.4 Hz, 3H), 0.88-0.80 (m, 4H); MS (ESI) m/z 374.30 [C₂₃H₂₃N₃O₂+H]⁺.

Preparation of 3-fluoro-4-(3-(3-(2-methyl-1H-imidazol-1-yl)phenoxy)butan-2-yloxy)benzonitrile, Compound 63

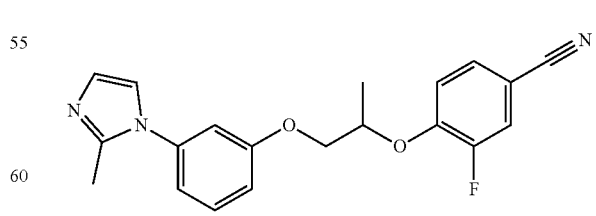

1H NMR (400 MHz, CDCl₃) δ (ppm): 7.40-7.33 (m, 3H), 7.11-7.03 (m, 3H), 6.98-6.87 (m, 2H), 6.81 (t, J=2.4 Hz, 1H), 4.65-4.56 (m, 2H), 2.37 (d, J=5.2 Hz, 3H), 1.57-1.40 (m, 6H); MS (ESI) m/z 366.15 [C₂₁H₂₀FN₃O₂+H]⁺.

Preparation of 3-fluoro-4-((1-(3-(isoxazol-5-yl)phenoxy)propan-2-yl)oxy)benzonitrile, Compound 64

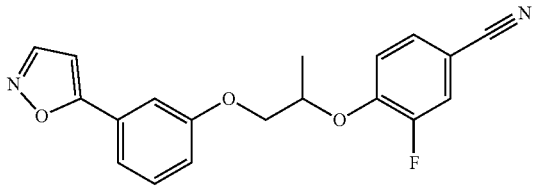 [SMILES: CC(COc1cccc(-c2ccno2)c1)Oc1ccc(C#N)cc1F]

1H NMR (400 MHz, DMSO-d$_6$) δ (ppm): 8.62 (d, J=4.0 Hz, 1H), 7.82 (dd, J=2.0, 11.6 Hz, 1H), 7.65 (d, J=8.8 Hz, 1H), 7.51-7.39 (m, 4H), 7.04 (dd, i=1.6, 5.2 Hz 2H), 5.10-5.06 (m, 1H), 4.30-4.23 (m, 2H), 1.35 (d, J=5.6 Hz, 3H); MS (ESI) m/z 339.19 [C$_{19}$H$_{15}$FN$_3$O$_2$+H]$^+$.

Preparation of (R)-3-fluoro-4-((1-(3-(isoxazol-5-yl)phenoxy)propan-2-yl)oxy)benzonitrile, Compound 65

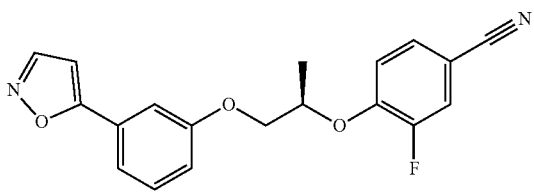 [SMILES: C[C@H](COc1cccc(-c2ccno2)c1)Oc1ccc(C#N)cc1F]

1H NMR (400 MHz, DMSO-d$_6$) δ (ppm): 8.62 (d, J=4.0 Hz, 1H), 7.82 (dd, J=2.0, 11.6 Hz, 1H), 7.65 (d, J=8.8 Hz, 1H), 7.51-7.39 (m, 4H), 7.04 (dd, J=1.6, 5.2 Hz 2H), 5.10-5.06 (m, 1H), 4.30-4.23 (m, 2H), 1.35 (d, J=5.6 Hz, 3H); MS (ESI) m/z 339.19 [C$_{19}$H$_{15}$FN$_3$O$_2$+H]$^+$.

Preparation of (S)-3-fluoro-4-((1-(3-(isoxazol-5-yl)phenoxy)propan-2-yl)oxy)benzonitrile, Compound 66

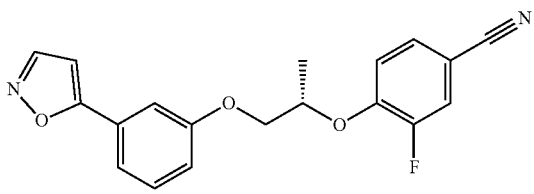 [SMILES: C[C@@H](COc1cccc(-c2ccno2)c1)Oc1ccc(C#N)cc1F]

1H NMR (400 MHz, DMSO-d$_6$) δ (ppm): 8.62 (d, J=4.0 Hz, 1H), 7.82 (dd, J=2.0, 11.6 Hz, 1H), 7.65 (d, J=8.8 Hz, 1H), 7.51-7.39 (m, 4H), 7.04 (dd, J=1.6, 5.2 Hz 2H), 5.10-5.06 (m, 1H), 4.30-4.23 (m, 2H), 1.35 (d, J=5.6 Hz, 3H); MS (ESI) m/z 339.19 [C$_{18}$H$_{15}$FN$_4$O$_2$+H]$^+$.

Preparation of (R)-4-((1-(3-(2-cyclopropyl-1H-imidazol-1-yl)phenoxy)propan-2-yl)oxy)-3-methylbenzonitrile, Compound 68

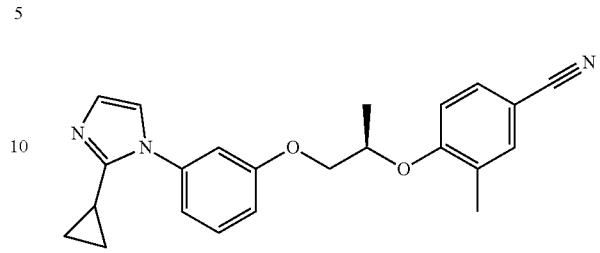

1H NMR (400 MHz, DMSO-d$_6$) δ (ppm): 7.62 (t, J=8.4 Hz, 2H), 7.43 (t, J=8.0 Hz, 1H), 7.24 (d, J=7.6 Hz, 2H), 7.05 (t, J=10.8 Hz, 3H), 6.84 (s, 1H), 4.99 (d, J=4.4 Hz, 1H), 4.27 (d, J=13.2 Hz, 2H), 2.09 (s, 3H), 1.76 (dd, J=4.8, 10 Hz, 1H), 1.37 (d, J=6.4 Hz, 3H), 0.88-0.80 (m, 4H); MS (ESI) m/z 374.30 [C$_{23}$H$_{23}$N$_3$O$_2$+H]$^+$.

Preparation of 3-fluoro-4-(2-((2-(1-methyl-1H-pyrazol-5-yl)pyridin-4-yl)oxy)ethoxy)benzonitrile, Compound 69

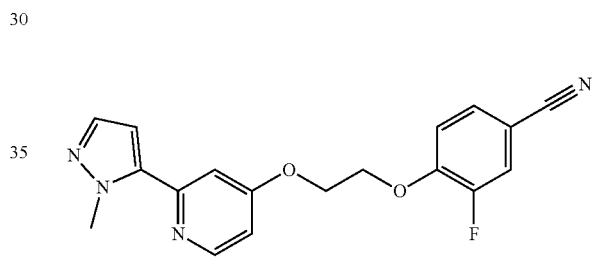

1H NMR (400 MHz, CDCl$_3$) δ (ppm): 8.52 (d, J=6.0 Hz, 1H), 7.5 (d, J=1.6 Hz, 1H), 7.41 (dd, J=8.8 Hz, 19.6 Hz, 2H), 7.12-7.07 (m, 2H), 6.83-6.81 (m, 1H), 6.54 (d, J=2 Hz, 1H), 4.48 (s, 4H), 4.20 (s, 3H); MS (ESI) m/z 339.19 [C$_{18}$H$_{15}$FN$_4$O$_2$+H]$^+$.

Preparation of 6-(2-((2-(2-methyl-1H-imidazol-1-yl)pyridin-4-yl)oxy)ethoxy)nicotinonitrile, Compound 70

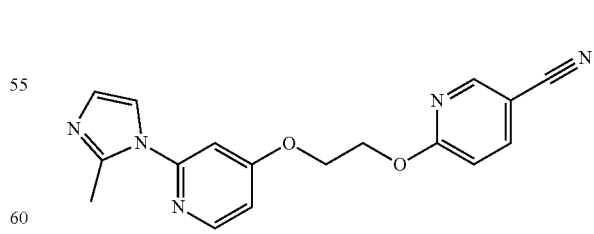

1H NMR (400 MHz, DMSO-d$_6$) δ (ppm): 8.72 (d, J=2.0 Hz, 1H), 8.37 (d, J=5.6 Hz, 1H), 8.19-8.17 (dd, J=2.4, 8.8 Hz, 1H), 7.57 (s, 1H), 7.21 (d, J=2.0 Hz, 1H), 7.08-7.06 (m, 2H), 6.93 (s, 1H), 4.73-4.71 (m, 2H), 4.56-4.54 (m, 2H), 2.50 (s, 3H); MS (ESI) m/z 322.29 [C$_{17}$H$_{15}$N$_5$O$_2$+H]$^+$.

Preparation of 6-(2-((2-(1-methyl-1H-pyrazol-5-yl)pyridin-4-yl)oxy)ethoxy)nicotinonitrile, Compound 71

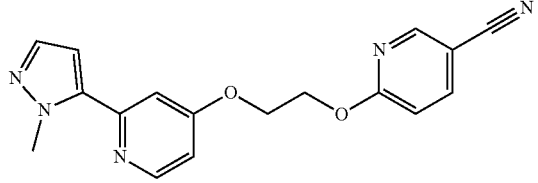 [SMILES: Cn1nccc1-c1cc(OCCOc2ccc(C#N)cn2)ccn1]

1H NMR (400 MHz, CDCl$_3$) δ (ppm): 8.60 (d, J=5.6 Hz, 2H), 7.8 (dd, J=1.6, 8 Hz, 1H), 7.49 (d, J=1.6 Hz, 1H), 7.12 (d, J=2.0 Hz, 1H), 6.88 (d, J=4.8 Hz, 1H), 6.81 (t, J=6.0 Hz, 1H), 6.53 (d, J=2.0 Hz, 1H), 4.78 (t, J=4.4 Hz, 2H), 4.42 (t, J=4.8 Hz, 2H), 4.20 (s, 3H); (MS (ESI) m/z 322.12 [C$_{17}$H$_{15}$N$_5$O$_2$+H]$^+$.

Preparation of (S)-3-methoxy-4-((1-(3-(2-methyl-1H-imidazol-1-yl)phenoxy)propan-2-yl)oxy)benzonitrile, Compound 72

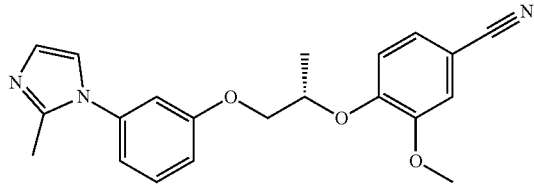 [SMILES: COc1cc(C#N)ccc1O[C@@H](C)COc1cccc(-n2ccnc2C)c1]

1H NMR (400 MHz, CDCl$_3$) δ (ppm): 7.36 (t, J=8.0 Hz, 1H), 7.26-7.24 (m, 1H), 7.10 (d, J=8.8 Hz, 1H), 7.06-6.88 (m, 5H), 6.83 (s, 1H), 4.86-4.82 (m, 1H), 4.26-4.22 (m, 1H), 4.12-4.09 (m, 1H), 3.84 (s, 3H), 2.36 (s, 3H) 1.49 (d, J=6.4 Hz, 3H); MS (ESI) m/z 364.16 [C$_{21}$H$_{21}$N$_3$O$_3$+H]$^+$.

Preparation of 6-(2-(3-(2-methyl-1H-imidazol-1-yl)phenoxy)ethoxy)pyridazine-3-carbonitrile, Compound 73

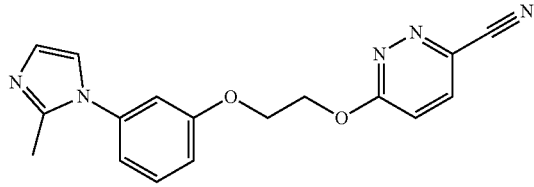 [SMILES: Cc1nccn1-c1cccc(OCCOc2ccc(C#N)nn2)c1]

1H NMR (400 MHz, DMSO-d$_6$) δ 8.25 (d, J=9.2 Hz, 1H), 7.56 (d, J=9.2 Hz, 1H), 7.44 (t, J=8.8 Hz, 1H), 7.28 (d, J=1.2 Hz, 1H), 7.08-7.07 (m, 2H), 7.02 (d, J=8.4 Hz, 1H), 6.89 (d, J=1.2 Hz, 1H), 4.89 (d, J=4.0 Hz, 2H), 4.48 (d, J=4.4 Hz, 2H), 2.30 (s, 3H); MS (ESI) m/z 321.9 [C$_{17}$H$_{15}$N$_5$O$_2$+H]$^+$.

Preparation of 5-fluoro-6-(2-(3-(2-methyl-1H-imidazol-1-yl)phenoxy)ethoxy)nicotinonitrile, Compound 74

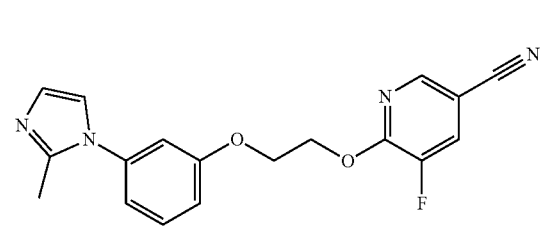 [SMILES: Cc1nccn1-c1cccc(OCCOc2ncc(C#N)cc2F)c1]

1H NMR (400 MHz, DMSO-d$_6$) δ 8.53 (d, J=3.2 Hz, 1H), 8.45-8.43 (m, 1H), 7.44 (t, J=8.0 Hz, 1H), 7.28 (d, J=1.2 Hz, 1H), 7.08-7.01 (m, 3H), 6.89 (d, J=1.2 Hz, 1H), 4.74 (t, J=4.0 Hz, 2H), 4.44 (t, J=5.2 Hz, 2H), 2.29 (s, 3H); MS (ESI) m/z 339.9 [C$_{18}$H$_{15}$FN$_4$O$_2$+H]$^+$.

Preparation of 6-(2-(3-(1-methyl-1H-pyrazol-5-yl)phenoxy)ethoxy)nicotinonitrile, Compound 75

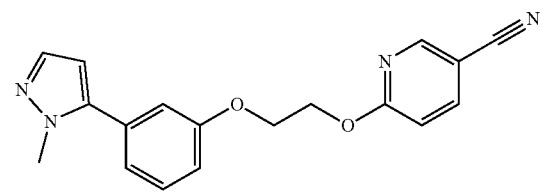

1H NMR (400 MHz, DMSO-d$_6$) δ 8.71 (d, J=2.0 Hz, 1H), 8.19-8.16 (m, 1H), 7.46-7.39 (m, 2H), 7.11-7.04 (m, 4H), 6.40 (d, J=2.0 Hz, 1H), 4.70 (d, J=4.4 Hz, 2H), 4.41 (d, J=4.4 Hz, 2H), 3.85 (s, 3H); MS (ESI) m/z 320.9 [C$_{18}$H$_{16}$N$_4$O$_2$+H]$^+$.

Preparation of 4-(2-((2-(2-cyclopropyl-1H-imidazol-1-yl)pyridin-4-yl)oxy)ethoxy)-3-fluorobenzonitrile, Compound 76

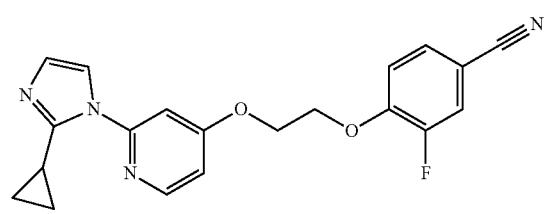

1H NMR (400 MHz, CDCl$_3$) δ (ppm): 8.42 (d, J=5.6 Hz, 1H), 7.46-7.38 (m, 2H), 7.29 (d, J=1.2 Hz, 1H), 7.08 (t, J=8.4 Hz, 2H), 6.98-6.97 (m, 1H), 6.88 (dd, J=2.4, 6.0 Hz, 1H), 4.50 (s, 4H), 2.19-2.14 (m, 1H), 1.17-1.13 (m, 2H), 0.98-0.94 (m, 2H); MS (ESI) m/z 365.23 [C$_{20}$H$_{17}$FN$_4$O$_2$+H]$^+$.

Preparation of (R)-3-methoxy-4-((1-(3-(2-methyl-1H-imidazol-1-yl)phenoxy)propan-2-yl)oxy)benzonitrile, Compound 77

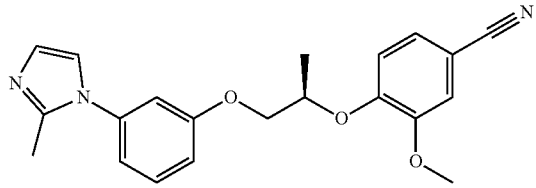 [SMILES: COc1cc(C#N)ccc1O[C@H](C)COc1cccc(-n2ccnc2C)c1]

1H NMR (400 MHz, CDCl$_3$) δ (ppm): 7.36 (t, J=8.0 Hz, 1H), 7.26-7.24 (m, 1H), 7.10 (d, J=8.8 Hz, 1H), 7.06-6.88 (m, 5H), 6.83 (s, 1H), 4.86-4.82 (m, 1H), 4.26-4.22 (m, 1H), 4.12-4.09 (m, 1H), 3.84 (s, 3H), 2.36 (s, 3H) 1.49 (d, J=6.4 Hz, 3H); MS (ESI) m/z 364.16 [C$_{21}$H$_{21}$N$_3$O$_3$+H]$^+$.

Preparation of (R)-3-fluoro-4-((1-(3-(2-methyl-1H-imidazol-1-yl)phenoxy)propan-2-yl)oxy)benzonitrile, Compound 78

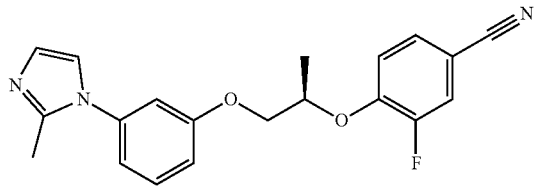 [SMILES: Cc1nccn1-c1cccc(OC[C@@H](C)Oc2ccc(C#N)cc2F)c1]

1H NMR (400 MHz, CDCl$_3$) δ (ppm): 7.42-7.35 (m, 3H), 7.14 (t, J=8.4 Hz, 1H), 7.02-6.89 (m, 4H), 6.81 (t, J=2.0 Hz, 1H), 2.36 (s, 3H), 1.50 (d, J=6.4 Hz, 3H); MS (ESI) m/z 352.14 [C$_{20}$H$_{18}$FN$_3$O$_2$+H]$^+$.

Preparation of (S)-3-fluoro-4-((1-(3-(2-methyl-1H-imidazol-1-yl)phenoxy)propan-2-yl)oxy)benzonitrile, Compound 79

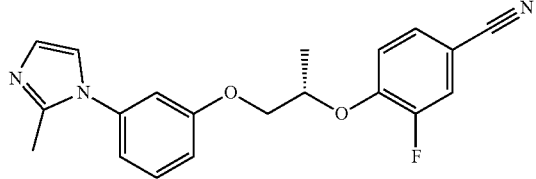

1H NMR (400 MHz, CDCl$_3$) δ (ppm): 7.42-7.35 (m, 3H), 7.14 (t, J=8.4 Hz, 1H), 7.02-6.89 (m, 4H), 6.81 (t, J=2.0 Hz, 1H), 2.36 (s, 3H), 1.50 (d, J=6.4 Hz, 3H); MS (ESI) m/z 352.14 [C$_{20}$H$_{18}$FN$_3$O$_2$+H]$^+$.

Preparation of 4-((1-(3-(2-cyclopropyl-1H-imidazol-1-yl)phenoxy)propan-2-yl)oxy)-3-methoxybenzonitrile, Compound 80

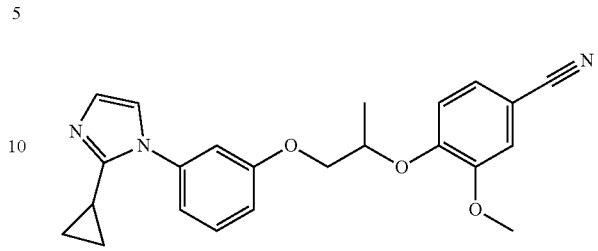

1H NMR (400 MHz, CDCl$_3$) δ (ppm): 7.41-7.36 (m, 1H), 7.04-6.96 (m, 4H), 4.25-4.20 (m, 1H), 3.95 (dd, J=3.2, 9.2 Hz, 1H), 3.85 (t, J=8.0 Hz, 1H), 2.37 (s, 1H), 1.82-1.75 (m, 1H), 1.30 (d, J=6.4 Hz, 3H), 1.12-1.08 (m, 2H), 0.92-0.87 (m, 2H); MS (ESI) m/z 259.21 [C$_{15}$H$_{18}$N$_2$O$_2$+H]$^+$.

Preparation of (S)-4-((1-(3-(2-cyclopropyl-1H-imidazol-1-yl)phenoxy)propan-2-yl)oxy)-3-methoxybenzonitrile, Compound 81

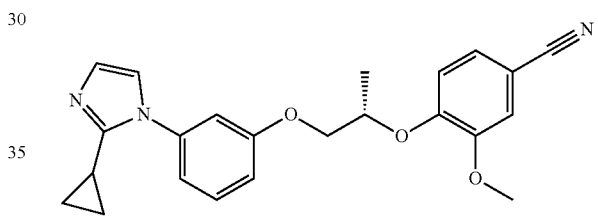

1H NMR (400 MHz, CDCl$_3$) δ (ppm): 7.41-7.36 (m, 1H), 7.04-6.96 (m, 4H), 4.25-4.20 (m, 1H), 3.95 (dd, J=3.2, 9.2 Hz, 1H), 3.85 (t, J=8.0 Hz, 1H), 2.37 (s, 1H), 1.82-1.75 (m, 1H), 1.30 (d, J=6.4 Hz, 3H), 1.12-1.08 (m, 2H), 0.92-0.87 (m, 2H); MS (ESI) m/z 259.21 [C$_{15}$H$_{18}$N$_2$O$_2$+H]$^+$.

Preparation of 5-fluoro-6-(2-(3-(1-methyl-1H-pyrazol-5-yl)phenoxy)ethoxy)nicotinonitrile, Compound 82

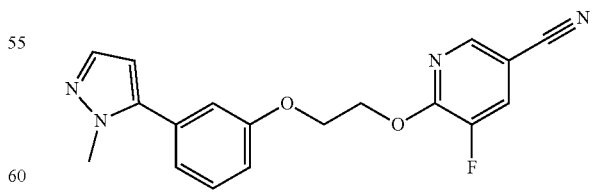

1H NMR (400 MHz, DMSO-d$_6$) δ 8.53 (d, J=3.2 Hz, 1H), 8.45-8.42 (m, 1H), 7.46-7.39 (m, 2H), 7.12-7.05 (m, 3H), 6.41 (d, J=1.6 Hz, 1H), 4.74 (d, J=4.0 Hz, 2H), 4.43 (d, J=4.8 Hz, 2H), 3.85 (s, 3H); MS (ESI) m/z 339.1 [C$_{18}$H$_{15}$FN$_4$O$_2$+H]$^+$.

Preparation of 6-(2-(3-(2-cyclopropyl-1H-imidazol-1-yl)phenoxy)ethoxy)-5-fluoronicotinonitrile, Compound 83

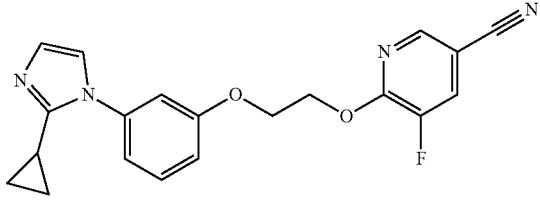

1H NMR (400 MHz, DMSO-d$_6$) δ 8.53 (d, J=3.2 Hz, 1H), 8.45-8.42 (m, 1H), 7.46 (t, J=7.6 Hz, 1H), 7.26 (d, J=1.2 Hz, 1H), 7.10-7.08 (m, 3H), 6.84 (d, J=0.8 Hz, 1H), 4.74 (t, J=4.0 Hz, 1H), 4.45 (t, J=4.4 Hz, 1H); MS (ESI) m/z 365.1 [C$_{20}$H$_{17}$FN$_4$O$_2$+H]$^+$.

Preparation of 3-fluoro-4-(2-(3-(isoxazol-4-yl)phenoxy)ethoxy)benzonitrile, Compound 84

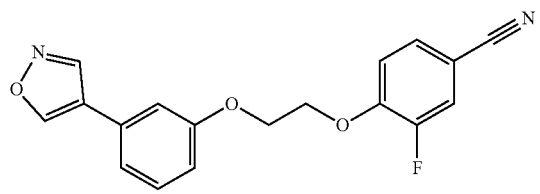 [SMILES: N#Cc1ccc(OCCOc2cccc(-c3cnoc3)c2)c(F)c1]

1H NMR (400 MHz, CDCl$_3$) δ (ppm): 8.66 (s, 1H), 8.54 (s, 1H), 7.45-7.33 (m, 3H), 7.08 (dd, J=17.6, 8.0 Hz, 3H), 6.90 (dd, J=8.4, 1.2 Hz, 1H), 4.49 (t, J=3.6 Hz, 2H), 4.42 (t, J=4.8 Hz, 2H); MS (ESI) m/z 325.24 [C$_{18}$H$_{13}$FN$_2$O$_3$+H]$^+$.

Preparation of 6-(2-((2-(2-cyclopropyl-1H-imidazol-1-yl)pyridin-4-yl)oxy)ethoxy)-5-fluoronicotinonitrile, Compound 90

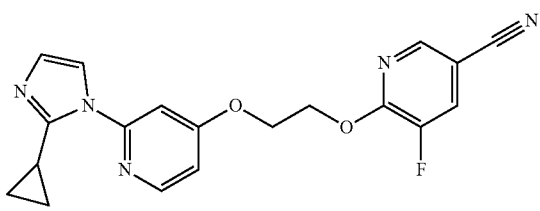 [SMILES: N#Cc1cnc(OCCOc2ccnc(-n3ccnc3C3CC3)c2)c(F)c1]

1H NMR (400 MHz, DMSO-d$_6$) δ 8.54 (d, J=2.8 Hz, 1H), 8.46-8.43 (m, 1H), 8.39 (d, J=6.0 Hz, 1H), 7.48 (s, 1H), 7.24 (d, J=2.0 Hz, 1H), 7.11-7.10 (m, 1H), 6.85 (s, 1H), 4.77 (t, J=4.0 Hz, 2H), 4.59 (t, J=4.0 Hz, 2H), 2.37-2.33 (m, 1H), 0.90-0.87 (m, 4H); MS (ESI) m/z 366.1 [C$_{19}$H$_{16}$FN$_5$O$_2$+H]$^+$.

Preparation of 5-fluoro-6-(2-((2-(2-methyl-1H-imidazol-1-yl)pyridin-4-yl)oxy)ethoxy)nicotinonitrile, Compound 91

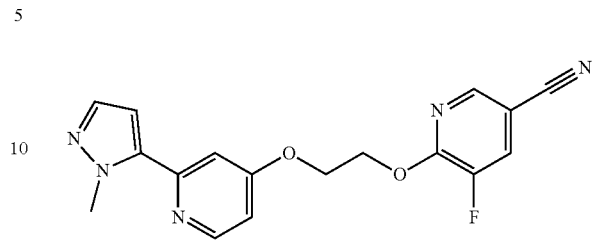

1H NMR (400 MHz, CDCl$_3$) δ8.39 (d, J=6.0 Hz, 1H), 8.23 (d, J=2.8 Hz, 1H), 7.69-7.67 (m, 1H), 7.26-7.25 (m, 1H), 7.01 (d, J=1.6 Hz, 1H), 6.89-6.87 (m, 1H), 6.84 (d, J=0.8 Hz, 1H), 4.80 (t, J=4.4 Hz, 2H), 4.47 (t, J=4.8 Hz, 2H), 2.59 (s, 3H); MS (ESI) m/z 340.1 [C$_{17}$H$_{14}$FN$_5$O$_2$]$^+$.

Preparation of 4-(2-(4-fluoro-3-(1-methyl-1H-pyrazol-5-yl)phenoxy)ethoxy)benzonitrile, Compound 93

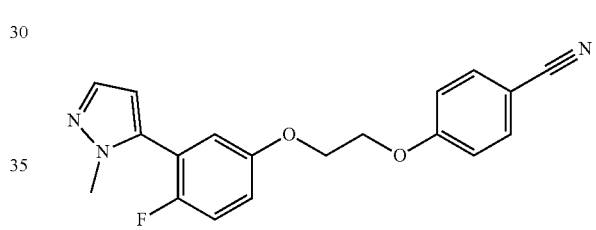

1H NMR (CDCl$_3$, 400 MHz): δ 7.61 (d, J=8.8 Hz, 2H), 7.54 (s, 1H), 7.12 (t, J=9.2 Hz, 1H), 7.02-6.88 (m, 4H), 6.31 (s, 1H), 4.35 (d, J=7.2 Hz, 4H), 3.81 (s, 3H); MS (ESI) m/z 338.12 [C$_{19}$H$_{16}$FN$_3$O$_2$+H]$^+$.

Preparation of 5-chloro-2-(2-((2-(1-methyl-1H-pyrazol-5-yl)pyridin-4-yl)oxy)ethoxy)benzonitrile, Compound 98

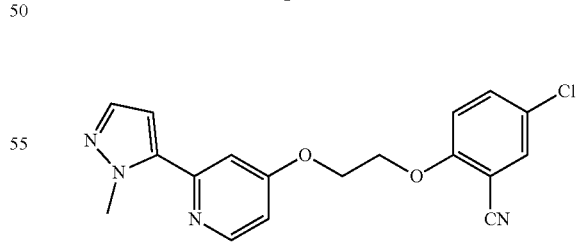

1H NMR (400 MHz, DMSO-d$_6$) δ 8.50 (d, J=6.0 Hz, 1H), 7.92 (d, J=2.4 Hz, 1H), 7.77-7.75 (m, 1H), 7.47 (d, J=2.0 Hz, 1H), 7.40-7.37 (m, 2H), 7.05-7.03 (m, 1H), 6.82 (d, J=2.0 Hz, 1H), 4.55 (s, 4H), 4.12 (s, 3H); MS (ESI) m/z 355.1 [C$_{18}$H$_{15}$ClN$_4$O$_2$+H]$^+$.

Preparation of 5-chloro-2-(2-((2-(2-methyl-1H-imidazol-1-yl)pyridin-4-yl)oxy)ethoxy)benzonitrile, Compound 99

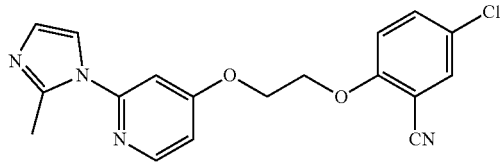 [SMILES: Cc1nccn1-c1cc(OCCOc2ccc(Cl)cc2C#N)ccn1]

1H NMR (400 MHz, CDCl₃) δ8.41 (d, J=5.6 Hz, 1H), 7.56-7.52 (m, 2H), 7.27 (s, 1H), 7.05 (s, 1H), 6.99 (d, J=8.8 Hz, 1H), 6.92 (d, J=6.0 Hz, 1H), 6.86 (s, 1H), 4.52-4.51 (m, 2H), 4.48-4.47 (m, 2H), 2.63 (s, 3H); MS (ESI) m/z 355.0 [C₁₈H₁₅ClN₄O₂+H]⁺.

Preparation of 3-chloro-4-(2-((2-(1-methyl-1H-pyrazol-5-yl)pyridin-4-yl)oxy)ethoxy)benzonitrile, Compound 100

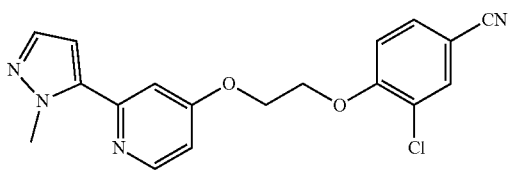 [SMILES: Cn1nccc1-c1cc(OCCOc2ccc(C#N)cc2Cl)ccn1]

1H NMR (400 MHz, DMSO-d₆) δ 8.50 (d, J=5.6, 1H), 8.03 (d, J=1.6 Hz, 1H), 7.88-7.80 (m, 1H), 7.50-7.39 (m, 3H), 7.06-7.00 (s, 1H), 6.83 (d, J=2.0 Hz, 1H), 4.58 (s, 4H), 4.12 (s, 3H); MS (ESI) m/z 355.1 [C₁₈H₁₅ClN₄O₂+H]⁺.

Preparation of 3-fluoro-4-(2-(3-fluoro-5-(1-methyl-1H-pyrazol-5-yl)phenoxy)ethoxy)benzonitrile, Compound 105

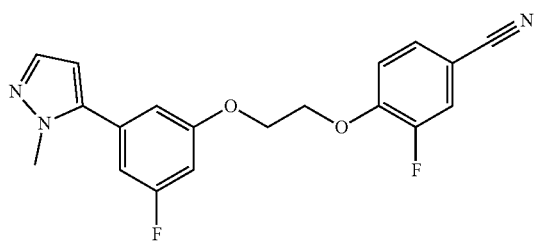 [SMILES: Cn1nccc1-c1cc(F)cc(OCCOc2ccc(C#N)cc2F)c1]

1H NMR (CDCl₃, 400 MHz): δ 7.508 (d, 1H, J=2.0 Hz), 7.460-7.376 (m, 2H), 7.092 (t, 1H, J=8.4 Hz), 6.783-6.700 (m, 3H), 6.310 (d, 1H, J=1.6 Hz), 4.485-4.463 (m, 2H), 4.413-4.391 (m, 2H), 3.902 (s, 3H); MS (ESI) m/z 356.1 [C₁₈H₁₅F₂N₃O₂+H]⁺.

Preparation of 3-fluoro-4-(2-((6-(1-methyl-1H-pyrazol-5-yl)pyridin-2-yl)oxy)ethoxy)benzonitrile, Compound 106

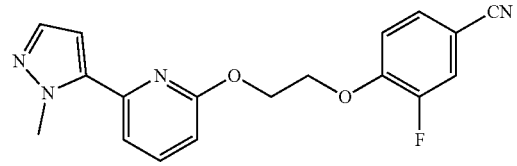 [SMILES: Cn1nccc1-c1cccc(OCCOc2ccc(C#N)cc2F)n1]

1H NMR (CDCl₃, 400 MHz) δ 7.662 (dd, 1H, J=7.6 & 7.2 Hz), 7.497 (d, 1H, J=2.0 Hz), 7.418 (dt, 1H, J=8.4 & 2.0 Hz), 7.375 (dd, 1H, J=10.4 & 2.0 Hz), 7.225 (dd, 1H, J=7.6 & 0.8 Hz), 7.086 (t, 1H, J=8.0 Hz), 6.747 (dd, 1H, J=8.0 & 0.8 Hz), 6.578 (d, 1H, J=2.0 Hz), 4.772 (t, 2H, J=4.8 Hz), 4.481 (t, 2H, J=4.8 Hz), 4.238 (s, 3H); MS (ESI) m/z 339.1 [C₁₈H₁₅FN₄O₂+H]⁺.

Preparation of 4-(2-(4-fluoro-3-(2-methyl-1H-imidazol-1-yl)phenoxy)ethoxy)benzonitrile, Compound 108

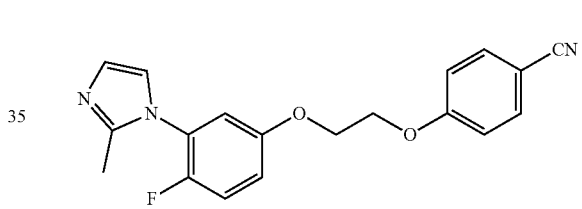

1H NMR (CDCl₃, 400 MHz) δ 7.62 (m, 1H), 7.60 (m, 1H), 7.19 (t, J=9.2 Hz, 1H), 7.06-7.05 (d, J=1.2 Hz, 1H), 7.02-6.97 (m, 3H), 6.95 (s, 1H), 6.87-6.85 (dd, J=6.4, 3.0 Hz, 1H), 4.36 (m, 2H), 4.34 (m, 2H), 2.31 (s, 3H); MS (ESI) m/z 338.2 [C₁₉H₁₆FN₃O₂+H]⁺.

Preparation of 4-(2-(3-(2-methyl-1H-imidazol-1-yl)phenoxy)ethoxy)-3-(trifluoromethyl)benzonitrile, Compound 111

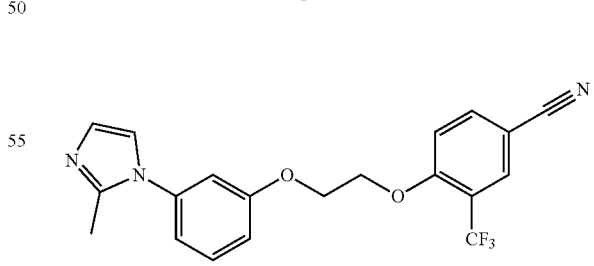

1H NMR (CDCl₃, 400 MHz): δ 7.89-7.88 (d, J=2.0 Hz, 1H), 7.84-7.81 (dd, J=8.4, 2.0 Hz, 1H), 7.40 (t, J=8.2 Hz, 1H), 7.18-7.16 (d, J=8.8 Hz, 1H), 7.03-6.99 (m, 3H), 6.92-6.91 (m, 1H), 6.84 (t, J=2.2 Hz, 1H), 4.55-4.50 (m, 2H), 4.49-4.40 (m, 2H), 2.37 (s, 3H). MS (ESI) m/z 388.1 [C₂₀H₁₆F₃N₃O₂+H]⁺.

Preparation of 5-fluoro-2-(2-(3-(2-methyl-1H-imidazol-1-yl)phenoxy)ethoxy)benzonitrile, Compound 114

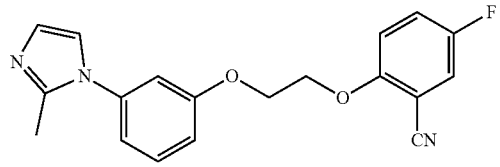

1H NMR (DMSO-d$_6$, 400 MHz): δ 7.77-7.74 (dd, J=8.0, 3.2 Hz, 1H), 7.61-7.56 (dt, J=8.8, 3.2 Hz, 1H), 7.44 (t, J=8.0 Hz, 1H), 7.39-7.35 (dd, J=9.2, 4.0 Hz, 1H), 7.29 (d, J=1.2 Hz, 1H), 7.09-7.01 (m, 3H), 6.90 (s, 1H), 4.51-4.49 (m, 2H), 4.43-4.41 (m, 2H), 2.29 (s, 3H); MS (ESI) m/z 338.2 [C$_{19}$H$_{16}$FN$_3$O$_2$+H]$^+$.

Preparation of 4-(2-(3-(1-cyclopropyl-1H-pyrazol-5-yl)phenoxy)ethoxy)-3-fluorobenzonitrile, Compound 116

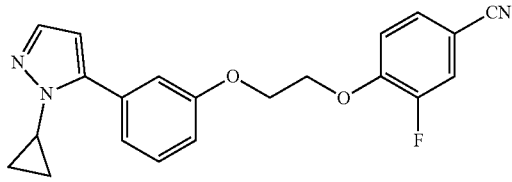 [SMILES: N#Cc1ccc(OCCOc2cccc(-c3ccnn3C3CC3)c2)c(F)c1]

1H NMR (DMSO-d$_6$, 400 MHz): δ 7.88-7.84 (dd, J=11.4, 2.0, 1H), (td, J=8.8, 1.4, 1H), 4.47-7.30 (m, 3H), 7.24-7.22 (m, 2H), 7.06-7.03 (m, 1H), 6.43-6.42 (d, J=1.6, 1H), 4.55-4.52 (m, 2H), 4.44-4.42 (m, 2H), 3.77-3.72 (m, 1H), 0.97-0.91 (m, 4H); MS (ESI) m/z 364.2 [C$_{21}$H$_{18}$FN$_3$O$_2$+H]$^+$.

Preparation of 4-(2-(3-(1-cyclopropyl-1H-pyrazol-5-yl)phenoxy)ethoxy)benzonitrile, Compound 117

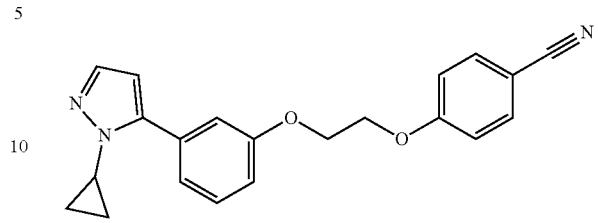

1H NMR (DMSO-d$_6$, 400 MHz): δ 7.63-7.61 (d, J=8.8, 2H), 7.47 (s, 1H), 7.40 (t, J=8.0, 1H), 7.22-7.20 (d, J=7.6, 1H), 7.14 (s, 1H), 7.04-7.02 (d, J=8.8, 2H), 7.01-6.98 (d, J=8.8, 1H), 6.32 (s, 1H), 4.41 (s, 4H), 3.62 (m, 1H), 1.17 (m, 2H), 0.98-0.97 (m, 2H); MS (ESI) m/z 346.2 [C$_{21}$H$_{19}$N$_3$O$_2$+H]$^+$.

Preparation of 3-chloro-4-(2-(3-(1-cyclopropyl-1H-pyrazol-5-yl)phenoxy)ethoxy)benzonitrile, Compound 118

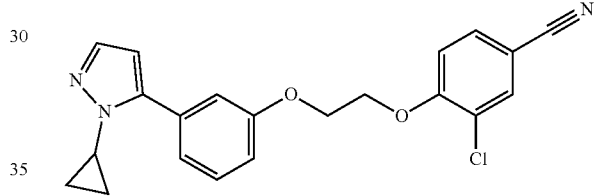

1H NMR (DMSO-d$_6$, 400 MHz): δ 7.69-7.68 (d, J=1.6, 1H), 7.59-7.56 (dd, J=8.4, 1.6, 1H), 7.47 (s, 1H), 7.40 (t, J=8.0, 1H), 7.23-7.21 (d, J=7.2, 1H), 7.16 (s, 1H), 7.09-7.07 (d, J=8.8, 1H), 7.02-7.00 (d, J=7.6, 1H), 6.32 (s, 1H), 4.48 (s, 4H), 3.62 (m, 1H), 1.17 (m, 2H), 0.98-0.97 (m, 2H); MS (ESI) m/z 380.2 [C$_{21}$H$_{18}$ClN$_3$O$_2$+H]$^+$.

Example 8: Compound List

The following Table 2 shows a list representing the exemplified compounds of this disclosure, together with the biological activity data.

TABLE 2

Table listing the structure and IC50 of exemplified compounds

| Compound # | Structure | IUPAC Name | ICMT IC50 (μM) |
|---|---|---|---|
| 1 | 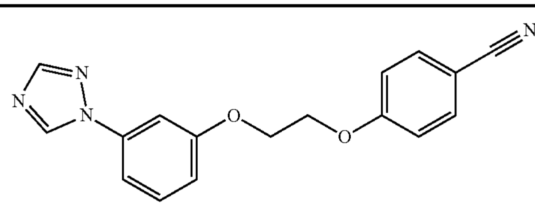 | 4-(2-(3-(1H-1,2,4-triazol-1-yl)phenoxy)ethoxy)benzonitrile | 0.56 |

TABLE 2-continued

Table listing the structure and IC50 of exemplified compounds

| Compound # | Structure | IUPAC Name | ICMT IC50 (μM) |
|---|---|---|---|
| 2 | 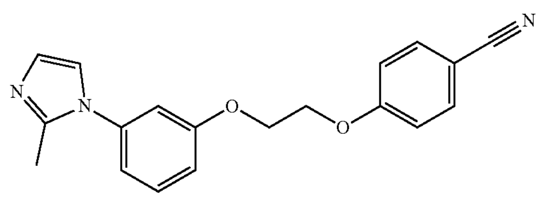 [SMILES: Cc1nccn1-c1cccc(OCCOc2ccc(C#N)cc2)c1] | 4-(2-(3-(2-methyl-1H-imidazol-1-yl)phenoxy)ethoxy)benzonitrile | 0.027 |
| 3 | 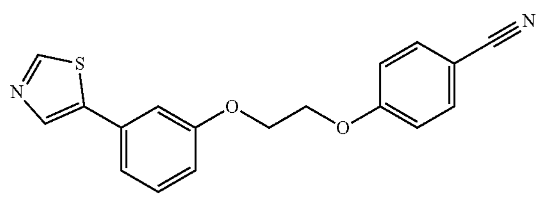 [SMILES: N#Cc1ccc(OCCOc2cccc(-c3cncs3)c2)cc1] | 4-(2-(3-(thiazol-5-yl)phenoxy)ethoxy)benzonitrile | 0.63; 0.49 |
| 4 | 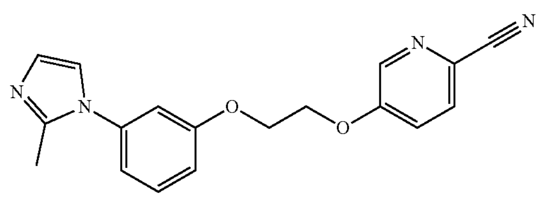 [SMILES: Cc1nccn1-c1cccc(OCCOc2ccc(C#N)nc2)c1] | 5-(2-(3-(2-methyl-1H-imidazol-1-yl)phenoxy)ethoxy)picolinonitrile | 0.26; 0.22; 0.39 |
| 5 | 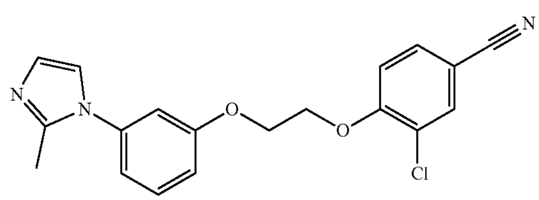 [SMILES: Cc1nccn1-c1cccc(OCCOc2ccc(C#N)cc2Cl)c1] | 3-chloro-4-(2-(3-(2-methyl-1H-imidazol-1-yl)phenoxy)ethoxy)benzonitrile | 0.003; 0.0002; 0.0004 |
| 6 | 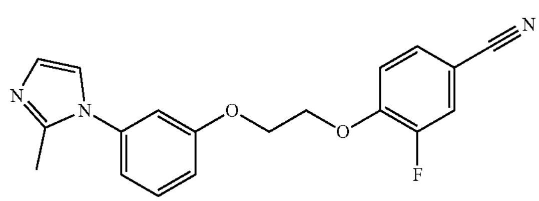 [SMILES: Cc1nccn1-c1cccc(OCCOc2ccc(C#N)cc2F)c1] | 3-fluoro-4-(2-(3-(2-methyl-1H-imidazol-1-yl)phenoxy)ethoxy)benzonitrile | 0.002; 0.001; 0.0024 |
| 7 | 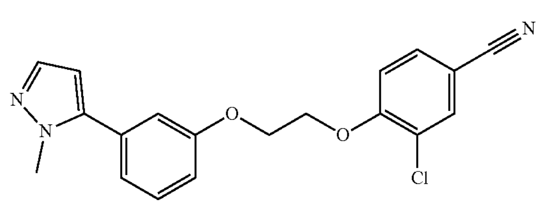 [SMILES: Cn1nccc1-c1cccc(OCCOc2ccc(C#N)cc2Cl)c1] | 3-chloro-4-(2-(3-(1-methyl-1H-pyrazol-5-yl)phenoxy)ethoxy)benzonitrile | 0.003; 0.003 |
| 8 | 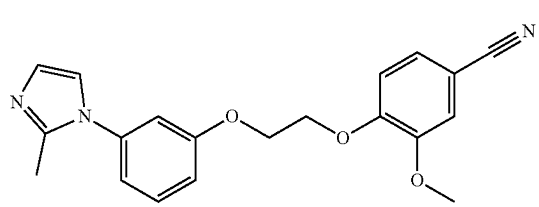 [SMILES: COc1cc(C#N)ccc1OCCOc1cccc(-n2ccnc2C)c1] | 3-methoxy-4-(2-(3-(2-methyl-1H-imidazol-1-yl)phenoxy)ethoxy)benzonitrile | 0.0002; 0.00036 |

TABLE 2-continued

Table listing the structure and IC50 of exemplified compounds

| Compound # | Structure | IUPAC Name | ICMT IC50 (μM) |
|---|---|---|---|
| 9 | 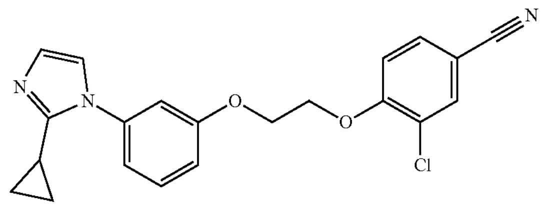 [SMILES: N#Cc1ccc(OCCOc2cccc(-n3ccnc3C3CC3)c2)c(Cl)c1] | 3-chloro-4-(2-(3-(2-cyclopropyl-1H-imidazol-1-yl)phenoxy)ethoxy)benzonitrile | 0.0001; 0.00018 |
| 10 | 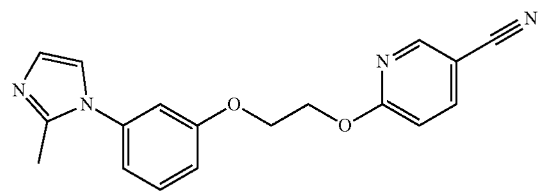 [SMILES: Cc1nccn1-c1cccc(OCCOc2ccc(C#N)cn2)c1] | 6-(2-(3-(2-methyl-1H-imidazol-1-yl)phenoxy)ethoxy)nicotinonitrile | 0.08 |
| 11 | 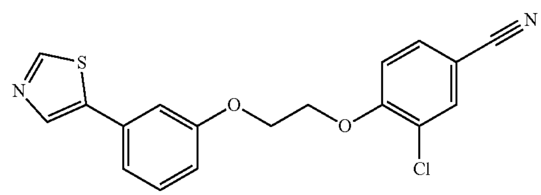 [SMILES: N#Cc1ccc(OCCOc2cccc(-c3cncs3)c2)c(Cl)c1] | 3-chloro-4-(2-(3-(thiazol-5-yl)phenoxy)ethoxy)benzonitrile | 0.02 |
| 12 | 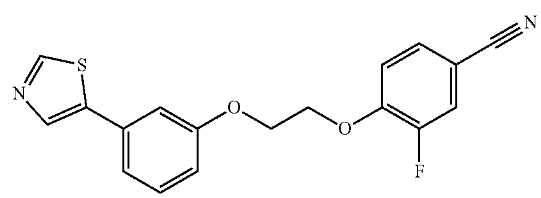 [SMILES: N#Cc1ccc(OCCOc2cccc(-c3cncs3)c2)c(F)c1] | 3-fluoro-4-(2-(3-(thiazol-5-yl)phenoxy)ethoxy)benzonitrile | 0.21 |
| 13 | 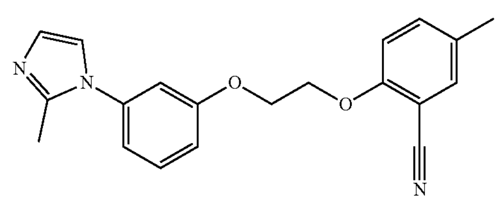 [SMILES: Cc1ccc(OCCOc2cccc(-n3ccnc3C)c2)c(C#N)c1] | 5-methyl-2-(2-(3-(2-methyl-1H-imidazol-1-yl)phenoxy)ethoxy)benzonitrile | 0.011 |
| 14 | 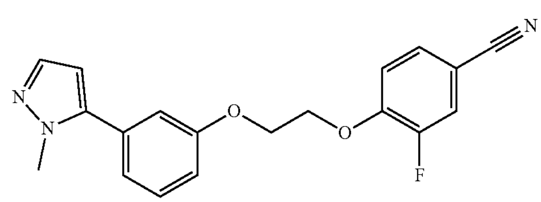 | 3-fluoro-4-(2-(3-(1-methyl-1H-pyrazol-5-yl)phenoxy)ethoxy)benzonitrile | 0.015 |
| 15 | 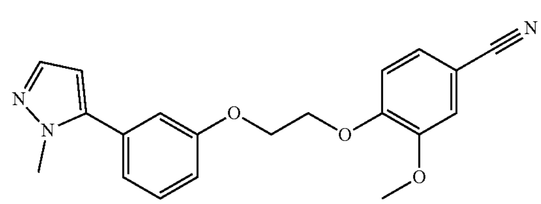 [SMILES: COc1cc(C#N)ccc1OCCOc1cccc(-c2ccnn2C)c1] | 3-methoxy-4-(2-(3-(1-methyl-1H-pyrazol-5-yl)phenoxy)ethoxy)benzonitrile | 0.0011; 0.0009 |

TABLE 2-continued

Table listing the structure and IC50 of exemplified compounds

| Compound # | Structure | IUPAC Name | ICMT IC50 (μM) |
|---|---|---|---|
| 16 | 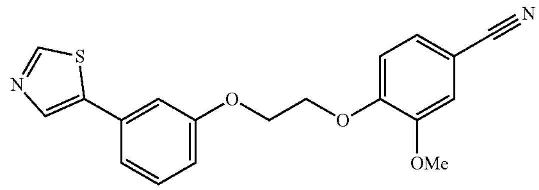 [SMILES: COc1cc(C#N)ccc1OCCOc1cccc(-c2cncs2)c1] | 3-methoxy-4-(2-(3-(thiazol-5-yl)phenoxy)ethoxy)benzonitrile | 0.008; 0.011 |
| 17 | 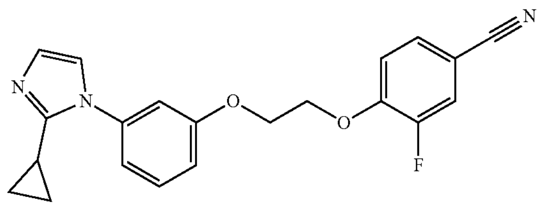 [SMILES: N#Cc1ccc(OCCOc2cccc(-n3ccnc3C3CC3)c2)c(F)c1] | 4-(2-(3-(2-cyclopropyl-1H-imidazol-1-yl)phenoxy)ethoxy)-3-fluorobenzonitrile | 0.016 |
| 18 | 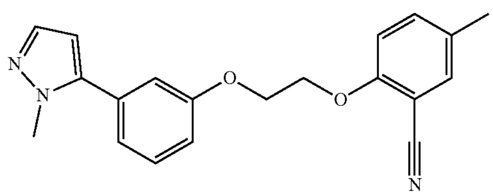 [SMILES: Cc1ccc(OCCOc2cccc(-c3ccnn3C)c2)c(C#N)c1] | 5-methyl-2-(2-(3-(1-methyl-1H-pyrazol-5-yl)phenoxy)ethoxy)benzonitrile | 0.003 |
| 19 | 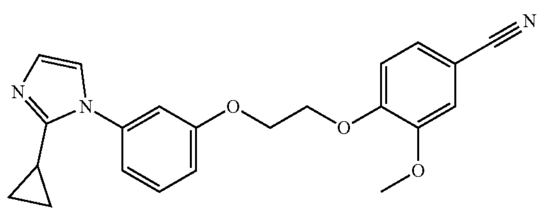 [SMILES: COc1cc(C#N)ccc1OCCOc1cccc(-n2ccnc2C2CC2)c1] | 4-(2-(3-(2-cyclopropyl-1H-imidazol-1-yl)phenoxy)ethoxy)-3-methoxybenzonitrile | 0.0045 |
| 20 | 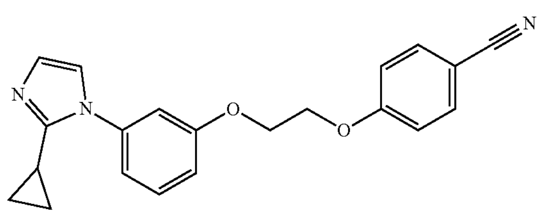 [SMILES: N#Cc1ccc(OCCOc2cccc(-n3ccnc3C3CC3)c2)cc1] | 4-(2-(3-(2-cyclopropyl-1H-imidazol-1-yl)phenoxy)ethoxy)benzonitrile | 0.00017; 0.00016 |
| 21 | 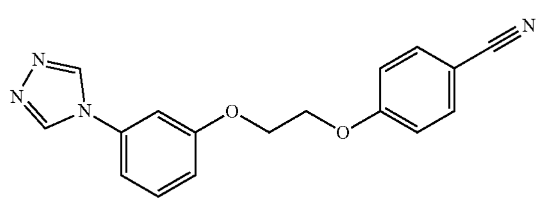 [SMILES: N#Cc1ccc(OCCOc2cccc(-n3cnnc3)c2)cc1] | 4-(2-(3-(4H-1,2,4-triazol-4-yl)phenoxy)ethoxy)benzonitrile | 0.298 |
| 22 | 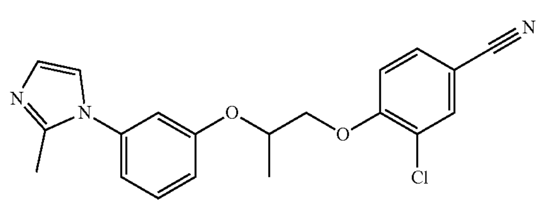 [SMILES: Cc1nccn1-c1cccc(OC(C)COc2ccc(C#N)cc2Cl)c1] | 3-chloro-4-(2-(3-(2-methyl-1H-imidazol-1-yl)phenoxy)propoxy)benzonitrile | 0.003 |

TABLE 2-continued

Table listing the structure and IC50 of exemplified compounds

| Compound # | Structure | IUPAC Name | ICMT IC50 (μM) |
|---|---|---|---|
| 23 | 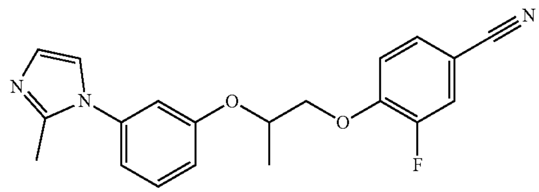 [SMILES: Cc1nccn1-c1cccc(OC(C)COc2ccc(C#N)cc2F)c1] | 3-fluoro-4-(2-(3-(2-methyl-1H-imidazol-1-yl)phenoxy)propoxy)benzonitrile | 0.061 |
| 24 | 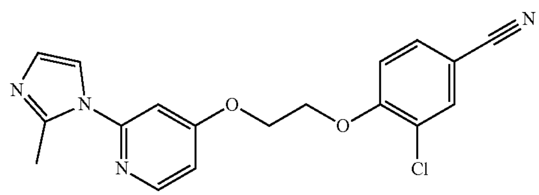 [SMILES: Cc1nccn1-c1cc(OCCOc2ccc(C#N)cc2Cl)ccn1] | 3-chloro-4-(2-((2-(2-methyl-1H-imidazol-1-yl)pyridin-4-yl)oxy)ethoxy)benzonitrile | 0.001 |
| 25 | 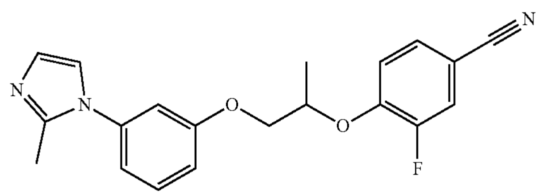 [SMILES: Cc1nccn1-c1cccc(OCC(C)Oc2ccc(C#N)cc2F)c1] | 3-fluoro-4-((1-(3-(2-methyl-1H-imidazol-1-yl)phenoxy)propan-2-yl)oxy)benzonitrile | 0.023 |
| 26 | 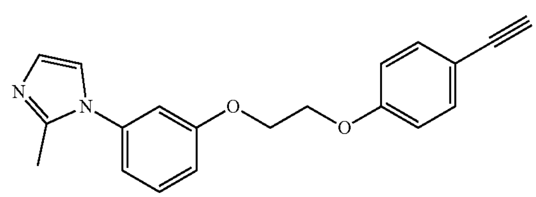 [SMILES: C#Cc1ccc(OCCOc2cccc(-n3ccnc3C)c2)cc1] | 1-(3-(2-(4-ethynylphenoxy)ethoxy)phenyl)-2-methyl-1H-imidazole | 0.069 |
| 27 | 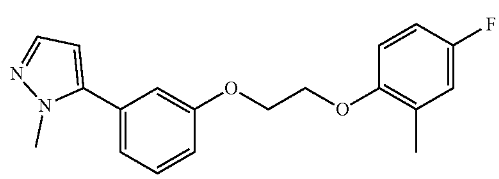 [SMILES: Cc1cc(F)ccc1OCCOc1cccc(-c2ccnn2C)c1] | 5-(3-(2-(4-fluoro-2-methylphenoxy)ethoxy)phenyl)-1-methyl-1H-pyrazole | 0.29 |
| 28 | 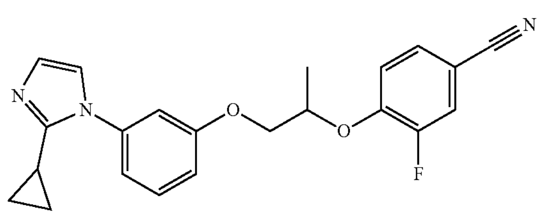 [SMILES: CC(COc1cccc(-n2ccnc2C2CC2)c1)Oc1ccc(C#N)cc1F] | 4-((1-(3-(2-cyclopropyl-1H-imidazol-1-yl)phenoxy)propan-2-yl)oxy)-3-fluorobenzonitrile | 0.0016 |
| 29 | 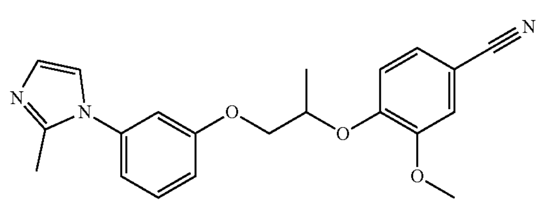 | 3-methoxy-4-((1-(3-(2-methyl-1H-imidazol-1-yl)phenoxy)propan-2-yl)oxy)benzonitrile | 0.00008 |

TABLE 2-continued

Table listing the structure and IC50 of exemplified compounds

| Compound # | Structure | IUPAC Name | ICMT IC50 (μM) |
|---|---|---|---|
| 30 | 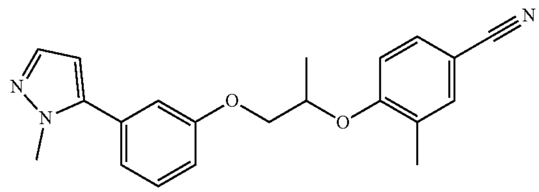 [SMILES: Cc1cc(C#N)ccc1OC(C)COc1cccc(-c2ccnn2C)c1] | 3-methyl-4-((1-(3-(1-methyl-1H-pyrazol-5-yl)phenoxy)propan-2-yl)oxy)benzonitrile | 0.0016 |
| 31 | 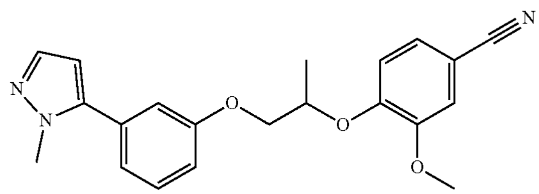 [SMILES: COc1cc(C#N)ccc1OC(C)COc1cccc(-c2ccnn2C)c1] | 3-methoxy-4-((1-(3-(1-methyl-1H-pyrazol-5-yl)phenoxy)propan-2-yl)oxy)benzonitrile | 0.0012 |
| 32 | 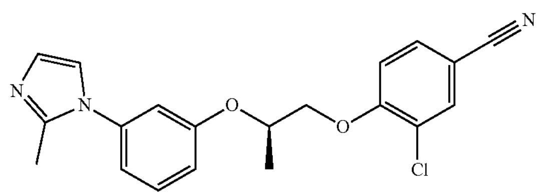 [SMILES: Cc1nccn1-c1cccc(O[C@H](C)COc2ccc(C#N)cc2Cl)c1] | (R)-3-chloro-4-(2-(3-(2-methyl-1H-imidazol-1-yl)phenoxy)propoxy)benzonitrile | 0.2 |
| 33 | 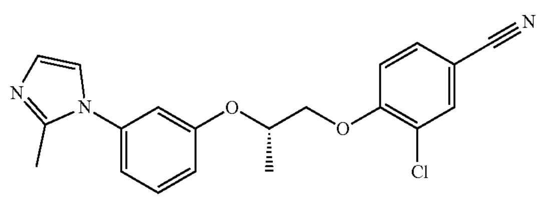 [SMILES: Cc1nccn1-c1cccc(O[C@@H](C)COc2ccc(C#N)cc2Cl)c1] | (S)-3-chloro-4-(2-(3-(2-methyl-1H-imidazol-1-yl)phenoxy)propoxy)benzonitrile | 0.0015 |
| 34 | 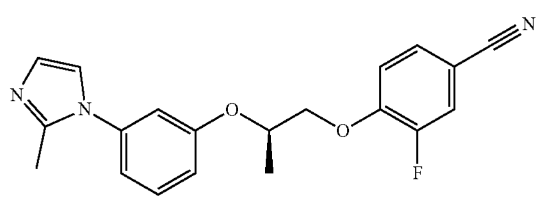 [SMILES: Cc1nccn1-c1cccc(O[C@H](C)COc2ccc(C#N)cc2F)c1] | (R)-3-fluoro-4-(2-(3-(2-methyl-1H-imidazol-1-yl)phenoxy)propoxy)benzonitrile | 1.47 |
| 35 | 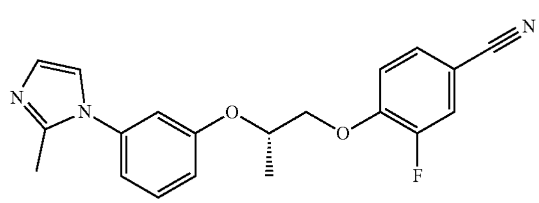 [SMILES: Cc1nccn1-c1cccc(O[C@@H](C)COc2ccc(C#N)cc2F)c1] | (S)-3-fluoro-4-(2-(3-(2-methyl-1H-imidazol-1-yl)phenoxy)propoxy)benzonitrile | 0.0036 |
| 36 | 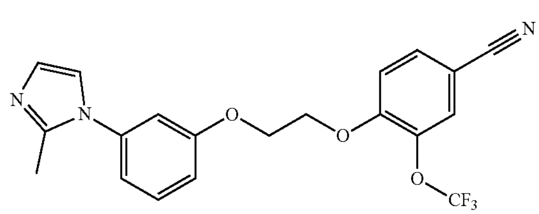 [SMILES: Cc1nccn1-c1cccc(OCCOc2ccc(C#N)cc2OC(F)(F)F)c1] | 4-(2-(3-(2-methyl-1H-imidazol-1-yl)phenoxy)ethoxy)-3-(trifluoromethoxy)benzonitrile | 0.14 |

TABLE 2-continued

Table listing the structure and IC50 of exemplified compounds

| Compound # | Structure | IUPAC Name | ICMT IC50 (μM) |
|---|---|---|---|
| 37 | 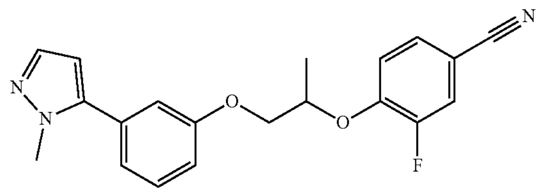 [SMILES: CC(COc1cccc(-c2ccnn2C)c1)Oc1ccc(C#N)cc1F] | 3-fluoro-4-((1-(3-(1-methyl-1H-pyrazol-5-yl)phenoxy)propan-2-yl)oxy)benzonitrile | 0.0007 |
| 38 | 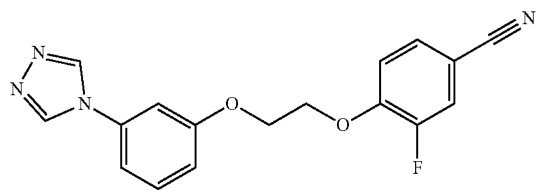 [SMILES: N#Cc1ccc(OCCOc2cccc(-n3cnnc3)c2)c(F)c1] | 4-(2-(3-(4H-1,2,4-triazol-4-yl)phenoxy)ethoxy)-3-fluorobenzonitrile | 0.31 |
| 39 | 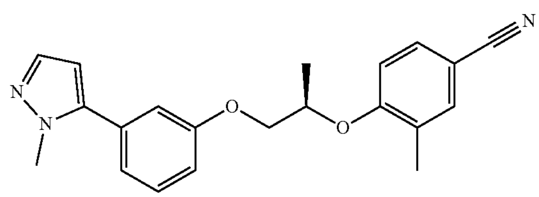 [SMILES: Cc1cc(C#N)ccc1O[C@H](C)COc1cccc(-c2ccnn2C)c1] | (R)-3-methyl-4-((1-(3-(1-methyl-1H-pyrazol-5-yl)phenoxy)propan-2-yl)oxy)benzonitrile | 0.0047 |
| 40 | 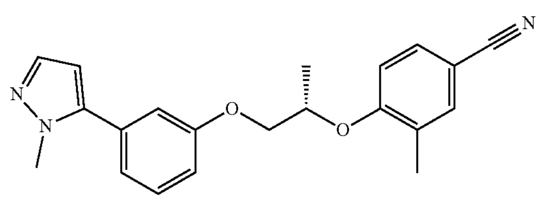 [SMILES: Cc1cc(C#N)ccc1O[C@@H](C)COc1cccc(-c2ccnn2C)c1] | (S)-3-methyl-4-((1-(3-(1-methyl-1H-pyrazol-5-yl)phenoxy)propan-2-yl)oxy)benzonitrile | 0.0095 |
| 41 | 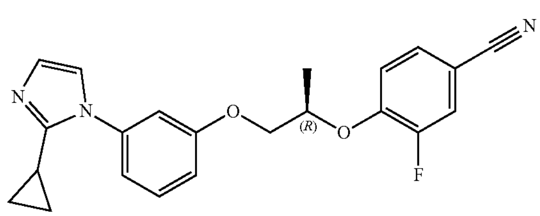 | (R)-4-((1-(3-(2-cyclopropyl-1H-imidazol-1-yl)phenoxy)propan-2-yl)oxy)-3-fluorobenzonitrile | 0.000002 |
| 42 | 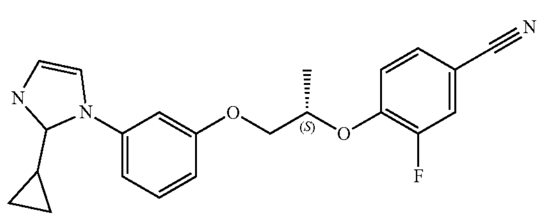 | (S)-4-((1-(3-(2-cyclopropyl-1H-imidazol-1-yl)phenoxy)propan-2-yl)oxy)-3-fluorobenzonitrile | 0.012 |
| 43 | 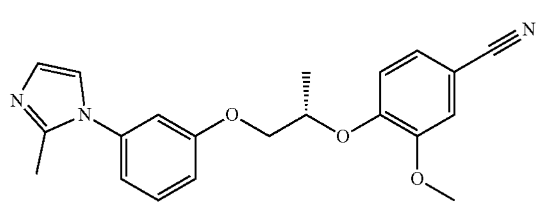 [SMILES: COc1cc(C#N)ccc1O[C@@H](C)COc1cccc(-n2ccnc2C)c1] | (S)-4-((1-(3-(2-cyclopropyl-1H-imidazol-1-yl)phenoxy)propan-2-yl)oxy)-3-methoxybenzonitrile | 0.00068 |

TABLE 2-continued

Table listing the structure and IC50 of exemplified compounds

| Compound # | Structure | IUPAC Name | ICMT IC50 (μM) |
|---|---|---|---|
| 44 | 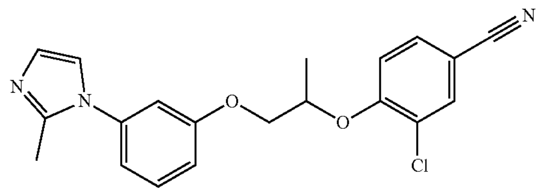 | 3-chloro-4-((1-(3-(2-methyl-1H-imidazol-1-yl)phenoxy)propan-2-yl)oxy)benzonitrile | 0.78 |
| 45 | 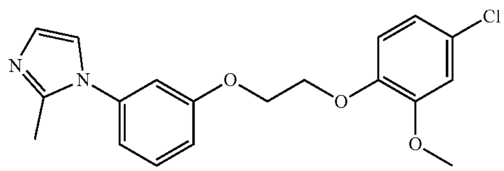 [SMILES: COc1cc(Cl)ccc1OCCOc1cccc(-n2ccnc2C)c1] | 1-(3-(2-(4-chloro-2-methoxyphenoxy)ethoxy)phenyl)-2-methyl-1H-imidazole | 0.076 |
| 46 | 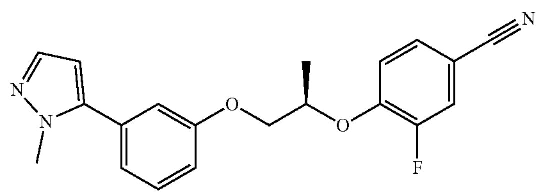 [SMILES: C[C@H](COc1cccc(-c2ccnn2C)c1)Oc1ccc(C#N)cc1F] | (R)-3-fluoro-4-((1-(3-(1-methyl-1H-pyrazol-5-yl)phenoxy)propan-2-yl)oxy)benzonitrile | 0.001 |
| 47 | 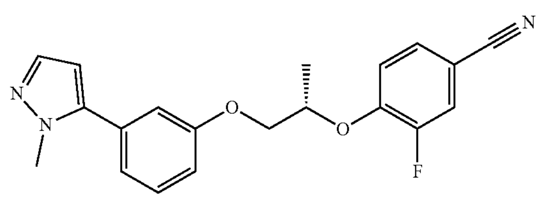 [SMILES: C[C@@H](COc1cccc(-c2ccnn2C)c1)Oc1ccc(C#N)cc1F] | (S)-3-fluoro-4-((1-(3-(1-methyl-1H-pyrazol-5-yl)phenoxy)propan-2-yl)oxy)benzonitrile | 0.0068; 0.00038 |
| 48 | 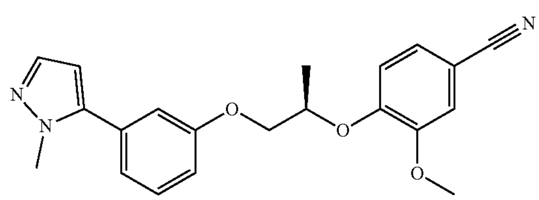 [SMILES: COc1cc(C#N)ccc1O[C@H](C)COc1cccc(-c2ccnn2C)c1] | (R)-3-methoxy-4-((1-(3-(1-methyl-1H-pyrazol-5-yl)phenoxy)propan-2-yl)oxy)benzonitrile | 0.00064 |
| 49 | 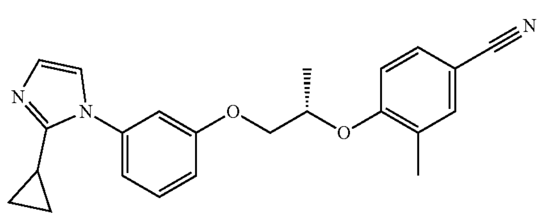 [SMILES: Cc1cc(C#N)ccc1O[C@@H](C)COc1cccc(-n2ccnc2C2CC2)c1] | (S)-4-((1-(3-(2-cyclopropyl-1H-imidazol-1-yl)phenoxy)propan-2-yl)oxy)-3-methylbenzonitrile | 0.0003 |
| 50 | 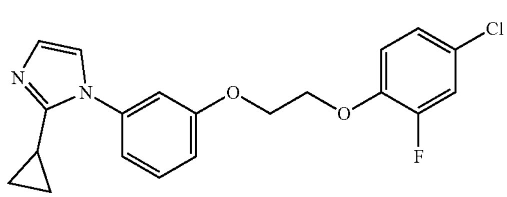 [SMILES: Fc1cc(Cl)ccc1OCCOc1cccc(-n2ccnc2C2CC2)c1] | 1-(3-(2-(4-chloro-2-fluorophenoxy)ethoxy)phenyl)-2-cyclopropyl-1H-imidazole | 0.012 |

TABLE 2-continued

Table listing the structure and IC50 of exemplified compounds

| Compound # | Structure | IUPAC Name | ICMT IC50 (µM) |
|---|---|---|---|
| 51 | 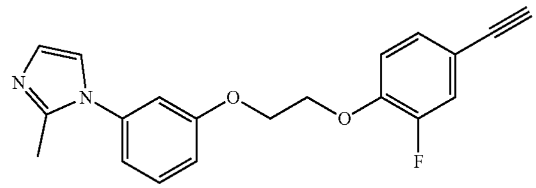 [SMILES: C#Cc1ccc(OCCOc2cccc(-n3ccnc3C)c2)c(F)c1] | 1-(3-(2-(4-ethynyl-2-fluorophenoxy)ethoxy)phenyl)-2-methyl-1H-imidazole | 0.02 |
| 52 | 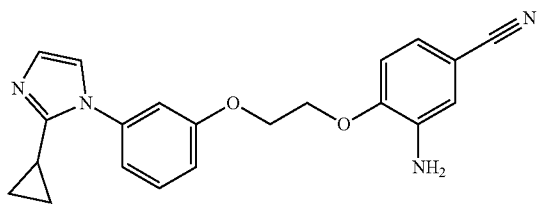 [SMILES: N#Cc1ccc(OCCOc2cccc(-n3ccnc3C3CC3)c2)c(N)c1] | 3-amino-4-(2-(3-(2-cyclopropyl-1H-imidazol-1-yl)phenoxy)ethoxy)benzonitrile | 0.0036 |
| 53 | 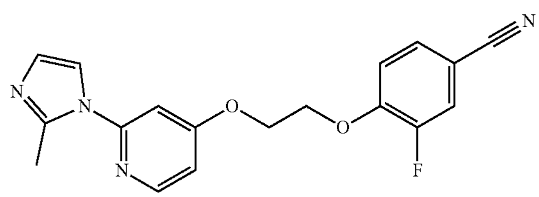 [SMILES: Cc1nccn1-c1cc(OCCOc2ccc(C#N)cc2F)ccn1] | 3-fluoro-4-(2-((2-(2-methyl-1H-imidazol-1-yl)pyridin-4-yl)oxy)ethoxy)benzonitrile | 0.00044 |
| 54 | 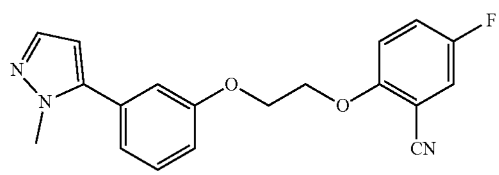 [SMILES: Cn1nccc1-c1cccc(OCCOc2ccc(F)cc2C#N)c1] | 5-fluoro-2-(2-(3-(1-methyl-1H-pyrazol-5-yl)phenoxy)ethoxy)benzonitrile | 0.032 |
| 55 | 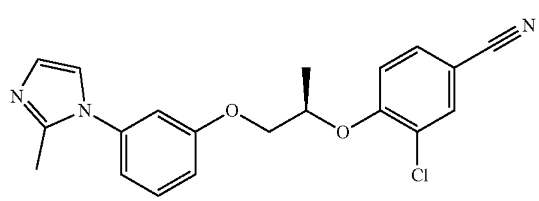 [SMILES: Cc1nccn1-c1cccc(OC[C@@H](C)Oc2ccc(C#N)cc2Cl)c1] | (R)-3-chloro-4-((1-(3-(2-methyl-1H-imidazol-1-yl)phenoxy)propan-2-yl)oxy)benzonitrile | 0.011 |
| 56 | 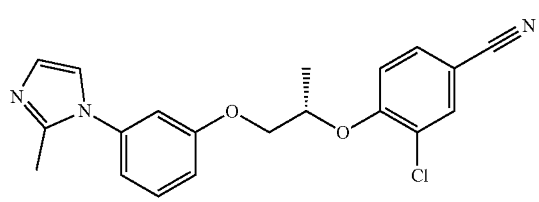 | (S)-3-chloro-4-((1-(3-(2-methyl-1H-imidazol-1-yl)phenoxy)propan-2-yl)oxy)benzonitrile | 0.00015 |
| 57 | 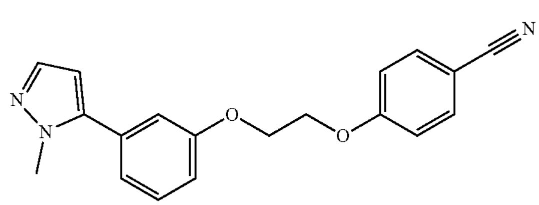 [SMILES: Cn1nccc1-c1cccc(OCCOc2ccc(C#N)cc2)c1] | 4-(2-(3-(1-methyl-1H-pyrazol-5-yl)phenoxy)ethoxy)benzonitrile | 0.009 |

TABLE 2-continued

Table listing the structure and IC50 of exemplified compounds

| Compound # | Structure | IUPAC Name | ICMT IC50 (μM) |
|---|---|---|---|
| 58 | 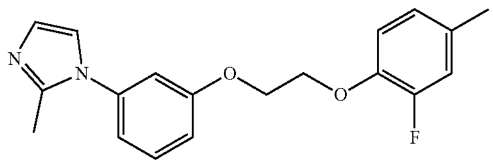 [SMILES: Cc1ccc(OCCOc2cccc(-n3ccnc3C)c2)c(F)c1] | 1-(3-(2-(2-fluoro-4-methylphenoxy)ethoxy)phenyl)-2-methyl-1H-imidazole | 0.06 |
| 59 | 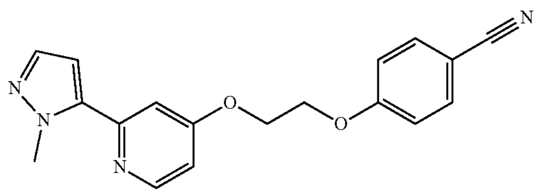 [SMILES: Cn1nccc1-c1cc(OCCOc2ccc(C#N)cc2)ccn1] | 4-(2-((2-(1-methyl-1H-pyrazol-5-yl)pyridin-4-yl)oxy)ethoxy)benzonitrile | 0.02 |
| 60 | 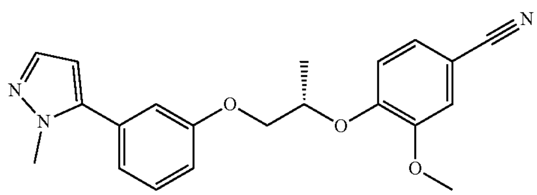 [SMILES: COc1cc(C#N)ccc1O[C@@H](C)COc1cccc(-c2ccnn2C)c1] | (S)-3-methoxy-4-((1-(3-(1-methyl-1H-pyrazol-5-yl)phenoxy)propan-2-yl)oxy)benzonitrile | 0.81 nM |
| 61 | 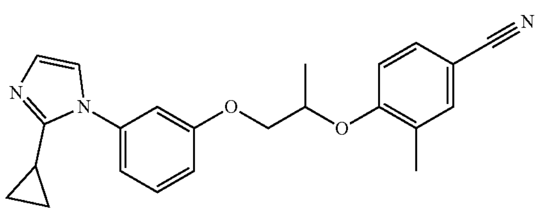 [SMILES: Cc1cc(C#N)ccc1OC(C)COc1cccc(-n2ccnc2C2CC2)c1] | 4-((1-(3-(2-cyclopropyl-1H-imidazol-1-yl)phenoxy)propan-2-yl)oxy)-3-methylbenzonitrile | 0.88 nM |
| 62 | 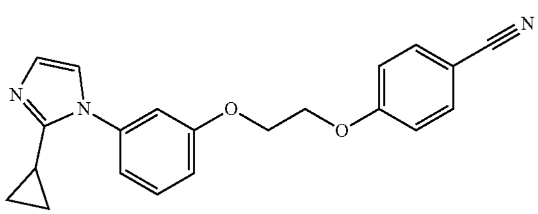 [SMILES: N#Cc1ccc(OCCOc2cccc(-n3ccnc3C3CC3)c2)cc1] | 4-(2-(3-(2-cyclopropyl-1H-imidazol-1-yl)phenoxy)ethoxy)benzonitrile | 0.0085 |
| 63 | 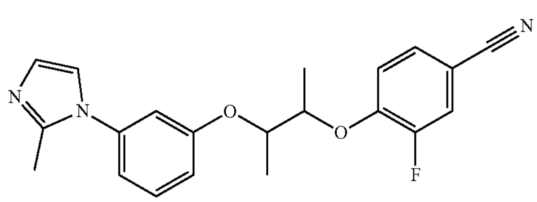 [SMILES: Cc1nccn1-c1cccc(OC(C)C(C)Oc2ccc(C#N)cc2F)c1] | 3-fluoro-4-((3-(3-(2-methyl-1H-imidazol-1-yl)phenoxy)butan-2-yl)oxy)benzonitrile | 0.018; 0.006 |
| 64 | 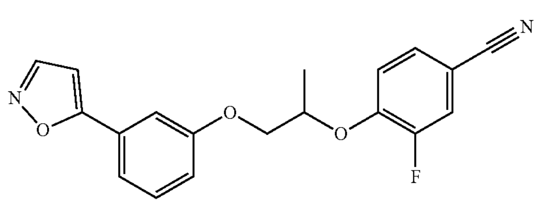 [SMILES: CC(COc1cccc(-c2ccno2)c1)Oc1ccc(C#N)cc1F] | 3-fluoro-4-((1-(3-(isoxazol-5-yl)phenoxy)propan-2-yl)oxy)benzonitrile | 0.27; 0.47 |

TABLE 2-continued

Table listing the structure and IC50 of exemplified compounds

| Compound # | Structure | IUPAC Name | ICMT IC50 (μM) |
|---|---|---|---|
| 65 | 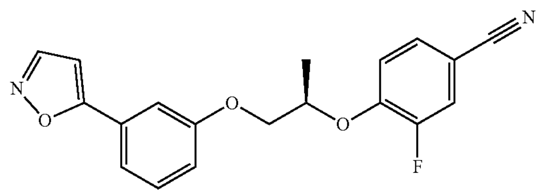 [SMILES: C[C@H](COc1cccc(-c2ccno2)c1)Oc1ccc(C#N)cc1F] | (R)-3-fluoro-4-((1-(3-(isoxazol-5-yl)phenoxy)propan-2-yl)oxy)benzonitrile | 4.67; 4.39 |
| 66 | 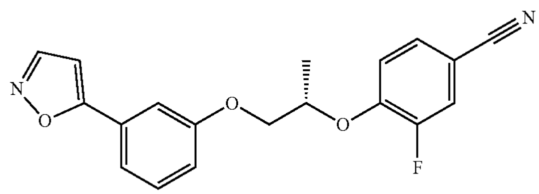 [SMILES: C[C@@H](COc1cccc(-c2ccno2)c1)Oc1ccc(C#N)cc1F] | (S)-3-fluoro-4-((1-(3-(isoxazol-5-yl)phenoxy)propan-2-yl)oxy)benzonitrile | 0.18; 0.19 |
| 67 | 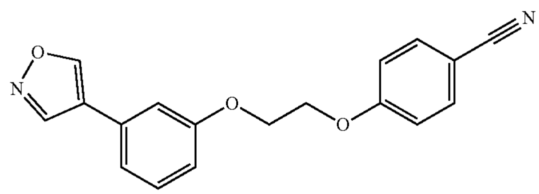 [SMILES: N#Cc1ccc(OCCOc2cccc(-c3cnoc3)c2)cc1] | 4-(2-(3-(isoxazol-4-yl)phenoxy)ethoxy)benzonitrile | 0.14; 0.10 |
| 68 | 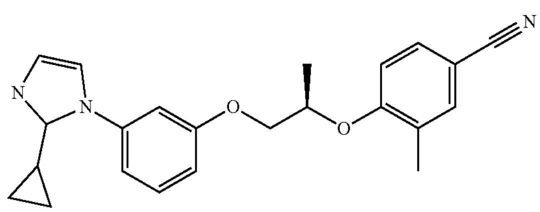 [SMILES: Cc1cc(C#N)ccc1O[C@H](C)COc1cccc(N2C=CNC2C2CC2)c1] | (R)-4-((1-(3-(2-cyclopropyl-1H-imidazol-1-yl)phenoxy)propan-2-yl)oxy)-3-methylbenzonitrile | 0.0015; 0.013 |
| 69 | 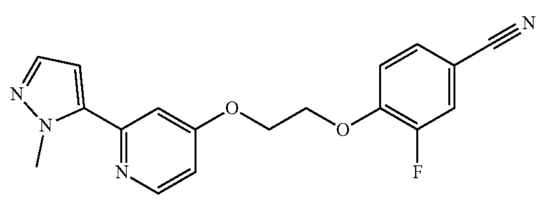 [SMILES: Cn1nccc1-c1cc(OCCOc2ccc(C#N)cc2F)ccn1] | 3-fluoro-4-(2-((2-(1-methyl-1H-pyrazol-5-yl)pyridin-4-yl)oxy)ethoxy)benzonitrile | 0.0028; 0.0014; 0.0015 |
| 70 | 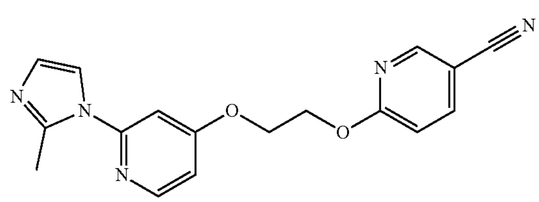 [SMILES: Cc1nccn1-c1cc(OCCOc2ccc(C#N)cn2)ccn1] | 6-(2-((2-(2-methyl-1H-imidazol-1-yl)pyridin-4-yl)oxy)ethoxy)nicotinonitrile | 0.027 |
| 71 | 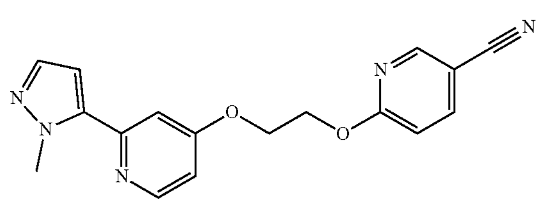 [SMILES: Cn1nccc1-c1cc(OCCOc2ccc(C#N)cn2)ccn1] | 6-(2-((2-(1-methyl-1H-pyrazol-5-yl)pyridin-4-yl)oxy)ethoxy)nicotinonitrile | 0.044; 0.041 |

TABLE 2-continued

Table listing the structure and IC50 of exemplified compounds

| Compound # | Structure | IUPAC Name | ICMT IC50 (μM) |
|---|---|---|---|
| 72 | 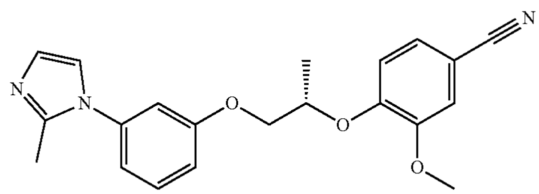 [SMILES: COc1cc(C#N)ccc1O[C@@H](C)COc1cccc(-n2ccnc2C)c1] | (S)-3-methoxy-4-((1-(3-(2-methyl-1H-imidazol-1-yl)phenoxy)propan-2-yl)oxy)benzonitrile | 0.0045 |
| 73 | 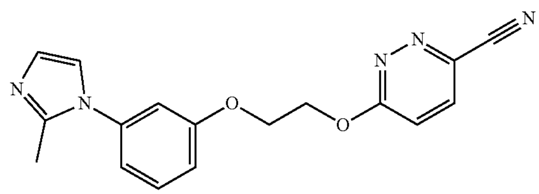 [SMILES: Cc1nccn1-c1cccc(OCCOc2ccc(C#N)nn2)c1] | 6-(2-(3-(2-methyl-1H-imidazol-1-yl)phenoxy)ethoxy)pyridazine-3-carbonitrile | 0.95 |
| 74 | 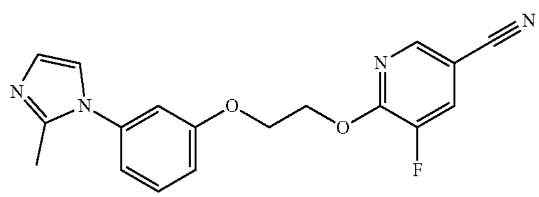 [SMILES: Cc1nccn1-c1cccc(OCCOc2ncc(C#N)cc2F)c1] | 5-fluoro-6-(2-(3-(2-methyl-1H-imidazol-1-yl)phenoxy)ethoxy)nicotinonitrile | 0.065 |
| 75 | 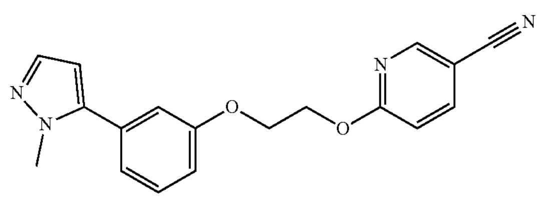 [SMILES: Cn1nccc1-c1cccc(OCCOc2ccc(C#N)cn2)c1] | 6-(2-(3-(1-methyl-1H-pyrazol-5-yl)phenoxy)ethoxy)nicotinonitrile | 0.06; 0.062 |
| 76 | 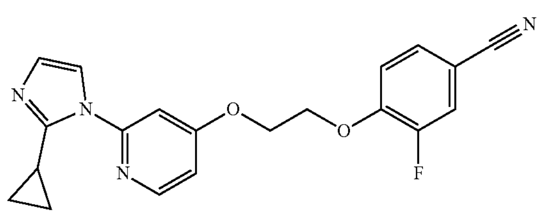 [SMILES: N#Cc1ccc(OCCOc2ccnc(-n3ccnc3C3CC3)c2)c(F)c1] | 4-(2-((2-(2-cyclopropyl-1H-imidazol-1-yl)pyridin-4-yl)oxy)ethoxy)-3-fluorobenzonitrile | 0.39 nM |
| 77 | 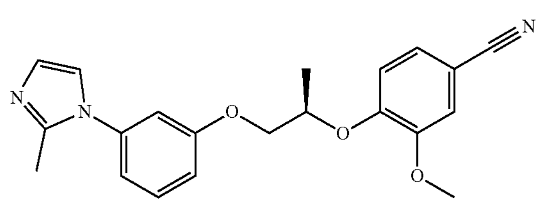 [SMILES: COc1cc(C#N)ccc1O[C@H](C)COc1cccc(-n2ccnc2C)c1] | (R)-3-methoxy-4-((1-(3-(2-methyl-1H-imidazol-1-yl)phenoxy)propan-2-yl)oxy)benzonitrile | 0.7 nM |
| 78 | 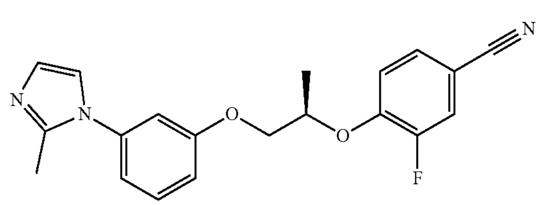 [SMILES: Cc1nccn1-c1cccc(OC[C@@H](C)Oc2ccc(C#N)cc2F)c1] | (R)-3-fluoro-4-((1-(3-(2-methyl-1H-imidazol-1-yl)phenoxy)propan-2-yl)oxy)benzonitrile | 75 pM |

TABLE 2-continued

Table listing the structure and IC50 of exemplified compounds

| Compound # | Structure | IUPAC Name | ICMT IC50 (μM) |
|---|---|---|---|
| 79 | 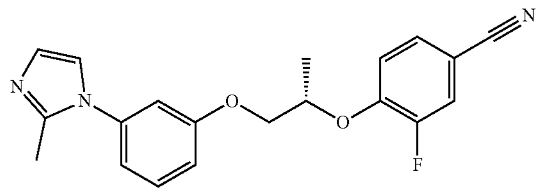 [SMILES: Cc1nccn1-c1cccc(OC[C@H](C)Oc2ccc(C#N)cc2F)c1] | (S)-3-fluoro-4-((1-(3-(2-methyl-1H-imidazol-1-yl)phenoxy)propan-2-yl)oxy)benzonitrile | 0.031 |
| 80 | 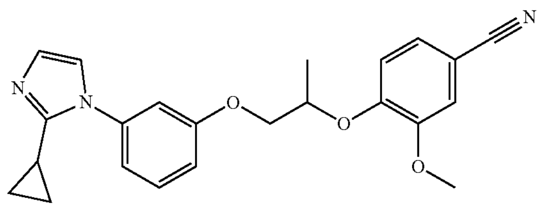 [SMILES: COc1cc(C#N)ccc1OC(C)COc1cccc(-n2ccnc2C2CC2)c1] | 4-((1-(3-(2-cyclopropyl-1H-imidazol-1-yl)phenoxy)propan-2-yl)oxy)-3-methoxybenzonitrile | 3 pM |
| 81 | 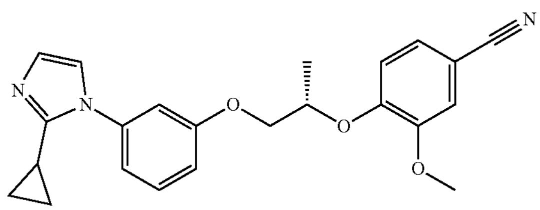 [SMILES: COc1cc(C#N)ccc1O[C@@H](C)COc1cccc(-n2ccnc2C2CC2)c1] | (S)-4-((1-(3-(2-cyclopropyl-1H-imidazol-1-yl)phenoxy)propan-2-yl)oxy)-3-methoxybenzonitrile | 0.001 |
| 82 | 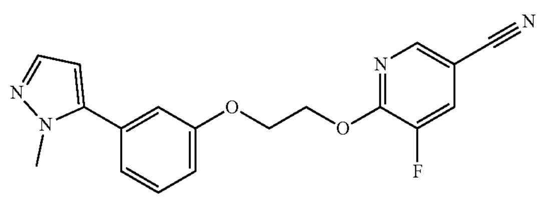 [SMILES: Cn1nccc1-c1cccc(OCCOc2ncc(C#N)cc2F)c1] | 5-fluoro-6-(2-(3-(1-methyl-1H-pyrazol-5-yl)phenoxy)ethoxy)nicotinonitrile | 0.21; 0.19 |
| 83 | 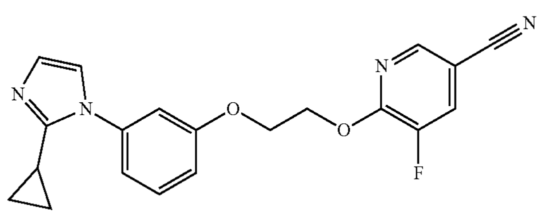 [SMILES: N#Cc1cnc(OCCOc2cccc(-n3ccnc3C3CC3)c2)c(F)c1] | 6-(2-(3-(2-cyclopropyl-1H-imidazol-1-yl)phenoxy)ethoxy)-5-fluoronicotinonitrile | 0.0037 |
| 84 | 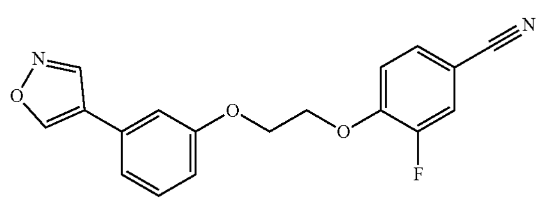 [SMILES: N#Cc1ccc(OCCOc2cccc(-c3cnoc3)c2)c(F)c1] | 3-fluoro-4-(2-(3-(isoxazol-4-yl)phenoxy)ethoxy)benzonitrile | 0.028 |
| 85 | 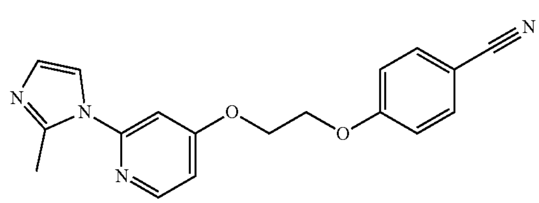 [SMILES: Cc1nccn1-c1cc(OCCOc2ccc(C#N)cc2)ccn1] | 4-(2-((2-(2-methyl-1H-imidazol-1-yl)pyridin-4-yl)oxy)ethoxy)benzonitrile | 0.015 |

TABLE 2-continued

Table listing the structure and IC50 of exemplified compounds

| Compound # | Structure | IUPAC Name | ICMT IC50 (μM) |
|---|---|---|---|
| 86 | 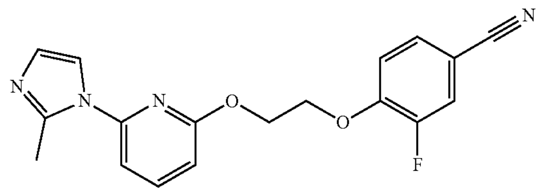 [SMILES: Cc1nccn1-c1cccc(OCCOc2ccc(C#N)cc2F)n1] | 3-fluoro-4-(2-((6-(2-methyl-1H-imidazol-1-yl)pyridin-2-yl)oxy)ethoxy)benzonitrile | 0.017 |
| 87 | 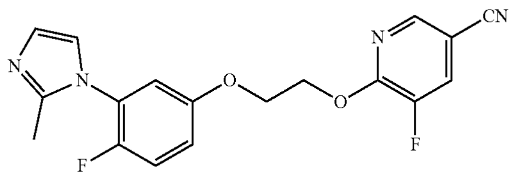 | 5-fluoro-6-(2-(4-fluoro-3-(2-methyl-1H-imidazol-1-yl)phenoxy)ethoxy)nicotinonitrile | 0.033 |
| 88 | 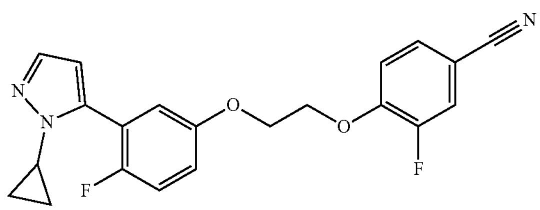 [SMILES: N#Cc1ccc(OCCOc2ccc(F)c(-c3ccnn3C3CC3)c2)c(F)c1] | 4-(2-(3-(1-cyclopropyl-1H-pyrazol-5-yl)-4-fluorophenoxy)ethoxy)-3-fluorobenzonitrile | 0.018 |
| 89 | 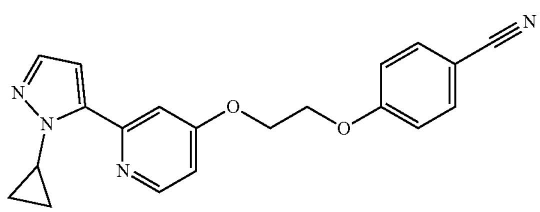 [SMILES: N#Cc1ccc(OCCOc2ccnc(-c3ccnn3C3CC3)c2)cc1] | 4-(2-((2-(2-cyclopropyl-1H-imidazol-1-yl)pyridin-4-yl)oxy)ethoxy)benzonitrile | 0.0028 |
| 90 | 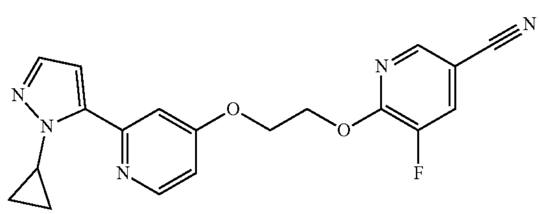 [SMILES: N#Cc1cnc(OCCOc2ccnc(-c3ccnn3C3CC3)c2)c(F)c1] | 6-(2-((2-(2-cyclopropyl-1H-imidazol-1-yl)pyridin-4-yl)oxy)ethoxy)-5-fluoronicotinonitrile | 0.037 |
| 91 | 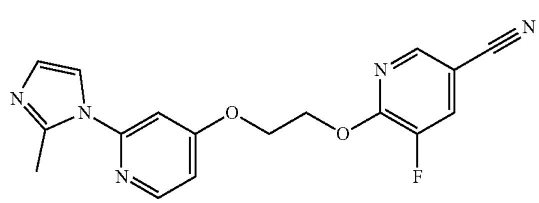 [SMILES: Cc1nccn1-c1cc(OCCOc2ncc(C#N)cc2F)ccn1] | 5-fluoro-6-(2-((2-(2-methyl-1H-imidazol-1-yl)pyridin-4-yl)oxy)ethoxy)nicotinonitrile | 0.12 |
| 92 | 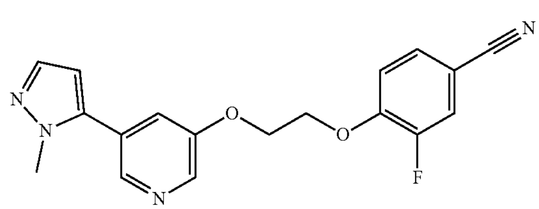 [SMILES: Cn1nccc1-c1cncc(OCCOc2ccc(C#N)cc2F)c1] | 3-fluoro-4-(2-((5-(1-methyl-1H-pyrazol-5-yl)pyridin-3-yl)oxy)ethoxy)benzonitrile | 0.3-1 |

TABLE 2-continued

Table listing the structure and IC50 of exemplified compounds

| Compound # | Structure | IUPAC Name | ICMT IC50 (μM) |
|---|---|---|---|
| 93 | 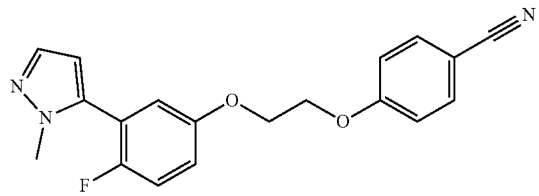 [SMILES: Cn1nccc1-c1cc(OCCOc2ccc(C#N)cc2)ccc1F] | 4-(2-(4-fluoro-3-(1-methyl-1H-pyrazol-5-yl)phenoxy)ethoxy)benzonitrile | 0.0066 |
| 94 | 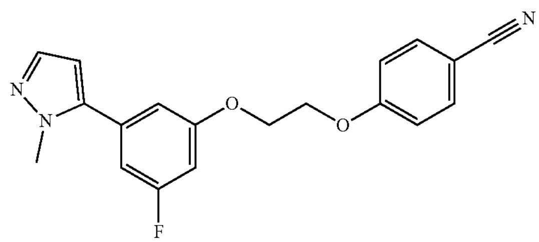 [SMILES: Cn1nccc1-c1cc(F)cc(OCCOc2ccc(C#N)cc2)c1] | 4-(2-(3-fluoro-5-(1-methyl-1H-pyrazol-5-yl)phenoxy)ethoxy)benzonitrile | 0.0016 |
| 95 | 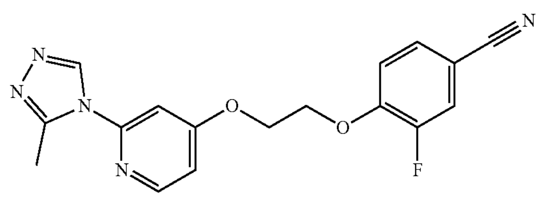 [SMILES: Cc1nncn1-c1cc(OCCOc2ccc(C#N)cc2F)ccn1] | 3-fluoro-4-(2-((2-(3-methyl-4H-1,2,4-triazol-4-yl)pyridin-4-yl)oxy)ethoxy)benzonitrile | 0.01 |
| 96 | 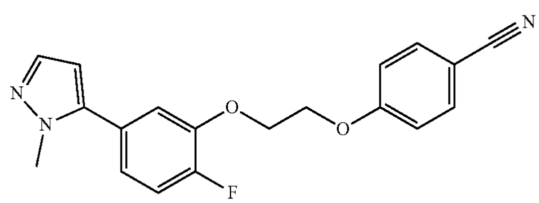 [SMILES: Cn1nccc1-c1ccc(F)c(OCCOc2ccc(C#N)cc2)c1] | 4-(2-(2-fluoro-5-(1-methyl-1H-pyrazol-5-yl)phenoxy)ethoxy)benzonitrile | 0.4-3 |
| 97 | 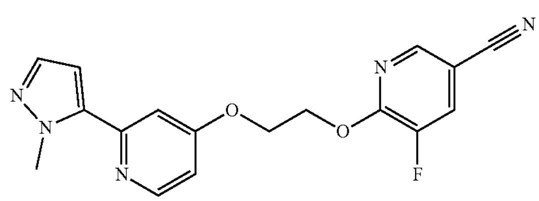 [SMILES: Cn1nccc1-c1cc(OCCOc2ncc(C#N)cc2F)ccn1] | 5-fluoro-6-(2-((2-(1-methyl-1H-pyrazol-5-yl)pyridin-4-yl)oxy)ethoxy)nicotinonitrile | 0.47-1 |
| 98 | 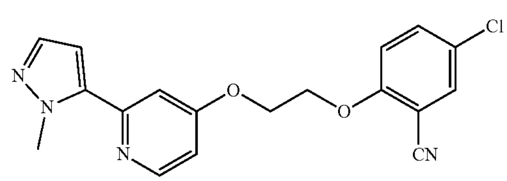 [SMILES: Cn1nccc1-c1cc(OCCOc2ccc(Cl)cc2C#N)ccn1] | 5-chloro-2-(2-((2-(1-methyl-1H-pyrazol-5-yl)pyridin-4-yl)oxy)ethoxy)benzonitrile | 0.01 |
| 99 | 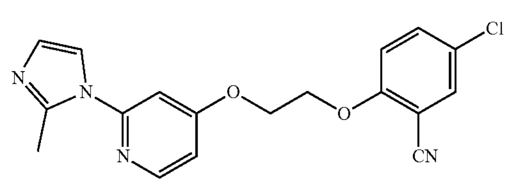 [SMILES: Cc1nccn1-c1cc(OCCOc2ccc(Cl)cc2C#N)ccn1] | 5-chloro-2-(2-((2-(2-methyl-1H-imidazol-1-yl)pyridin-4-yl)oxy)ethoxy)benzonitrile | 0.0026 |

TABLE 2-continued

Table listing the structure and IC50 of exemplified compounds

| Compound # | Structure | IUPAC Name | ICMT IC50 (μM) |
|---|---|---|---|
| 100 | 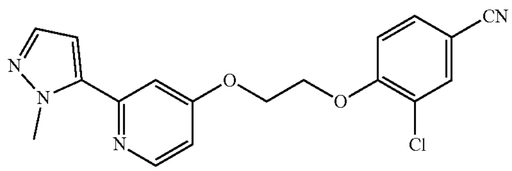 [SMILES: Cn1nccc1-c1cc(OCCOc2ccc(C#N)cc2Cl)ccn1] | 3-chloro-4-(2-((2-(1-methyl-1H-pyrazol-5-yl)pyridin-4-yl)oxy)ethoxy)benzonitrile | 0.0018 |
| 101 | 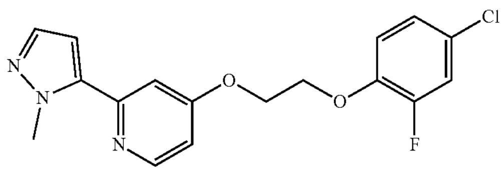 [SMILES: Cn1nccc1-c1cc(OCCOc2ccc(Cl)cc2F)ccn1] | 4-(2-(4-chloro-2-fluorophenoxy)ethoxy)-2-(1-methyl-1H-pyrazol-5-yl)pyridine | 0.029 |
| 102 | 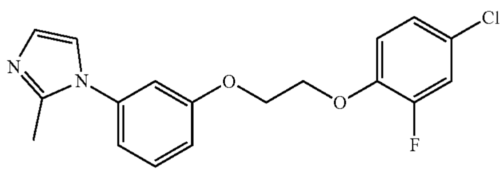 [SMILES: Cc1nccn1-c1cccc(OCCOc2ccc(Cl)cc2F)c1] | 1-(3-(2-(4-chloro-2-fluorophenoxy)ethoxy)phenyl)-2-methyl-1H-imidazole | 0.068 |
| 103 | 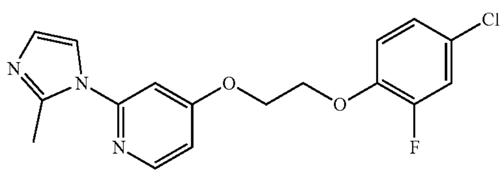 [SMILES: Cc1nccn1-c1cc(OCCOc2ccc(Cl)cc2F)ccn1] | 4-(2-(4-chloro-2-fluorophenoxy)ethoxy)-2-(2-methyl-1H-imidazol-1-yl)pyridine | 0.0031 |
| 104 | 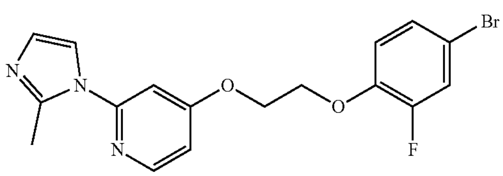 [SMILES: Cc1nccn1-c1cc(OCCOc2ccc(Br)cc2F)ccn1] | 4-(2-(4-bromo-2-fluorophenoxy)ethoxy)-2-(2-methyl-1H-imidazol-1-yl)pyridine | 0.0017 |
| 105 | 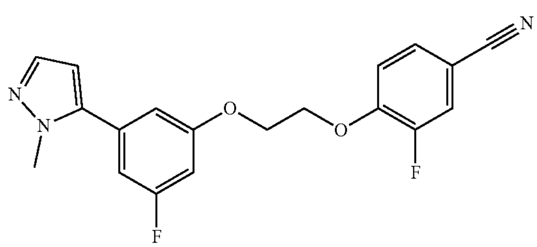 [SMILES: Cn1nccc1-c1cc(F)cc(OCCOc2ccc(C#N)cc2F)c1] | 3-fluoro-4-(2-(3-fluoro-5-(1-methyl-1H-pyrazol-5-yl)phenoxy)ethoxy)benzonitrile | 0.006 |
| 106 | 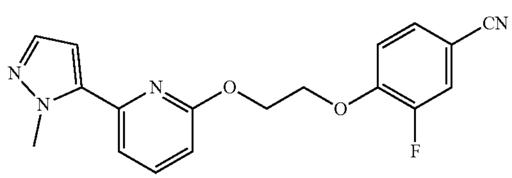 [SMILES: Cn1nccc1-c1cccc(OCCOc2ccc(C#N)cc2F)n1] | 3-fluoro-4-(2-((6-(1-methyl-1H-pyrazol-5-yl)pyridin-2-yl)oxy)ethoxy)benzonitrile | 0.3-1 |
| 107 | 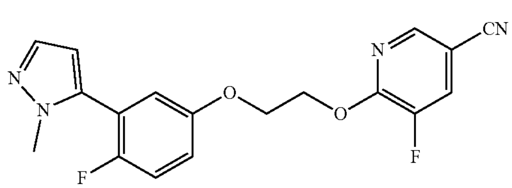 [SMILES: Cn1nccc1-c1cc(OCCOc2ncc(C#N)cc2F)ccc1F] | 5-fluoro-6-(2-(4-fluoro-3-(1-methyl-1H-pyrazol-5-yl)phenoxy)ethoxy)nicotinonitrile | 0.15 |

TABLE 2-continued

Table listing the structure and IC50 of exemplified compounds

| Compound # | Structure | IUPAC Name | ICMT IC50 (μM) |
|---|---|---|---|
| 108 | 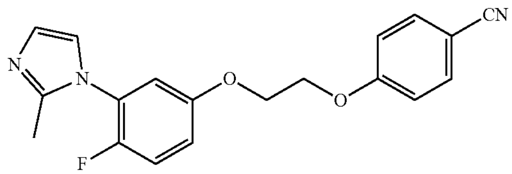 [SMILES: Cc1nccn1-c1cc(OCCOc2ccc(C#N)cc2)ccc1F] | 4-(2-(4-fluoro-3-(2-methyl-1H-imidazol-1-yl)phenoxy)ethoxy)benzonitrile | 0.051 |
| 109 | 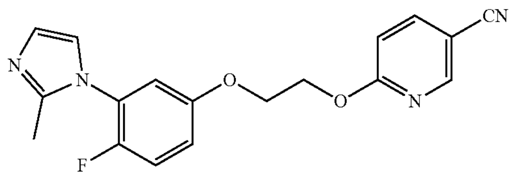 [SMILES: Cc1nccn1-c1cc(OCCOc2ccc(C#N)cn2)ccc1F] | 6-(2-(4-fluoro-3-(2-methyl-1H-imidazol-1-yl)phenoxy)ethoxy)nicotinonitrile | 0.17 |
| 110 | 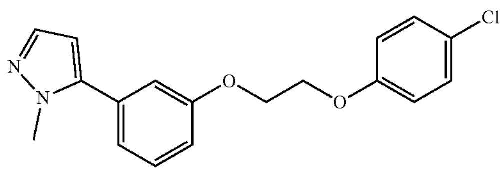 [SMILES: Cn1nccc1-c1cccc(OCCOc2ccc(Cl)cc2)c1] | 5-(3-(2-(4-chlorophenoxy)ethoxy)phenyl)-1-methyl-1H-pyrazole | 0.27 |
| 111 | 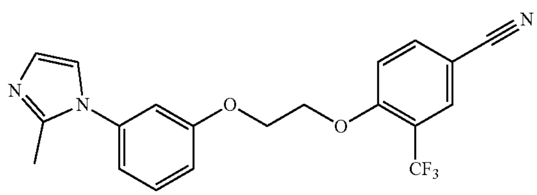 | 4-(2-(3-(2-methyl-1H-imidazol-1-yl)phenoxy)ethoxy)-3-(trifluoromethyl)benzonitrile | 0.18 |
| 112 | 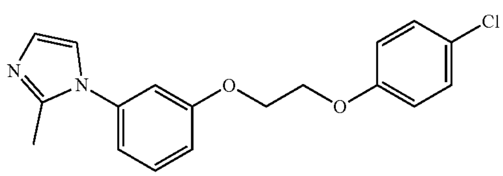 [SMILES: Cc1nccn1-c1cccc(OCCOc2ccc(Cl)cc2)c1] | 1-(3-(2-(4-chlorophenoxy)ethoxy)phenyl)-2-methyl-1H-imidazole | 0.25 |
| 113 | 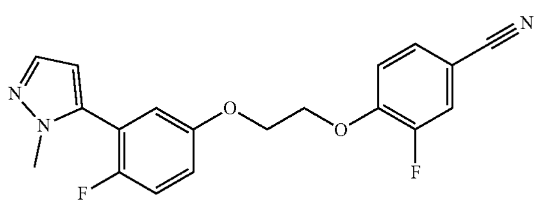 [SMILES: Cn1nccc1-c1cc(OCCOc2ccc(C#N)cc2F)ccc1F] | 3-fluoro-4-(2-(4-fluoro-3-(1-methyl-1H-pyrazol-5-yl)phenoxy)ethoxy)benzonitrile | 0.022 |
| 114 | 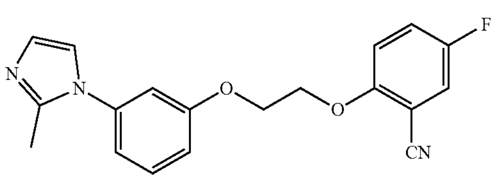 | 5-fluoro-2-(2-(3-(2-methyl-1H-imidazol-1-yl)phenoxy)ethoxy)benzonitrile | 0.082 |
| 115 | 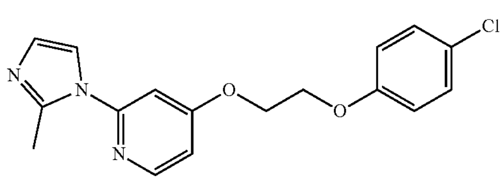 [SMILES: Cc1nccn1-c1cc(OCCOc2ccc(Cl)cc2)ccn1] | 4-(2-(4-chlorophenoxy)ethoxy)-2-(2-methyl-1H-imidazol-1-yl)pyridine | 0.16 |

TABLE 2-continued

Table listing the structure and IC50 of exemplified compounds

| Compound # | Structure | IUPAC Name | ICMT IC50 (µM) |
|---|---|---|---|
| 116 | 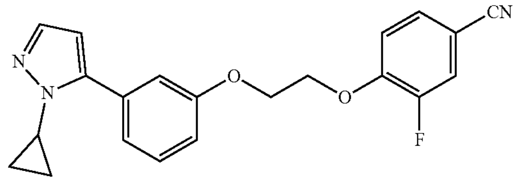 [SMILES: N#Cc1ccc(OCCOc2cccc(-c3ccnn3C3CC3)c2)c(F)c1] | 4-(2-(3-(1-cyclopropyl-1H-pyrazol-5-yl)phenoxy)ethoxy)-3-fluorobenzonitrile | 0.0095 |
| 117 | 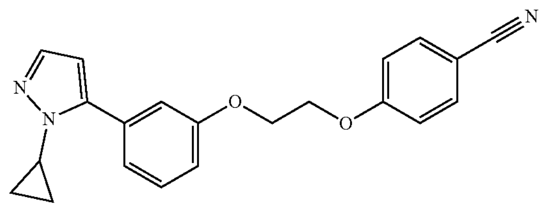 [SMILES: N#Cc1ccc(OCCOc2cccc(-c3ccnn3C3CC3)c2)cc1] | 4-(2-(3-(1-cyclopropyl-1H-pyrazol-5-yl)phenoxy)ethoxy)benzonitrile | 0.055 |
| 118 | 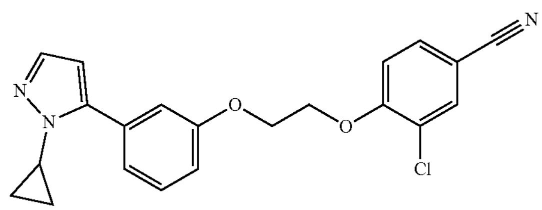 [SMILES: N#Cc1ccc(OCCOc2cccc(-c3ccnn3C3CC3)c2)c(Cl)c1] | 3-chloro-4-(2-(3-(1-cyclopropyl-1H-pyrazol-5-yl)phenoxy)ethoxy)benzonitrile | 0.0022 |
| 119 | 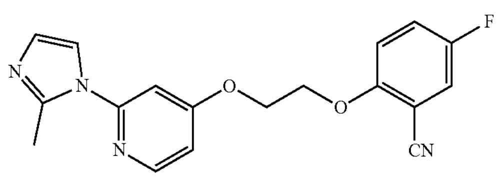 [SMILES: Cc1nccn1-c1cc(OCCOc2ccc(F)cc2C#N)ccn1] | 5-fluoro-2-(2-((2-(2-methyl-1H-imidazol-1-yl)pyridin-4-yl)oxy)ethoxy)benzonitrile | 0.08 |
| 120 | 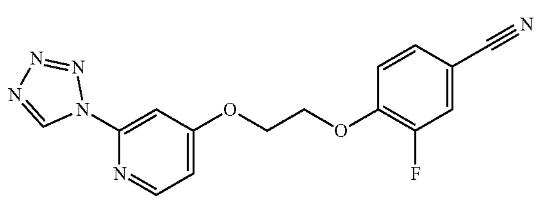 [SMILES: N#Cc1ccc(OCCOc2ccnc(-n3cnnn3)c2)c(F)c1] | 4-(2-((2-(1H-tetrazol-1-yl)pyridin-4-yl)oxy)ethoxy)-3-fluorobenzonitrile | 0.012 |
| 121 | 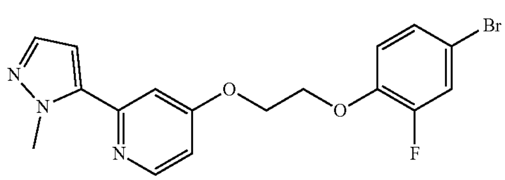 [SMILES: Cn1nccc1-c1cc(OCCOc2ccc(Br)cc2F)ccn1] | 4-(2-(4-bromo-2-fluorophenoxy)ethoxy)-2-(1-methyl-1H-pyrazol-5-yl)pyridine | 0.07 |

INDUSTRIAL APPLICABILITY

The compounds as defined above may find a multiple number of applications in which their ability to inhibit methyltransferases such as ICMT is useful. The compounds may also be used in treating or preventing a condition or disorder in which inhibition of a protein methyl transferase and/or co-factor thereof and/or via an unspecified mechanism prevents, inhibits or ameliorates apathology or a symptomology of the condition. The condition or disorder may be cancer or progeroid disease. The compounds may be particularly useful in treating cancer such as breast cancer, ovarian cancer, pancreatic cancer, leukemia, colorectal carcinoma, lung cancer, hepatocellular carcinoma cancer and other hypervascular tumors as well as angiogenic diseases.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:
1. A compound of Formula (I):

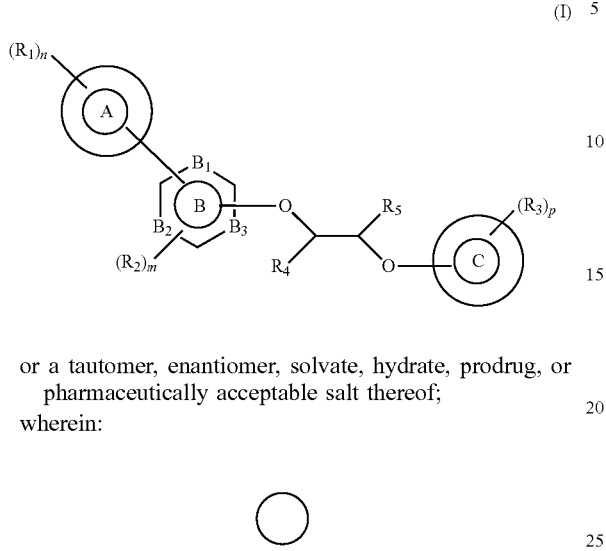

(I)

or a tautomer, enantiomer, solvate, hydrate, prodrug, or pharmaceutically acceptable salt thereof;
wherein:

◯ represents an aromatic ring system;
Ring A is selected from the group consisting of formulas (ab), (a1) to (a8), and (a1') to (a10''):
formula (ab):

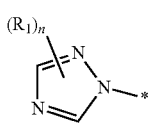

(ab)

wherein:
* represents the point of attachment to Ring B;
$A_1$ is N or C;
$A_2$ is N, S, or CH;
$A_3$ is CH or N;
$A_4$ is N; and
$A_5$ is C, CH, O, or N;
formulas (a1) to (a8):

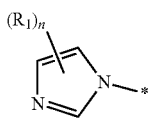

(a1)

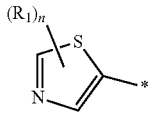

(a2)

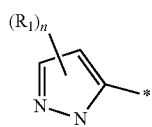

(a3)

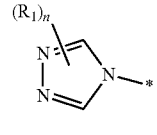

(a4)

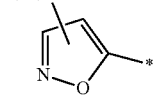

(a5)

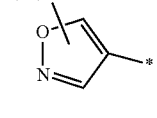

(a6)

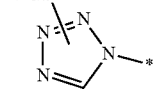

(a7)

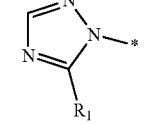

(a8)

wherein * represents the point of attachment to Ring B;
formulas (a1') to (a8'):

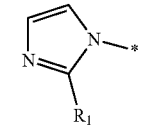

(a1')

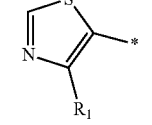

(a2')

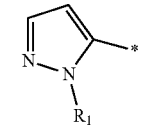

(a3')

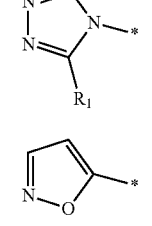

(a4')

(a5')

(a6')

-continued

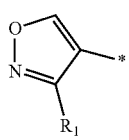
(a7′)

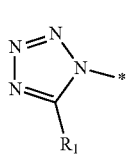
(a8′)

wherein * represents the point of attachment to Ring B; and formulas (a1″) to (a10″):

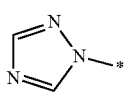
(a1″)

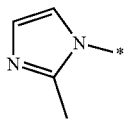
(a2″)

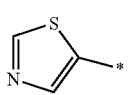
(a3″)

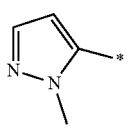
(a4″)

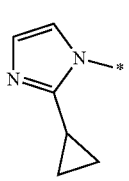
(a5″)

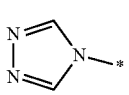
(a6″)

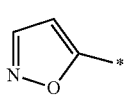
(a7″)

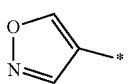
(a8″)

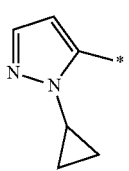
(a9″)

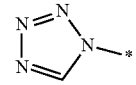
(a10″)

wherein * represents the point of attachment to Ring B;
$B_1$, $B_2$, and $B_3$ are independently selected from C, CH, or N, wherein one of $B_1$, $B_2$, or $B_3$ is N, and the remaining $B_1$, $B_2$, or $B_3$ is C or CH;

Ring B is of formula (bb1) or formula (bb2):

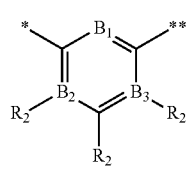
(bb1)

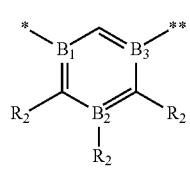
(bb2)

wherein:
* represents the point of attachment to Ring A, and
** represents the point of attachment to the —O(CHR$_4$)— moiety of formula (I);

Ring C is a 5- or 6-membered substituted or unsubstituted carbocyclic ring system, wherein 1 to 3 carbon atoms may be optionally replaced with a heteroatom;

$R_1$ is absent or selected from the group consisting of H, OH, halogen, optionally substituted alkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, and optionally substituted heteroaryl;

$R_2$ is absent or selected from the group consisting of H, OH, cyano, halogen, optionally substituted alkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, optionally substituted aryl, and optionally substituted heteroaryl;

$R_3$ is absent or selected from the group consisting of H, OH, cyano, halogen, optionally substituted alkyl, $CF_3$, $CHF_2$, optionally substituted alkenyl, optionally substituted alkynyl, optionally substituted alkoxy, optionally substituted amino, optionally substituted acyl, optionally substituted cycloalkyl, optionally substituted cycloalkenyl, optionally substituted heterocycloalkyl, and optionally substituted aryl;

$R_4$ and $R_5$ are independently selected from the group consisting of H and aliphatic;

n is an integer selected from 0 to 5, wherein when n is more than 1, and each $R_1$ substituted on Ring A may be the same or different;

m is an integer selected from 0 to 4, wherein when m is more than 1, each $R_2$ substituted on Ring B may be the same or different, and m is 1 when $R_2$ is halogen; and p is an integer selected from 0 to 5, wherein when p is more than 1, and each $R_3$ substituted on Ring C may be the same or different.

2. The compound of claim 1, wherein $R_1$ is alkyl or cycloalkyl.

3. The compound of claim 1, wherein Ring B is selected from the group consisting of formulas (b2) to (b5):

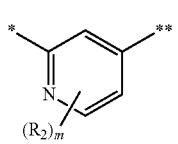
(b2)

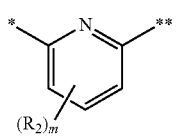
(b3)

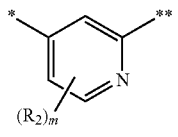
(b4)

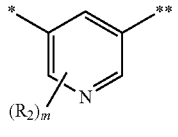
(b5)

wherein:
* represents the point of attachment to Ring A; and
represents the point of attachment to the —O(CHR$_4$)— moiety of formula (I).

4. The compound of claim 1, wherein Ring B is selected from the group consisting of formulas (b2') to (b4') and (b9'):

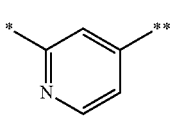
(b2')

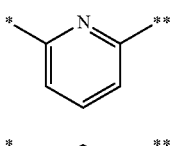
(b3')

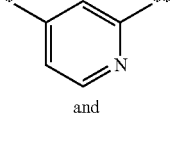
(b4')

and

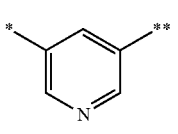
(b9')

wherein:
* represents the point of attachment to Ring A; and
** represents the point of attachment to the —O(CHR$_4$)— moiety of formula (I).

5. The compound of claim 1, wherein $R_2$ is H or F.

6. The compound of claim 1, wherein Ring C is selected from the group consisting of formulas (ca), (cb), (cc), (c1) to (c4), and (c1') to (c6'):

formula (ca):

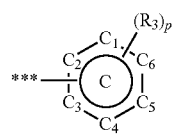
(ca)

wherein:

represents an aromatic ring system;
*** represents the point of attachment to the —O(CHR$_5$)— moiety of formula (I); and
$C_1$, $C_2$, $C_3$, $C_4$, $C_5$ and $C_6$ are independently selected from the group consisting of C, CH, and N, formula (cb):

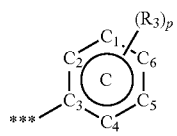
(cb)

wherein:

represents an aromatic ring system;
*** represents the point of attachment to the —O(CHR$_5$)— moiety of formula (I);
$C_1$ and $C_2$ are independently C, CH, or N;
$C_4$, $C_5$, and $C_6$ are C or CH; and
$C_3$ is C, formula (cc):

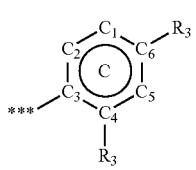
(cc)

wherein:

represents an aromatic ring system;
\*\*\* represents the point of attachment to the —O(CHR$_5$)— moiety of formula (I);
C$_1$ and C$_2$ are independently CH or N;
C$_5$ is CH; and
C$_3$, C$_4$, and C$_6$ are C,
formulas (c1) to (c4):

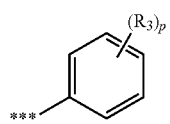 (c1)

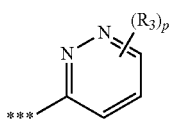 (c2)

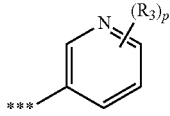 (c3)

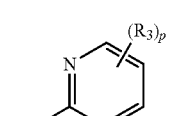 (c4)

wherein:
\*\*\* represents the point of attachment to the —O(CHR$_5$)— moiety of formula (I), and
formulas (c1') to (c6'):

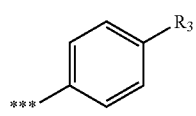 (c1')

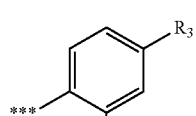 (c2')

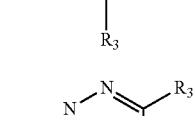 (c3')

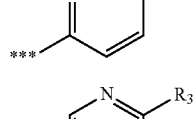 (c4')

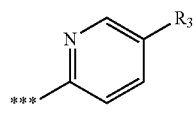 (c5')

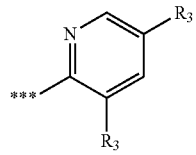 (c6')

wherein:
\*\*\* represents the point of attachment to the —O(CHR$_5$)— moiety of formula (I).

7. The compound of claim 1, wherein Ring C is selected from the group consisting of (c1″) to (c22″):

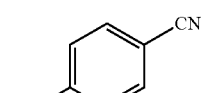 (c1″)

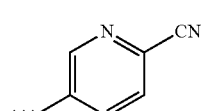 (c2″)

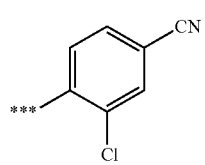 (c3″)

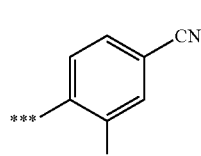 (c4″)

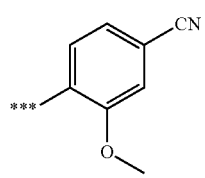 (c5″)

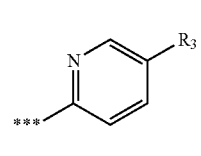 (c6″)

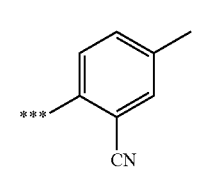 (c7″)

-continued

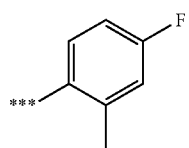 (c8″)

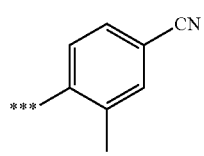 (c9″)

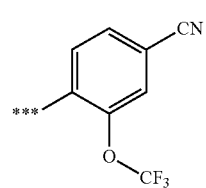 (c10″)

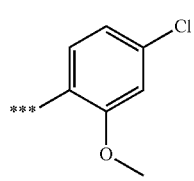 (c11″)

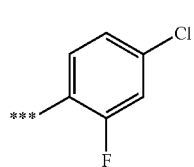 (c12″)

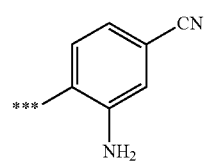 (c13″)

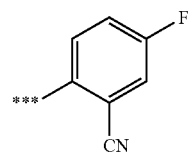 (c14″)

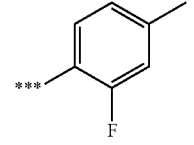 (c15″)

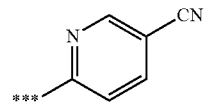 (c16″)

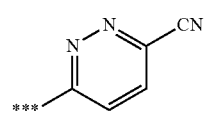 (c17″)

-continued

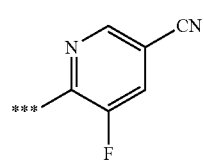 (c18″)

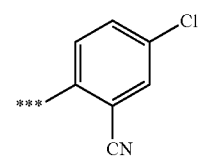 (c19″)

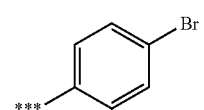 (c20″)

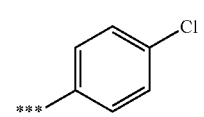 (c21″)

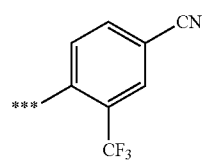 (c22″)

wherein:

*** represents the point of attachment to the —O(CHR$_5$)— moiety of formula (I).

8. The compound of claim 1, wherein R$_3$ is halogen, —CN, alkoxy, amino, haloalkyl, haloalkyloxy, or alkyl.

9. The compound of claim 1, wherein R$_3$ is fluoro, chloro, bromo, —CN, methoxy, methyl, —NH$_2$, —OCF$_3$, CF$_3$, or CHF$_2$.

10. The compound of claim 1, wherein R$_4$ and R$_5$ are independently H or alkyl.

11. The compound of claim 1, wherein R$_4$ and R$_5$ are H; or R$_4$ is H and R$_5$ is methyl; or R$_4$ is methyl and R$_5$ is H; or R$_4$ is methyl and R$_5$ is methyl.

12. The compound of claim 1, selected from the group consisting of:

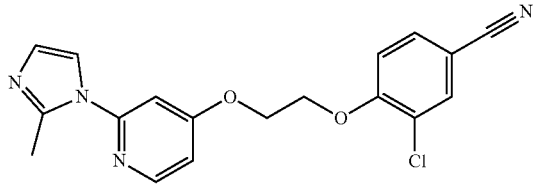

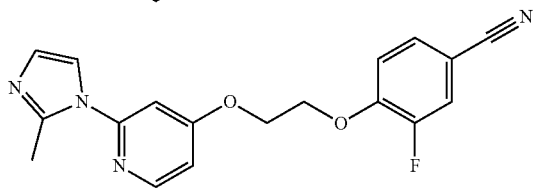

-continued

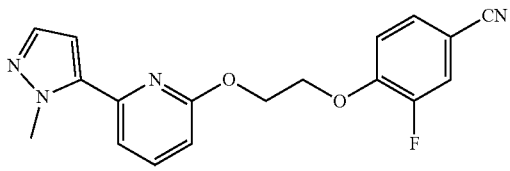

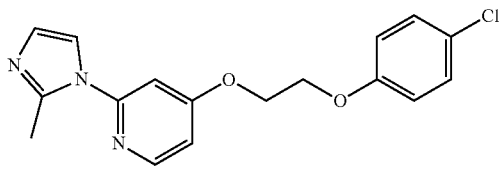

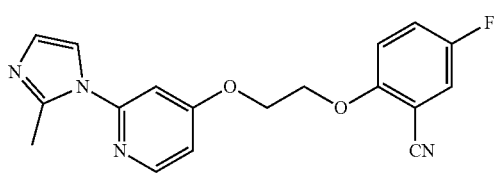

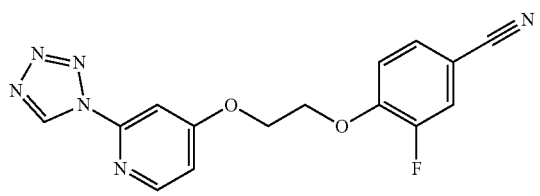 and

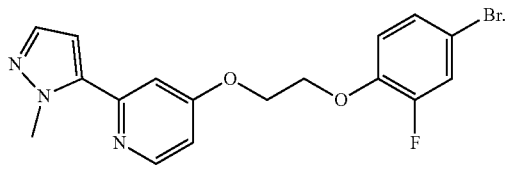 [SMILES: Cn1nccc1-c1cc(OCCOc2ccc(Br)cc2F)ccn1]

13. A pharmaceutical composition comprising a compound of claim 1 or prodrug thereof, and a pharmaceutically acceptable excipient.

14. A method of inhibiting methylation of isoprenylated cysteine or isoprenylcysteine caused by isoprenylcysteine carboxyl methyltransferase (ICMT) comprising contacting a compound of claim 1 with ICMT.

15. The method according to claim 14, comprising administering the compound to a subject having an ICMT-related disorder.

16. The method according to claim 15, wherein the disorder is selected from the group consisting of cancer, premature ageing, Hutchinson-Gilford progeria syndrome (HGPS), and linked to mutant Ras overactivity.

17. A process for synthesizing a compound according to claim 1, comprising:
(a) reacting a compound of formula (III):

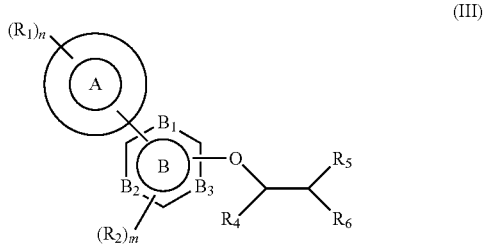

wherein $R_6$ is a leaving group,
in an organic solvent in the presence of a base with a compound of formula (IV):

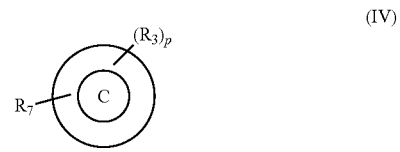

wherein $R_7$ is —OH to obtain the compound of claim 1; or
(b) reacting a compound of formula (III):

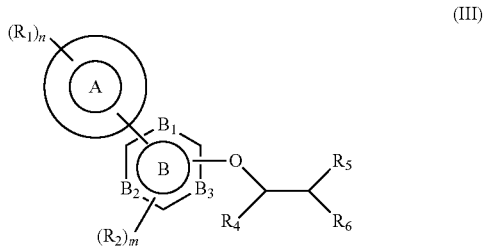

wherein $R_6$ is OH or an alkoxide,
in an organic solvent in the presence of a base with a compound of formula (IV):

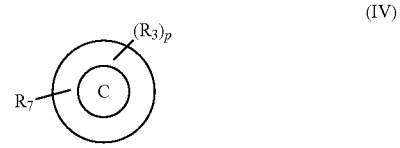

wherein $R_7$ is halogen to obtain the compound of claim 1.

18. The compound of claim 2, wherein $R_1$ is methyl or cyclopropyl.

19. The compound of claim 10, wherein $R_4$ and $R_5$ are independently H, methyl, ethyl, propyl, or butyl.

20. The method according to claim 16, wherein the cancer is selected from the group consisting of hepatocellular carcinoma cancer, breast cancer, ovarian cancer, colorectal carcinoma, lung cancer, pancreatic cancer, and leukemia.

* * * * *

UNITED STATES PATENT AND TRADEMARK OFFICE
CERTIFICATE OF CORRECTION

PATENT NO. : 11,834,430 B2  
APPLICATION NO. : 16/646693  
DATED : December 5, 2023  
INVENTOR(S) : Soo Yei Ho et al.

Page 1 of 1

It is certified that error appears in the above-identified patent and that said Letters Patent is hereby corrected as shown below:

In the Claims

At Column 139, Lines 24-29, " 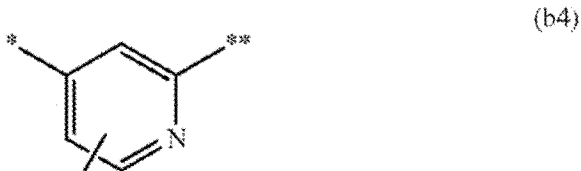 " should be -- 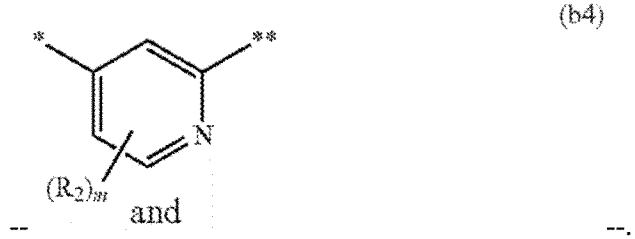 and --.

At Column 139, Line 39, "represents" should be -- ** represents --.

Signed and Sealed this  
Twelfth Day of November, 2024

Katherine Kelly Vidal  
*Director of the United States Patent and Trademark Office*